(12) United States Patent
Winston et al.

(10) Patent No.: US 11,352,403 B2
(45) Date of Patent: *Jun. 7, 2022

(54) ACTIVATABLE INTERLEUKIN-2 POLYPEPTIDES AND METHODS OF USE THEREOF

(71) Applicant: Werewolf Therapeutics, Inc., Cambridge, MA (US)

(72) Inventors: William Winston, West Newton, MA (US); Daniel Hicklin, Montclair, NJ (US); Vinay Bhaskar, San Francisco, CA (US); Luke Evnin, San Francisco, CA (US); Patrick Baeuerle, Gauting (DE); Jose Andres Salmeron Garcia, Westminster, MA (US); Heather Brodkin, West Newton, MA (US); Cynthia Seidel-Dugan, Belmont, MA (US)

(73) Assignee: Werewolf Therapeutics, Inc., Cambridge, MA (US)

( * ) Notice: Subject to any disclaimer, the term of this patent is extended or adjusted under 35 U.S.C. 154(b) by 171 days.

This patent is subject to a terminal disclaimer.

(21) Appl. No.: 16/880,606

(22) Filed: May 21, 2020

(65) Prior Publication Data
US 2020/0283490 A1 Sep. 10, 2020

Related U.S. Application Data

(63) Continuation of application No. 16/438,156, filed on Jun. 11, 2019, now Pat. No. 10,696,724, which is a continuation-in-part of application No. PCT/US2019/032321, filed on May 14, 2019.

(60) Provisional application No. 62/756,507, filed on Nov. 6, 2018, provisional application No. 62/756,504, filed on Nov. 6, 2018, provisional application No. 62/671,225, filed on May 14, 2018.

(51) Int. Cl.
| | |
|---|---|
| C07K 14/55 | (2006.01) |
| A61K 38/00 | (2006.01) |
| A61P 35/00 | (2006.01) |
| C07K 16/28 | (2006.01) |

(52) U.S. Cl.
CPC .............. *C07K 14/55* (2013.01); *A61P 35/00* (2018.01); *C07K 16/2809* (2013.01); *A61K 38/00* (2013.01); *C07K 2317/90* (2013.01); *C07K 2319/31* (2013.01); *C07K 2319/50* (2013.01)

(58) Field of Classification Search
CPC .......................... C07K 14/55; A61K 38/2013
See application file for complete search history.

(56) References Cited

U.S. PATENT DOCUMENTS

| | | | |
|---|---|---|---|
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland |
| 4,816,567 A | 3/1989 | Cabilly et al. |
| 4,927,762 A | 5/1990 | Darfier |
| 4,965,199 A | 10/1990 | Capon et al. |
| 5,089,261 A | 2/1992 | Nitecki et al. |
| 5,122,464 A | 6/1992 | Wilson et al. |
| 5,122,469 A | 6/1992 | Mather et al. |
| 5,208,020 A | 5/1993 | Chari et al. |
| 5,264,365 A | 11/1993 | Georgiou |
| 5,416,064 A | 5/1995 | Chari et al. |
| 5,508,192 A | 4/1996 | Georgiou et al. |
| 5,571,894 A | 11/1996 | Weis et al. |
| 5,587,458 A | 12/1996 | King et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter et al. |
| 5,648,260 A | 7/1997 | Winter et al. |
| 5,712,374 A | 1/1998 | Kunstmann et al. |
| 5,714,586 A | 2/1998 | Kunstmann et al. |
| 5,739,277 A | 4/1998 | Presta et al. |
| 5,767,285 A | 6/1998 | Hamann et al. |
| 5,770,701 A | 6/1998 | McGahren et al. |
| 5,770,710 A | 6/1998 | McGahren et al. |

(Continued)

FOREIGN PATENT DOCUMENTS

| | | |
|---|---|---|
| DE | 19701141 C1 | 4/1998 |
| EP | 0547163 B1 | 2/2002 |

(Continued)

OTHER PUBLICATIONS

Trinchieri et al "The IL-2 family of heterodimeric cytokines: new players in the regulation of T cell responses." Immunity 2003; 19: 641-644.

(Continued)

*Primary Examiner* — Prema M Mertz
(74) *Attorney, Agent, or Firm* — Hogan Lovells US LLP

(57) ABSTRACT

The disclosure features fusion proteins that are conditionally active variants of IL-2. In one aspect, the full-length polypeptides of the invention have reduced or minimal cytokine-receptor activating activity even though they contain a functional cytokine polypeptide. Upon activation, e.g., by cleavage of a linker that joins a blocking moiety, e.g., a steric blocking polypeptide, in sequence to the active cytokine, the cytokine can bind its receptor and effect signaling.

13 Claims, 48 Drawing Sheets

Specification includes a Sequence Listing.

(56) References Cited

U.S. PATENT DOCUMENTS

| | | |
|---|---|---|
| 5,773,001 A | 6/1998 | Hamann et al. |
| 5,780,588 A | 7/1998 | Pettit et al. |
| 5,834,597 A | 11/1998 | Tso et al. |
| 5,869,046 A | 2/1999 | Presta et al. |
| 5,877,296 A | 3/1999 | Hamann et al. |
| 5,891,693 A | 4/1999 | Bebbington et al. |
| 5,939,598 A | 8/1999 | Kucherlapati et al. |
| 6,027,888 A | 2/2000 | Georgiou et al. |
| 6,075,181 A | 6/2000 | Kucherlapati et al. |
| 6,083,715 A | 7/2000 | Georgiou et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,248,516 B1 | 6/2001 | Winter et al. |
| 6,602,684 B1 | 8/2003 | Umana et al. |
| 6,630,579 B2 | 10/2003 | Chari et al. |
| 6,670,147 B1 | 12/2003 | Heidtman et al. |
| 6,821,505 B2 | 11/2004 | Ward et al. |
| 6,942,853 B2 | 9/2005 | Chernajovsky et al. |
| 7,498,298 B2 | 3/2009 | Doronina et al. |
| 7,514,073 B2 | 4/2009 | Epstein et al. |
| 8,399,219 B2 | 3/2013 | Stagliano et al. |
| 8,563,269 B2 | 10/2013 | Stagliano et al. |
| 8,734,774 B2 | 5/2014 | Frelinger et al. |
| 8,809,504 B2 | 8/2014 | Lauermann et al. |
| 8,969,538 B2 | 3/2015 | Rosen et al. |
| 8,993,266 B2 | 3/2015 | Stagliano et al. |
| 9,206,243 B2 | 12/2015 | Leon Monzon et al. |
| 9,309,510 B2 | 4/2016 | La Porte et al. |
| 9,453,078 B2 | 9/2016 | Stagliano et al. |
| 9,487,590 B2 | 11/2016 | West et al. |
| 9,517,276 B2 | 12/2016 | Lowman et al. |
| 9,540,440 B2 | 1/2017 | Lowman et al. |
| 9,644,016 B2 | 5/2017 | Stagliano et al. |
| 9,708,412 B2 | 7/2017 | Baeuerle et al. |
| 9,737,623 B2 | 8/2017 | Desnoyers et al. |
| 9,856,314 B2 | 1/2018 | Lowman et al. |
| 9,861,705 B2 | 1/2018 | Bossard et al. |
| 9,889,211 B2 | 2/2018 | Lowman et al. |
| 10,059,762 B2 | 8/2018 | Stagliano et al. |
| 10,077,300 B2 | 9/2018 | Daugherty et al. |
| 10,100,106 B2 | 10/2018 | Dubridge et al. |
| 10,138,272 B2 | 11/2018 | Moore et al. |
| 10,179,817 B2 | 1/2019 | Sagert et al. |
| 10,233,244 B2 | 3/2019 | Sagert et al. |
| 10,301,380 B2 | 3/2019 | West et al. |
| 10,261,083 B2 | 4/2019 | Vasiljeva et al. |
| 10,513,549 B2 | 12/2019 | Stagliano et al. |
| 10,696,724 B2 * | 6/2020 | Winston ............ C07K 16/2809 |
| 2002/0164328 A1 | 11/2002 | Shinkawa et al. |
| 2003/0139575 A1 | 7/2003 | Gillies et al. |
| 2003/0157108 A1 | 8/2003 | Presta et al. |
| 2003/0190311 A1 | 10/2003 | Dall'Acqua et al. |
| 2004/0014652 A1 | 1/2004 | Trouet et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0132140 A1 | 7/2004 | Satoh et al. |
| 2004/0136952 A1 | 7/2004 | Bhaskaran et al. |
| 2005/0014934 A1 | 1/2005 | Hinton et al. |
| 2006/0166329 A1 | 7/2006 | Rosen et al. |
| 2006/0205926 A1 | 9/2006 | Ross et al. |
| 2006/0236411 A1 | 10/2006 | Dreher et al. |
| 2007/0048282 A1 | 3/2007 | Rosen et al. |
| 2007/0269422 A1 | 11/2007 | Beirnaert et al. |
| 2010/0254944 A1 | 10/2010 | Subramanian et al. |
| 2011/0190209 A1 | 8/2011 | Culbertson et al. |
| 2013/0064788 A1 | 3/2013 | Barnes et al. |
| 2013/0089516 A1 | 4/2013 | Frelinger et al. |
| 2015/0079088 A1 | 3/2015 | Lowman et al. |
| 2015/0087810 A1 | 3/2015 | Moore et al. |
| 2016/0152686 A1 | 6/2016 | Camphausen et al. |
| 2016/0194399 A1 | 7/2016 | Irving et al. |
| 2016/0289324 A1 | 10/2016 | Moore et al. |
| 2016/0311903 A1 | 10/2016 | West et al. |
| 2016/0354472 A1 | 12/2016 | Merchant et al. |
| 2016/0355587 A1 | 12/2016 | West et al. |
| 2017/0044259 A1 | 2/2017 | Tipton et al. |
| 2017/0096472 A1 | 4/2017 | Rosen et al. |
| 2017/0240608 A1 | 8/2017 | Stagliano et al. |
| 2018/0016316 A1 | 1/2018 | Garcia et al. |
| 2018/0119128 A1 | 5/2018 | Metzner et al. |
| 2018/0134789 A1 | 5/2018 | Baeuerle et al. |
| 2018/0200346 A1 | 7/2018 | Ballance et al. |
| 2018/0303952 A1 | 10/2018 | Sagert et al. |
| 2018/0344810 A1 | 12/2018 | Addepalli et al. |
| 2019/0008978 A1 | 1/2019 | Huang et al. |
| 2019/0016814 A1 | 1/2019 | Humphrey et al. |
| 2019/0117789 A1 | 4/2019 | Carman et al. |
| 2019/0135943 A1 | 5/2019 | Boustany et al. |
| 2019/0225702 A1 | 7/2019 | Baeuerle et al. |

FOREIGN PATENT DOCUMENTS

| | | |
|---|---|---|
| EP | 1867660 A1 | 12/2007 |
| EP | 2639241 A2 | 9/2013 |
| EP | 3134102 A4 | 11/2017 |
| EP | 3792277 A1 | 3/2021 |
| WO | 1987/00195 | 1/1987 |
| WO | 1990/03430 | 4/1990 |
| WO | 1991/01743 | 2/1991 |
| WO | 1993/08829 | 5/1993 |
| WO | 1993/16185 | 8/1993 |
| WO | 1994/11026 | 5/1994 |
| WO | 199429351 | 12/1994 |
| WO | 1996027011 | 9/1996 |
| WO | 1997/30087 | 8/1997 |
| WO | 1998/58964 | 12/1998 |
| WO | 1999/22764 | 5/1999 |
| WO | 1999/51642 | 10/1999 |
| WO | 2000/61739 | 10/2000 |
| WO | 2001/30460 A1 | 5/2001 |
| WO | 2001/079271 A1 | 10/2001 |
| WO | 2002022833 A1 | 3/2002 |
| WO | 2002/43478 | 6/2002 |
| WO | 2002076489 | 10/2002 |
| WO | 2003/011878 | 2/2003 |
| WO | 2003/59934 A2 | 7/2003 |
| WO | 2003/084570 | 10/2003 |
| WO | 2003/085119 | 10/2003 |
| WO | 2004/041865 | 5/2004 |
| WO | 2004/056312 | 7/2004 |
| WO | 2005/035586 | 4/2005 |
| WO | 2005/035778 | 4/2005 |
| WO | 2005/053742 | 6/2005 |
| WO | 2006/106905 A1 | 10/2006 |
| WO | 2006110728 A2 | 10/2006 |
| WO | 2008/147530 A1 | 12/2008 |
| WO | 2009103965 A1 | 8/2009 |
| WO | 2010020766 A2 | 2/2010 |
| WO | 2011/011797 A2 | 1/2011 |
| WO | 2011/124718 | 10/2011 |
| WO | 2011123683 A2 | 10/2011 |
| WO | 2012/059486 | 5/2012 |
| WO | 2013163631 A2 | 10/2013 |
| WO | 20131771897 A2 | 11/2013 |
| WO | 2014100014 A1 | 6/2014 |
| WO | 2014/120555 A1 | 8/2014 |
| WO | 2015066279 A2 | 5/2015 |
| WO | 2016/200645 A1 | 12/2016 |
| WO | 2017156178 A1 | 9/2017 |
| WO | 2018/071918 | 4/2018 |
| WO | 2018071777 A1 | 4/2018 |
| WO | 2018136725 A1 | 4/2018 |
| WO | 2018160754 A2 | 9/2018 |
| WO | 2018160877 A1 | 9/2018 |
| WO | 2018/085555 A1 | 11/2018 |
| WO | 2018204528 A1 | 11/2018 |
| WO | 2018204717 A1 | 11/2018 |
| WO | 2018213341 A1 | 11/2018 |
| WO | 2019/014586 A1 | 1/2019 |
| WO | 2019/018828 A1 | 1/2019 |
| WO | 2019036031 A2 | 2/2019 |

(56) References Cited

FOREIGN PATENT DOCUMENTS

| WO | 2019094396 A1 | 5/2019 |
|---|---|---|
| WO | 2019/173832 A2 | 9/2019 |
| WO | 2019/214757 A1 | 11/2019 |
| WO | 2019/222294 A1 | 11/2019 |
| WO | 2019/222295 A1 | 11/2019 |
| WO | 2019/246392 | 12/2019 |
| WO | 2020/069398 A1 | 4/2020 |
| WO | 2020/252264 A1 | 12/2020 |
| WO | 2021/016599 A1 | 1/2021 |
| WO | 2021/030483 A1 | 2/2021 |
| WO | 2021202673 A1 | 7/2021 |
| WO | 2021202675 A1 | 7/2021 |
| WO | 2021202678 A1 | 10/2021 |

OTHER PUBLICATIONS

Gillies, et al "Improved circulating half-life and efficacy of an antibody-interleukin 2 immunocytokine based on reduced intracellular proteolysis" Clinical Cancer Research, the American Association for Cancer Research, US, 8(1) Jan. 2002, 210-216.

Helguera, et al "Antibody-Cytokine fusion proteins: Harnessing the combined power of cytokines and antibodies for cancer therapy" Clinical immunology 105 (3) Dec. 2002, 233-246.

Jana et al "Interleukin-12 (IL-12), but not IL-23, induces the expression of IL-7 in microglia and macrophages: implications for multiple sclerosis." Immunology 2013; 141: 549-563.

Wang et al Structure of the Quaternary Complex of Interleukin-2 with its alpha, beta, and gamma-c receptors. Science Nov. 18, 2005 vol. 310, 1159-1163.

Lasek et al "Interleukin 12: still a promising candidate for tumor immunotherapy?" Cancer Immunol Immunother (2014) 63:419-435.

Montepaone et al "Profile of ustekinumab and its potential in the treatment of active psoriatic arthritis" Open Access Rheumatol. 2014; 6: 7-13.

Gerber et al Preferential attachment of peritoneal tumor metastases to omental immune aggregates and possible role of a unique vascular microenvironment in metastatic survival and growth. Am J Pathol 169(5): 1739-1752.

Marks-Konczalik et al "IL-2-induced cell death is inhibited in IL-15 transgenic mice." PNAS 2000; 97(21): 11445-11450.

Sadlack et al "Ulcerative colitis-like disease in mice with a disrupted interleukin 2 gene." Cell 1993; 75: 253-261.

Rochman et al. "New insights into the regulation of T cells by gamma-c family cytokines." Nat Rev Immunol 2009; 9(7): 480.

Hemar et al "Endocytosis of Interleukin 2 receptors in human T lymphocytes: distinct intracellular localization and fate of the receptor alpha, beta, and gamma chains." J. Cell Biol. 1995; 129(1): 55-64.

Gao et al "High-throughput screening using patient-derived tumor xenografts to predict clinical trial drug response." Nature Medicine 2015; 21(11): 1318-1325.

Suzuki et al. "Deregulated T cell activation and autoimmunity in Mice lacking interleukin-2 Receptor Beta." Science 1995; 268: 1472-1476.

Koreth et al "Interleukin-2 and Regulatory T Cells in Graft-versus-host disease." N. Engl. J. Med. 2011; 365(22): 2055-2066.

Saadoun, et al. "Regulatory T-Cell Responses to Low-Dose Interleukin-2 in HCV-Induced Vasculitis." N. Engl. J. Med. 2011; 365(22): 2067-2077.

Smith, T.F. and Waterman, M.S. "Comparison of biosequences." Advances in applied mathermatics 1981; 2: 482-489.

Willerford, et al "Interleukin-2 receptor alpha chain regulates the size and content of the peripheral lymphoid compartment." Immunity 1995; 3: 521-530.

Yu, A and Malek, T.R. "The Proteosome regulates receptor-mediated endocytosis of interleukin-2" The Journal of Biological Chemistry 2001; 276(1): 381-385.

Bessard et al High antitumor activity of RLI, an interleukin-15 (IL-15)-IL-15 receptor alpha fusion protein, in metastatic melanoma and colorectal cancer. Mol Cancer Ther 2009; 8(9): 2736-2745.

Desbois et al IL-15 Trans-signaling with the superagonist RLI Promotes Effector/Memory CD8+ T cell responses and enhances antitumor activity of PD-1 antagonists. 2016 J Immunol 1-11.

Malek, T.R. and Castro, I. Interleukin-2 receptor signaling: at the interface between tolerance and immunity. Immunity 2010 33(2): 153-165.

Berger et al "An Operational definition of epigenetics." Genes Dev 2009; 23: 781-783.

Klatzmann, D and Abbas, A.K. "The promise of low-dose interleukin-2 therapy for autoimmune and inflammatory diseases." Nat. Rev. Immunol. 2015; 15: 283-294.

Oh et al "IL-15 as a mediator of CD4+ help for CD8+ T cell longevity and avoidance of TRAIL-mediated apoptosis." PNAS 2008; 105(13): 5201-5206.

Berger et al "Safety and immunologic effects of IL-15 administration in nonhuman primates." Blood 2009; 114(12): 2417-2426.

Conlon et al "Redistribution, hyperproliferation, activation of natural killer cells and CD8 T cells, and cytokine production during first-in-human clinical trial of recombinant human interleukin-15 in patients with cancer." J Clin Oncol 2015; 33(1): 74-82.

Bernett et al., "Potency-reduced IL 15/IL 15Ra heterodimeric Fe-fusions display enhanced in vivo activity through increased exposure," Xencor, AACR (2018) Abstract #5565.

Caescu et al., "Active site determinants of substrate recognition by the metalloproteinases TACE and ADAM10," Biochem. J., 424(1):79-88 (2010).

Lindmark et al., "Binding of immunoglobulins to protein A and immunoglobulin levels in mammalian sera," J. Immunol. Meth., 62:1-13 (1983).

U.S. Appl. No. 17/279,407, filed (Int'l) Sep. 27, 2019, by Karow et al. (a copy is not submitted herewith pursuant to the waiver of 37 C.F.R. § 1.98(a)(2)(iii) issued by the Office on Sep. 21, 2004).

Arie et al. "Chaperone function of FkpA, a heat shock prolyl isomerase, in the periplasm of *Escherichia coli*,", Mol. Micro biol. 39:199-210 (2001).

Atwell et al., "Stable heterodimers from remodeling the domain interface of a homodimer using a phage display library," J. Mol. Biol., 270(1):26-35 (1997).

Bachmann, Cellular and Molecular Biology, vol. 2 (Washington, D.C.: American Society for Microbiology), pp. 1190-1219 (1987_.

Barnes et al., "Methods for growth of cultured cells in serum-free medium," Anal. Biochem. 102:255 (1980).

Bass et al., "Hormone phage: an enrichment method for variant proteins with altered binding properties," Proteins, 8:309-314 (1990).

Boerner et al., "Production of antigen-specific human monoclonal antibodies from in vitro-primed human splenocytes," J. Immunol., 147: 86 (1991).

Bothmann and Pluckthun. "Improving Expression of scFv Fragments by Coexpression of Periplasmic Chaperones," J. Biol. Chem. 275:17100-17105 (2000).

Brennan et al., "Preparation of bispecific antibodies by chemical recombination of monoclonal immunoglobulin G1 fragments," Science, 229:81 (1985).

Brodeur et al., Monoclonal Antibody Production Techniques and Applications, pp. 51-63 Marcel Dekker, Inc., New York, (1987).

Carter et al., "High level *Escherichia coli* expression and production of a bivalent humanized antibody fragment," BioTechnology 10: 163-167 (1992).

Carter et al., "Bispecific human IgG by design," J. Immunol. Methods, 248: 7-15 (2001).

Chapman et al. "Therapeutic antibody fragments with prolonged in vivo half-lives," Nature Biotechnol., 17:780-783 (1999).

Chari et al., "Immunoconjugates containing novel maytansinoids: promising anticancer drugs," Cancer Res. 52:127-131 (1992).

Chen et al., "Chaperone activity of DsbC," J. Biol Chem. 274:19601-19605 (1999).

Choe et al., "Fe-Binding Ligands of Immunoglobulin G: An Overview of High Affinity Proteins and Peptides," Materials 9(12): 994 (2016).

(56) References Cited

OTHER PUBLICATIONS

Cunningham and Wells, "High-resolution epitope mapping of hGH-receptor interactions by alanine-scanning mutagenesis," Science, 244:1081-1085 (1989).
Davies et al., "Antibody-antigen complexes," Annual Rev Biochem. 59:439-473, (1990).
Dennis et al., "Albumin binding as a general strategy for improving the pharmacokinetics of proteins," JBC 277(38): 35035-35043 (2002).
Dubowchik et al., "Doxorubicin Immunoconjugates Containing Bivalent, Lysosomally-Cleavable Dipeptide Linkages," Bioorg. & Med. Chem. Letters 12:1529-1532 (2002).
Duncan and Winter, "The binding site for C1q on IgG," Nature 322:738-40 (1988).
Damodaran, "Protein PEGylation: An overview of chemistry and process considerations," European Pharmaceutical Review, 15(1): 18-26 (2010).
Firan, M., et al., "The MHC class I-related receptor, FcRn, plays an essential role in the maternofetal transfer of y-globulin in humans," Int. Immunol. 13: 993-1002 (2001).
Fishwild, D. et al.,"High-avidity human IgG kappa monoclonal antibodies from a novel strain of minilocus transgenic mice," Nature Biotechnology 14: 845-851 (1996).
Graham et al., "Characteristics of a human cell line transformed by DNA from human adenovirus type 5," J. Gen Virol. 36:59 (1977).
Gunasekaran et al., "Enhancing antibody Fc heterodimer formation through electrostatic steering effects: applications to bispecific molecules and monovalent IgG," J Biol Chem., 285(25): 19637-19646 (2010).
Guss et al., "Structure of the IgG-binding regions of streptococcal protein G.," EMBO J. 5:15671575 (1986).
Guyer et al., "Immunoglobulin Binding by Mouse Intestinal Epithelial Cell Receptors," J. Immunol. 117:587 (1976).
Ham et al., "Media and Growth Requirements," Meth. Enz. 58:44 (1979).
Hara et al., "Overproduction of Penicillin-Binding Protein 7 Suppresses Thermosensitive Growth Defect at Low Osmolarty due to an spr Mutation of *Escherichia coli*," Microbial Drug Resistance, 2:63-72 (1996).
Hinman et al., "Preparation and characterization of monoclonal antibody conjugates of the calicheamicins: a novel and potent family of antitumor antibiotics," Cancer Res. 53:3336-3342 (1993).
Hudson et al., "Engineered antibodies," Nat. Med., 9:129-134 (2003).
Idusogie et al., "Mapping of the C1q Binding Site on Rituxan, a Chimeric Antibody with a Human IgG1 Fc," J. Immunol., 164:4178-4184, (2000).
Imai-Nishiya et al., "Double knockdown of a1,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnol., 7:84, 13 pages (2007).
Jefferis et al., "Human immunoglobulin allotypes: Possible implications for immunogenicity," mAbs, 1 (4):332-8 (2009).
Jeffrey et al., "Dipeptide-based highly potent doxorubicin antibody conjugates," Bioorganic & Med. Chem. Letters, 16:358-362 (2006).
Jones et al., "Replacing the complementarity-determining regions in a human antibody with those from a mouse," Nature, 321 :522-525 (1986).
Kim et al., "Localization of the site of the murine IgG1 molecule that is involved in binding to the murine intestinal Fc receptor," European Journal of Immunology, 24:2429-2434 (1994).
King et al., "Monoclonal Antibody Conjugates of Doxorubicin Prepared with Branched Peptide Linkers: Inhibition of Aggregation by Methoxytriethyleneglycol Chains," J. Med. Chem., 45:4336-4343 (2002).
Klein et al., "Progress in overcoming the chain association issue in bispecific heterodimeric IgG antibodies," MAbs, 4(6):653-663 (2012).
Kontermann et al., "Bispecific antibodies," Drug Discovery Today, 20(7) :838-84 7 (2015).

Kozbor et al., "A human hybrid myeloma for production of human monoclonal antibodies," J. Immunol., 133:3001-5 (1984).
Kratz et al., "Prodrugs of anthracyclines in cancer chemotherapy," Current Med. Chem. 13:477-523 (2006).
Krieg et al., "Improved IL-2 immunotherapy by selective stimulation of IL-2 receptors on lymphocytes and endothelial cells," PNAS, 107(26):11906-11911 (2010).
Lehninger, in Biochemistry, second ed., pp. 73-75, Worth Publishers, New York (1975).
Lin et al., Targeting Drug Conjugates to the Tumor Microenvironment: Probody Drug Conjugates, Innovations for Next-Generation Antibody-Drug Conjugates, 2018, 281-298, Humana Press, USA.
Wong et al., In vivo imaging of protease activity by Probody therapeutic activation, Biochimie, Nov. 4, 2015, 62-67, vol. 122, Elsevier, USA.
Desnoyers et al., Tumor-Specific Activation of an EGFR-Targeting Probody Enhances Therapeutic Index, Science Translational Medicine, Oct. 16, 2013, , vol. 5, Issue 207, American Association for the Advancement of Science, USA.
Lebeau et al., Imaging a functional tumorigenic biomarker in the transformed epithelium, PNAS, Jan. 2, 2013, 93-98, vol. 110, Issue 1, National Academy of Sciences, USA.
Jabaiah et al., Identification of protease exosite-interacting peptides that enhance substrate cleavage kinetics, Biol Chem., Sep. 2012, 933-941, vol. 393, Issue 9, ASBMB Publications, USA.
Erster et al., Site-specific targeting of antibody activity in vivo mediated by disease-associated proteases, Journal of Controlled Release, Aug. 10, 2012, 804-812, vol. 161, Issue 3, Elsevier, USA.
Drag et al., Emerging principles in protease-based drug discovery, Nat Rev Drug Discov., Nov. 5, 2010, 690-701, vol. 9, Issue 9, Springer Nature, USA.
Boulware et al., Evolutionary optimization of peptide substrates for proteases that exhibit rapid hydrolysis kinetics, Biotechnol Bioeng., Jun. 15, 2010, 339-46, vol. 106, Issue 3, Wiley, USA.
Darragh et al., Specific targeting of proteolytic activity for tumor detection in vivo, Cancer Res., Feb. 15, 2010, 1505-1512, vol. 70, Issue 5, AACR, USA.
Agard et al., Methods for the proteomic identification of protease substrates, Curr Opin Chem Biol., Dec. 2009, 503-509, vol. 12, Issue 5-6, Elsevier, USA.
Ulisse et al., The urokinase plasminogen activator system: a target for anti-cancer therapy, Curr Cancer Drug Targets, Feb. 2009, 32-71, vol. 9, Issue 1, Bentham Science.
Vartak et al. Matrix metalloproteases: underutilized targets for drug delivery, J Drug Target, Jan. 2007, 1-20, vol. 15, Issue 1.
Uhland, Matriptase and its putative role in cancer, Cell Mol Life Sci., Dec. 2006, 2968-2978, vol. 63, Issue 24.
Boulware et al., Protease specificity determination by using cellular libraries of peptide substrates (CLiPS), PNAS, May 16, 2006, 7583-7588, vol. 103, Issue 20, National Academy of Sciences, USA.
Rice et al., Bacterial display using circularly permuted outer membrane protein OmpX yields high affinity peptide ligands, Protein Sci., 825-836, Apr. 2006, vol. 15, Issue 4, Wiley.
Declerck et al., Proteases, extracellular matrix, and cancer: a workshop of the path B study section, Am J Pathol., Apr. 2004, 1131-1139, vol. 164, Issue 4, Elsevier, USA.
Geletu et al., Effect of Caveolin-1 upon Stat3-ptyr705 levels in breast and lung carcinoma cells., Biochem Cell Biol., Apr. 15, 2019, 1-19, Canadian Science Publishing.
Vasiljeva et al., The multifaceted roles of tumor-associated proteases and harnessing their activity for prodrug activation, Biological Chemistry, Apr. 22, 2019, Walter de Gruyter GmbH, (abstract only).
Giesen et al., 8089Zr-labeled anti-PD-L1 CX-072 PET imaging in human xenograft and syngeneic tumors, Annals of Oncology, Feb. 27, 2019, vol. 30, Issue Supplement 1, Oxford Academic.
Zhao et al., FGFR1β is a driver isoform of FGFR1 alternative splicing in breast cancer cells, Oncotarget, Jan. 1, 2019, 30-44, vol. 10, Issue 1, Impact Journals, LLC.
Osorio et al., Understanding and quantifying the immune microenvironment in hepatocellular carcinoma, Transl Gastroenterol Hepatol. Dec. 24, 2018, 3:107, AME Publishing Company.

(56) References Cited

OTHER PUBLICATIONS

Zavrsnik et al., Cystatin C deficiency suppresses tumor growth in a breast cancer model through decreased proliferation of tumor cells, Oncotarget, Apr. 24, 2017, 73793-73809, vol. 8, Issue 43, Impact Journals, LLC.
Manuale L. Penichet, "Antibody-cytokine fusion proteins for the therapy of cancer", Immunology, 2001, pp. 91-101.
Irving et al., A Clue to Antigen Receptor Tails, J Immunol, May 1, 2014, 4013-4014, vol. 192, Issue 9, The American Association of Immunologists, Inc., USA.
Polu et al., Probody therapeutics for targeting antibodies to diseased tissue, May 20, 2014, Expert Opinion on Biological Therapy, 1049-1053, vol. 14, Issue 8, Taylor & Francis Online.
Lebeau et al., Imaging Active Urokinase Plasminogen Activator in Prostate Cancer, Cancer Res, 1225-1235, vol. 75, Issue 7, AACR, USA (2015).
Pandya et al., PKCα Attenuates Jagged-1-Mediated Notch Signaling in ErbB-2-Positive Breast Cancer to Reverse Trastuzumab Resistance, Clin Cancer Res, 175-186, Jan. 1, 2016, vol. 22 Issue 1, AACR, USA.
Hoos et al., CCR 20th Anniversary Commentary: Immune-Related Response Criteria—Capturing Clinical Activity in Immuno-Oncology, Clin Cancer Res. Nov. 15, 2015, 4989-4991, vol. 21, Issue 22, American Association of Cancer Research, USA.
Adusumilli et al., New Cancer Immunotherapy Agents in Development: a report from an associated program of the 31stAnnual Meeting of the Society for Immunotherapy of Cancer, 2016, J Immunother Cancer, Jun. 20, 2017, 1-9, vol. 5, Issue 50, BioMed Central, USA.
Afonina et al., Proteolytic Processing of Interleukin-1 Family Cytokines: Variations on a Common Theme, Immunity Review16 Jun. 2015, 991-1004, vol. 42, Issue 6, Elsevier, USA.
Halin et al., Synergistic Therapeutic Effects of a Tumor Targeting Antibody Fragment, Fused to Interleukin 12 and to Tumor Necrosis Factor α, Cancer Research, Jun. 2003, 3202-3210, vol. 63, Issue 12, AACR, USA.
Deluca et al., Potentiation of PD-L1 blockade with a potency-matched dual cytokine-antibody fusion protein leads to cancer eradication in BALB/c-derived tumors but not in other mouse strains, Cancer Immunol Immunother, Sep. 6, 2018, 1381-1391, vol. 67, Issue 9, Springer.
Fercher et al., Evolution of the magic bullet: Single chain antibody fragments for the targeted delivery of immunomodulatory proteins, Exp Biol Med, Jan. 2018, 166-183, vol. 243, Issue 2, Sage Journals.
De Luca et al., Potency-matched Dual Cytokine-Antibody Fusion Proteins for Cancer Therapy, Mol Cancer Ther, Nov. 2017, 2442-2451, vol. 16, Issue 11, AACR, USA.
Kim et al., Novel immunocytokine IL12-SS1 (Fv) inhibits mesothelioma tumor growth in nude mice, PLoS One, Nov. 15, 2013, 1-11, vol. 8, Issue 11, PLOS.
Pedretti et al, Combination of temozolomide with immunocytokine F16-IL2 for the treatment of glioblastoma, Br J Cancer, Sep. 7, 2010, 827-836, vol. 103, Issue 6, SpringerNature, UK.
Kaspar et al., The antibody-mediated targeted delivery of interleukin-15 and GM-CSF to the tumor neovasculature inhibits tumor growth and metastasis, Cancer Res, May 15, 2007, 4940-4098, vol. 67 Issue 10, AACR. USA.
Mitsiades et al., Matrix Metalloproteinase-7-mediated Cleavage of Fas Ligand Protects Tumor Cells from Chemotherapeutic Drug Cytotoxicity, Cancer Research, Jan. 15, 2001, 577-581, vol. 61, AACR, USA.
John Puskas et al., Development of an attenuated interleukin-2 fusion protein that can be activated by tumour-expressed proteases, Jun. 23, 2011, Immunology, vol. 133, No. 2, pp. 206-220.
Denise Skrombolas et al., Challenges and developing solutions for increasing the benefits of IL-2 treatment in tumor therapy, Expert Review of Clinical Immunology, vol. 10, No. 2, Feb. 1, 2014, pp. 207-217.

William R. Strohl, Fusion Proteins for Half-Life Extension of Biologics as a Strategy to Make Biobetters, Biodrugs, vol. 29, No. 4, Jul. 16, 2015, pp. 215-239.
Rodrigo Vazquez-Lombardi et al., Molecular Engineering of Therapeutic Cytokines, Antibodies, vol. 2 No. 3, Jul. 3, 2013, pp. 426-451.
Skrombolas, et al. "Development of protease activated interleukin-12 cytokine fusion proteins for tumor immunotherapy (TUM7P. 946)," The Journal of Immunology; 203:28, 192 (1 Supplement) (2014).
Skrombolas, etl al. "Development of an Interleukin-12 Fusion Protein That is Activated by Cleavage with Matrix Metalloproteinase 9," Journal of Interferon & Cytokine Research, 39(4):233-245 (2019).
Lonberg, et al., "Antigen-specific human antibodies from mice comprising four distinct genetic modifications," Nature 368:856-859 (1994).
Mather et al., "Culture of testicular cells in hormone-supplemented serum-free medium," Annals N.Y. Acad. Sci., 383:44-68 (1982).
Mather, "Establishment and characterization of two distinct mouse testicular epithelial cell lines," Biol. Reprod. 23:243-251 (1980).
Merchant et al., "An efficient route to human bispecific IgG," Nat. Biotechnol., 16(7):677-681 (1988).
Milstein et al., "Hybrid hybridomas and their use in immunohistochemistry," Nature, 305:537 (1983).
Moore et al. "A novel bispecific antibody format enables simultaneous bivalent and monovalent co-engagement of distinct target antigens," MAbs., 3(6): 546-557 (2011).
Mori et al., "Engineering Chinese hamster ovary cells to maximize effector function of produced antibodies using FUT8 siRNA," Biotechnol. Bioeng. 88(7):901-908 (2004).
Morimoto et al., "Single-step purification of F(ab12 fragments of mouse monoclonal antibodies (immunoglobulins G1) by hydrophobic interaction high performance liquid chromatography using TSKgel Phenyl-5PW," Journal of Biochemical and Biophysical Methods, 24:107-117 (1992).
Nagy et al., ("Stability of cytotoxic luteinizing hormone-releasing hormone conjugate (AN-152) containing doxorubicin 14-O-hemiglutarate in mouse and human serum in vitro: Implications for the design of preclinical studies," Proc. Natl. Acad. Sci. USA, 97:829-834 (2000).
Nilvebrant et al., "The albumin-binding domain as a scaffold for protein engineering," Comput. Struct. Biotechol. J., 6:e201303009, 8 pages (2013).
Nygren et al., "Analysis and use of the serum albumin binding domains of streptococcal protein G," J. Mal. Recogn., 1 (2):69-74 (1988).
Okazaki et al., "Fucose depletion from human IgG1 oligosaccharide enhances binding enthalpy and association rate between IgG1 and FcgammaRIIIa," J. Mal. Biol., 336:1239-1249 (2004).
Omasa et al., "Decrease in antithrombin III fucosylation by expressing GDP-fucose transporter siRNA in Chinese hamster ovary cells," J. Biosci. Bioeng., 106(2):168-173 (2008).
Podust et al., "Extension of in vivo half-life of biologically active molecules by XTEN protein polymers," J. Controlled Release, 240:52-66 (2016).
Proba et al., "Functional antibody single-chain fragments from the cytoplasm of *Escherichia coli*: influence of thioredoxin reductase (TrxB)," Gene, 159:203-207 (1995).
Ramm et al., "The periplasmic *Escherichia coli* peptidylprolyl cis, trans-isomerase FkpA II. Isomerase-independent chaperone activity in vitro," J. Biol. Chem., 275:17106-17113 (2000).
Reyes et al., "Expression of human 13-interferon cDNA under the control of a thymidine kinase promoter from herpes simplex virus," Nature, 297:598-601 (1982).
Riechmann et al.,"Reshaping human antibodies for therapy," Nature, 332:323-327 (1988).
Ridgway et al., "'Knobs-into-holes' engineering of antibody CH3 domains for heavy chain heterodimerization," Protein Eng., 9(7):617-621 (1996).
Ripka et al., "Two Chinese hamster ovary glycosylation mutants affected in the conversion of GDP-man nose to GDP-fucose," Arch. Biochem. Biophys., 249:533-545 (1986).

(56) References Cited

OTHER PUBLICATIONS

Roux et al., "Comparisons of the ability of human IgG3 hinge mutants, IgM, IgE, and IgA2, to form small immune complexes: a role for flexibility and geometry," J Immunol, 161 :4083-90 (1998).
Sali et al.. "Characterization of a Novel Human-Specific STING Agonist that Elicits Antiviral Activity Against Emerging Alphaviruses," PloS Pathog., 11(12):e1005324, 30 pages (2015).
Schlapschy et al., "PASylation: a biological alternative to PEGylation for extending the plasma half-life of pharmaceutically active proteins," Protein Eng. Des. Sel., 26(8):489-501 (2013).
Shields et al., High resolution mapping of the binding site on human IgG1 for Fc gamma RI, Fc gamma RII, Fc gamma RIii, and FcRn and design of IgG1 variants with improved binding to the Fc gamma R, J. Biol. Chem., 276:6591-6604. (2001).
Shields et al., "Lack of fucose on human IgG1 N-linked oligosaccharide improves binding to human Fcgamma RIii and antibody-dependent cellular toxicity," J. Biol. Chem., 277(30):26733-40 (2002).
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J. Biol. Chem., 278(5):3466-73 (2003).
Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-3473 (2003).
Simmons et al., "Expression of full-length immunoglobulins in *Escherichia coli*: rapid and efficient production of aglycosylated antibodies," J. Immunol. Methods, 263:133-147 (2002).
Sola et al. "Modulation of protein biophysical properties by chemical glycosylation: biochemical insights and biomedical implications," Cell. Mol. Life Sci., 64(16):2133-2152 (2007).
Sola et al., "Effects of Glycosylation on the Stability of Protein Pharmaceuticals," J. Pharm. Sci., 98(4):1223-1245 (2009).
Sties et al. (eds), Basic and Clinical Immunology, 8th Edition, Appleton & Lange, Nmwalk, CT, p. 71 and Chapter 6 (1994).
Suresh et al., "Bispecific monoclonal antibodies from hybrid hybridomas," Methods in Enzymology, 121:210-228 (1986).
Tomizuka et al., "Double trans-chromosomic mice: Maintenance of two individual human chromosome fragments containing Ig heavy and K loci and expression of fully human antibodies," Proc. Natl. Acad. Sci. USA, 97:722-727 (2000).
Torgov et al., "Generation of an Intensely Potent Anthracycline by a Monoclonal Antibody-[3-Galactosidase Conjugate," Bioconj. Chem., 16:717-721 (2005).
Traunecker et al., "Bispecific single chain molecules (Janusins) target cytotoxic lymphocytes on HIV infected cells," EMBO J., 10:3655-3656 (1991).
Urlaub et al., "Isolation of Chinese hamster cell mutants deficient in dihydrofolate reductase activity," Proc. Natl. Acad. Sci. USA, 77:4216-4220 (1980).
Verhoeven et al., "Reshaping human antibodies: grafting an antilysozyme activity," Science, 239:1534-1536 (1988).
Vitetta et al., "Redesigning nature's poisons to create anti-tumor reagents," Science, 238:1098-1104 (1987).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng., 87:614-22 (2004).
Yamane-Ohnuki et al., "Production of therapeutic antibodies with controlled fucosylation," MAbs, 1 (3):230-236 (2009).
Yaniv, "Enhancing elements for activation of eukaryotic promoters," Nature 297:17-18 (1982).
Yeung et al., "Engineering Human IgG1 Affinity to Human Neonatal Fc Receptor: Impact of Affinity Improvement on Pharmacokinetics in Primates," J. Immunol., 182:7667-7671 (2009).
Zapata et al., "Engineering linear F(ab')2 fragments for efficient production in *Escherichia coli* and enhanced antiproliferative activity," Protein Eng., 8(10):1057-1062 (1995).
Xue et al., "A tumor-specific pro-IL-12 activates preexisting cytotoxic T cells to control established tumors," Science Immunology, vol. 7, pp. 1-14, (2022).
Xue et al., "Supplementary Materials for A tumor-specific pro-IL-12 activates preexisting cytotoxic T cells to control established tumors," Science Immunology, vol. 7, pp. 1-26, (2022).
Cao, et al., "Next generation of tumor-activating type I IFN enhances anti-tumor immune responses to overcome therapy resistance," Nature Communications, 12:5866, pp. 1-11 (2021).

\* cited by examiner

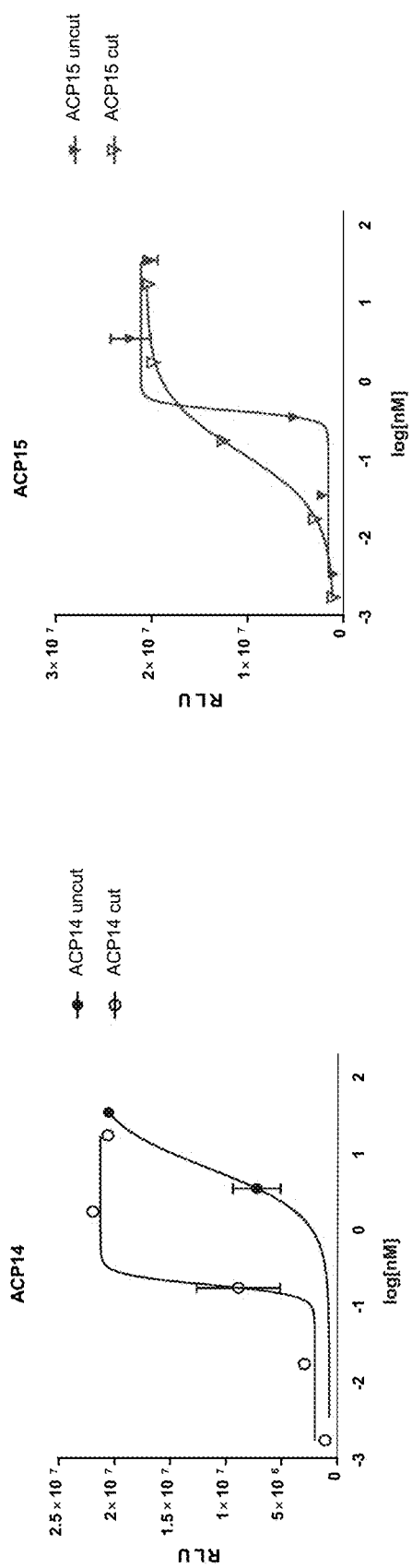
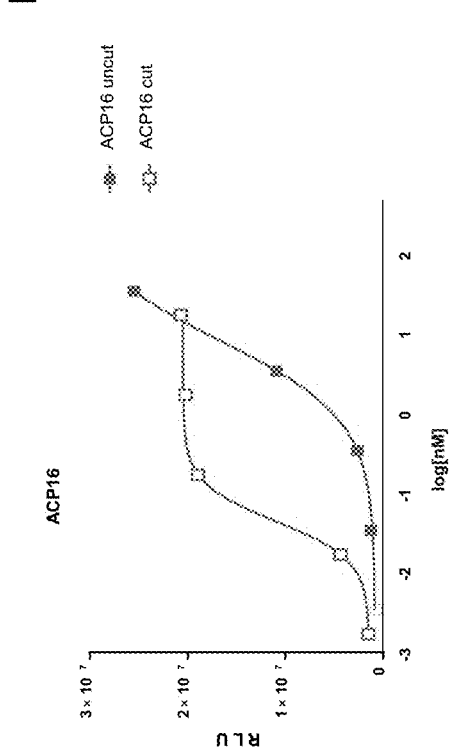
FIG. 8a
FIG. 8b
FIG. 8c

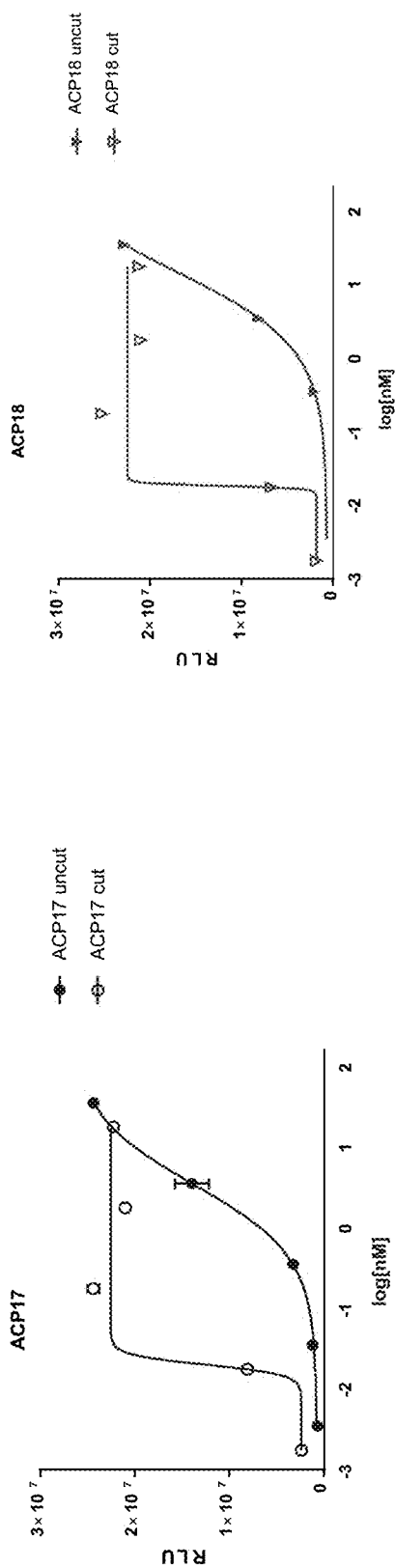
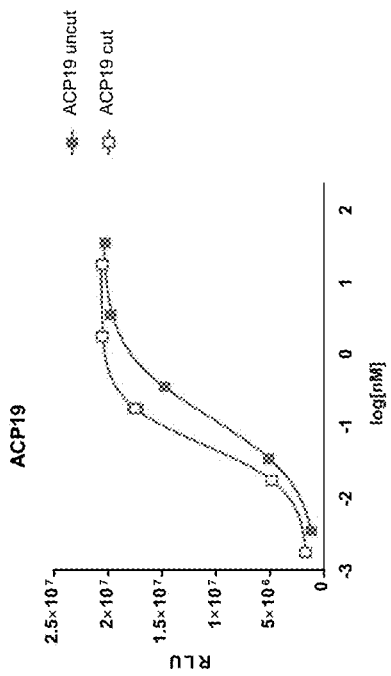
FIG. 8d
FIG. 8e
FIG. 8f

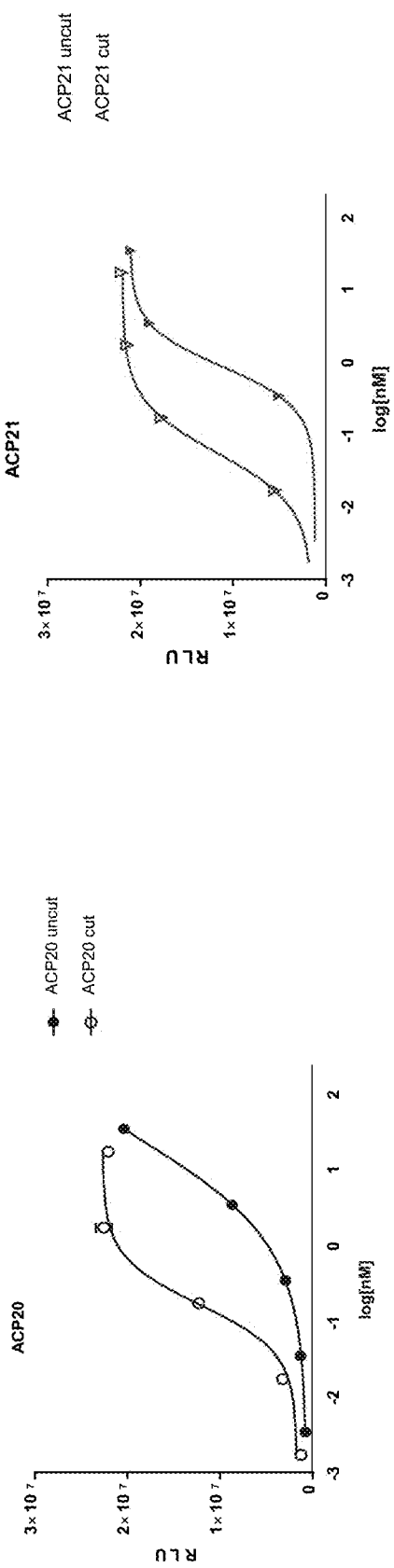
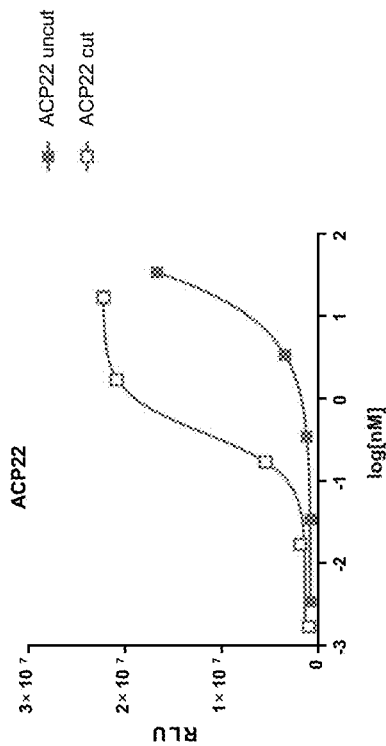
FIG. 9a
FIG. 9b
FIG. 9c

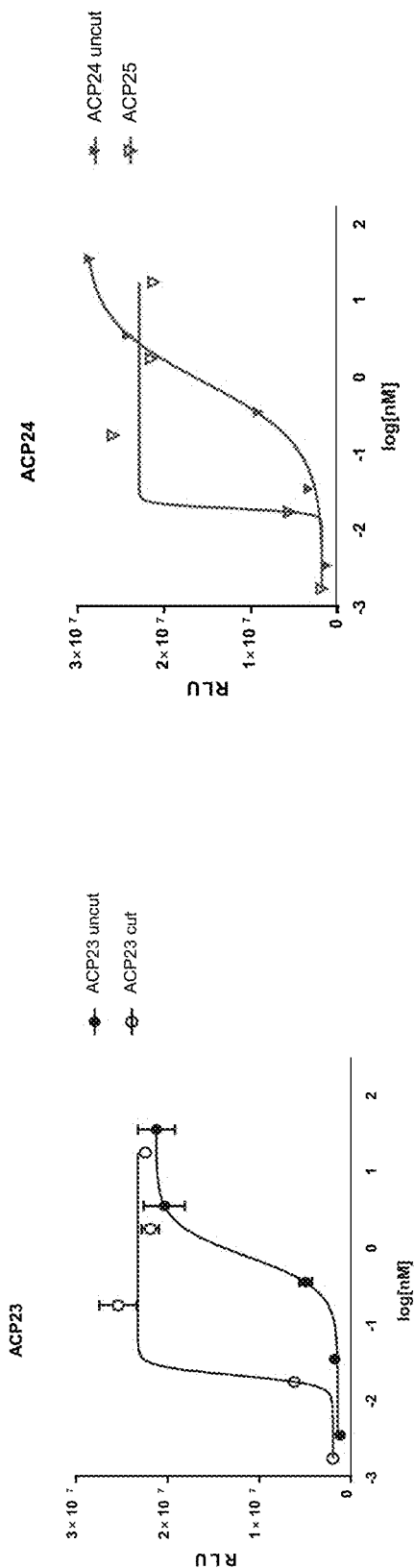
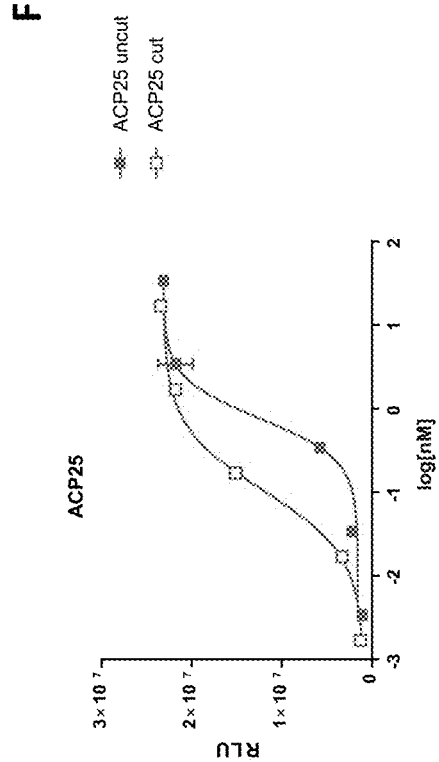
FIG. 9d
FIG. 9e
FIG. 9f

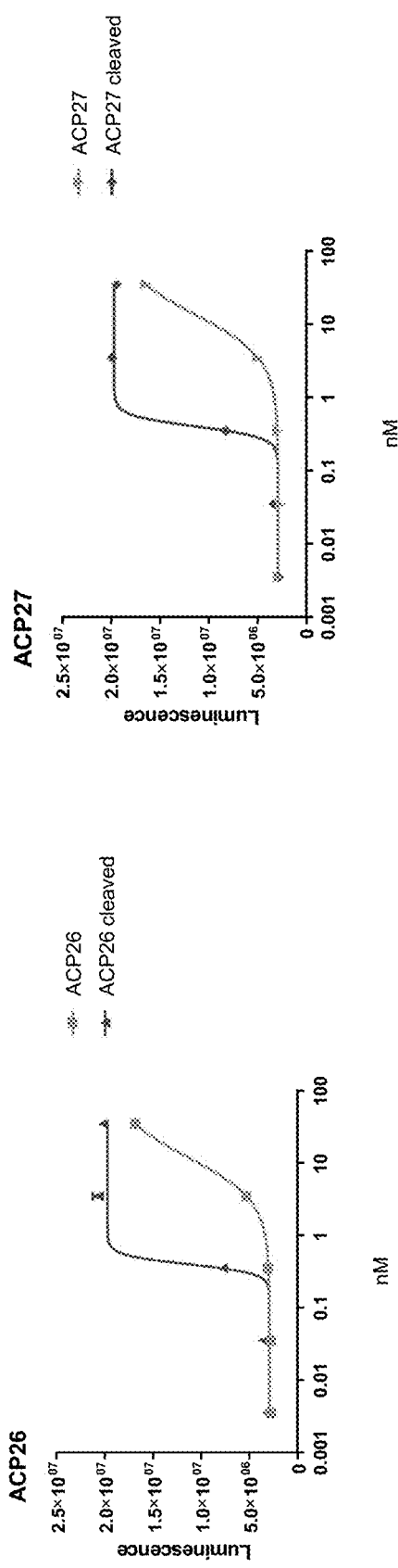
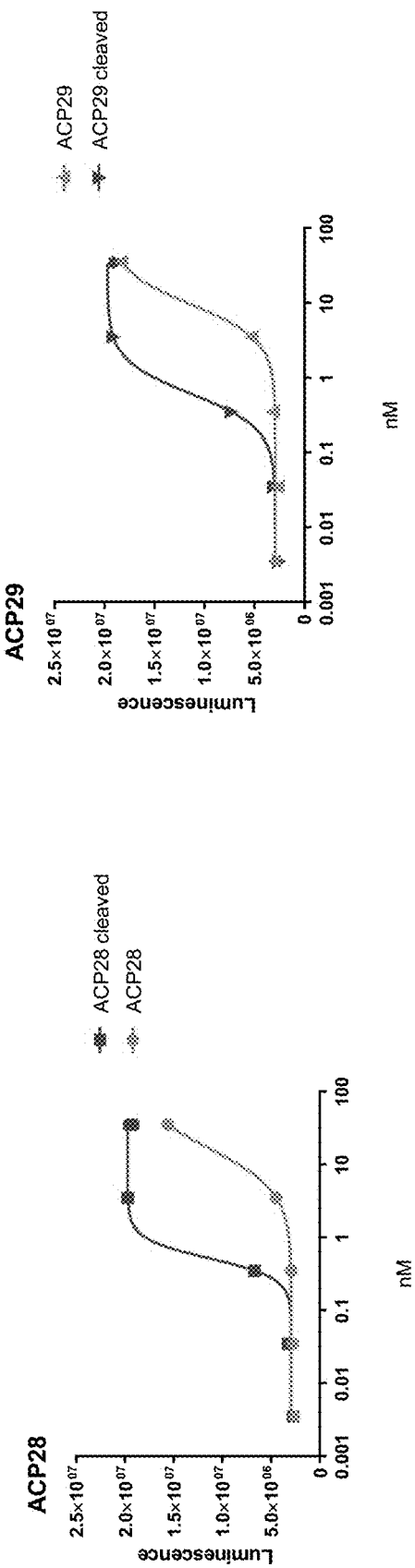
FIG. 9g
FIG. 9h
FIG. 9i
FIG. 9j

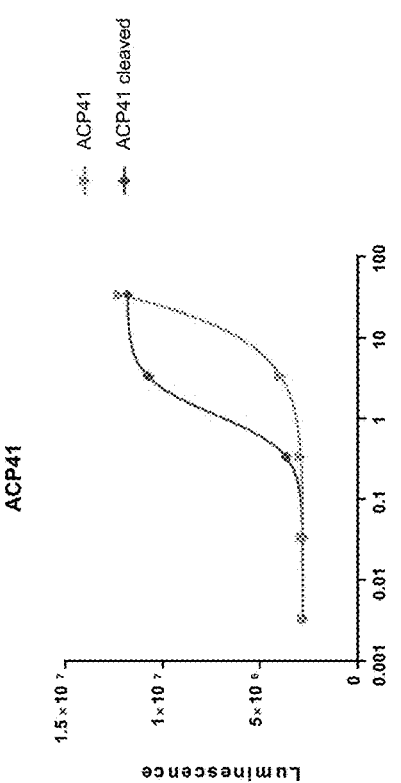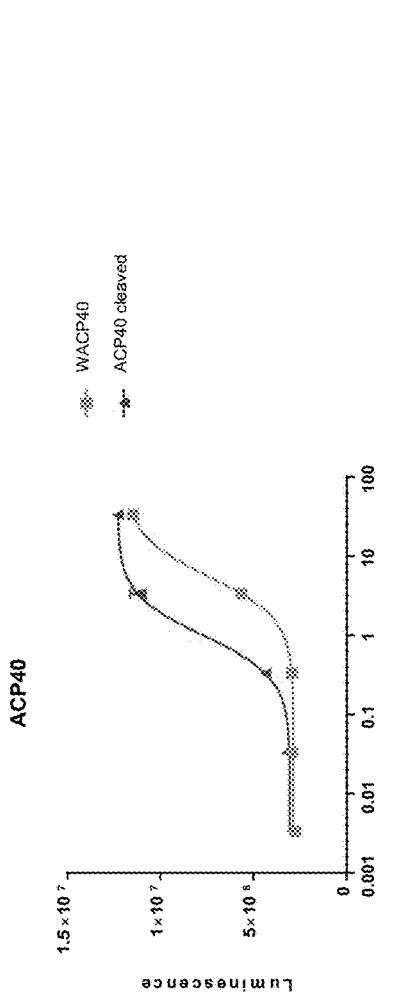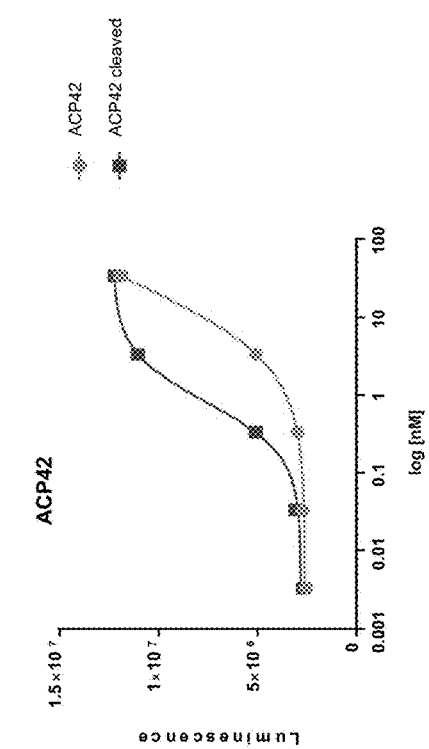
FIG. 9k
FIG. 9l
FIG. 9m

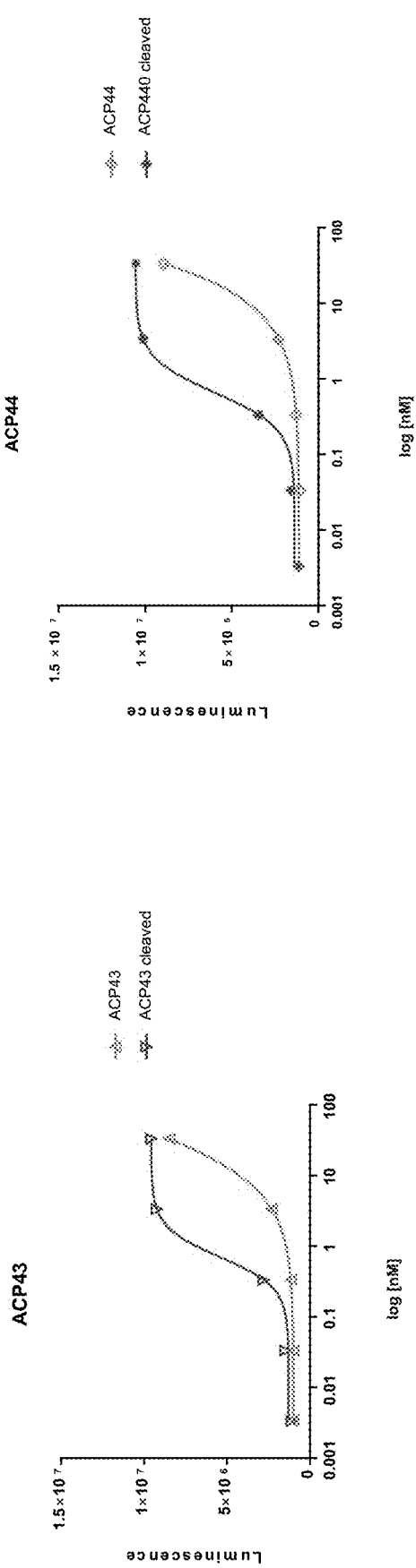
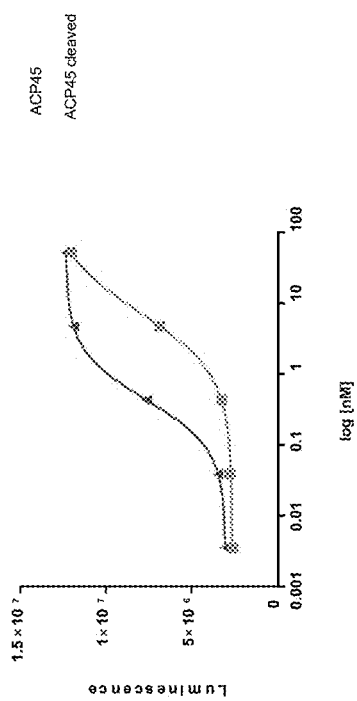
FIG. 9n
FIG. 9o
FIG. 9p

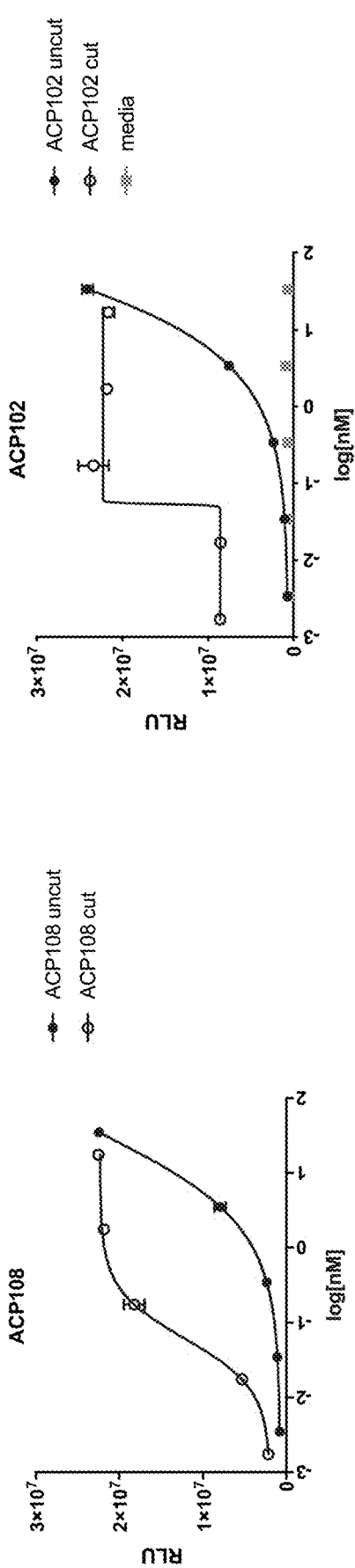
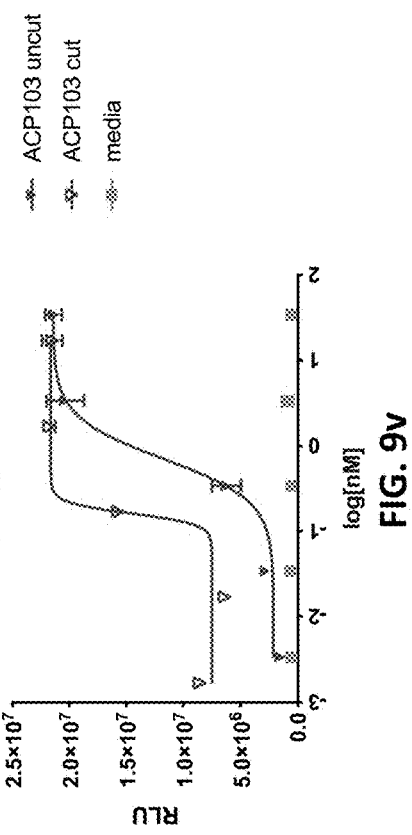
FIG. 9t
FIG. 9u
FIG. 9v

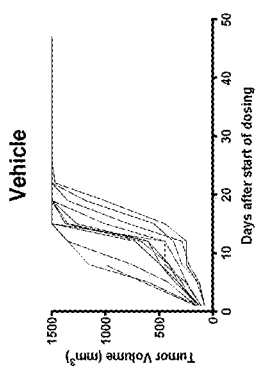
FIG. 14a
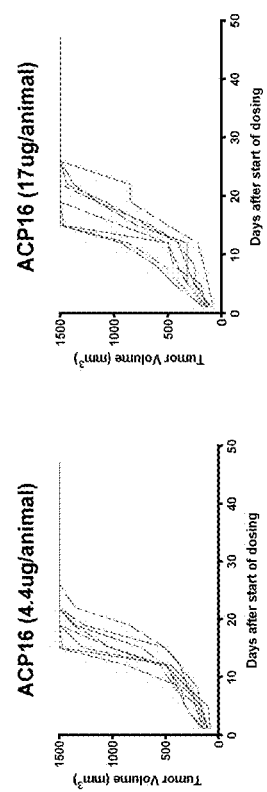
FIG. 14b
FIG. 14c
FIG. 14d
FIG. 14e
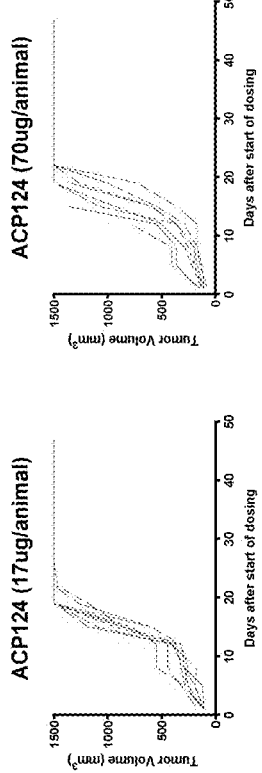
FIG. 14f
FIG. 14g
FIG. 14h
FIG. 14i

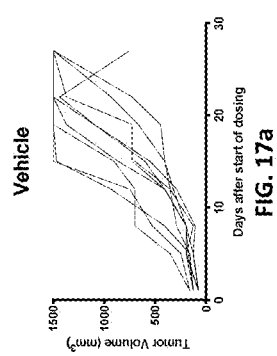
FIG. 17a Vehicle

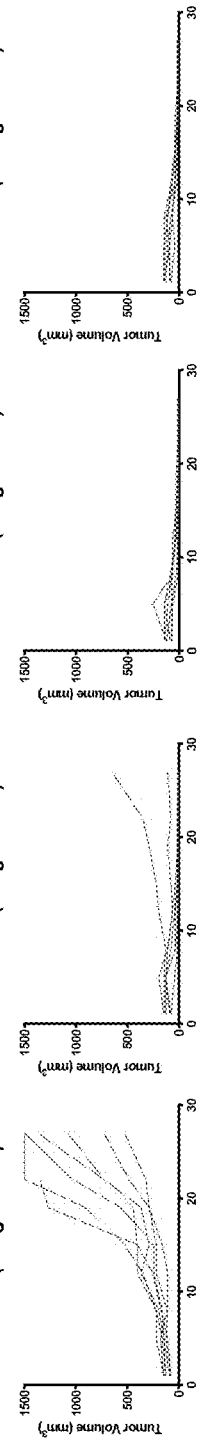

FIG. 17b ACP16 (17ug/animal)
FIG. 17c ACP16 (55ug/animal)
FIG. 17d ACP16 (70ug/animal)
FIG. 17e ACP16 (230ug/animal)

FIG. 17f APC132 (9ug/animal)
FIG. 17g APC132 (28ug/animal) 5/7 dead 2 days after 2nd dose
FIG. 17h APC132 (36ug/animal) 5/7 dead 2 days after 2nd dose
FIG. 17i APC132 (119ug/animal) 7/7 dead 1 day after 2nd dose FIG. 17j ACP21 (13ug/animal)
FIG. 17k ACP21 (42ug/animal)
FIG. 17l ACP21 (54ug/animal)
FIG. 17m ACP21 (177ug/animal)

All groups dosed 2 weeks (4 doses total) except ACP132 top three groups. Fatal toxicity was detected after 1 week (2 doses)

Differential Activity Supported by Various In Vitro Assays
250X Differential in CD3 Binding (ELISA)
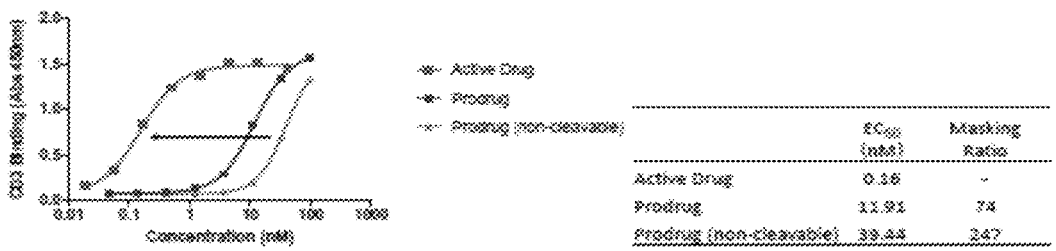
>1000X Differential in Human Primary T Cell Binding (FACS)
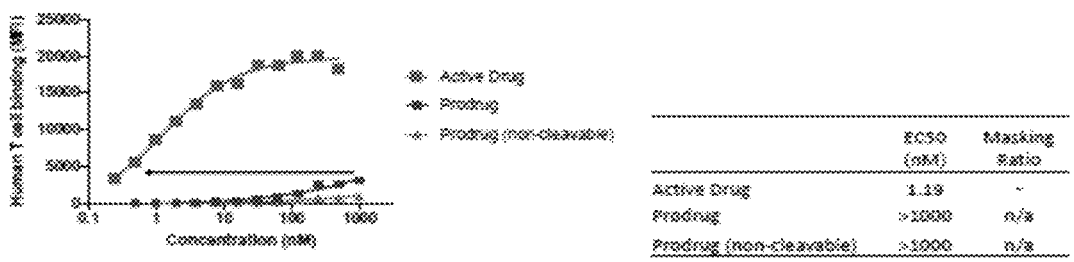
550X Differential in T Cell Killing Activity (TDCC)
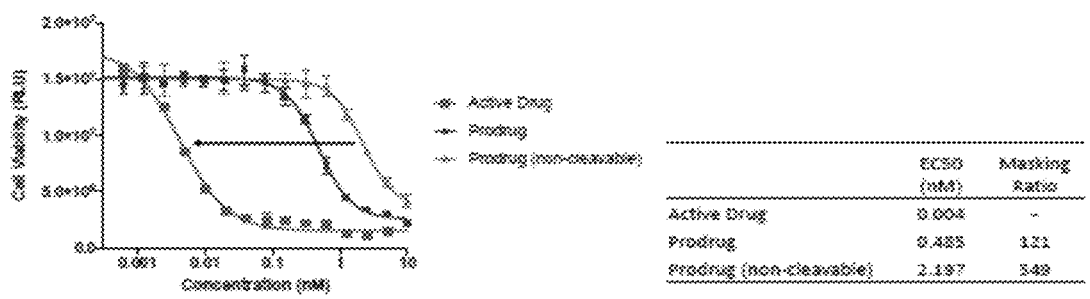
- Plug-and-play: masking demonstrated with >20 binders to 5 different targets
FIG. 19

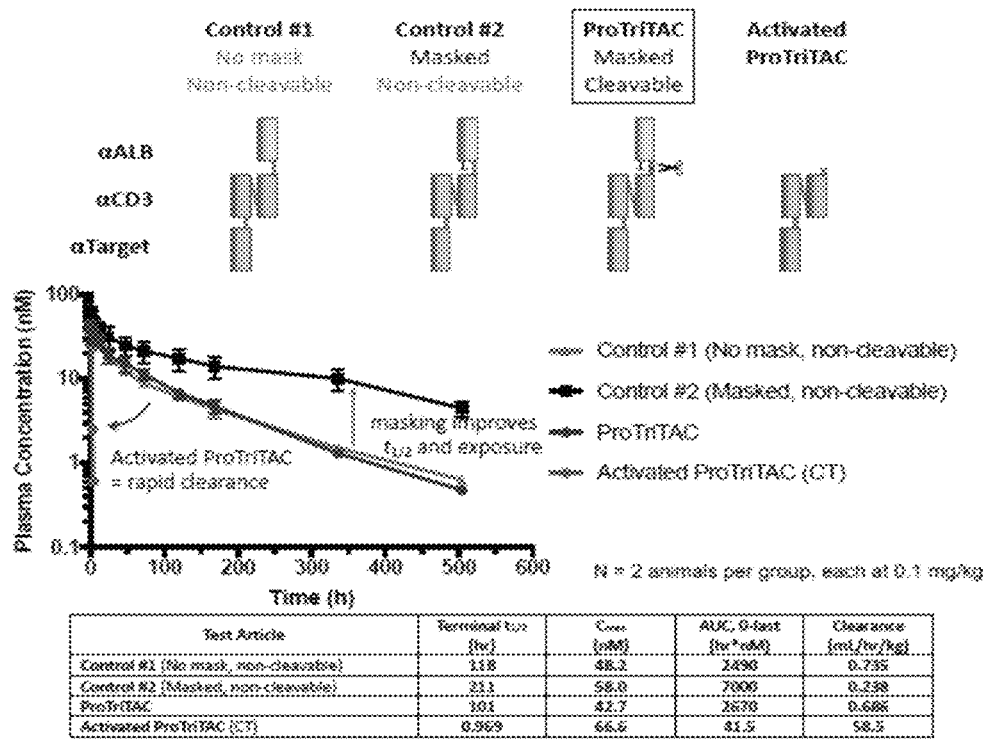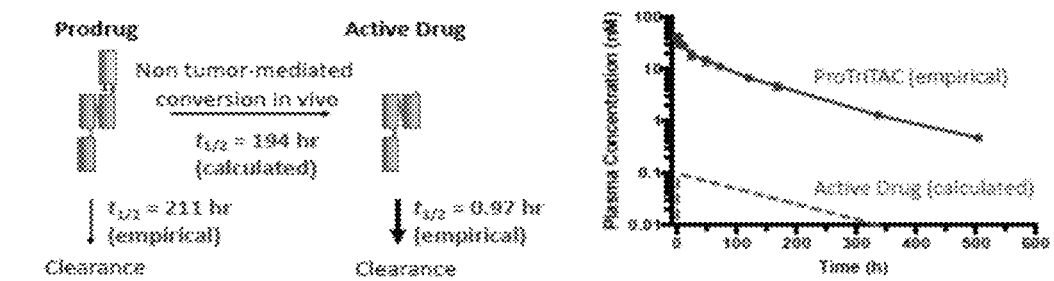
FIG. 23

ACTIVATABLE INTERLEUKIN-2 POLYPEPTIDES AND METHODS OF USE THEREOF

RELATED APPLICATIONS

This application is a continuation of U.S. application Ser. No. 16/438,156 filed Jun. 11, 2019, which is a continuation-in-part of International Patent Application No. PCT/US2019/032321, filed May 14, 2019, which claims the benefit of U.S. Provisional Application 62/671,225, filed on May 14, 2018, U.S. Provisional Application No. 62/756,504, filed on Nov. 6, 2018, and U.S. Provisional Application No. 62/756,507, filed on Nov. 6, 2018. The entire teachings of the above applications are incorporated herein by reference.

SEQUENCE LISTING

The instant application contains a Sequence Listing, which has been submitted electronically in ASCII format and is hereby incorporated by reference in its entirety. Said ASCII copy, created on May 31, 2019, is named 761146_000138_SL.txt and is 405,194 bytes in size.

BACKGROUND

The development of mature immunocompetent lymphoid cells from less-committed precursors, their subsequent antigen-driven immune responses, and the suppression of these and unwanted autoreactive responses are highly dependent and regulated by cytokines (including interleukin-2 [IL-2], IL-4, IL-7, IL-9, IL-15, and IL-21) that utilize receptors in the common γ-chain (γc) family (Rochman et al., 2009) and family members including IL-12, 18 and 23. IL-2 is essential for thymic development of Treg cells and critically regulates several key aspects of mature peripheral Treg and antigen-activated conventional T cells. Because of its potent T cell growth factor activity in vitro, IL-2 has been extensively studied in part because this activity offered a potential means to directly boost immunity, e.g., in cancer and AIDS-HIV patients, or a target to antagonize unwanted responses, e.g., transplantation rejection and autoimmune diseases. Although in vitro studies with IL-2 provided a strong rationale for these studies, the function of IL-2 in vivo is clearly much more complex as first illustrated in IL-2-deficient mice, where a rapid lethal autoimmune syndrome, not lack of immunity, was observed (Sadlack et al., 1993, 1995). Similar observations were later made when the gene encoding IL-2Rα(Il2ra) and IL-2Rβ (Il2rb) were individually ablated (Suzuki et al., 1995; Willerford et al., 1995).

The present invention refers to conditionally active and/or targeted cytokines for use in the treatment of cancer and other diseases dependent on immune up or down regulation. For example, the antitumoral activity of some cytokines is well known and described and some cytokines have already been used therapeutically in humans. Cytokines such as interleukin-2 (IL-2) have shown positive antitumoral activity in patients with different types of tumors, such as kidney metastatic carcinoma, hairy cell leukemia, Kaposi sarcoma, melanoma, multiple myeloma, and the like. Other cytokines like IFNβ, the Tumor Necrosis Factor (TNF) α, TNFβ, IL-1, 4, 6, 12, 15 and the CSFs have shown a certain antitumoral activity on some types of tumors and therefore are the object of further studies.

SUMMARY

Provided herein are therapeutic proteins, nucleic acids that encode the proteins, and compositions and methods of using the proteins and nucleic acids for the treatment of a disease or disorder, such as proliferative disease, a tumorous disease, an inflammatory disease, an immunological disorder, an autoimmune disease, an infectious disease, a viral disease, an allergic reaction, a parasitic reaction, graft-versus-host disease and the like.

The invention features fusion proteins that are conditionally active variants of IL-2. In one aspect, the full-length polypeptides of the invention have reduced or minimal IL-2-receptor activating activity even though they contain a functional cytokine polypeptide. Upon activation, e.g., by cleavage of a linker that joins a blocking moiety, e.g., a steric blocking polypeptide, in sequence to the active cytokine, IL-2 or functional fragment or mutein thereof, can bind its receptor and effect signaling. If desired, the full-length polypeptides can include a blocking polypeptide moiety that also provides additional advantageous properties. For example, the full-length polypeptide can contain a blocking polypeptide moiety that also extends the serum half-life and/or targets the full-length polypeptide to a desired site of IL-2 activity. Alternatively, the full-length fusion polypeptides can contain a serum half-life extension element and/or targeting domain that are distinct from the blocking polypeptide moiety. Preferably, the fusion protein contains at least one element or domain capable of extending in vivo circulating half-life. Preferably, this element is removed enzymatically in the desired body location (e.g., protease cleavage in the tumor microenvironment), restoring pharmacokinetic properties to the payload molecule (e.g., IL-2) substantially similar to the naturally occurring payload molecule. Preferably, the fusion proteins are targeted to a desired cell or tissue. As described herein targeting is accomplished through the action of a blocking polypeptide moiety that also binds to a desired target, or through a targeting domain. The domain that recognizes a target antigen on a preferred target (for example a tumor-specific antigen), may be attached to the cytokine via a cleavable or non-cleavable linker. If attached by a non-cleavable linker, the targeting domain may further aid in retaining the cytokine in the tumor, and may be considered a retention domain. The targeting domain does not necessarily need to be directly linked to the payload molecule, and may be linked directly to another element of the fusion protein. This is especially true if the targeting domain is attached via a cleavable linker.

In one aspect is provided a fusion polypeptide comprising an IL-2 polypeptide, or functional fragment or mutein thereof, and a blocking moiety, e.g., a steric blocking domain. The blocking moiety is fused to the IL-2 polypeptide, directly or through a linker, and can be separated from the cytokine polypeptide by cleavage (e.g., protease-mediated cleavage) of the fusion polypeptide at or near the fusion site or linker or in the blocking moiety. For example, when the cytokine polypeptide is fused to a blocking moiety through a linker that contains a protease cleavage site, the cytokine polypeptide is released from the blocking moiety and can bind its receptor, upon protease-mediated cleavage of the linker. The linker is designed to be cleaved at the site of desired cytokine activity, for example in the tumor microenvironment, avoiding off-target cytokine activity and reducing overall toxicity of cytokine therapy.

In one embodiment, a fusion polypeptide is provided that includes at least one of each of a human interleukin 2 (IL-2) polypeptide [A], an IL-2 blocking moiety [D], and a protease-cleavable polypeptide linker [L], where the IL-2 polypeptide and the IL-2 blocking moiety are operably linked by the protease-cleavable polypeptide linker and the fusion polypeptide has attenuated IL-2-receptor activating activity.

Typically, the IL-2-receptor activating activity of the fusion polypeptide is at least about 10 fold less than the IL-2-receptor activating activity of the polypeptide that contains the IL-2 polypeptide that is produced by cleavage of the protease-cleavable linker.

In another embodiment, a fusion polypeptide is provided that has at least one of each of a human interleukin 2 (IL-2) polypeptide [A], a half-life extension element [B], an IL-2 blocking moiety [D], and a protease-cleavable polypeptide linker [L], where the IL-2 polypeptide and the IL-2 blocking moiety can be operably linked by the protease-cleavable polypeptide linker and the fusion polypeptide has attenuated IL-2-receptor activating activity. Typically, the IL-2-receptor activating activity of the fusion polypeptide is at least about 10 fold less than the IL-2-receptor activating activity of the polypeptide that contains the IL-2 polypeptide that is produced by cleavage of the protease-cleavable linker. The serum half-life of the IL-2 polypeptide that is produced by cleavage of the protease-cleavable polypeptide linker is typically comparable to the half-life of naturally occurring IL-2.

The fusion polypeptide can have the formula:

[A]-[L1]-[B]-[L2]-[D],

[A]-[L1]-[D]-[L2]-[B],

[D]-[L2]-[B]-[L1]-[A],

[B]-[L2]-[D]-[L1]-[A],

[D]-[L1]-[B]-[L1]-[A],

[B]-[L1]-[D]-[L1]-[A],

[B]-[L1]-[A]-[L1]-[D], or

[D]-[L1]-[A]-[L1]-[B], where A is an interleukin 2 (IL-2) polypeptide; B is a half-life extension element; L1 and L2 are each independently a polypeptide linker, where L1 is a protease-cleavable polypeptide linker and L2 is optionally a protease-cleavable polypeptide linker; D is an IL-2 blocking moiety. In a further embodiment, the fusion polypeptide has attenuated IL-2-receptor activating activity. In some embodiments, the IL-2-receptor activating activity of the fusion polypeptide is at least about 10 fold less than the IL-2-receptor activating activity of the polypeptide that contains the IL-2 polypeptide that is produced by cleavage of the protease-cleavable polypeptide linker L1.

The fusion polypeptide can further include a tumor-specific antigen binding peptide. For example, the tumor-specific antigen binding peptide of the fusion polypeptide can be linked to any one of [A], [B], or [D] by a non-cleavable linker. The tumor-specific antigen binding peptide can be linked to any one of [A], [B], or [D] by a cleavable linker. The tumor-specific antigen binding peptide of the fusion polypeptide can be linked to the IL-2 polypeptide by a non-cleavable linker and the IL-2 polypeptide can be linked to the half-life extension element or the IL-2 blocking moiety by a cleavable linker.

The fusion polypeptide can bind IL-2 receptor alpha (IL-2Rα) in a manner substantially similar to the naturally occurring IL-2. In some embodiments, the blocking moiety of the fusion polypeptide inhibits activation of IL-2 receptor alpha/beta/gamma (IL-2Rαβγ) and IL-2 receptor beta/gamma (IL-2Rβγ) by the IL-2 polypeptide in the uncleaved fusion polypeptide.

The IL-2-receptor activating activity of the fusion polypeptide can be assessed, for example, using a CTLL-2 proliferation assay, a phospho STAT ELISA, or HEK Blue reporter cell assay and using equal amounts on a mole basis of the IL-2 polypeptide and the fusion polypeptide.

The fusion polypeptide may include a plurality of protease-cleavable polypeptide linkers, where each protease-cleavable polypeptide linker independently comprises at least one sequence that is capable of being cleaved by a protease such as a kallikrein, thrombin, chymase, carboxypeptidase A, cathepsin G, cathepsin L, an elastase, PR-3, granzyme M, a calpain, a matrix metalloproteinase (MMP), a fibroblast activation protein (FAP), an ADAM metalloproteinase, a plasminogen activator, a cathepsin, a caspase, a tryptase, or a tumor cell surface protease. Each protease-cleavable polypeptide of the fusion polypeptide can independently comprise two or more cleavage sites for the same protease, or two or more cleavage sites that can be cleaved by different proteases, or at least one of the protease-cleavable polypeptides can comprises a cleavage site for two or more different proteases.

In some embodiments, the IL-2 blocking moiety of the fusion polypeptides of the invention inhibits activation of the IL-2 receptor by the fusion polypeptide. In some embodiments, the IL-2 blocking moiety can comprise, for example, a ligand-binding domain or fragment of a cognate receptor for the IL-2, a single domain antibody, Fab or scFv that binds the IL-2 polypeptide, or an antibody or antibody fragment that binds a receptor of the IL-2.

The half-life extension element of the fusion polypeptide can be, for example, human serum albumin, an antigen-binding polypeptide that binds human serum albumin, or an immunoglobulin Fc.

In some embodiments, the blocking moiety can also function as a serum half-life extension element. In some other embodiments, the fusion polypeptide further comprises a separate serum half-life extension element. In some embodiments, the fusion polypeptide further comprises a targeting domain. In various embodiments, the serum half-life extension element is a water-soluble polypeptide such as optionally branched or multi-armed polyethylene glycol (PEG), full length human serum albumin (HSA) or a fragment that preserves binding to FcRn, an Fc fragment, or a nanobody that binds to FcRn directly or to human serum albumin.

In addition to serum half-life extension elements, the pharmaceutical compositions described herein preferably comprise at least one, or more targeting domains that bind to one or more target antigens or one or more regions on a single target antigen. It is contemplated herein that a polypeptide construct of the invention is cleaved, for example, in a disease-specific microenvironment or in the blood of a subject at the protease cleavage site and that the targeting domain(s) will bind to a target antigen on a target cell. At least one target antigen is involved in and/or associated with a disease, disorder or condition. Exemplary target antigens include those associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

In some embodiments, a target antigen is a cell surface molecule such as a protein, lipid or polysaccharide. In some embodiments, a target antigen is a on a tumor cell, virally infected cell, bacterially infected cell, damaged red blood cell, arterial plaque cell, or fibrotic tissue cell.

Target antigens, in some cases, are expressed on the surface of a diseased cell or tissue, for example a tumor or a cancer cell. Target antigens for tumors include but are not limited to Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, c-Met, FOLR1, and CEA. Pharmaceutical compositions disclosed herein, also include proteins comprising two antigen binding domains that bind to two different target antigens known to be expressed on a diseased cell or tissue. Exemplary pairs of antigen binding domains include but are not limited to EGFR/CEA, EpCAM/CEA, and HER-2/HER-3.

In some embodiments, the targeting polypeptides independently comprise a scFv, a VH domain, a VL domain, a non-Ig domain, or a ligand that specifically binds to the target antigen. In some embodiments, the targeting polypeptides specifically bind to a cell surface molecule. In some embodiments, the targeting polypeptides specifically bind to a tumor antigen. In some embodiments, the targeting polypeptides specifically and independently bind to a tumor antigen selected from at least one of EpCAM, EGFR, HER-2, HER-3, cMet, CEA, and FOLR1. In some embodiments, the targeting polypeptides specifically and independently bind to two different antigens, wherein at least one of the antigens is a tumor antigen selected from EpCAM, EGFR, HER-2, HER-3, cMet, CEA, and FOLR1. In some embodiments, the targeting polypeptide serves as a retention domain and is attached to the cytokine via a non-cleavable linker.

As described herein, the cytokine blocking moiety can bind to IL-2 and thereby block activation of the IL-2 cognate receptor.

This disclosure also related to nucleic acids, e.g., DNA, RNA, mRNA, that encode the conditionally active proteins described herein, as well as vectors and host cells that contain such nucleic acids.

This disclosure also relates to pharmaceutical compositions that contain a conditionally active protein, nucleic acid that encodes the conditionally active protein, and vectors and host cells that contain such nucleic acids. Typically, the pharmaceutical composition contains one or more physiologically acceptable carriers and/or excipients. The disclosure also relates to methods of making a pharmaceutical composition that include culturing host cell that contain nucleic acids encoding the fusion polypeptides of the invention under suitable conditions for expression and collection of the fusion polypeptides.

The disclosure also relates to therapeutic methods that include administering to a subject in need thereof an effective amount of a conditionally active protein, nucleic acid that encodes the conditionally active protein, vector or host cells that contain such a nucleic acid, and pharmaceutical compositions of any of the foregoing. Typically, the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure further relates methods for treating a tumor or cancer that include administering to a subject in need thereof an effective amount of a fusion polypeptide of the invention. In some embodiments, the method for treating a tumor or cancer can include administering effective amount of the fusion polypeptide intravenously. In some embodiments, the method can further include administration of an additional chemotherapeutic agent.

The disclosure also relates to the use of a conditionally active protein, nucleic acid that encodes the conditionally active protein, vector or host cells that contain such a nucleic acid, and pharmaceutical compositions of any of the foregoing, for treating a subject in need thereof. Typically the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure also relates to the use of a conditionally active protein, nucleic acid that encodes the conditionally active protein, vector or host cells that contain such a nucleic acid for the manufacture of a medicament for treating a disease, such as a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

BRIEF DESCRIPTION OF THE DRAWINGS

FIGS. 8a-8f are a series of graphs showing activity of exemplary IL-2 fusion proteins in IL-2 dependent cytotoxic T lymphocyte cell line CTLL-2. Each graph shows results of the IL-2 proliferation assay as quantified by CellTiter-Glo (Promega) luminescence-based cell viability assay. Both uncleaved and MMP9 protease cleaved versions of the fusion protein were used in each assay.

FIG. 11g is a schematic showing the structure of the fusion protein ACP16.

FIG. 13a shows tumor volume over time in mice treated with 4.4 µg ACP16 (squares), 17 µg ACP16 (triangles), 70 µg ACP16 (downward triangles), 232 µg ACP16 (dark circles), and as a comparator, 12 µg wild type IL-2 (dashed line, triangles) and 36 µg wild type IL-2 (dashed line, diamonds). Vehicle alone is indicated by large open circles. The data show tumor volume decreasing over time in a dose-dependent manner in mice treated with ACP16 at higher concentrations. FIG. 13b shows tumor volume over time in mice treated with 17 µg ACP124 (squares), 70 µg ACP124 (triangles), 230 µg ACP124 (downward triangles), and 700 µg ACP124. Vehicle alone is indicated by large open circles. FIG. 13c shows tumor volume over time in mice treated with 17 µg ACP16 (triangles), 70 µg ACP16 (circles), 232 µg ACP16 (dark circles), and as a comparator 17 µg ACP124 (dashed line, triangles) 70 µg ACP124 (dashed line, diamonds), 230 µg ACP124 (dashed line, diamonds). Vehicle alone is indicated by dark downward triangles. The data show tumor volume decreasing over time in a dose-dependent manner in mice treated with ACP16, but not ACP124.

FIGS. 14a-14l are a series of "spaghetti" plots showing activity of fusion proteins in an MC38 mouse xenograft model corresponding to the data shown in FIGS. 13a-13c. Each line in the plots represents a single mouse. Shown are vehicle alone (FIG. 14a), 4.4, 17, 70, and 232 µg ACP16 (FIG. 14b, FIG. 14c, FIG. 14d, and FIG. 14e), and 17, 70, 230, and 700 µg ACP124 (FIG. 14f, FIG. 14g, FIG. 14h, and FIG. 14i).

FIG. 16a shows data for mice treated with vehicle alone (gray line), 17 µg ACP16 (dark line), and 17 µg ACP124 (dashed line). FIG. 16b shows data for mice treated with vehicle alone (gray line), 70 µg ACP16 (dark line), and 70 µg ACP124 (dashed line). FIG. 16c shows data for mice treated with vehicle alone (gray line), 232 µg ACP16 (dark line), and 230 µg ACP124 (dashed line). FIG. 16d shows data for mice treated with vehicle alone (gray line), 232 µg ACP16 (dark line), and 700 µg ACP124 (dashed line).

FIG. 17a-17m are a series of "spaghetti" plots showing activity of fusion proteins in an MC38 mouse xenograft model. All mouse groups were given four doses total except for the highest three doses of APC132, wherein fatal toxicity was detected after 1 week/2 doses. Shown are vehicle alone (FIG. 17a), 17, 55, 70, and 230 µg ACP16 (FIG. 17b, FIG. 17c, FIG. 17d, and FIG. 17e), 9, 28, 36, and 119 µg ACP132 (FIG. 17f, FIG. 17g, FIG. 17h, and FIG. 17l), and 13, 42, 54, and 177 µg ACP21 (FIG. 17j, FIG. 17k, FIG. 17l, and FIG. 17m). Each line in the plots represents an individual animal.

FIG. 19 illustrates differential activities of ProTriTAC proteins measured by ELISA, flow cytometry, and T cell-dependent cellular cytotoxicity assay.

FIG. 23 demonstrates functional masking and stability of ProTriTAC in cynomolgus monkey pharmacokinetic study.

DETAILED DESCRIPTION

Figure 1A:
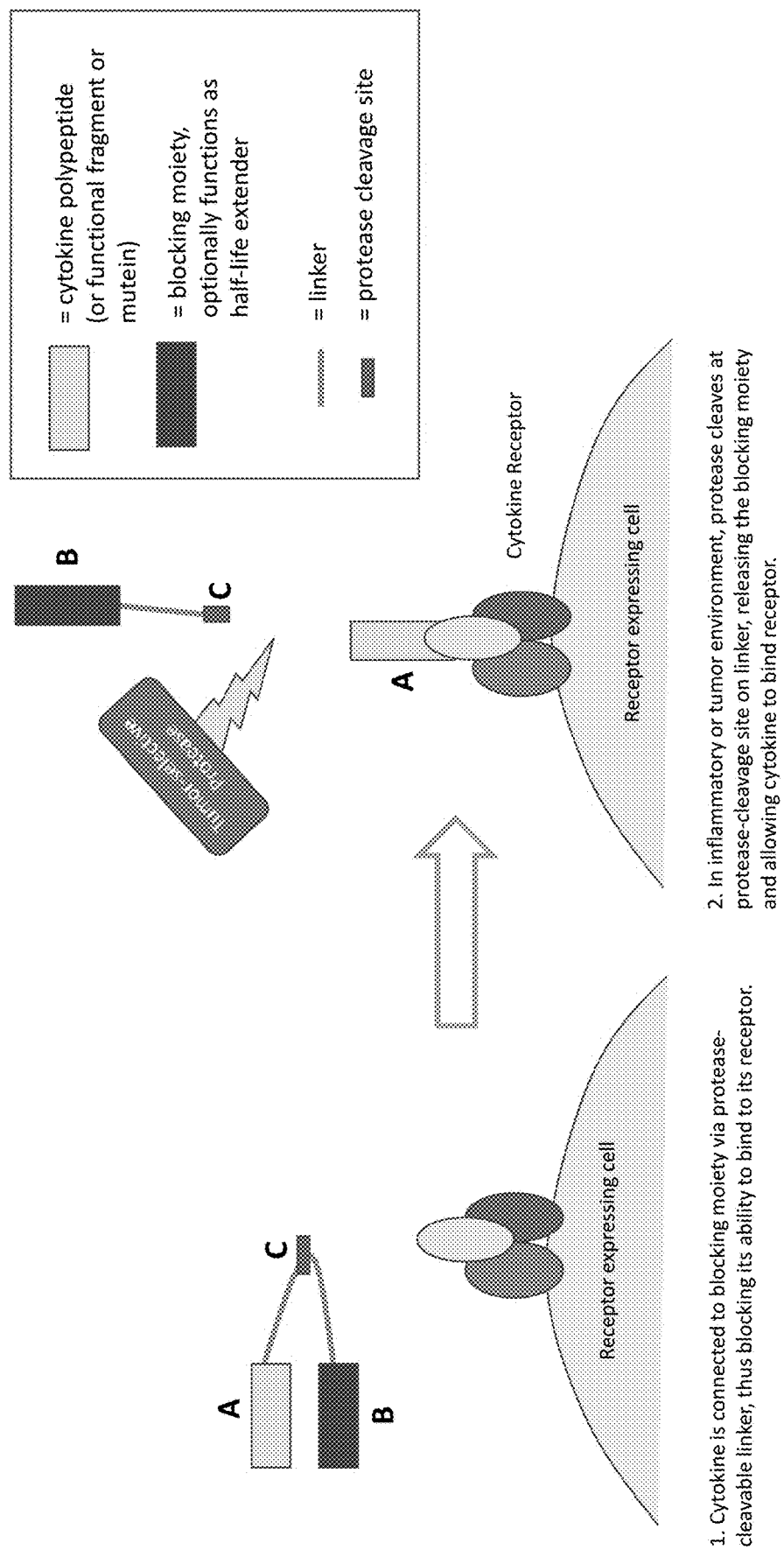
FIG. 1a is a schematic illustrating a protease-activated cytokine or chemokine that includes a blocking moiety. The blocking moiety may optionally function as a serum half-life extending domain. To the left of the arrow the drawing shows that a cytokine is connected to a blocking moiety via a protease-cleavable linker, thus blocking its ability to bind to its receptor. To the right of the arrow the drawing shows that in an inflammatory or tumor environment a protease cleaves at a protease-cleavage site on the linker, releasing the blocking moiety and allowing the cytokine to bind to its receptor.
Figure 1B:
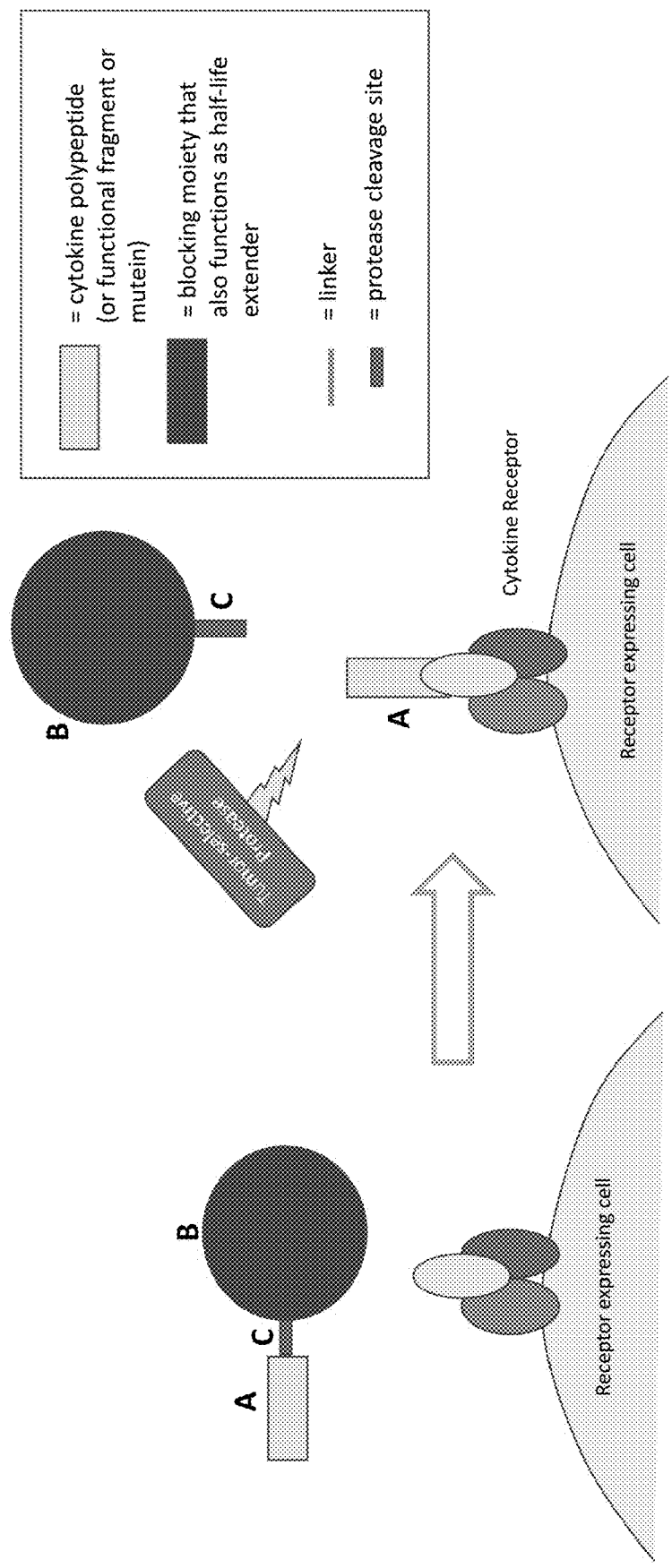
FIG. 1b is a schematic illustrating a protease-activated cytokine or chemokine wherein HSA (blocking moiety) is directly bound to the cytokine or chemokine of interest, with a protease cleavage site between the HSA and a cytokine or chemokine of interest. To the left of the arrow the drawing shows that a cytokine is connected to a blocking moiety via a protease-cleavable linker, thus blocking its ability to bind to its receptor. To the right of the arrow the drawing shows that in an inflammatory or tumor environment, the protease cleaves at a protease-cleavage site on linker, releasing the blocking moiety and allowing the cytokine to bind to its receptor.
Figure 1C:
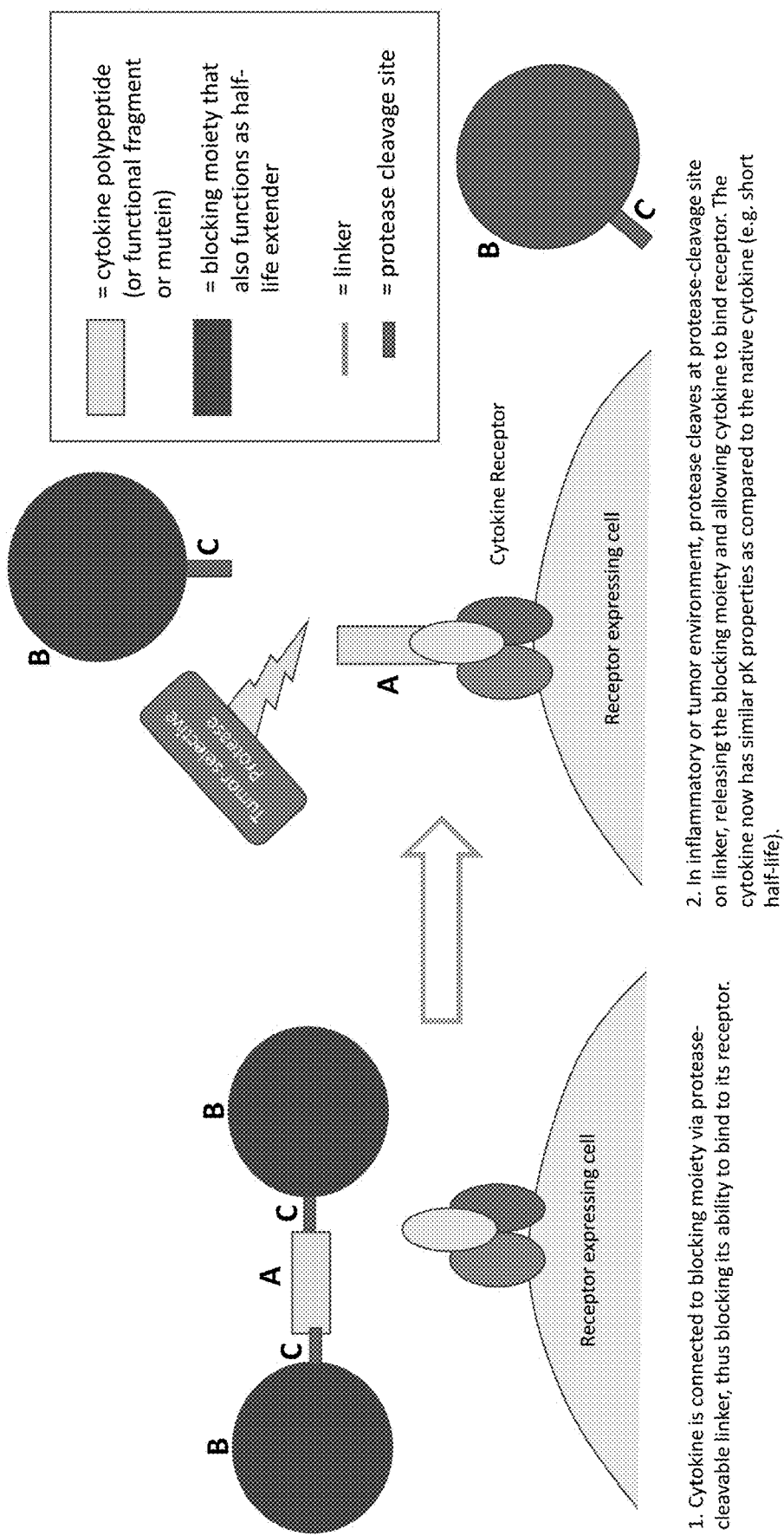
FIG. 1c is a schematic illustrating a protease-activated cytokine or chemokine wherein more than one HSA (blocking moiety) is bound directly to the molecule of interest. If desired, one or more of the HSA can be bonded to the cytokine or chemokine through a linker, such as a linker that contains a protease cleavage site. To the left of the arrow the drawing shows that a cytokine is connected to a blocking moiety via a protease-cleavable linker, thus blocking its ability to bind to its receptor. To the right of the arrow the drawing shows that in an inflammatory or tumor environment, protease cleaves at protease-cleavage site on linker, releasing the blocking moiety and allowing cytokine to bind receptor. The cytokine now has similar pK properties as compared to the native cytokine (e.g., has a short half-life).
Figure 1D:
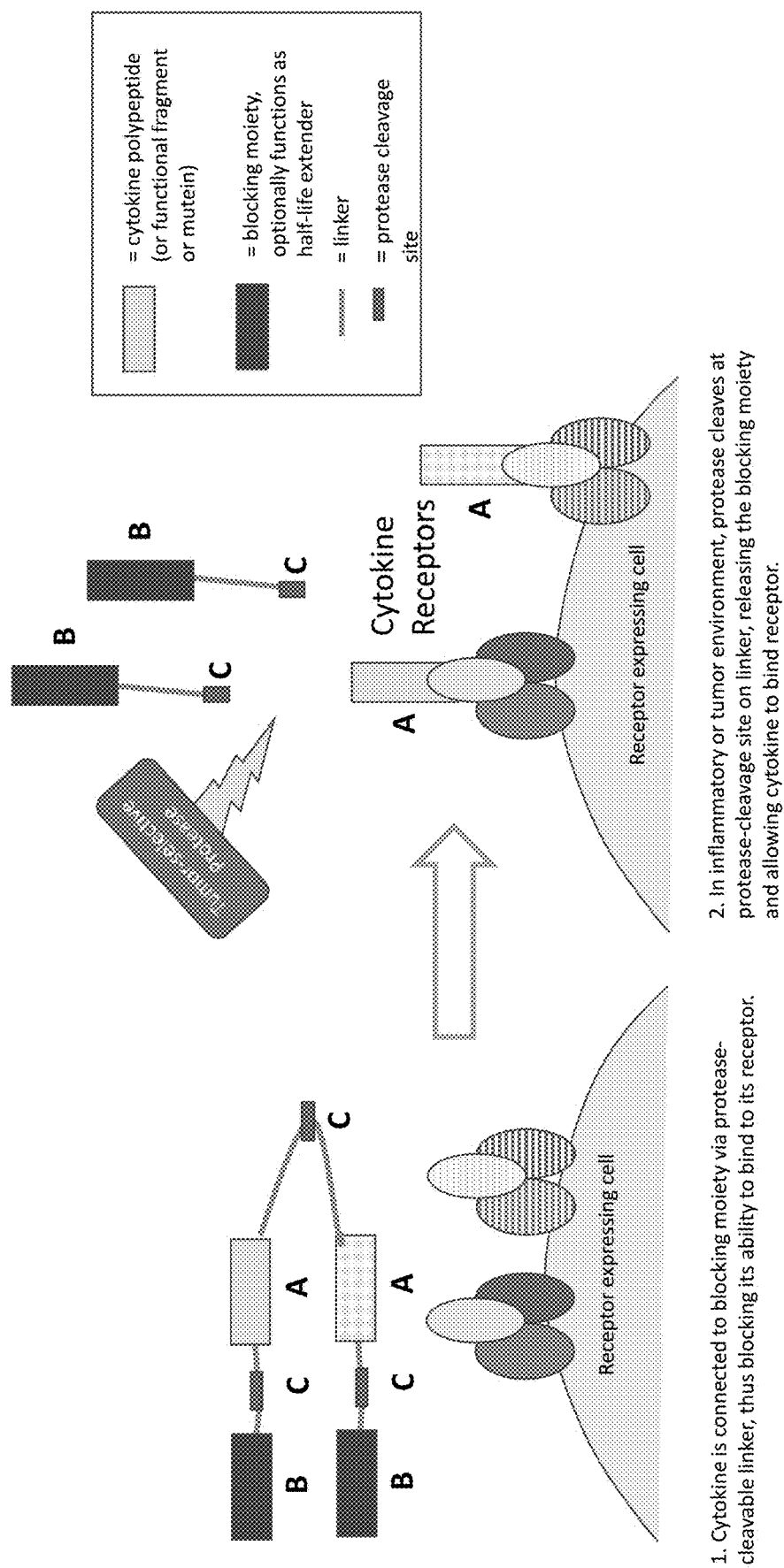
FIG. 1d is a schematic illustrating a protease-activated cytokine or chemokine comprising more than one cytokine, of the same type or different type, each of which is bonded to a binding domain through a protease-cleavable linker. To the left of the arrow the drawing shows that a cytokine is connected to a blocking moiety via a protease-cleavable linker, thus blocking its ability to bind to its receptor. To the right of the arrow the drawing shows that in an inflammatory or tumor environment a protease cleaves at a protease cleavage site on linker, releasing the blocking moiety and allowing the cytokine to bind to its receptor.
Figure 2:
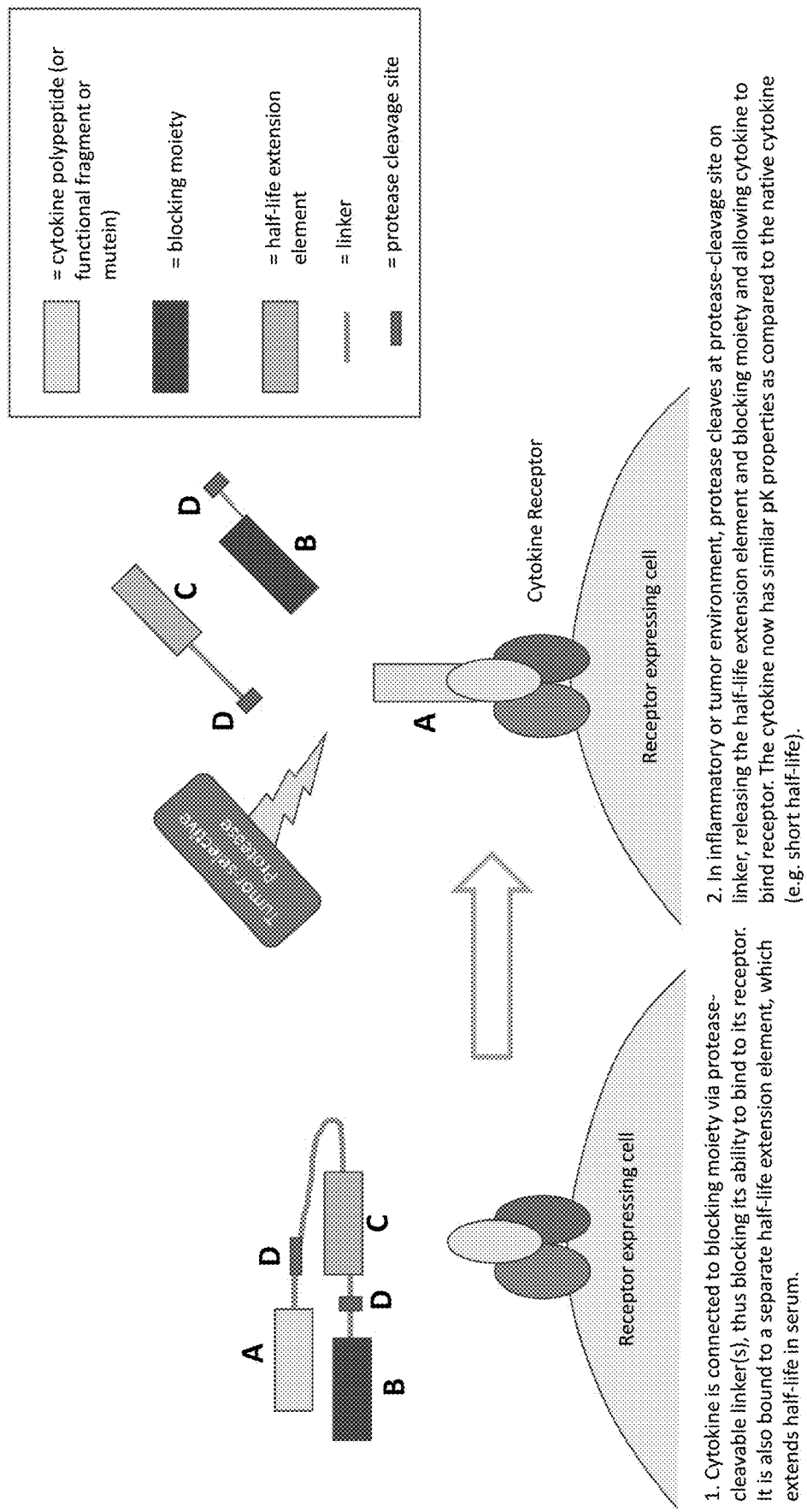
FIG. 2 is a schematic illustrating a protease-activated cytokine or chemokine comprising a cytokine or chemokine polypeptide, a blocking moiety, and a serum half-life extending domain connected by at least one protease-cleavable linker. To the left of the arrow the drawing shows that a cytokine is connected to a blocking moiety via protease-cleavable linkers, thus blocking its ability to bind to its receptor. It is also bound to a separate half-life extension element, which extends half-life in serum. To the right of the arrow the drawing shows that in an inflammatory or tumor environment a protease cleaves at a protease-cleavage site on linker, thus releasing the serum half-life extension element and the blocking moiety and allowing the cytokine to bind to its receptor. The cytokine now has similar pK properties as compared to the native cytokine (e.g., a short half-life).
Figure 3:
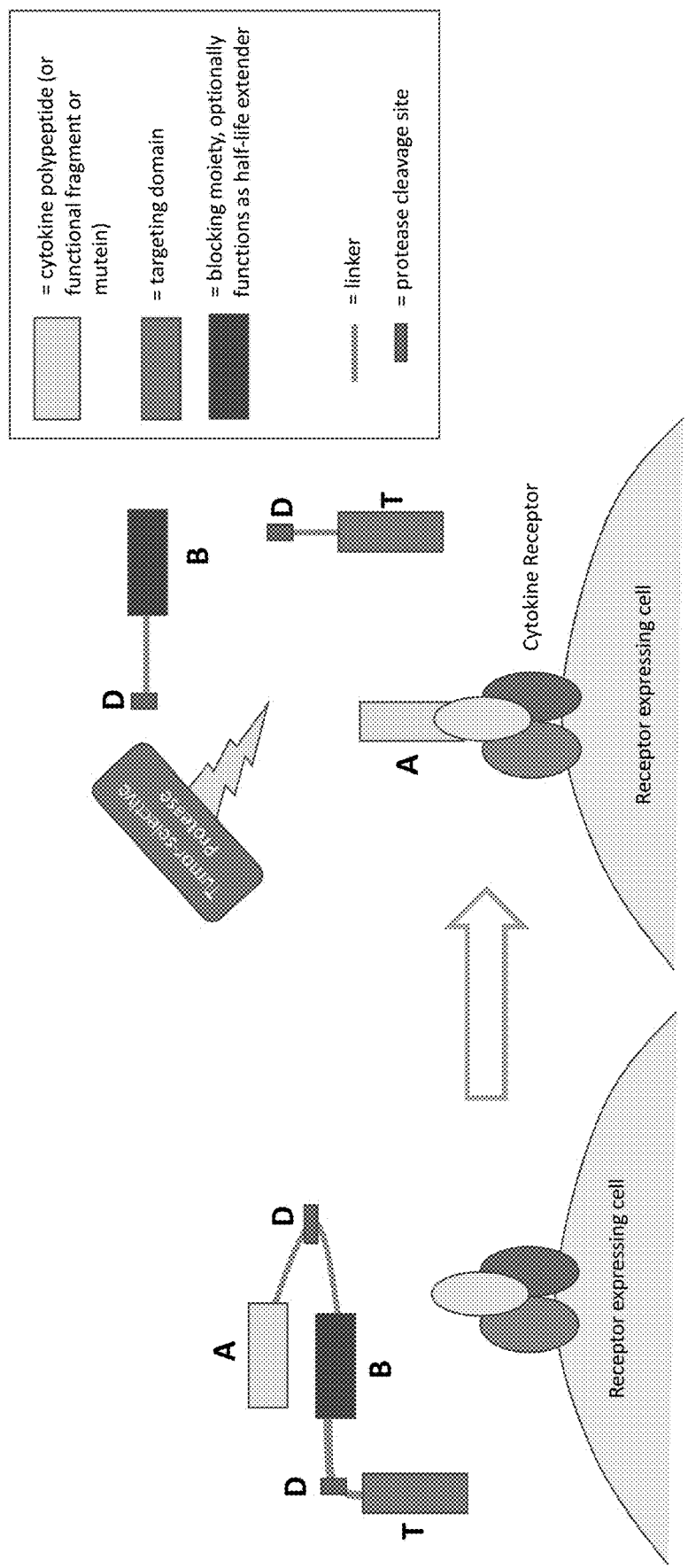
FIG. 3 is a schematic illustrating a protease-activated cytokine or chemokine comprising a cytokine or chemokine polypeptide, a blocking moiety, and a targeting domain connected by at least one protease-cleavable linker. To the left of the arrow the drawing shows that a cytokine is connected to a blocking moiety and a targeting domain via a protease-cleavable linker, thus blocking its ability to bind to its receptor. To the right of the arrow the drawing shows that in an inflammatory or tumor microenvironment a protease cleaves at the protease cleavage site in the linker, releasing the targeting domain and the blocking moiety and allowing the cytokine to bind to its receptor.
Figure 4A:
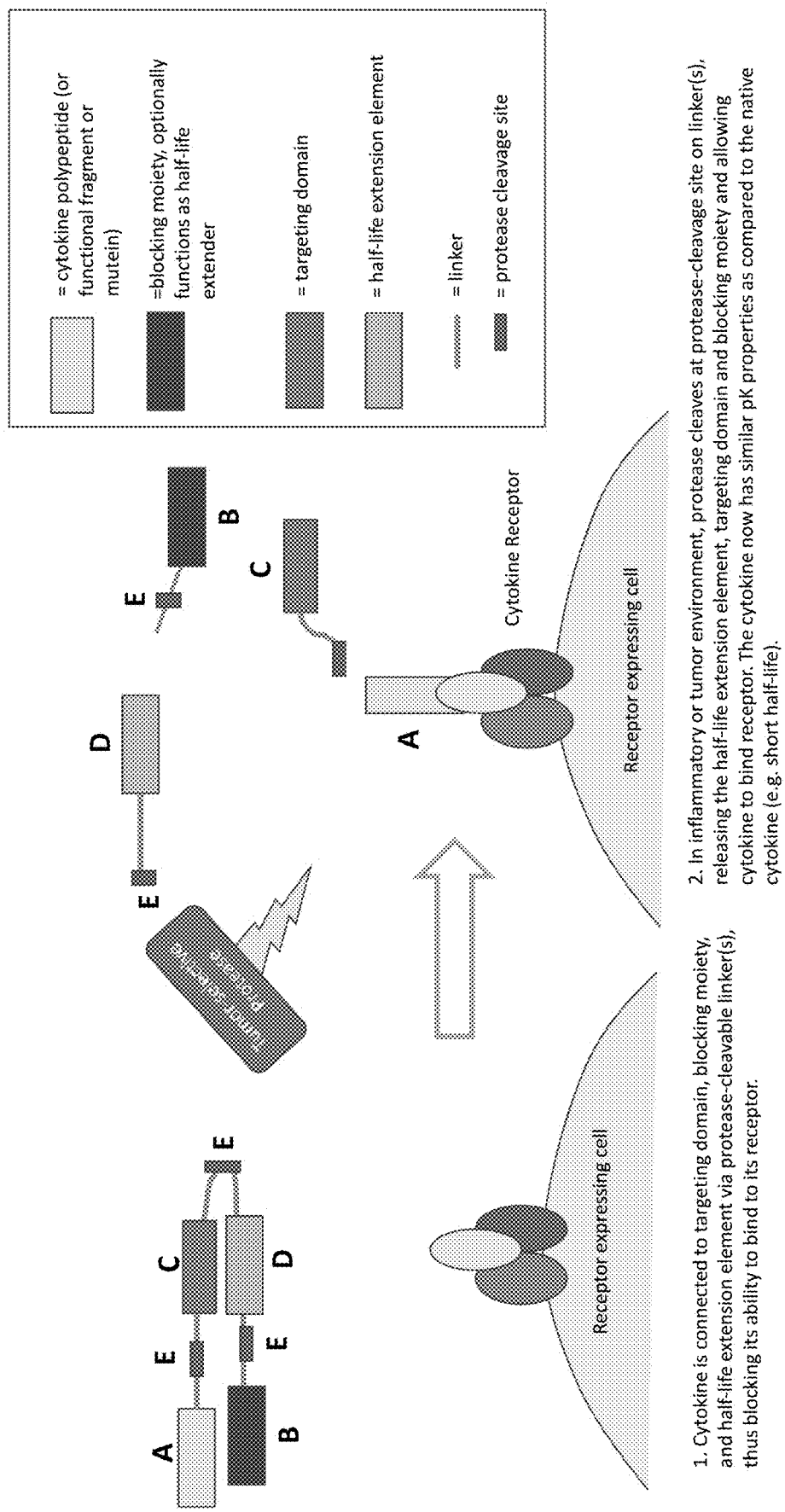
FIG. 4a is a schematic illustrating a protease-activated cytokine or chemokine comprising a cytokine or chemokine polypeptide, a blocking moiety, a targeting domain, and a serum half-life extending domain connected by at least one protease-cleavable linker, wherein the cytokine polypeptide and the targeting domain are connected by a protease-cleavable linker. To the left of the arrow, the drawing shows that a cytokine is connected to targeting domain, blocking moiety, and half-life extension element via protease-cleavable linker(s), thus blocking its ability to bind to its receptor. To the right of the arrow the drawing shows that in an inflammatory or tumor environment, the protease cleaves at a protease-cleavage site on linker(s), releasing the half-life extension element, the targeting domain, and the blocking moiety, and allowing the cytokine to bind to its receptor. The cytokine now has similar pK properties as compared to the native cytokine (e.g., short half-life).
Figure 4B:
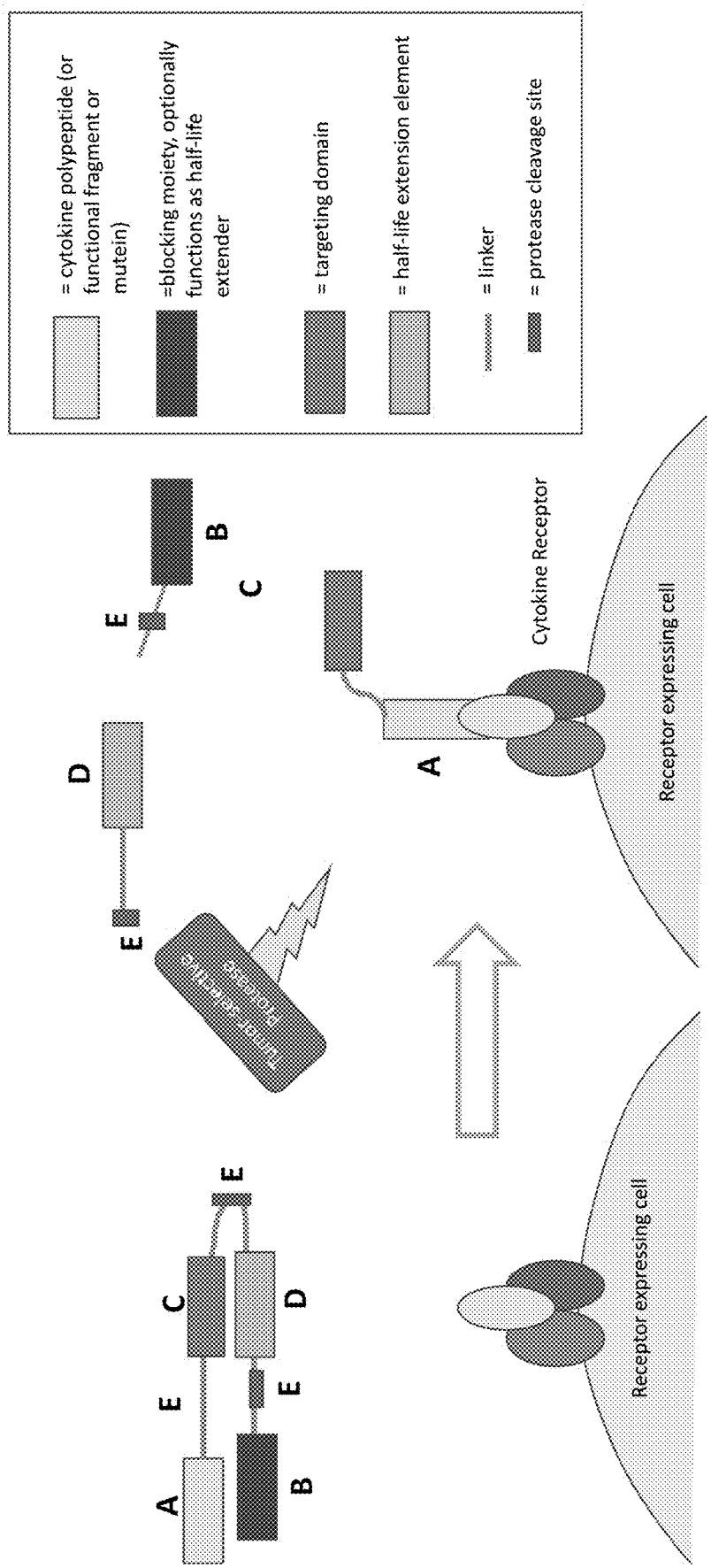
FIG. 4b is a schematic illustrating a protease-activated cytokine or chemokine comprising a cytokine or chemokine polypeptide, a blocking moiety, a targeting domain, and a serum half-life extending domain connected by at least one protease-cleavable linker. To the left of the arrow, the drawing shows that a cytokine is connected to targeting domain, a blocking moiety, and a half-life extension element via protease-cleavable linker(s), thus blocking its ability to bind to its receptor. To the right of the arrow the drawing shows that in an inflammatory or tumor environment, the protease cleaves at a protease-cleavage site on linker(s), releasing the half-life extension element and the blocking moiety and allowing the cytokine to bind to the receptor. The targeting moiety remains bound, keeping the cytokine in the tumor microenvironment. The cytokine now has similar pK properties as compared to the native cytokine (e.g., a short half-life).

Disclosed herein are methods and compositions to engineer and use constructs comprising inducible cytokines. Cytokines are potent immune agonists, which lead to them being considered promising therapeutic agents for oncology. However, cytokines proved to have a very narrow therapeutic window. Cytokines have short serum half-lives and are also considered to be highly potent. Consequently, therapeutic administration of cytokines produced undesirable systemic effects and toxicities. These were exacerbated by the need to administer large quantities of cytokine in order to achieve the desired levels of cytokine at the intended site of cytokine action (e.g., a tumor). Unfortunately, due to the biology of cytokines and inability to effectively target and control their activity, cytokines did not achieve the hoped for clinical advantages in the treatment of tumors.

Disclosed herein are fusion proteins that overcome the toxicity and short half-life problems that have severely limited the clinical use of cytokines in oncology. The fusion proteins contain cytokine polypeptides that have receptor agonist activity. But in the context of the fusion protein, the cytokine receptor agonist activity is attenuated and the circulating half-life is extended. The fusion proteins include protease cleave sites, which are cleaved by proteases that are associated with a desired site of cytokine activity (e.g., a tumor), and are typically enriched or selectively present at the site of desired activity. Thus, the fusion proteins are preferentially (or selectively) and efficiently cleaved at the desired site of activity to limit cytokine activity substantially to the desired site of activity, such as the tumor microenvironment. Protease cleavage at the desired site of activity, such as in a tumor microenvironment, releases a form of the cytokine from the fusion protein that is much more active as a cytokine receptor agonist than the fusion protein (typically at least about 100× more active than the fusion protein). The form of the cytokine that is released upon cleavage of the fusion protein typically has a short half-life, which is often substantially similar to the half-life of the naturally occurring cytokine, further restricting cytokine activity to the tumor microenvironment. Even though the half-life of the fusion protein is extended, toxicity is dramatically reduced or eliminated because the circulating fusion protein is attenuated and active cytokine is targeted to the tumor microenvironment. The fusion proteins described herein, for the first time, enable the administration of an effective therapeutic dose of a cytokine to treat tumors with the activity of the cytokine substantially limited to the tumor microenvironment, and dramatically reduces or eliminates unwanted systemic effects and toxicity of the cytokine.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

"Cytokine" is a well-known term of art that refers to any of a class of immunoregulatory proteins (such as interleukin or interferon) that are secreted by cells especially of the immune system and that are modulators of the immune system. Cytokine polypeptides that can be used in the fusion proteins disclosed herein include, but are not limited to transforming growth factors, such as TGF-α and TGF-β (e.g., TGFbeta1, TGFbeta2, TGFbeta3); interferons, such as interferon-α, interferon-β, interferon-γ, interferon-kappa and interferon-omega; interleukins, such as IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21 and IL-25; tumor necrosis factors, such as tumor necrosis factor alpha and lymphotoxin; chemokines (e.g., C—X—C motif chemokine 10 (CXCL10), CCL19, CCL20, CCL21), and granulocyte macrophage-colony stimulating factor (GM-CS), as well as fragments of such polypeptides that active the cognate receptors for the cytokine (i.e., functional fragments of the foregoing). "Chemokine" is a term of art that refers to any of a family of small cytokines with the ability to induce directed chemotaxis in nearby responsive cells.

Cytokines are well-known to have short serum half-lives that frequently are only a few minutes or hours. Even forms of cytokines that have altered amino acid sequences intended to extend the serum half-life yet retain receptor agonist activity typically also have short serum half-lives. As used herein, a "short-half-life cytokine" refers to a cytokine that has a substantially brief half-life circulating in the serum of a subject, such as a serum half-life that is less than 10, less than 15, less than 30, less than 60, less than 90, less than 120, less than 240, or less than 480 minutes. As used herein, a short half-life cytokine includes cytokines which have not been modified in their sequence to achieve a longer than usual half-life in the body of a subject and polypeptides that have altered amino acid sequences intended to extend the serum half-life yet retain receptor agonist activity. Typically a short half-life cytokine polypeptide, such as an IL-2 polypeptide has a serum half-life that is comparable to naturally occurring IL-2, e.g., within 5 fold, 4 fold, 3 fold or 2 fold of naturally occurring IL-2. This latter case is not meant to include the addition of heterologous protein domains, such as a bona fide half-life extension element, such as serum albumin.

"Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID NO: 125) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

As used herein, the term "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. A steric blocker may also block by virtue of recruitment of a large protein binding partner. An example of this is an antibody, which binds to serum albumin; while the antibody itself may or may not be large enough to block activation or binding on its own, recruitment of albumin allows for sufficient steric blocking.

As used herein, the term "operably linked" in the context of a fusion polypeptide refers to orientation of the components of a fusion polypeptide that permits the components to function in their intended manner. For example, an IL-2 polypeptide and an IL-2 blocking moiety are operably linked by a protease-cleavable polypeptide linker in a fusion polypeptide when the IL-2 blocking moiety is capable of inhibiting the IL-2 receptor-activating activity of the IL-2 polypeptide in the fusion polypeptide, for example by binding to the IL-2 polypeptide, but upon cleavage of the protease-cleavable polypeptide linker the inhibition of the IL-2 receptor-activating activity of the IL-2 polypeptide by the IL-2 blocking moiety is decreased or eliminated, for example because the IL-2 blocking moiety can diffuse away from the IL-2 polypeptide.

As used and described herein, a "half-life extension element" is a part of the chimeric polypeptide that increases the serum half-life and improve pK, for example, by altering its size (e.g., to be above the kidney filtration cutoff), shape, hydrodynamic radius, charge, or parameters of absorption, biodistribution, metabolism, and elimination.

As used herein, the terms "activatable," "activate," "induce," and "inducible" refer to the ability of a protein, i.e. a cytokine, that is part of a fusion protein, to bind its receptor and effectuate activity upon cleavage of additional elements from the fusion protein.

As used herein, "plasmids" or "viral vectors" are agents that transport the disclosed nucleic acids into the cell without degradation and include a promoter yielding expression of the nucleic acid molecule and/or polypeptide in the cells into which it is delivered.

As used herein, the terms "peptide", "polypeptide", or "protein" are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, "subject" can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered.

As used herein, "patient" or "subject" may be used interchangeably and can refer to a subject with a disease or disorder (e.g., cancer). The term patient or subject includes human and veterinary subjects.

As used herein the terms "treatment", "treat", or "treating" refers to a method of reducing the effects of a disease or condition or symptom of the disease or condition. Thus, in the disclosed method, treatment can refer to at least about 10%, at least about 20%, at least about 30%, at least about 40%, at least about 50%, at least about 60%, at least about 70%, at least about 80%, at least about 90%, or substantially complete reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms "prevent", "preventing", and "prevention" of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder.

As used herein, references to "decreasing", "reducing", or "inhibiting" include a change of at least about 10%, of at least about 20%, of at least about 30%, of at least about 40%, of at least about 50%, of at least about 60%, of at least about 70%, of at least about 80%, of at least about 90% or greater as compared to a suitable control level. Such terms can include but do not necessarily include complete elimination of a function or property, such as agonist activity.

An "attenuated cytokine receptor agonist" is a cytokine receptor agonist that has decreased receptor agonist activity as compared to the cytokine receptor's naturally occurring agonist. An attenuated cytokine agonist may have at least about 10×, at least about 50×, at least about 100×, at least about 250×, at least about 500×, at least about 1000× or less agonist activity as compared to the receptor's naturally occurring agonist. When a fusion protein that contains a cytokine polypeptide as described herein is described as "attenuated" or having "attenuated activity", it is meant that the fusion protein is an attenuated cytokine receptor agonist.

An "intact fusion protein" is a fusion protein in which no domain has been removed, for example by protease cleavage. A domain may be removable by protease cleavage or other enzymatic activity, but when the fusion protein is "intact", this has not occurred.

As used herein "moiety" refers to a portion of a molecule that has a distinct function within that molecule, and that function may be performed by that moiety in the context of another molecule. A moiety may be a chemical entity with a particular function, or a portion of a biological molecule with a particular function. For example, a "blocking moiety" within a fusion protein is a portion of the fusion protein which is capable of blocking the activity of some or all of the fusion polypeptide. This may be a protein domain, such as serum albumin. Blocking may be accomplished by a steric blocker or a specific blocker. A steric blocker blocks by virtue of size and position and not based upon specific binding; an examples is serum albumin. A specific blocker blocks by virtue of specific interactions with the moiety to be blocked. A specific blocker must be tailored to the particular cytokine or active domain; a steric blocker can be used regardless of the payload, as long as it is large enough.

In general, the therapeutic use of cytokines is strongly limited by their systemic toxicity. TNF, for example, was originally discovered for its capacity of inducing the hemorrhagic necrosis of some tumors, and for its in vitro cytotoxic effect on different tumoral lines, but it subsequently proved to have strong pro-inflammatory activity, which can, in case of overproduction conditions, dangerously affect the human body. As the systemic toxicity is a fundamental problem with the use of pharmacologically active amounts of cytokines in humans, novel derivatives and therapeutic strategies are now under evaluation, aimed at reducing the toxic effects of this class of biological effectors while keeping their therapeutic efficacy.

IL-2 exerts both stimulatory and regulatory functions in the immune system and is, along with other members of the common γ chain (γc) cytokine family, central to immune homeostasis. IL-2 mediates its action by binding to IL-2 receptors (IL-2R), consisting of either trimeric receptors made of IL-2Rα (CD25), IL-2Rβ (CD122), and IL-2Rγ (γc, CD132) chains or dimeric βγ IL-2Rs (1, 3). Both IL-2R variants are able to transmit signal upon IL-2 binding. However, trimeric αβγ IL-2Rs have a roughly 10-100 times higher affinity for IL-2 than dimeric βγ IL-2Rs (3), implicating that CD25 confers high-affinity binding of IL-2 to its receptor but is not crucial for signal transduction. Trimeric IL-2Rs are found on activated T cells and CD4+ forkhead box P3 (FoxP3)+ T regulatory cells (Treg), which are sensitive to IL-2 in vitro and in vivo. Conversely, antigen-experienced (memory) CD8+, CD44 high memory-phenotype (MP) CD8+, and natural killer (NK) cells are endowed with high levels of dimeric βγ IL-2Rs and these cells also respond vigorously to IL-2 in vitro and in vivo.

Expression of the high-affinity IL-2R is critical for endowing T cells to respond to low concentrations of IL-2 that is transiently available in vivo. IL-2Rα expression is absent on naive and memory T cells but is induced after antigen activation. IL-2Rβ is constitutively expressed by NK, NKT, and memory CD8+ T cells but is also induced on naive T cells after antigen activation. γc is much less stringently regulated and is constitutively expressed by all lymphoid cells. Once the high-affinity IL-2R is induced by antigen, IL-2R signaling upregulates the expression of IL-2Rα in part through Stat5-dependent regulation of Il2ra transcription (Kim et al., 2001). This process represents a mechanism to maintain expression of the high-affinity IL-2R and sustain IL-2 signaling while there remains a source of IL-2.

IL-2 is captured by IL-2Rα through a large hydrophobic binding surface surrounded by a polar periphery that results in a relatively weak interaction (Kd 10-8 M) with rapid on-off binding kinetics. However, the IL-2Rα-IL-2 binary complex leads to a very small conformational change in IL-2 that promotes association with IL-2Rβ through a distinct polar interaction between IL-2 and IL-2Rβ. The pseudo-high affinity of the IL-2/α/β trimeric complex (i.e. Kd~300 pM) clearly indicates that the trimeric complex is more stable than either IL-2 bound to the α chain alone (Kd=10 nM) or to the β chain alone (Kd=450 nM) as shown by Ciardelli's data. In any event, the IL-2/α/β timer then recruits the γ chain into the quaternary complex capable of signaling, which is facilitated by the large composite binding site on the IL-2-bound β chain for the γ chain.

In other words, the ternary IL-2Rα-IL-2Rβ-IL-2 complex then recruits γc through a weak interaction with IL-2 and a stronger interaction with IL-2Rβ to produce a stable quaternary high-affinity IL-2R (Kd 10-11 M which is 10 pM). The formation of the high-affinity quaternary IL-2-IL-2R complex leads to signal transduction through the tyrosine kinases Jak1 and Jak3, which are associated with IL-2Rβ and γc, respectively (Nelson and Willerford, 1998). The quaternary IL-2-IL-2R complex is rapidly internalized, where IL-2, IL-2Rβ, and γc are rapidly degraded, but IL-2Rα is recycled to the cell surface (Hémar et al., 1995; Yu and Malek, 2001). Thus, those functional activities that require sustained IL-2R signaling require a continued source of IL-2 to engage IL-2Rα and form additional IL-2-IL-2R signaling complexes.

Regulatory T cells actively suppress activation of the immune system and prevent pathological self-reactivity and consequent autoimmune disease. Developing drugs and methods to selectively activate regulatory T cells for the treatment of autoimmune disease is the subject of intense research and, until the development of the present invention, which can selectively deliver active interleukins at the site of inflammation, has been largely unsuccessful. Regulatory T cells (Treg) are a class of CD4+CD25+ T cells that suppress the activity of other immune cells. Treg are central to immune system homeostasis, and play a major role in maintaining tolerance to self-antigens and in modulating the immune response to foreign antigens. Multiple autoimmune and inflammatory diseases, including Type 1 Diabetes (T1D), Systemic Lupus Erythematosus (SLE), and Graft-versus-Host Disease (GVHD) have been shown to have a deficiency of Treg cell numbers or Treg function.

Consequently, there is great interest in the development of therapies that boost the numbers and/or function of Treg cells. One treatment approach for autoimmune diseases being investigated is the transplantation of autologous, ex vivo-expanded Treg cells (Tang, Q., et al, 2013, Cold Spring Harb. Perspect. Med., 3:1-15). While this approach has shown promise in treating animal models of disease and in several early stage human clinical trials, it requires personalized treatment with the patient's own T cells, is invasive, and is technically complex. Another approach is treatment with low dose Interleukin-2 (IL-2). Treg cells characteristically express high constitutive levels of the high affinity IL-2 receptor, IL-2Rαβγ, which is composed of the subunits IL-2Rα (CD25), IL-2Rβ (CD122), and IL-2Rγ (CD132), and Treg cell growth has been shown to be dependent on IL-2 (Malek, T. R., et al., 2010, Immunity, 33:153-65).

Conversely, immune activation has also been achieved using IL-2, and recombinant IL-2 (Proleukin®) has been approved to treat certain cancers. High-dose IL-2 is used for the treatment of patients with metastatic melanoma and metastatic renal cell carcinoma with a long-term impact on overall survival.

Clinical trials of low-dose IL-2 treatment of chronic GVHD (Koreth, J., et al., 2011, N Engl J Med., 365:2055-66) and HCV-associated autoimmune vasculitis patients (Saadoun, D., et al., 2011, N Engl J Med., 365:2067-77) have demonstrated increased Treg levels and signs of clinical efficacy. New clinical trials investigating the efficacy of IL-2 in multiple other autoimmune and inflammatory diseases have been initiated. The rationale for using so-called low dose IL-2 was to exploit the high IL-2 affinity of the trimeric IL-2 receptor which is constitutively expressed on Tregs while leaving other T cells which do not express the high affinity receptor in the inactivated state. Aldesleukin (marketed as Proleukin® by Prometheus Laboratories, San Diego, Calif.), the recombinant form of IL-2 used in these trials, is associated with high toxicity. Aldesleukin is approved for the treatment of metastatic melanoma and metastatic renal cancer, but its side effects are so severe that its use is only recommended in a hospital setting with access to intensive care (Web address: www.proleukin.com/assets/pdf/proleukin.pdf).

The clinical trials of IL-2 in autoimmune diseases have employed lower doses of IL-2 in order to target Treg cells, because Treg cells respond to lower concentrations of IL-2 than many other immune cell types due to their expression of IL-2Rα (Klatzmann D, 2015 Nat Rev Immunol. 15:283-94). However, even these lower doses resulted in safety and tolerability issues, and the treatments used have employed daily subcutaneous injections, either chronically or in intermittent 5-day treatment courses. Therefore, there is a need for an autoimmune disease therapy that potentiates Treg cell numbers and function, that targets Treg cells more specifically than IL-2, that is safer and more tolerable, and that is administered less frequently.

One approach that has been suggested for improving the therapeutic index of IL-2-based therapy for autoimmune diseases is to use variants of IL-2 that are selective for Treg cells relative to other immune cells. IL-2 receptors are expressed on a variety of different immune cell types, including T cells, NK cells, eosinophils, and monocytes, and this broad expression pattern likely contributes to its pleiotropic effect on the immune system and high systemic toxicity. In particular, activated T effector cells express IL-2Rαβγ, as do pulmonary epithelial cells. But, activating T effector cells runs directly counter to the goal of down-modulating and controlling an immune response, and activating pulmonary epithelial cells leads to known dose-limiting side effects of IL-2 including pulmonary edema. In fact, the major side effect of high-dose IL-2 immunotherapy is vascular leak syndrome (VLS), which leads to accumulation of intravascular fluid in organs such as lungs and liver with subsequent pulmonary edema and liver cell damage. There is no treatment of VLS other than withdrawal of IL-2. Low-dose IL-2 regimens have been tested in patients to avoid VLS, however, at the expense of suboptimal therapeutic results.

According to the literature, VLS is believed to be caused by the release of proinflammatory cytokines from IL-2-activated NK cells. However, there is strong evidence that pulmonary edema results from direct binding of IL-2 to lung endothelial cells, which expressed low to intermediate levels of functional αβγ IL-2Rs. The pulmonary edema associated with interaction of IL-2 with lung endothelial cells was abrogated by blocking binding to CD25 with an anti-CD25 monoclonal antibody (mAb), in CD25-deficient host mice, or by the use of CD122-specific IL-2/anti-IL-2 mAb (IL-2/mAb) complexes, thus preventing VLS.

Treatment with interleukin cytokines other than IL-2 has been more limited. IL-15 displays immune cell stimulatory activity similar to that of IL-2 but without the same inhibitory effects, thus making it a promising immunotherapeutic candidate. Clinical trials of recombinant human IL-15 for the treatment of metastatic malignant melanoma or renal cell cancer demonstrated appreciable changes in immune cell distribution, proliferation, and activation and suggested potential antitumor activity (Conlon et. al., 2014). IL-15 is currently in clinical trials to treat various forms of cancer.

However, IL-15 therapy is known to be associated with undesired and toxic effects, such as exacerbating certain leukemias, graft-versus-host disease, hypotension, thrombocytopenia, and liver injury. (Mishra A., et al., Cance Cell, 2012, 22(5):645-55; Alpdogan O. et al., Blood, 2005, 105 (2):866-73; Conlon K C et al., J Clin Oncol, 2015, 33(1): 74-82.)

The direct use of IL-2 as an agonist to bind the IL-2R and modulate immune responses therapeutically has been problematic due its well-documented therapeutic risks, e.g., its short serum half-life and high toxicity. These risks have also limited the therapeutic development and use of other cytokines. New forms of cytokines that reduce these risks are needed. Disclosed herein are compositions and methods comprising IL-2 and IL-15 and other cytokines, functional fragments and muteins of cytokines as well as conditionally active cytokines designed to address these risks and provide needed immunomodulatory therapeutics.

The present invention is designed to address the shortcomings of direct IL-2 therapy and therapy using other cytokines, for example using cytokine blocking moieties, e.g., steric blocking polypeptides, serum half-life extending polypeptides, targeting polypeptides, linking polypeptides, including protease cleavable linkers, and combinations thereof. Cytokines, including interleukins (e.g., IL-2, IL-7, IL-12, IL-15, IL-18, IL-21 IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (C—X—C motif chemokine 10 (CXCL10), CCL19, CCL20, CCL21), and granulocyte macrophage-colony stimulating factor (GM-CS) are highly potent when administered to patients. As used herein, "chemokine" means a family of small cytokines with the ability to induce directed chemotaxis in nearby responsive cells Cytokines can provide powerful therapy, but are accompanied by undesired effects that are difficult to control clinically and which have limited the clinical use of cytokines. This disclosure relates to new forms of cytokines that can be used in patients with reduced or eliminated undesired effects. In particular, this disclosure relates to pharmaceutical compositions including chimeric polypeptides (fusion proteins), nucleic acids encoding fusion proteins and pharmaceutical formulations of the foregoing that contain cytokines or active fragments or muteins of cytokines that have decreased cytokine receptor activating activity in comparison to the corresponding cytokine. However, under selected conditions or in a selected biological environment the chimeric polypeptides activate their cognate receptors, often with the same or higher potency as the corresponding naturally occurring cytokine. As described herein, this is typically achieved using a cytokine blocking moiety that blocks or inhibits the receptor activating function of the cytokine, active fragment or mutein thereof under general conditions but not under selected conditions, such as those present at the desired site of cytokine activity (e.g., an inflammatory site or a tumor).

The chimeric polypeptides and nucleic acids encoding the chimeric polypeptides can be made using any suitable method. For example, nucleic acids encoding a chimeric polypeptide can be made using recombinant DNA techniques, synthetic chemistry or combinations of these techniques, and expressed in a suitable expression system, such as in CHO cells. Chimeric polypeptides can similarly be made, for example by expression of a suitable nucleic acid, using synthetic or semi-synthetic chemical techniques, and the like. In some embodiments, the blocking moiety can be attached to the cytokine polypeptide via sortase-mediated conjugation. "Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID NO: 125) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

To form the cytokine-blocking moiety fusion protein, the cytokine polypeptide is first tagged at the N-terminus with a polyglycine sequence, or alternatively, with at the C-terminus with a LPXTG motif (SEQ ID NO: 125). The blocking moiety or other element has respective peptides attached that serve as acceptor sites for the tagged polypeptides. For conjugation to domains carrying a LPXTG acceptor peptide (SEQ ID NO: 125) attached via its N-terminus, the polypeptide will be tagged with an N-terminal poly-glycine stretch. For conjugation to domain carrying a poly-glycine peptide attached via its C-terminus, the polypeptide will be tagged at its C-terminus with a LPXTG sortase recognition sequence (SEQ ID NO: 125). Recognizing poly-glycine and LPXTG (SEQ ID NO: 125) sequences, sortase will form a peptide bond between polymer-peptide and tagged polypeptides. The sortase reaction cleaves off glycine residues as intermediates and occurs at room temperature.

A variety of mechanisms can be exploited to remove or reduce the inhibition caused by the blocking moiety. For example, the pharmaceutical compositions can include an IL-2 polypeptide and a blocking moiety, e.g., a steric blocking moiety, with a protease cleavable linker comprising a protease cleavage site located between the IL-2 polypeptide and IL-2 blocking moiety or within the IL-2 blocking moiety. When the protease cleavage site is cleaved, the blocking moiety can dissociate from cytokine, and the cytokine can then activate cytokine receptor. A cytokine moiety can also be blocked by a specific blocking moiety, such as an antibody, which binds an epitope found on the relevant cytokine.

Any suitable linker can be used. For example, the linker can comprise glycine-glycine, a sortase-recognition motif, or a sortase-recognition motif and a peptide sequence $(Gly_4Ser)_n$ (SEQ ID NO: 126) or $(Gly_3Ser)_n$ (SEQ ID NO: 127), wherein n is 1, 2, 3, 4 or 5. Typically, the sortase-recognition motif comprises a peptide sequence LPXTG (SEQ ID NO: 125), where X is any amino acid. In some embodiments, the covalent linkage is between a reactive lysine residue attached to the C-terminal of the cytokine polypeptide and a reactive aspartic acid attached to the N-terminal of the blocker or other domain. In other embodiments, the covalent linkage is between a reactive aspartic acid residue attached to the N-terminal of the cytokine polypeptide and a reactive lysine residue attached to the C-terminal of said blocker or other domain.

Accordingly, as described in detail herein, the cytokine blocking moieties (e.g., IL-2 blocking moieties) used can be steric blockers. As used herein, a "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. The steric inhibition of the cytokine moiety can be removed by spatially separating the cytokine moiety from the steric blocker, such as by enzymatically cleaving a fusion protein that contains a steric blocker and a cytokine polypeptide at a site between the steric blocker and the cytokine polypeptide.

As described in greater detail herein, the blocking function can be combined with or due to the presence of additional functional components in the pharmaceutical composition, such as a targeting domain, a serum half-life extension element, and protease-cleavable linking polypeptides. For example, a serum half-life extending polypeptide can also be a steric blocker.

Various elements ensure the delivery and activity of IL-2 preferentially at the site of desired IL-2 activity and to severely limit systemic exposure to the interleukin via a blocking and/or a targeting strategy preferentially linked to a serum half-life extension strategy. In this serum half-life extension strategy, the blocked version of interleukin circulates for extended times (preferentially 1-2 or more weeks) but the activated version has the typical serum half-life of the interleukin.

By comparison to a serum half-life extended version, the serum half-life of IL-2 administered intravenously is only ~10 minutes due to distribution into the total body extracellular space, which is large, ~15 L in an average sized adult. Subsequently, IL-2 is metabolized by the kidneys with a half-life of ~2.5 hours. (Smith, K. "Interleukin 2 immunotherapy." *Therapeutic Immunology* 240 (2001)). By other measurements, IL-2 has a very short plasma half-life of 85 minutes for intravenous administration and 3.3 hours subcutaneous administration (Kirchner, G. I., et al., 1998, Br J Clin Pharmacol. 46:5-10). In some embodiments of this invention, the half-life extension element is linked to the interleukin via a linker which is cleaved at the site of action (e.g., by inflammation-specific or tumor-specific proteases) releasing the interleukin's full activity at the desired site and also separating it from the half-life extension of the uncleaved version. In such embodiments, the fully active and free interleukin would have very different pharmacokinetic (pK) properties—a half-life of hours instead of weeks. In addition, exposure to active cytokine is limited to the site of desired cytokine activity (e.g., an inflammatory site or tumor) and systemic exposure to active cytokine, and associated toxicity and side effects, are reduced.

Other cytokines envisioned in this invention have similar pharmacology (e.g., IL-15 as reported by Blood 2011 117: 4787-4795; doi: doi.org/10.1182/blood-2010-10-311456) as IL-2 and accordingly, the designs of this invention address the shortcomings of using these agents directly, and provide chimeric polypeptides that can have extended half-life and/or be targeted to a site of desired activity (e.g., a site of inflammation or a tumor).

If desired, IL-2 can be engineered to bind the IL-2R complex generally or one of the three IL-2R subunits specifically with an affinity that differs from that of the corresponding wild-type IL-2, for example toto selectively activate Tregs or Teff. For example, IL-2 polypeptides that are said to have higher affinity for the trimeric form of the IL-2 receptor relative to the dimeric beta/gamma form of the IL-2 receptor in comparison to wild type IL-2 can have an amino acid sequence that includes one of the following sets of mutations with respect to SEQ ID NO: 1 (a mature IL-2 protein comprising amino acids 21-153 of human IL-2 having the Uniprot Accession No. P60568-1): (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (l) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54R, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and I89V. This approach can also be applied to prepare muteins of other cytokines including interleukins (e.g., IL-2, IL-7, IL-12, IL-15, IL-18, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3) and granulocyte macrophage-colony stimulating factor (GM-CS). For example, muteins can be prepared that have desired binding affinity for a cognate receptor.

As noted above, any of the mutant IL-2 polypeptides disclosed herein can include the sequences described; they can also be limited to the sequences described and otherwise identical to SEQ ID NO:1. Moreover, any of the mutant IL-2 polypeptides disclosed herein can optionally include a substitution of the cysteine residue at position 125 with another residue (e.g., serine) and/or can optionally include a deletion of the alanine residue at position 1 of SEQ ID NO: 1.

Another approach to improving the therapeutic index of an IL-2 based therapy is to optimize the pharmacokinetics of the molecule to maximally activate Treg cells. Early studies of IL-2 action demonstrated that IL-2 stimulation of human T cell proliferation in vitro required a minimum of 5-6 hours exposure to effective concentrations of IL-2 (Cantrell, D. A., et. al., 1984, Science, 224: 1312-1316). When administered to human patients, IL-2 has a very short plasma half-life of 85 minutes for intravenous administration and 3.3 hours subcutaneous administration (Kirchner, G. I., et al., 1998, Br J Clin Pharmacol. 46:5-10). Because of its short half-life, maintaining circulating IL-2 at or above the level necessary to stimulate T cell proliferation for the necessary duration necessitates high doses that result in peak IL-2 levels significantly above the EC50 for Treg cells or will require frequent administration. These high IL-2 peak levels can activate IL-2Rβγ receptors and have other unintended or adverse effects, for example VLS as noted above. An IL-2 analog, or a multifunctional protein with IL-2 attached to a domain that enables binding to the FcRn receptor, with a longer circulating half-life than IL-2 can achieve a target drug concentration for a specified period of time at a lower dose than IL-2, and with lower peak levels. Such an IL-2 analog will therefore require either lower doses or less frequent administration than IL-2 to effectively stimulate Treg cells. Less frequent subcutaneous administration of an IL-2 drug will also be more tolerable for patients. A therapeutic with these characteristics will translate clinically into improved pharmacological efficacy, reduced toxicity, and improved patient compliance with therapy. Alternatively, IL-2 or muteins of IL-2 (herein, "IL-2*") can be selectively targeted to the intended site of action (e.g., sites of inflammation). This targeting can be achieved by one of several strategies, including the addition of domains to the administered agent that comprise blockers of the IL-2 (or muteins) that are cleaved away or by targeting domains or a combination of the two.

In some embodiments, IL-2* partial agonists can be tailored to bind with higher or lower affinity depending on the desired target; for example, an IL-2* can be engineered to bind with enhanced affinity to one of the receptor subunits and not the others. These types of partial agonists, unlike full agonists or complete antagonists, offer the ability to tune the signaling properties to an amplitude that elicits desired functional properties while not meeting thresholds for undesired properties. Given the differential activities of the partial agonists, a repertoire of IL-2 variants could be engineered to exhibit an even finer degree of distinctive signaling activities, ranging from almost full to partial agonism to complete antagonism.

In some embodiments, the IL-2* has altered affinity for IL-2Rα. In some embodiments, the IL-2* has a higher affinity for IL-2Rα than wild-type IL-2. In other embodiments, the IL-2* has altered affinity for IL-2Rβ. In one embodiment, IL-2* has enhanced binding affinity for IL-2Rβ, e.g., the N-terminus of IL-2Rβ, that eliminates the functional requirement for IL-2Rα. In another embodiment, an IL-2* is generated that has increased binding affinity for IL-2Rβ but that exhibited decreased binding to IL-2Rγ, and thereby is defective IL-2Rβγ heterodimerization and signaling.

Blocking moieties, described in further detail below, can also be used to favor binding to or activation of one or more receptors. In one embodiment, blocking moieties are added such that IL-2Rβγ binding or activation is blocked but IL-2Rα binding or activation is not changed. In another embodiment, blocking moieties are added such that IL-2Rα binding or activation is diminished. In another embodiment, blocking moieties are added such that binding to and or activation of all three receptors is inhibited. This blocking may be relievable by removal of the blocking moieties in a particular environment, for example by proteolytic cleavage of a linker linking one or more blocking moieties to the cytokine.

A similar approach can be applied to improve other cytokines, particularly for use as immunostimulatory agents, for example for treating cancer. For example, in this aspect, the pharmacokinetics and/or pharmacodynamics of the cytokine (e.g., IL-2, IL-7, IL-12, IL-15, IL-18, IL-21 IL-23, IFNalpha, IFNbeta and IFNgamma, TNFalpha, lymphotoxin, TGFbeta1, TGFbeta2, TGFbeta3 GM-CSF, CXCL10, CCL19, CCL20, and CCL21 can be tailored to maximally activate effector cells (e.g., effect T cells, NK cells) and/or cytotoxic immune response promoting cells (e.g., induce dendritic cell maturation) at a site of desired activity, such as in a tumor, but preferably not systemically.

Thus, provided herein are pharmaceutical compositions comprising at least one cytokine polypeptide, such as interleukins (e.g., IL-2, IL-7, IL-12, IL-15, IL-18, IL-21, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (e.g., CXCL10, CCL19, CCL20, CCL21) and granulocyte macrophage-colony stimulating factor (GM-CS) or a functional fragment or mutein of any of the foregoing. The polypeptide typically also includes at least one linker amino acid sequence, wherein the amino acid sequence is in certain embodiments capable of being cleaved by an endogenous protease. In one embodiment, the linker comprises an amino acid sequence comprising HSSKLQ (SEQ ID NO: 25), GPLGVRG (SEQ ID NO: 128), IPVSLRSG (SEQ ID NO: 129), VPLSLYSG (SEQ ID NO: 130), or SGESPAYYTA (SEQ ID NO: 131). In other embodiments, the chimeric polypeptide further contains a blocking moiety, e.g., a steric blocking polypeptide moiety, capable of blocking the activity of the interleukin polypeptide. The blocking moiety, for example, can comprise a human serum albumin (HSA) binding domain or an optionally branched or multi-armed polyethylene glycol (PEG). Alternatively, the pharmaceutical composition comprises a first cytokine polypeptide or a fragment thereof, and blocking moiety, e.g., a steric blocking polypeptide moiety, wherein the blocking moiety blocks the activity of the cytokine polypeptide on the cytokine receptor, and wherein the blocking moiety in certain embodiments comprises a protease cleavable domain. In some embodiments, blockade and reduction of cytokine activity is achieved simply by attaching additional domains with very short linkers to the N or C terminus of the interleukin domain. In such embodiments, it is anticipated the blockade is relieved by protease digestion of the blocking moiety or of the short linker that tethers the blocker to the interleukin. Once the domain is clipped or is released, it will no longer be able to achieve blockade of cytokine activity.

The pharmaceutical composition e.g., chimeric polypeptide can comprise two or more cytokines, which can be the same cytokine polypeptide or different cytokine polypeptides. For example, the two or more different types of cytokines have complementary functions. In some examples, a first cytokine is IL-2 and a second cytokine is IL-12. In some embodiments, each of the two or more different types of cytokine polypeptides have activities that modulate the activity of the other cytokine polypeptides. In some examples of chimeric polypeptides that contain two cytokine polypeptides, a first cytokine polypeptide is T-cell activating, and a second cytokine polypeptide is non-T-cell-activating. In some examples of chimeric polypeptides that contain two cytokine polypeptides, a first cytokine is a chemoattractant, e.g., CXCL10, and a second cytokine is an immune cell activator.

Preferably, the cytokine polypeptides (including functional fragments) that are included in the fusion proteins disclosed herein are not mutated or engineered to alter the properties of the naturally occurring cytokine, including receptor binding affinity and specificity or serum half-life. However, changes in amino acid sequence from naturally occurring (including wild type) cytokine are acceptable to facilitate cloning and to achieve desired expression levels, for example.

CD25 Binding

CD25 binding is often discouraged in modified IL-2 constructs. In contrast, the IL-2 polypeptides described herein preferably are not modified to avoid CD25 binding. Preferably, the IL-2 polypeptides described herein bind CD25. Typically, the IL-2 fusion proteins described herein are capable of CD25 binding and blocking is directed to interactions with IL-2R beta and gamma (CD122 and CD132).

Blocking Moiety

The blocking moiety can be any moiety that inhibits the ability of the cytokine to bind and/or activate its receptor. The blocking moiety can inhibit the ability of the cytokine to bind and/or activate its receptor sterically blocking and/or by noncovalently binding to the cytokine. Examples of suitable blocking moieties include the full length or a cytokine-binding fragment or mutein of the cognate receptor of the cytokine. Antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like that bind the cytokine can also be used. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of suitable blocking polypeptides include polypeptides that sterically inhibit or block binding of the cytokine to its cognate receptor. Advantageously, such moieties can also function as half-life extending elements. For example, a peptide that is modified by conjugation to a water-soluble polymer, such as PEG, can sterically inhibit or prevent binding of the cytokine to its receptor. Polypeptides, or fragments thereof, that have long serum half-lives can also be used, such as serum albumin (human serum albumin), immunoglobulin Fc, transferrin and the like, as well as fragments and muteins of such polypeptides.

Antibodies and antigen-binding domains that bind to, for example, a protein with a long serum half-life such as HSA, immunoglobulin or transferrin, or to a receptor that is recycled to the plasma membrane, such as FcRn or transferrin receptor, can also inhibit the cytokine, particularly when bound to their antigen. Examples of such antigen-binding polypeptides include a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds.

In illustrative examples, when IL-2 is the cytokine in the chimeric polypeptide, the blocking moiety can be the full length or fragment or mutein of the alpha chain of IL-2 receptor (IL-2Rα) or beta (IL-2Rβ) or gamma chain of IL-2 receptor (IL-2Rγ), an anti-IL-2 single-domain antibody (dAb) or scFv, a Fab, an anti-CD25 antibody or fragment thereof, and anti-HAS dAb or scFv, and the like.

Additional Aspects of the Invention
1. A fusion protein comprising a cytokine moiety that is operably linked to a binding moiety, the binding moiety comprising a non-CDR loop and a cleavable linker, wherein the binding moiety is capable of masking the binding the cytokine to its receptor and/or the activation of the receptor by the cytokine.
2. The fusion protein of aspect 1, wherein the binding moiety is a natural peptide, a synthetic peptide, an engineered scaffold, or an engineered bulk serum protein.
3. The fusion protein of aspect 1 or 2, wherein the engineered scaffold comprises a sdAb, a scFv, a Fab, a VHH, a fibronectin type III domain, immunoglobulin-like scaffold, DARPin, cystine knot peptide, lipocalin, three-helix bundle scaffold, protein G-related albumin-binding module, or a DNA or RNA aptamer scaffold.
4. The fusion protein of any one of aspects 1-2, wherein the binding moiety is capable of binding to a bulk serum protein.
5. The fusion protein of any one of aspects 1-3, wherein the non-CDR loop is from a variable domain, a constant domain, a C1-set domain, a C2-set domain, an I-domain, or any combinations thereof
6. The fusion protein of any one of aspects 1-4, wherein the binding moiety further comprises complementarity determining regions (CDRs).
7. The fusion protein of aspect 5, wherein the binding moiety is capable of binding to the bulk serum protein.
8. The fusion protein of aspect 6, wherein the bulk serum protein is a half-life extending protein.
9. The fusion protein of aspect 6 or 7, wherein the bulk serum protein is albumin, transferrin, Factor XIII, or Fibrinogen.
10. The fusion protein of any one of aspects 5-8, wherein the CDR loop provides the binding site specific for the bulk serum protein or the immunoglobulin light chain, or any combinations thereof
11. The fusion protein of any one of aspects 1-9, wherein the cleavable linker comprises a cleavage site.
12. The fusion protein of aspect 10, wherein the cleavage site is recognized by a protease.
13. The fusion protein of aspect 11, wherein the binding moiety is bound to the cytokine.
14. The fusion protein of aspect 11 or 13, wherein the binding moiety is covalently linked to the cytokine.
15. The fusion protein of aspect 11, 13, or 14, wherein the binding moiety is capable of masking the binding of the cytokine to its target via specific intermolecular interactions between the binding moiety and the cytokine.
16. The fusion protein of any one of aspects 11-14, wherein the non-CDR loop provides a binding site specific for binding of the moiety to the cytokine.
17. The fusion protein of any one of aspects 11-15, wherein upon cleavage of the cleavable linker, the binding moiety is separated from the cytokine and the cytokine binds to its target.
18. The fusion protein of any one of aspects 1-16, wherein the cytokine binds to a cytokine receptor.
19. The fusion protein of aspect 17, wherein the cytokine receptor comprises a type I cytokine receptor, a type I IL receptor, a type II IL receptor, a chemokine receptor, or a tumor necrosis receptor superfamily receptor.
20. The fusion protein of any one of aspects 1-18, wherein the cleavable linker comprises a cleavage site.
21. The fusion protein of aspect 20, wherein the cleavage site is recognized by a protease.
22. The fusion protein of aspect 21, wherein the protease cleavage site is recognized by a serine protease, a cysteine protease, an aspartate protease, a threonine protease, a glutamic acid protease, a metalloproteinase, a gelatinase, or a asparagine peptide lyase.
23. The fusion protein of aspect 21, wherein the protease cleavage site is recognized by a Cathepsin B, a Cathepsin C, a Cathepsin D, a Cathepsin E, a Cathepsin K, a Cathepsin L, a kallikrein, a hK1, a hK10, a hK15, a plasmin, a collagenase, a Type IV collagenase, a stromelysin, a Factor Xa, a chymotrypsin-like protease, a trypsin-like protease, a elastase-like protease, a subtilisin-like protease, an actinidain, a bromelain, a calpain, a caspase, a caspase-3, a Mir1-CP, a papain, a HIV-1 protease, a HSV protease, a CMV protease, a chymosin, a renin, a pepsin, a matriptase, a legumain, a plasmepsin, a nepenthesin, a metalloexopeptidase, a metalloendopeptidase, a matrix metalloprotease (MMP), a MMP1, a MMP2, a MMP3, a MMP8, a MMP9, a MMP10, a MMP11, a MMP12, a MMP13, a MMP14, an ADAM10, an ADAM17, an ADAM12, an urokinase plasminogen activator (uPA), an enterokinase, a prostate-specific target (PSA, hK3), an interleukin-1β converting enzyme, a thrombin, a FAP (FAP-α), a dipeptidyl peptidase, or dipeptidyl peptidase IV (DPPIV/CD26), a type II transmembrane serine protease (TTSP), a neutrophil elastase, a cathepsin G, a proteinase 3, a neutrophil serine protease 4, a mast cell chymase, a mast cell tryptase, a dipeptidyl peptidase, and a dipeptidyl peptidase IV (DPPIV/CD26).

24. A conditionally active binding protein comprising a binding moiety (M) which comprises a non-CDR loop, a cytokine, and a cleavable linker (L), wherein the non-CDR loop is capable of binding to the cytokine, and wherein the binding moiety is capable of inhibiting the binding of the cytokine to its receptor and/or inhibiting activation of the receptor by the cytokine.

25. The conditionally active binding protein of aspect 24, wherein the binding moiety is capable of binding to a half-life extending protein.

26. The conditionally active binding protein of aspect 24 or 25, wherein the binding moiety is a natural peptide, a synthetic peptide, an engineered scaffold, or an engineered serum bulk protein.

27. The conditionally active binding protein of aspect 26, wherein the engineered scaffold comprises a sdAb, a scFv, a Fab, a VHH, a fibronectin type III domain, immunoglobulin-like scaffold, DARPin, cystine knot peptide, lipocalin, three-helix bundle scaffold, protein G-related albumin-binding module, or a DNA or RNA aptamer scaffold.

28. The conditionally active binding protein of any one of aspects 24-27, wherein the non-CDR-loop is from a variable domain, a constant domain, a C1-set domain, a C2-set domain, an I-domain, or any combinations thereof 29. The conditionally active binding protein of any one of aspects 24-28, wherein the binding moiety further comprises complementarity determining regions (CDRs).

30. The conditionally active binding protein of any one of aspects 24-29, wherein the binding moiety comprises a binding site specific for a bulk serum protein.

31. The conditionally active binding protein of aspect 30, wherein the bulk serum protein is albumin, transferrin, Factor XIII, or Fibrinogen.

32. The conditionally active binding protein of any one of aspects 29-31, wherein the CDRs provide the binding site specific for the bulk serum protein or the immunoglobulin light chain, or any combinations thereof 33. The conditionally active binding protein of any one of aspects 29-32, wherein the binding moiety is capable of masking the binding of the cytokine to its target via specific intermolecular interactions between the binding moiety and the cytokine.

34. The conditionally active binding protein of any one of aspects 29-33, wherein the non-CDR loop provides a binding site specific for binding of the binding moiety to the cytokine.

35. The conditionally active binding protein of any one of aspects 24-34, wherein the cytokine binds to a cytokine receptor.

36. The conditionally active binding protein of aspect 35, wherein the cytokine receptor comprises a type I cytokine receptor, a type I IL receptor, a type II IL receptor, a chemokine receptor, or a tumor necrosis receptor superfamily receptor.

37. The conditionally active binding protein of aspect 24-36, wherein the cleavable linker comprises a cleavage site.

38. The conditionally active binding protein of aspect 37, wherein the cleavage site is recognized by a protease.

39. The conditionally active binding protein of aspect 38, wherein the protease cleavage site is recognized by a serine protease, a cysteine protease, an aspartate protease, a threonine protease, a glutamic acid protease, a metalloproteinase, a gelatinase, or a asparagine peptide lyase.

40. The conditionally active binding protein of aspect 38, wherein the protease cleavage site is recognized by a Cathepsin B, a Cathepsin C, a Cathepsin D, a Cathepsin E, a Cathepsin K, a Cathepsin L, a kallikrein, a hK1, a hK10, a hK15, a plasmin, a collagenase, a Type IV collagenase, a stromelysin, a Factor Xa, a chymotrypsin-like protease, a trypsin-like protease, a elastase-like protease, a subtilisin-like protease, an actinidain, a bromelain, a calpain, a caspase, a caspase-3, a Mir1-CP, a papain, a HIV-1 protease, a HSV protease, a CMV protease, a chymosin, a renin, a pepsin, a matriptase, a legumain, a plasmepsin, a nepenthesin, a metalloexopeptidase, a metalloendopeptidase, a matrix metalloprotease (MMP), a MMP1, a MMP2, a MMP3, a MMP8, a MMP9, a MMP10, a MMP11, a MMP12, a MMP13, a MMP14, an ADAM10, an ADAM17, an ADAM12, an urokinase plasminogen activator (uPA), an enterokinase, a prostate-specific target (PSA, hK3), an interleukin-1β converting enzyme, a thrombin, a FAP (FAP-α), a dipeptidyl peptidase, or dipeptidyl peptidase IV (DPPIV/CD26), a type II transmembrane serine protease (TTSP), a neutrophil elastase, a cathepsin G, a proteinase 3, a neutrophil serine protease 4, a mast cell chymase, a mast cell tryptase, a dipeptidyl peptidase, and a dipeptidyl peptidase IV (DPPIV/CD26).

41. The conditionally active binding protein of aspect 24, further comprising a half-life extension domain bound to the binding moiety, wherein the half-life extension domain provides the binding protein with a safety switch, and wherein upon cleavage of the linker the binding protein is activated by separation of the binding moiety and the half-life extension domain from the cytokine, and the binding protein is thereby separated from the safety switch.

42. The conditionally active binding protein of aspect 41, wherein the cleavage of the linker is in a tumor microenvironment.

43. A conditionally active binding protein, comprising a binding moiety that binds a cytokine via a non-CDR loop within the binding moiety, wherein the binding moiety is further linked to a half-life extension domain and comprises a cleavable linker, wherein the binding protein has an extended half-life prior to its activation by cleavage of the linker, and wherein upon activation the binding moiety and the half-life extension domain are separated from the cytokine, and wherein the binding protein, in its activated state, does not have an extended half-life.

44. The conditionally active binding protein of aspect 43, wherein the cleavage of the linker is in a tumor microenvironment.

In Vivo Half-Life Extension Elements

Preferably, the chimeric polypeptides comprise an in vivo half-life extension element. Increasing the in vivo half-life of therapeutic molecules with naturally short half-lives allows for a more acceptable and manageable dosing regimen without sacrificing effectiveness. As used herein, a "half-life extension element" is a part of the chimeric polypeptide that increases the in vivo half-life and improve pK, for example, by altering its size (e.g., to be above the kidney filtration cutoff), shape, hydrodynamic radius, charge, or parameters of absorption, biodistribution, metabolism, and elimination. An exemplary way to improve the pK of a polypeptide is by expression of an element in the polypeptide chain that binds to receptors that are recycled to the plasma membrane of cells rather than degraded in the lysosomes, such as the FcRn receptor on endothelial cells and transferrin receptor. Three types of proteins, e.g., human IgGs, HSA (or fragments), and transferrin, persist for much longer in human serum than would be predicted just by their size, which is a function of their ability to bind to receptors that are recycled rather than degraded in the lysosome. These proteins, or fragments of them that retain the FcRn binding are routinely linked to other polypeptides to extend their serum half-life. In one embodiment, the half-life extension element is a human serum albumin (HSA) binding domain. HSA (SEQ ID NO: 2) may also be directly bound to the pharmaceutical compositions or bound via a short linker. Fragments of HSA may also be used. HSA and fragments thereof can function as both a blocking moiety and a half-life extension element Human IgGs and Fc fragments can also carry out a similar function.

The serum half-life extension element can also be antigen-binding polypeptide that binds to a protein with a long serum half-life such as serum albumin, transferrin and the like. Examples of such polypeptides include antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of antigen-binding polypeptides include a ligand for a desired receptor, a ligand-binding portion of a receptor, a lectin, and peptides that binds to or associates with one or more target antigens.

Figure 5:
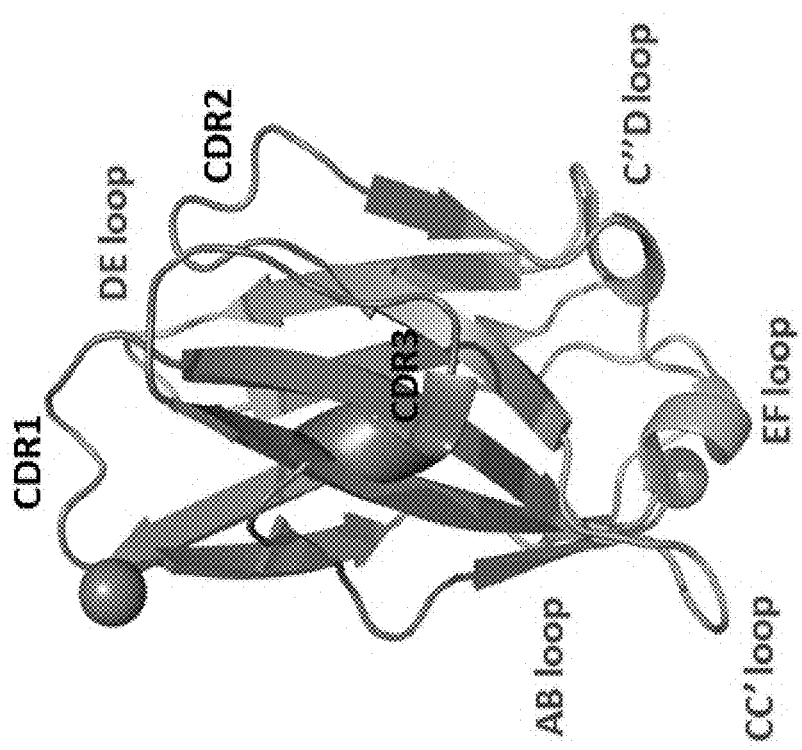
FIG. 5 is a schematic illustrating the structure of a variable domain of an immunoglobulin molecule. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops.
Figure 6:
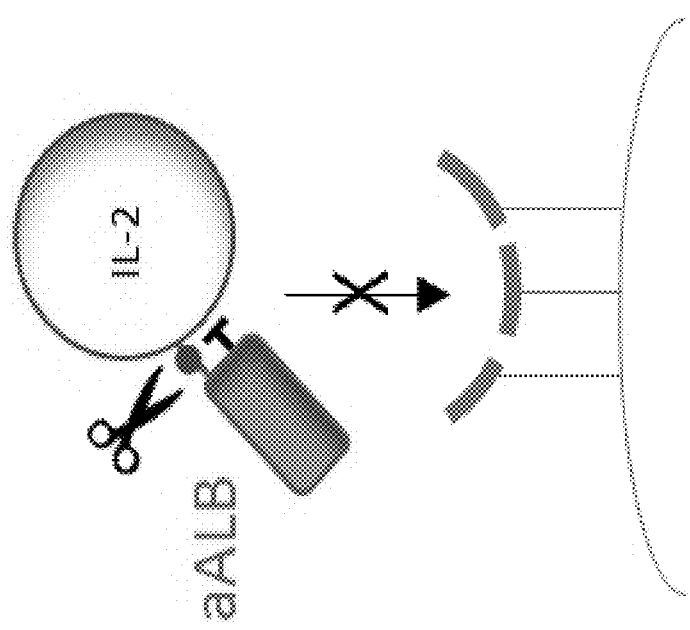
FIG. 6 is a schematic illustrating a protease-activated cytokine or chemokine comprising a cytokine or chemokine polypeptide, a blocking moiety that is a serum albumin binding domain (e.g., a dAb), and a protease-cleavable linker. In the illustrated example, the non-CDR loops in a serum albumin binding domain (e.g., a sdAb) can form a binding site for the cytokine IL-2. In this example, the binding site for serum albumin can be formed by the CDRs of the serum albumin binding domain.
Figure 7B:
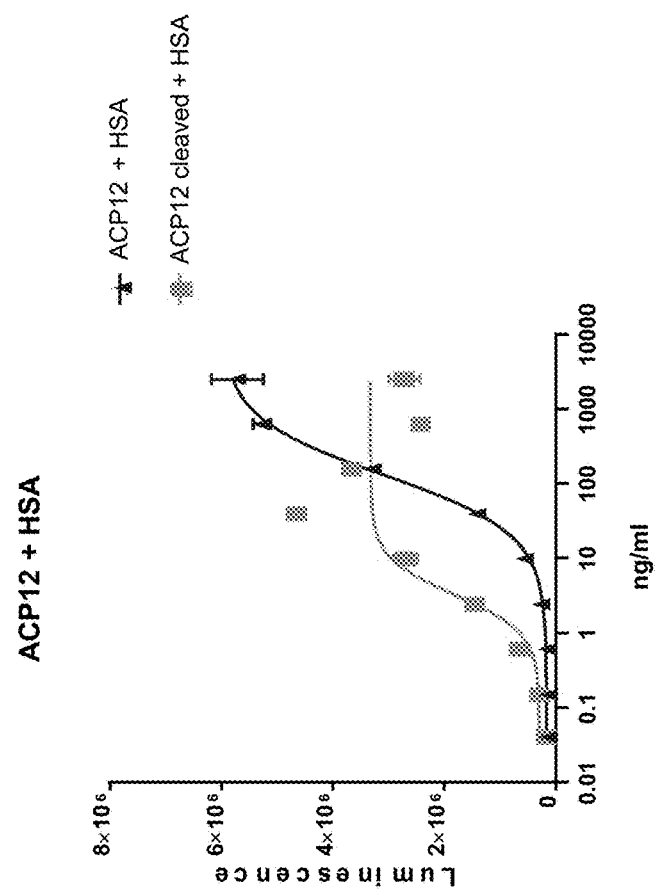
FIGS. 7a-7h are a series of graphs showing activity of exemplary IL-2 fusion proteins in IL-2 dependent cytotoxic T lymphocyte cell line CTLL-2. Each graph shows results of the IL-2 proliferation assay as quantified by CellTiter-Glo® (Promega) luminescence-based cell viability assay. Each proliferation assay was performed with HSA (FIG. 7b, FIG. 7d, FIG. 7f, and FIG. 7h) or without (FIG. 7a, FIG. 7c, FIG. 7e, and FIG. 7g). Each fusion protein comprises an anti-HSA binder, and both uncleaved and MMP9 protease cleaved versions of the fusion protein were used in each assay.
Figure 7A:
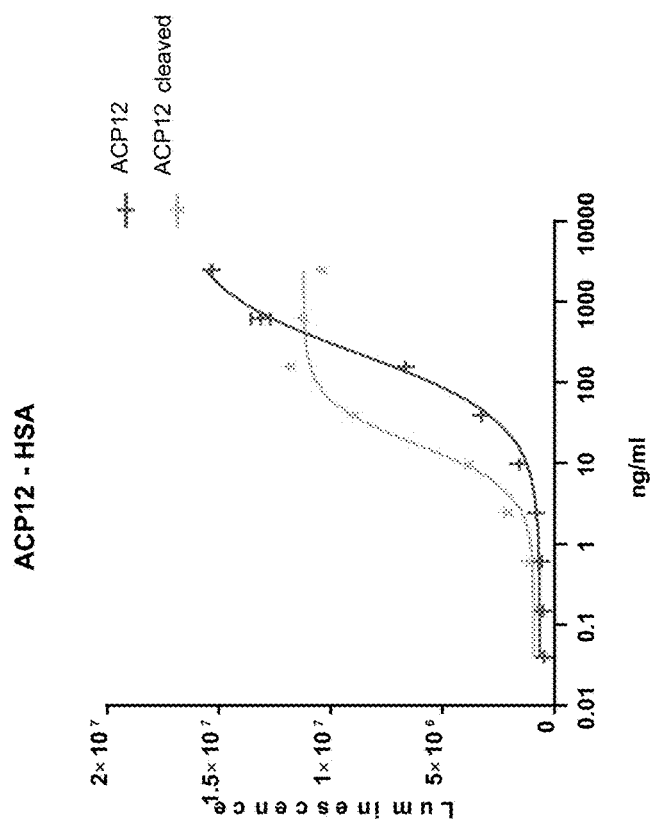
Figures 7C, 7D:
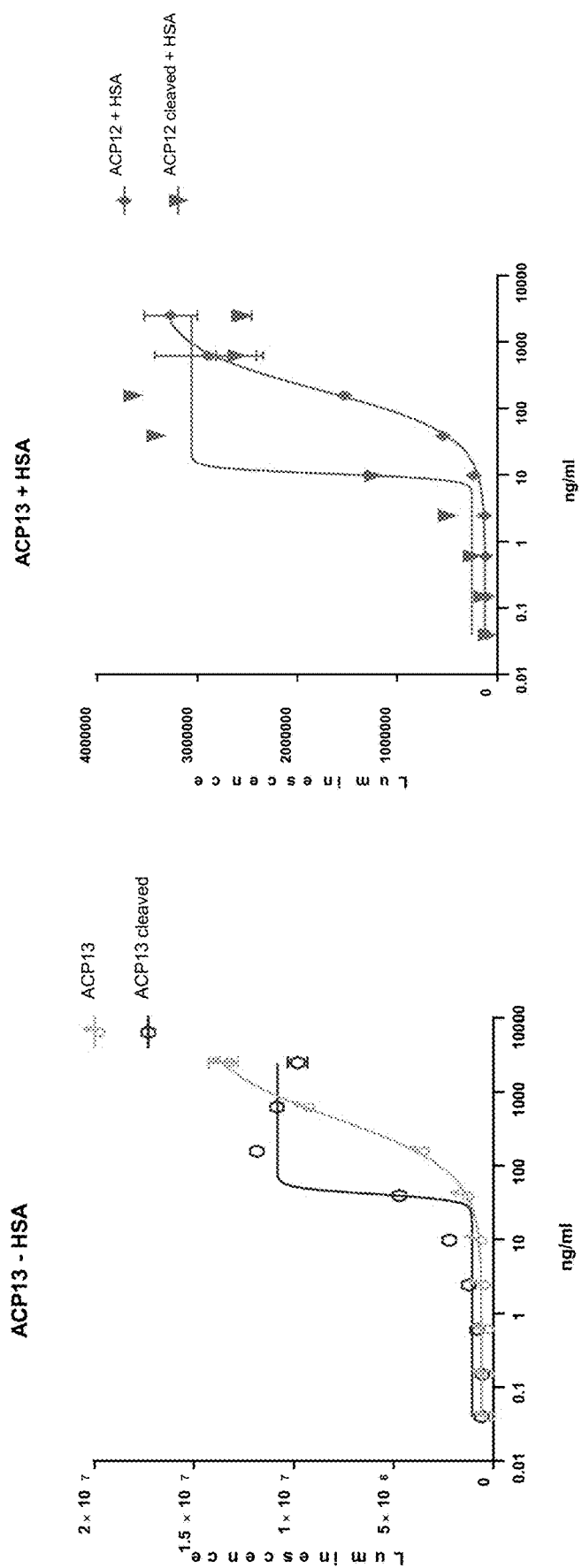
Figure 7F:
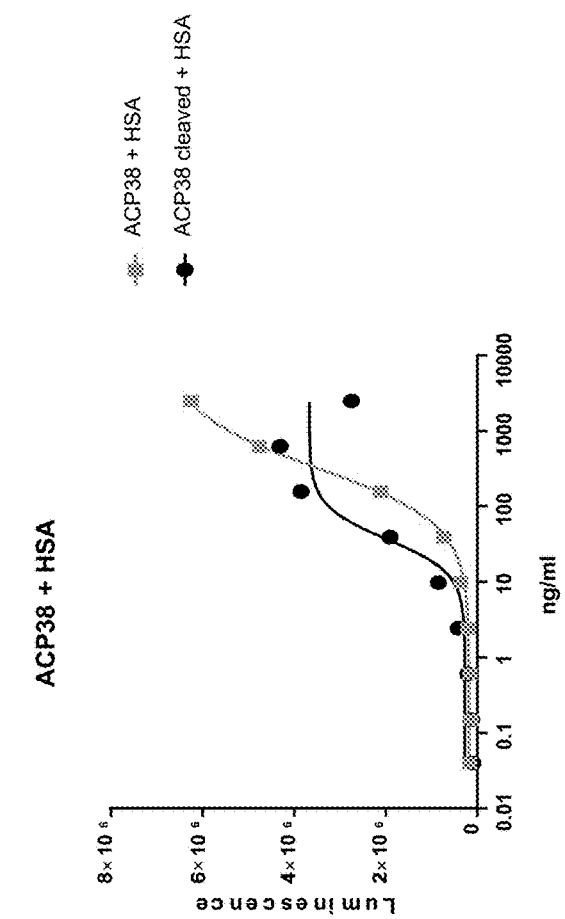
Figure 7E:
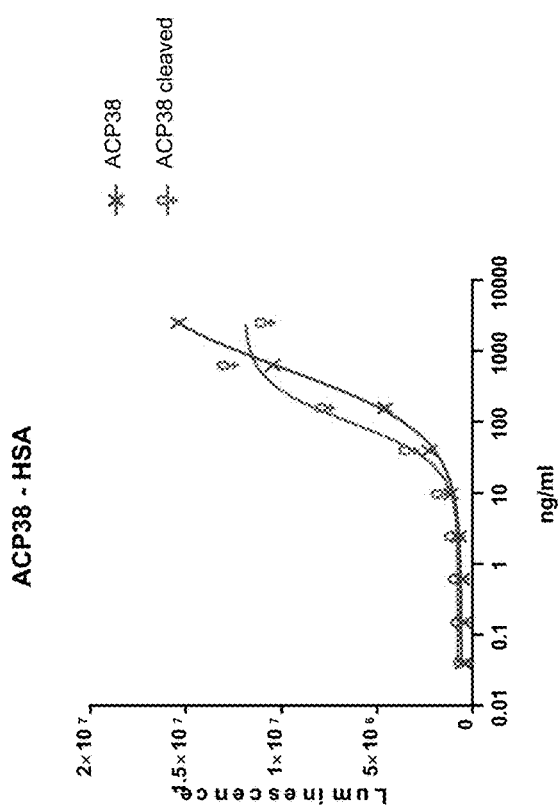
Figures 7G, 7H:
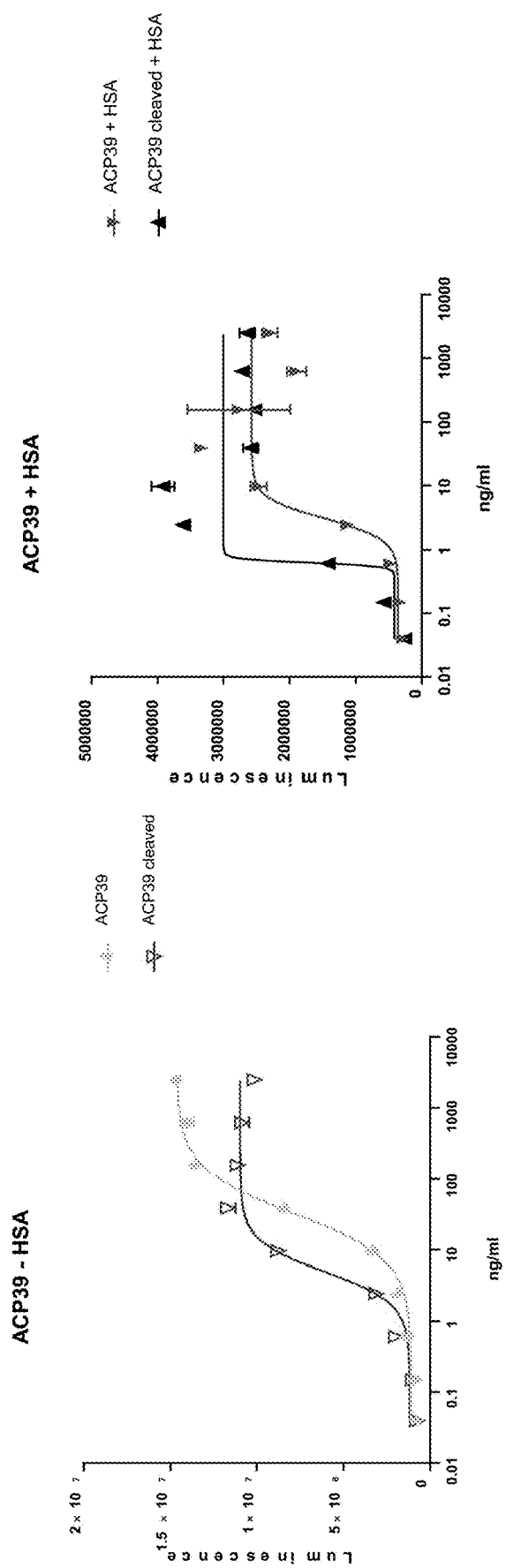
Figure 9R:
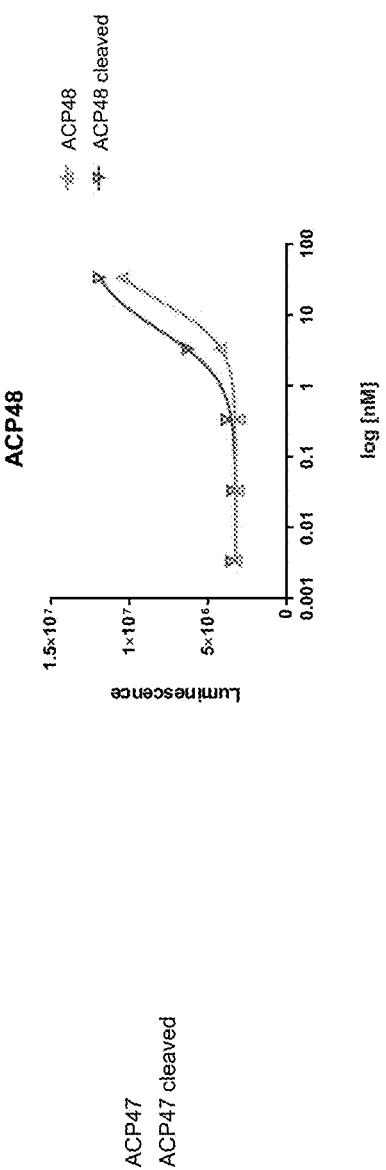
FIGS. 9a-9z are a series of graphs showing activity of exemplary IL-2 fusion proteins in IL-2 dependent cytotoxic T lymphocyte cell line CTLL-2. Each graph shows results of the IL-2 proliferation assay as quantified by CellTiter-Glo (Promega) luminescence-based cell viability assay. Both uncleaved and MMP9 protease cleaved versions of the fusion protein were used in each assay.
Figure 9S:
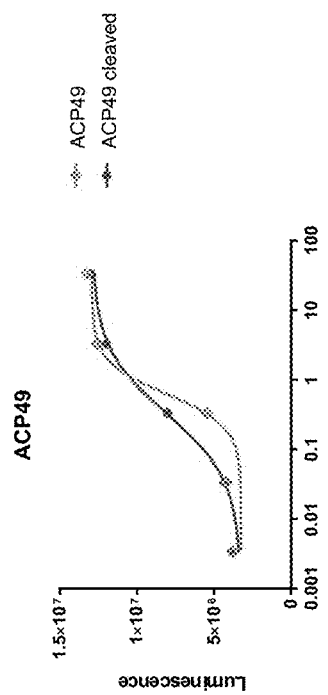
Figure 9Q:
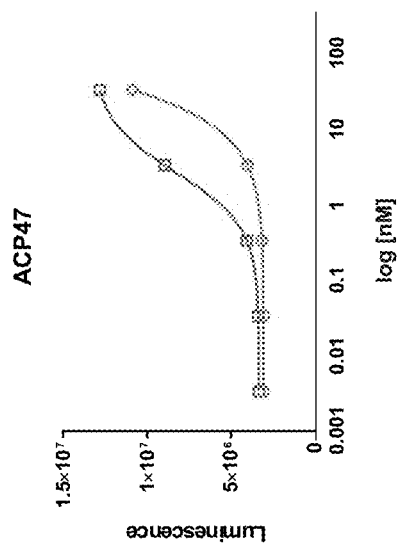
Figure 9X:
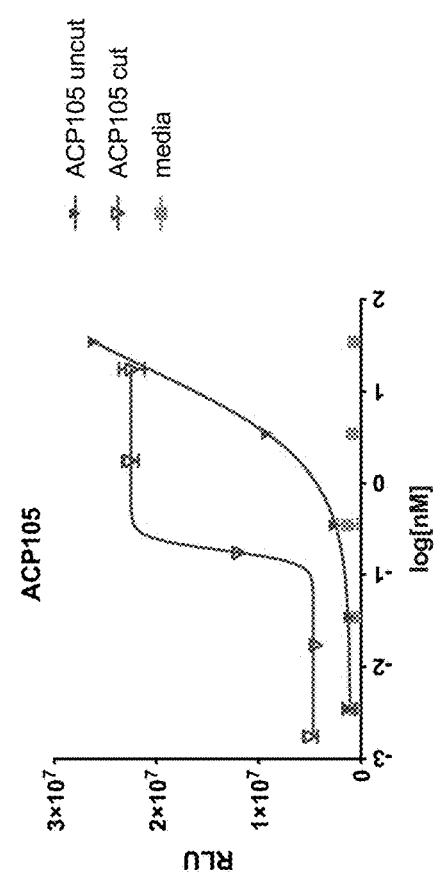
Figure 9W:
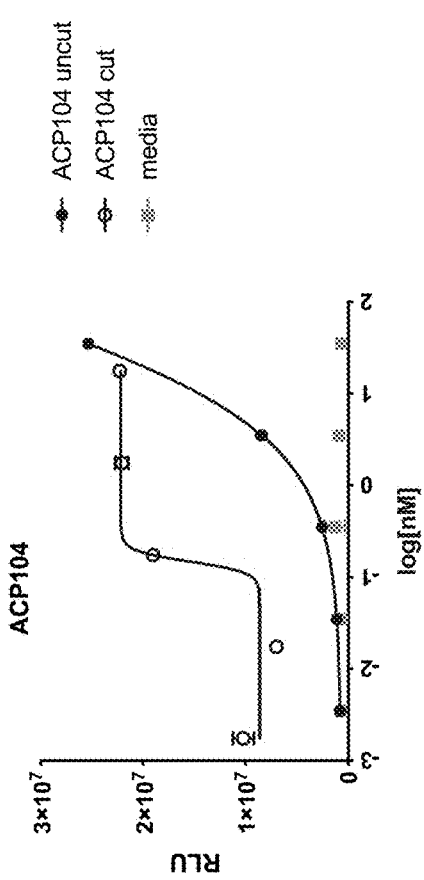
Figure 9Z:
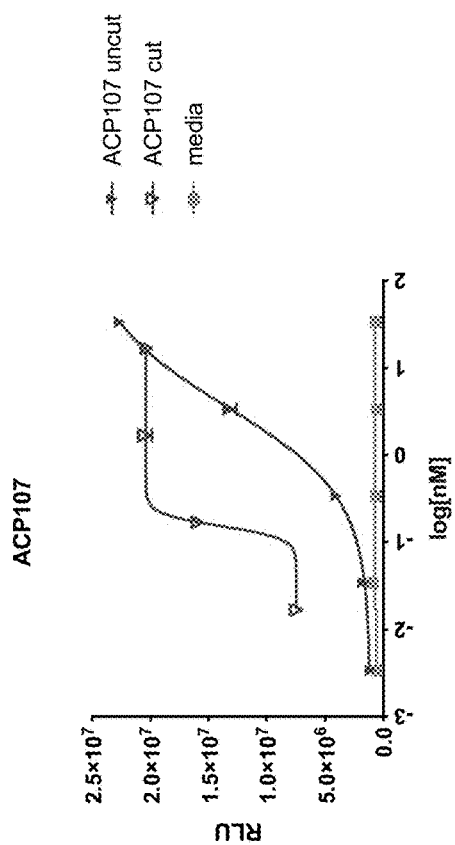
Figure 9Y:
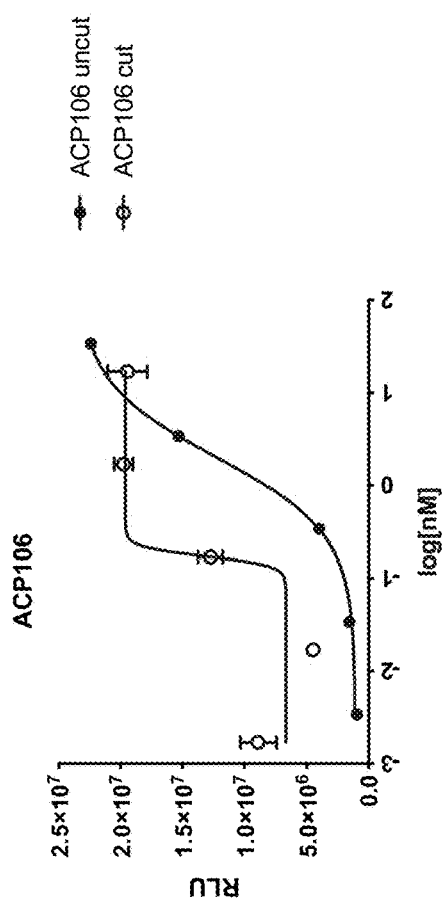

Some preferred serum half-life extension elements are polypeptides that comprise complementarity determining regions (CDRs), and optionally non-CDR loops. Advantageously, such serum half-life extension elements can extend the serum half-life of the cytokine, and also function as inhibitors of the cytokine (e.g., via steric blocking, non-covalent interaction or combination thereof) and/or as targeting domains. In some instances, the serum half-life extension elements are domains derived from an immunoglobulin molecule (Ig molecule) or engineered protein scaffolds that mimic antibody structure and/or binding activity. The Ig may be of any class or subclass (IgG1, IgG2, IgG3, IgG4, IgA, IgE, IgM etc). A polypeptide chain of an Ig molecule folds into a series of parallel beta strands linked by loops. In the variable region, three of the loops constitute the "complementarity determining regions" (CDRs) which determine the antigen binding specificity of the molecule. An IgG molecule comprises at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs) with are hypervariable in sequence and/or involved in antigen recognition and/or usually form structurally defined loops, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments of this disclosure, at least some or all of the amino acid sequences of FR1, FR2, FR3, and FR4 are part of the "non-CDR loop" of the binding moieties described herein. As shown in FIG. 5, a variable domain of an immunoglobulin molecule has several beta strands that are arranged in two sheets. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops. In some embodiments of this disclosure, at least some amino acid residues of a constant domain, CH1, CH2, or CH3, are part of the "non-CDR loop" of the binding moieties described herein. Non-CDR loops comprise, in some embodiments, one or more of AB, CD, EF, and DE loops of a C1-set domain of an Ig or an Ig-like molecule; AB, CC', EF, FG, BC, and EC' loops of a C2-set domain of an Ig or an Ig-like molecule; DE, BD, GF, A(A1A2)B, and EF loops of I(Intermediate)-set domain of an Ig or Ig-like molecule.

Within the variable domain, the CDRs are believed to be responsible for antigen recognition and binding, while the FR residues are considered a scaffold for the CDRs. However, in certain cases, some of the FR residues play an important role in antigen recognition and binding. Framework region residues that affect Ag binding are divided into two categories. The first are FR residues that contact the antigen, thus are part of the binding-site, and some of these residues are close in sequence to the CDRs. Other residues are those that are far from the CDRs in sequence, but are in close proximity to it in the 3-D structure of the molecule, e.g., a loop in heavy chain. The serum half-life extension domain (e.g., a domain that comprises CDRs) can comprise at least one non-CDR loop. In some embodiments, a non-CDR loop provides a binding site for binding to a cytokine, bulk serum protein or other target antigen.

The serum half-life extension element, in addition to or alternatively to containing CDRs, comprises a non-CDR loop. In some embodiments, the non-CDR loop is modified to generate an antigen binding site specific for a desired target antigen, such as a bulk serum protein, such as albumin, or for the cytokine moiety or other targeting antigen. It is contemplated that various techniques can be used for modifying the non-CDR loop, e.g., site-directed mutagenesis, random mutagenesis, insertion of at least one amino acid that is foreign to the non-CDR loop amino acid sequence, amino acid substitution. An antigen peptide is inserted into a non-CDR loop, in some examples. In some examples, an antigenic peptide is substituted for the non-CDR loop. The modification, to generate an antigen binding site, is in some cases in only one non-CDR loop. In other instances, more than one non-CDR loop are modified. For instance, the modification is in any one of the non-CDR loops shown in FIG. 5, i.e., AB, CC', C" D, EF, and D-E. In some cases, the modification is in the DE loop. In other cases the modifications are in all four of AB, CC', C"-D, E-F loops.

In some examples, the serum half-life extension element has dual binding specificity and contains CDRs that specifically bind a bulk serum proteins, such as serum albumin, and non-CDR loops that specifically bind and block the cytokine domain. In other examples, the serum half-life extension element contains CDRs that specifically bind a target antigen, such as the cytokine domain or other target antigen, and non-CDR loops that specifically bind a bulk serum protein, such as serum albumin. Preferably, the serum half-life extension element inhibits binding of the cytokine domain to the cognate cytokine receptor, e.g., via steric occlusion, via specific intermolecular interactions, or a combination of both.

In some embodiments, the serum half-life extension element noncovalently binds directly to the cytokine and inhibit its activity.

In certain examples, the binding moiety binds to a cytokine via one or more of AB, CC', C" D, and E-F loop and binds to a bulk-serum protein, such as albumin, via one or more of BC, C'C", and FG loop. In certain examples, the binding moiety binds to a bulk serum protein, such as albumin, via its AB, CC', C" D, or EF loop and binds to a cytokine via its BC, C'C", or FG loop. In certain examples, the binding moiety of the binds to a bulk serum protein, such as albumin, via its AB, CC', C" D, and EF loop and is bound to a cytokine via its BC, C'C", and FG loop. In certain examples, the binding moiety binds to a bulk serum protein, such as albumin, via one or more of AB, CC', C" D, and E-F loop and binds to a cytokine, via one or more of BC, C'C", and FG loop.

The binding moieties are any kinds of polypeptides. For example, in certain instances the binding moieties are natural peptides, synthetic peptides, or fibronectin scaffolds, or engineered bulk serum proteins. The bulk serum protein comprises, for example, albumin, fibrinogen, or a globulin. In some embodiments, the binding moieties are an engineered scaffolds. Engineered scaffolds comprise, for example, sdAb, a scFv, a Fab, a VHH, a fibronectin type III domain, immunoglobulin-like scaffold (as suggested in Halaby et al., 1999. Prot Eng 12(7):563-571), DARPin, cystine knot peptide, lipocalin, three-helix bundle scaffold, protein G-related albumin-binding module, or a DNA or RNA aptamer scaffold.

In some cases, the serum half-life extension element binds to the cytokine domain via its non-CDR loops and the cytokine domain is further connected to a targeting domain as described herein. In some cases, the serum half-life extending element comprises a binding site for a bulk serum protein. In some embodiments, the CDRs provide the binding site for the bulk serum protein. The bulk serum protein is, in some examples, a globulin, albumin, transferrin, IgG1, IgG2, IgG4, IgG3, IgA monomer, Factor XIII, Fibrinogen, IgE, or pentameric IgM. In some embodiments, the CDR form a binding site for an immunoglobulin light chain, such as an Igκ free light chain or an Igλ free light chain.

One exemplary conditionally active protein is shown in FIG. 6. In the illustrated example, the non-CDR loops in a serum albumin binding domain (e.g., a dAb) can form a binding site for the cytokine IL-2. In this example, the binding site for serum albumin can be formed by the CDRs of the serum albumin binding domain.

The serum half-life extension element can be any type of binding domain, including but not limited to, domains from a monoclonal antibody, a polyclonal antibody, a recombinant antibody, a human antibody, a humanized antibody. In some embodiments, the binding moiety is a single chain variable fragment (scFv), single-domain antibody such as a heavy chain variable domain (VH), a light chain variable domain (VL) and a variable domain (VHH) of camelid derived nanobody. In other embodiments, the binding moieties are non-Ig binding domains, i.e., antibody mimetic, such as anticalins, affilins, affibody molecules, affimers, affitins, alphabodies, avimers, DARPins, fynomers, kunitz domain peptides, and monobodies.

In other embodiments, the serum half-life extension element can be a water-soluble polymer or a peptide that is conjugated to a water-soluble polymer, such as PEG. "PEG," "polyethylene glycol" and "poly(ethylene glycol)" as used herein, are interchangeable and encompass any nonpeptidic water-soluble poly(ethylene oxide). The term "PEG" also means a polymer that contains a majority, that is to say, greater than 50%, of $-OCH_2CH_2-$ repeating subunits. With respect to specific forms, the PEG can take any number of a variety of molecular weights, as well as structures or geometries such as "branched," "linear," "forked," "multifunctional," and the like, to be described in greater detail below. The PEG is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the PEG can be organized in any number of different repeat patterns and can be selected from the group consisting of homopolymer, alternating copolymer, random copolymer, block copolymer, alternating tripolymer, random tripolymer, and block tripolymer. PEGs can be conjugated to polypeptide and peptides through any suitable method. Typically a reactive PEG derivative, such as N-hydroxysuccinamidyl ester PEG, is reacted with a peptide or polypeptide that includes amino acids with a side chain that contains an amine, sulfhydryl, carboxylic acid or hydroxyl functional group, such as cysteine, lysine, asparagine, glutamine, theonine, tyrosine, serine, aspartic acid, and glutamic acid.

Targeting and Retention Domains

For certain applications, it may be desirable to maximize the amount of time the construct is present in its desired location in the body. This can be achieved by including one further domain in the chimeric polypeptide (fusion protein) to influence its movements within the body. For example, the chimeric nucleic acids can encode a domain that directs the polypeptide to a location in the body, e.g., tumor cells or a site of inflammation; this domain is termed a "targeting domain" and/or encode a domain that retains the polypeptide in a location in the body, e.g., tumor cells or a site of inflammation; this domain is termed a "retention domain". In some embodiments a domain can function as both a targeting and a retention domain. In some embodiments, the targeting domain and/or retention domain are specific to a protease-rich environment. In some embodiments, the encoded targeting domain and/or retention domain are specific for regulatory T cells (Tregs), for example targeting the CCR4 or CD39 receptors. Other suitable targeting and/or retention domains comprise those that have a cognate ligand that is overexpressed in inflamed tissues, e.g., the IL-1 receptor, or the IL-6 receptor. In other embodiments, the suitable targeting and/or retention domains comprise those who have a cognate ligand that is overexpressed in tumor tissue, e.g., Epcam, CEA or mesothelin. In some embodiments, the targeting domain is linked to the interleukin via a linker which is cleaved at the site of action (e.g., by inflammation or cancer specific proteases) releasing the interleukin full activity at the desired site. In some embodiments, the targeting and/or retention domain is linked to the interleukin via a linker which is not cleaved at the site of action (e.g., by inflammation or cancer specific proteases), causing the cytokine to remain at the desired site.

Antigens of choice, in some cases, are expressed on the surface of a diseased cell or tissue, for example a tumor or a cancer cell. Antigens useful for tumor targeting and retention include but are not limited to EpCAM, EGFR, HER-2, HER-3, c-Met, FOLR1, and CEA. Pharmaceutical compositions disclosed herein, also include proteins comprising two targeting and/or retention domains that bind to two different target antigens known to be expressed on a diseased cell or tissue. Exemplary pairs of antigen binding domains include but are not limited to EGFR/CEA, EpCAM/CEA, and HER-2/HER-3.

Suitable targeting and/or retention domains include antigen-binding domains, such as antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of antigen-binding polypeptides include a ligand for a desired receptor, a ligand-binding portion of a receptor, a lectin, and peptides that binds to or associates with one or more target antigens.

In some embodiments, the targeting and/or retention domains specifically bind to a cell surface molecule. In some embodiments, the targeting and/or retention domains specifically bind to a tumor antigen. In some embodiments, the targeting polypeptides specifically and independently bind to a tumor antigen selected from at least one of Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, cMet, CEA, and FOLR1. In some embodiments, the targeting polypeptides specifically and independently bind to two different antigens, wherein at least one of the antigens is a tumor antigen selected from Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, cMet, CEA, and FOLR1.

The targeting and/or retention antigen can be a tumor antigen expressed on a tumor cell. Tumor antigens are well known in the art and include, for example, EpCAM, EGFR, HER-2, HER-3, c-Met, FOLR1, PSMA, CD38, BCMA, and CEA. 5T4, AFP, B7-H3, Cadherin-6, CAIX, CD117, CD123, CD138, CD166, CD19, CD20, CD205, CD22, CD30, CD33, CD352, CD37, CD44, CD52, CD56, CD70, CD71, CD74, CD79b, DLL3, EphA2, FAP, FGFR2, FGFR3, GPC3, gpA33, FLT-3, gpNMB, HPV-16 E6, HPV-16 E7, ITGA2, ITGA3, SLC39A6, MAGE, mesothelin, Muc1, Muc16, NaPi2b, Nectin-4, P-cadherin, NY-ESO-1, PRLR, PSCA, PTK7, ROR1, SLC44A4, SLTRK5, SLTRK6, STEAP1, TIM1, Trop2, WT1.

The targeting and/or retention antigen can be an immune checkpoint protein. Examples of immune checkpoint proteins include but are not limited to CD27, CD137, 2B4, TIGIT, CD155, ICOS, HVEM, CD40L, LIGHT, TIM-1, OX40, DNAM-1, PD-L1, PD1, PD-L2, CTLA-4, CD8, CD40, CEACAM1, CD48, CD70, A2AR, CD39, CD73, B7-H3, B7-H4, BTLA, IDO1, IDO2, TDO, KIR, LAG-3, TIM-3, or VISTA.

The targeting and/or retention antigen can be a cell surface molecule such as a protein, lipid or polysaccharide. In some embodiments, a targeting and/or retention antigen is a on a tumor cell, virally infected cell, bacterially infected cell, damaged red blood cell, arterial plaque cell, inflamed or fibrotic tissue cell. The targeting and/or retention antigen can comprise an immune response modulator. Examples of immune response modulator include but are not limited to granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), GITRL, CD3, or GITR.

The targeting and/or retention antigen can be a cytokine receptor. Examples, of cytokine receptors include but are not limited to Type I cytokine receptors, such as GM-CSF receptor, G-CSF receptor, Type I IL receptors, Epo receptor, LIF receptor, CNTF receptor, TPO receptor; Type II Cytokine receptors, such as IFN-alpha receptor (IFNAR1, IFNAR2), IFB-beta receptor, IFN-gamma receptor (IFNGR1, IFNGR2), Type II IL receptors; chemokine receptors, such as CC chemokine receptors, CXC chemokine receptors, CX3C chemokine receptors, XC chemokine receptors; tumor necrosis receptor superfamily receptors, such as TNFRSF5/CD40, TNFRSF8/CD30, TNFRSF7/CD27, TNFRSF1A/TNFR1/CD120a, TNFRSF1B/TNFR2/CD120b; TGF-beta receptors, such as TGF-beta receptor 1, TGF-beta receptor 2; Ig super family receptors, such as IL-1 receptors, CSF-1R, PDGFR (PDGFRA, PDGFRB), SCFR.

Linkers

As stated above, the pharmaceutical compositions comprise one or more linker sequences. A linker sequence serves to provide flexibility between polypeptides, such that, for example, the blocking moiety is capable of inhibiting the activity of the cytokine polypeptide. The linker sequence can be located between any or all of the cytokine polypeptide, the serum half-life extension element, and/or the blocking moiety. As described herein at least one of the linkers is protease cleavable, and contains a (one or more) cleavage site for a (one or more) desired protease. Preferably, the desired protease is enriched or selectively expressed at the desired site of cytokine activity (e.g., the tumor microenvironment). Thus, the fusion protein is preferentially or selectively cleaved at the site of desired cytokine activity.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

The orientation of the components of the pharmaceutical composition, are largely a matter of design choice and it is recognized that multiple orientations are possible and all are intended to be encompassed by this disclosure. For example, a blocking moiety can be located C-terminally or N-terminally to a cytokine polypeptide.

Proteases known to be associated with diseased cells or tissues include but are not limited to serine proteases, cysteine proteases, aspartate proteases, threonine proteases, glutamic acid proteases, metalloproteases, asparagine peptide lyases, serum proteases, cathepsins, Cathepsin B, Cathepsin C, Cathepsin D, Cathepsin E, Cathepsin K, Cathepsin L, kallikreins, hK1, hK10, hK15, plasmin, collagenase, Type IV collagenase, stromelysin, Factor Xa, chymotrypsin-like protease, trypsin-like protease, elastase-like protease, subtilisin-like protease, actinidain, bromelain, calpain, caspases, caspase-3, Mir1-CP, papain, HIV-1 protease, HSV protease, CMV protease, chymosin, renin, pepsin, matriptase, legumain, plasmepsin, nepenthesin, metalloexopeptidases, metalloendopeptidases, matrix metalloproteases (MMP), MMP1, MMP2, MMP3, MMP8, MMP9, MMP13, MMP11, MMP14, urokinase plasminogen activator (uPA), enterokinase, prostate-specific antigen (PSA, hK3), interleukin-1β converting enzyme, thrombin, FAP (FAP-α), dipeptidyl peptidase, meprins, granzymes and dipeptidyl peptidase IV (DPPIV/CD26). Proteases capable of cleaving amino acid sequences encoded by the chimeric nucleic acid sequences provided herein can, for example, be selected from the group consisting of a prostate specific antigen (PSA), a matrix metalloproteinase (MMP), an A Disintigrin and a Metalloproteinase (ADAM), a plasminogen activator, a cathepsin, a caspase, a tumor cell surface protease, and an elastase. The MMP can, for example, be matrix metalloproteinase 2 (MMP2) or matrix metalloproteinase 9 (MMP9).

Proteases useful in the methods disclosed herein are presented in Table 1, and exemplary proteases and their cleavage site are presented in Table 1a:

TABLE 1

Proteases relevant to inflammation and cancer

| Protease | Specificity | Other aspects |
| --- | --- | --- |
| Secreted by killer T cells: | | |
| Granzyme B (grB) | Cleaves after Asp residues (asp-ase) | Type of serine protease; strongly implicated in inducing perforin-dependent target cell apoptosis |
| Granzyme A (grA) | trypsin-like, cleaves after basic residues | Type of serine protease; |
| Granzyme H (grH) | Unknown substrate specificity | Type of serine protease; Other granzymes are also secreted by killer T cells, but not all are present in humans |
| Caspase-8 | Cleaves after Asp residues | Type of cysteine protease; plays essential role in TCR-induced cellular expansion-exact molecular role unclear |
| Mucosa-associated lymphoid tissue (MALT1) | Cleaves after arginine residues | Type of cysteine protease; likely acts both as a scaffold and proteolytically active enzyme in the CBM-dependent signaling pathway |
| Tryptase | Targets: angiotensin I, fibrinogen, prourokinase, TGFβ; preferentially cleaves proteins after lysine or arginine residues | Type of mast cell-specific serine protease; trypsin-like; resistant to inhibition by macromolecular protease inhibitors expressed in mammals due to their tetrameric structure, with all sites facing narrow central pore; also associated with inflammation |
| Associated with inflammation: | | |
| Thrombin | Targets: FGF-2, HB-EGF, Osteo-pontin, PDGF, VEGF | Type of serine protease; modulates activity of vascular growth factors, chemokines and extracellular proteins; strengthens VEGF-induced proliferation; induces cell migration; angiogenic factor; regulates hemostasis |
| Chymase | Exhibit chymotrypsin-like specificity, cleaving proteins after aromatic amino acid residues | Type of mast cell-specific serine protease |
| Carboxypeptidase A (MC-CPA) | Cleaves amino acid residues from C-terminal end of peptides and proteins | Type of zinc-dependent metalloproteinase |
| Kallikreins | Targets: high molecular weight kininogen, pro-urokinase | Type of serine protease; modulate relaxation response; contribute to inflammatory response; fibrin degradation |
| Elastase | Targets: E-cadherin, GM-CSF, IL-1, IL-2, IL-6, IL8, $p38^{MAPK}$, TNFα, VE-cadherin | Type of neutrophil serine protease; degrades ECM components; regulates inflammatory response; activates pro-apoptotic signaling |

TABLE 1-continued

Proteases relevant to inflammation and cancer

| Protease | Specificity | Other aspects |
| --- | --- | --- |
| Cathepsin G | Targets: EGF, ENA-78, IL-8, MCP-1, MMP-2, MT1-MMP, PAI-1, RANTES, TGF|L TNFa | Type of serine protease; degrades ECM components; chemo-attractant of leukocytes; regulates inflammatory response; promotes apoptosis |
| PR-3 | Targets: ENA-78, IL-8, IL-18, JNK, p38$^{MAPK}$, TNFα | Type of serine protease; promotes inflammatory response; activates pro-apoptotic signaling |
| Granzyme M (grM) | Cleaves after Met and other long, unbranched hydrophobic residues | Type of serine protease; only expressed in NK cells |
| Calpains | Cleave between Arg and Gly | Family of cysteine proteases; calcium-dependent; activation is involved in the process of numerous inflammation-associated diseases |

TABLE 1a

Exemplary Proteases and Protease Recognition Sequences

| Protease | Cleavage Domain Sequence | SEQ ID NO: |
| --- | --- | --- |
| MMP7 | KRALGLPG | 3 |
| MMP7 | (DE)$_8$RPLALWRS(DR)$_8$ | 4 |
| MMP9 | PR(S/T)(L/I)(S/T) | 5 |
| MMP9 | LEATA | 6 |
| MMP11 | GGAANLVRGG | 7 |
| MMP14 | SGRIGFLRTA | 8 |
| MMP | PLGLAG | 9 |
| MMP | PLGLAX | 10 |
| MMP | PLGC(me)AG | 11 |
| MMP | ESPAYYTA | 12 |
| MMP | RLQLICL | 13 |
| MMP | RLQLKAC | 14 |
| MMP2, MMP9, MMP14 | EP(Cit)G(Hof)YL | 15 |
| Urokinase plasminogen activator (uPA) | SGRSA | 16 |
| Urokinase plasminogen activator (uPA) | DAFK | 17 |
| Urokinase plasminogen activator (uPA) | GGGRR | 18 |
| Lysosomal Enzyme | GFLG | 19 |
| Lysosomal Enzyme | ALAL | 20 |
| Lysosomal Enzyme | FK | 21 |
| Cathepsin B | NLL | 22 |
| Cathepsin D | PIC(Et)FF | 23 |
| Cathepsin K | GGPRGLPG | 24 |
| Prostate Specific Antigen | HSSICLQ | 25 |
| Prostate Specific Antigen | HSSICLQL | 26 |
| Prostate Specific Antigen | HSSICLQEDA | 27 |
| Herpes Simplex Virus Protease | LVLASSSFGY | 28 |
| HIV Protease | GVSQNYPIVG | 29 |
| CMV Protease | GVVQASCRLA | 30 |
| Thrombin | F(Pip)RS | 31 |
| Thrombin | DPRSFL | 32 |
| Thrombin | PPRSFL | 33 |
| Caspase-3 | DEVD | 34 |
| Caspase-3 | DEVDP | 35 |
| Caspase-3 | KGSGDVEG | 36 |
| Interleukin 1β converting enzyme | GWEHDG | 37 |
| Enterokinase | EDDDDKA | 38 |
| FAP | KQEQNPGST | 39 |
| Kallikrein 2 | GKAFRR | 40 |
| Plasmin | DAFK | 41 |
| Plasmin | DVLK | 42 |
| Plasmin | DAFK | 43 |
| TOP | ALLLALL | 44 |

Provided herein are pharmaceutical compositions comprising polypeptide sequences. As with all peptides, polypeptides, and proteins, including fragments thereof, it is understood that additional modifications in the amino acid sequence of the chimeric polypeptides (amino acid sequence variants) can occur that do not alter the nature or function of the peptides, polypeptides, or proteins. Such modifications include conservative amino acid substitutions and are discussed in greater detail below.

The compositions provided herein have a desired function. The compositions are comprised of at least an IL-2 polypeptide, a blocking moiety, e.g., a steric blocking polypeptide, and an optional serum half-life extension element, and an optional targeting polypeptide, with one or more linkers connecting each polypeptide in the composition. The first polypeptide, e.g., an IL-2 mutein, is provided to be an active agent. The blocking moiety is provided to block the activity of the interleukin. The linker polypeptide, e.g., a protease cleavable polypeptide, is provided to be cleaved by a protease that is specifically expressed at the intended target of the active agent. Optionally, the blocking moiety blocks the activity of the first polypeptide by binding the interleukin polypeptide. In some embodiments, the blocking moiety, e.g., a steric blocking peptide, is linked to the interleukin via a protease-cleavable linker which is cleaved at the site of action (e.g., by inflammation specific or tumor-specific proteases) releasing the cytokine full activity at the desired site.

The protease cleavage site may be a naturally occurring protease cleavage site or an artificially engineered protease cleavage site. The artificially engineered protease cleavage site can be cleaved by more than one protease specific to the desired environment in which cleavage will occur, e.g., a tumor. The protease cleavage site may be cleavable by at least one protease, at least two proteases, at least three proteases, or at least four proteases.

In some embodiments, the linker comprises glycine-glycine, a sortase-recognition motif, or a sortase-recognition motif and a peptide sequence $(Gly_4Ser)_n$ (SEQ ID NO: 126) or $(Gly_3Ser)_n$, (SEQ ID NO: 127) wherein n is 1, 2, 3, 4 or 5. In one embodiment, the sortase-recognition motif comprises a peptide sequence LPXTG (SEQ ID NO: 125), where X is any amino acid. In one embodiment, the covalent linkage is between a reactive lysine residue attached to the C-terminal of the cytokine polypeptide and a reactive aspartic acid attached to the N-terminal of the blocking or other moiety. In one embodiment, the covalent linkage is between a reactive aspartic acid residue attached to the N-terminal of the cytokine polypeptide and a reactive lysine residue attached to the C-terminal of the blocking or other moiety.

Cleavage and Inducibility

As described herein, the activity of the cytokine polypeptide the context of the fusion protein is attenuated, and protease cleavage at the desired site of activity, such as in a tumor microenvironment, releases a form of the cytokine from the fusion protein that is much more active as a cytokine receptor agonist than the fusion protein. For example, the cytokine-receptor activating (agonist) activity of the fusion polypeptide can be at least about 10×, at least about 50×, at least about 100×, at least about 250×, at least about 500×, or at least about 1000× less than the cytokine receptor activating activity of the cytokine polypeptide as a separate molecular entity. The cytokine polypeptide that is part of the fusion protein exists as a separate molecular entity when it contains an amino acid that is substantially identical to the cytokine polypeptide and does not substantially include additional amino acids and is not associated (by covalent or non-covalent bonds) with other molecules. If necessary, a cytokine polypeptide as a separate molecular entity may include some additional amino acid sequences, such as a tag or short sequence to aid in expression and/or purification.

In other examples, the cytokine-receptor activating (agonist) activity of the fusion polypeptide is at least about 10×, at least about 50×, at least about 100×, at least about 250×, at least about 500×, or about 1000× less than the cytokine receptor activating activity of the polypeptide that contains the cytokine polypeptide that is produced by cleavage of the protease-cleavable linker in the fusion protein. In other words, the cytokine receptor activating (agonist) activity of the polypeptide that contains the cytokine polypeptide that is produced by cleavage of the protease-cleavable linker in the fusion protein is at least about 10×, at least about 50×, at least about 100×, at least about 250×, at least about 500×, or at least about 1000× greater than the cytokine receptor activating activity of the fusion protein.

Polypeptide Substitutions

The polypeptides described herein can include components (e.g., the cytokine, the blocking moiety) that have the same amino acid sequence of the corresponding naturally occurring protein (e.g., IL-2, IL-15, HSA) or can have an amino acid sequence that differs from the naturally occurring protein so long as the desired function is maintained. It is understood that one way to define any known modifications and derivatives or those that might arise, of the disclosed proteins and nucleic acids that encode them is through defining the sequence variants in terms of identity to specific known reference sequences. Specifically disclosed are polypeptides and nucleic acids which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the chimeric polypeptides provided herein. For example, provided are polypeptides or nucleic acids that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the sequence of any of the nucleic acids or polypeptides described herein. Those of skill in the art readily understand how to determine the identity of two polypeptides or two nucleic acids. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism), may arise due to environmental influence (e.g., by exposure to ultraviolet light), or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations. Amino acid sequence modifications typically fall into one or more of three classes: substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 2 and are referred to as conservative substitutions.

TABLE 2

Exemplary amino acid substitutions

| Amino Acid | Exemplary Substitutions |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. For example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Modifications can be selected to optimize binding. For example, affinity maturation techniques can be used to alter binding of the scFv by introducing random mutations inside the complementarity determining regions (CDRs). Such random mutations can be introduced using a variety of techniques, including radiation, chemical mutagens or error-prone PCR. Multiple rounds of mutation and selection can be performed using, for example, phage display.

The disclosure also relates to nucleic acids that encode the chimeric polypeptides described herein, and to the use of such nucleic acids to produce the chimeric polypeptides and for therapeutic purposes. For example, the invention includes DNA and RNA molecules (e.g., mRNA, self-replicating RNA) that encode a chimeric polypeptide and to the therapeutic use of such DNA and RNA molecules.

Exemplary Compositions

Exemplary fusion proteins of the invention combine the above described elements in a variety of orientations. The orientations described in this section are meant as examples and are not to be considered limiting.

In some embodiments, the fusion protein comprises an IL-2 polypeptide, a blocking moiety and a half-life extension element. In some embodiments, the IL-2 polypeptide is positioned between the half-life extension element and the blocking moiety. In some embodiments, the IL-2 polypeptide is N-terminal to the blocking moiety and the half-life extension element. In some such embodiments, the IL-2 polypeptide is proximal to the blocking moiety; in some such embodiments, the IL-2 polypeptide is proximal to the half-life extension element. At least one protease-cleavable linker must be included in all embodiments, such that the IL-2 polypeptide may be active upon cleavage. In some embodiments, the IL-2 polypeptide is C-terminal to the blocking moiety and the half-life extension element. Additional elements may be attached to one another by a cleavable linker, a non-cleavable linker, or by direct fusion. In some cases it is beneficial to include two of the same cytokine to facilitate dimerization.

In some embodiments, the blocking domains used are capable of extending half-life, and the IL-2 polypeptide is positioned between two such blocking domains. In some embodiments, the IL-2 polypeptide is positioned between two blocking domains, one of which is capable of extending half-life.

In some embodiments, two cytokines are included in the same construct, at least one being IL-2. In some embodiments, the cytokines are connected to two blocking domains each (three in total in one molecule), with a blocking domain between the two cytokine domains. In some embodiments, one or more additional half-life extension domains may be included to optimize pharmacokinetic properties.

In some embodiments, three cytokines are included in the same construct. In some embodiments, the third cytokine may function to block the other two in place of a blocking domain between the two cytokines.

Preferred half-life extension elements for use in the fusion proteins are human serum albumin (HSA), an antibody or antibody fragment (e.g., scFV, dAb) which binds serum albumin, a human or humanized IgG, or a fragment of any of the foregoing. In some preferred embodiments, the blocking moiety is human serum albumin (HSA), or an antibody or antibody fragment which binds serum albumin, an antibody which binds the cytokine and prevents activation of binding or activation of the cytokine receptor, another cytokine, or a fragment of any of the foregoing. In preferred embodiments comprising an additional targeting domain, the targeting domain is an antibody which binds a cell surface protein which is enriched on the surface of cancer cells, such as EpCAM, FOLR1, and Fibronectin.

Methods of Treatment and Pharmaceutical Compositions

Further provided are methods of treating a subject with or at risk of developing an of a disease or disorder, such as proliferative disease, a tumorous disease, an inflammatory disease, an immunological disorder, an autoimmune disease, an infectious disease, a viral disease, an allergic reaction, a parasitic reaction, or graft-versus-host disease. The methods administering to a subject in need thereof an effective amount of a fusion protein as disclosed herein that is typically administered as a pharmaceutical composition. In some embodiments, the method further comprises selecting a subject with or at risk of developing such a disease or disorder. The pharmaceutical composition preferably comprises a blocked cytokine, fragment or mutein thereof that is activated at a site of inflammation or a tumor. In one embodiment, the chimeric polypeptide comprises a cytokine polypeptide, fragment or mutein thereof and a serum half-life extension element. In another embodiment, the chimeric polypeptide comprises a cytokine polypeptide, fragment or mutein thereof and a blocking moiety, e.g., a steric blocking polypeptide, wherein the steric blocking polypeptide is capable of sterically blocking the activity of the cytokine polypeptide, fragment or mutein thereof. In another embodiment, the chimeric polypeptide comprises a cytokine polypeptide, fragment or mutein thereof, a blocking moiety, and a serum half-life extension element.

Inflammation is part of the complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair. Inflammation can occur from infection, as a symptom or a disease, e.g., cancer, atherosclerosis, allergies, myopathies, HIV, obesity, or an autoimmune disease. An autoimmune disease is a chronic condition arising from an abnormal immune response to a self-antigen. Autoimmune diseases that may be treated with the polypeptides disclosed herein include but are not limited to lupus, celiac disease, diabetes mellitus type 1, Graves disease, inflammatory bowel disease, multiple sclerosis, psoriasis, rheumatoid arthritis, and systemic lupus erythematosus.

The pharmaceutical composition can comprise one or more protease-cleavable linker sequences. The linker sequence serves to provide flexibility between polypeptides, such that each polypeptide is capable of inhibiting the activity of the first polypeptide. The linker sequence can be located between any or all of the cytokine polypeptide, fragment or mutein thereof, the blocking moiety, and serum half-life extension element. Optionally, the composition comprises, two, three, four, or five linker sequences. The linker sequence, two, three, or four linker sequences can be the same or different linker sequences. In one embodiment, the linker sequence comprises GGGGS (SEQ ID NO: 132), GSGSGS (SEQ ID NO: 133), or G(SGGG)$_2$SGGT (SEQ ID NO: 134). In another embodiment, the linker comprises a protease-cleavable sequence selected from group consisting of HSSKLQ (SEQ ID NO: 25), GPLGVRG (SEQ ID NO: 128), IPVSLRSG (SEQ ID NO: 129), VPLSLYSG (SEQ ID NO: 130), and SGESPAYYTA (SEQ ID NO: 131).

In some embodiments, the linker is cleaved by a protease selected from the group consisting of a kallikrein, thrombin, chymase, carboxypeptidase A, cathepsin G, an elastase, PR-3, granzyme M, a calpain, a matrix metalloproteinase (MMP), a plasminogen activator, a cathepsin, a caspase, a tryptase, or a tumor cell surface protease.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

Further provided are methods of treating a subject with or at risk of developing cancer. The methods comprise administering to the subject in need thereof an effective amount of a chimeric polypeptide (a fusion protein) as disclosed herein that is typically administered as a pharmaceutical composition. In some embodiments, the method further comprises selecting a subject with or at risk of developing cancer. The pharmaceutical composition preferably comprises a blocked cytokine, fragment or mutein thereof that is activated at a tumor site. Preferably, the tumor is a solid tumor. The cancer may be, but is not limited to, a colon cancer, a lung cancer, a melanoma, a sarcoma, a renal cell carcinoma, and a breast cancer.

The method can further involve the administration of one or more additional agents to treat cancer, such as chemotherapeutic agents (e.g., Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine), immuno-oncology agents (e.g., anti-PD-L1, anti-CTLA4, anti-PD-1, anti-CD47, anti-GD2), cellular therapies (e.g., CAR-T, T-cell therapy), oncolytic viruses and the like.

Provided herein are pharmaceutical formulations or compositions containing the chimeric polypeptides and a pharmaceutically acceptable carrier. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical formulation or composition in which it is contained. The carrier is selected to minimize degradation of the active ingredient and to minimize adverse side effects in the subject.

Suitable carriers and their formulations are described in *Remington: The Science and Practice of Pharmacy,* 21$^{st}$ Edition, David B. Troy, ed., Lippincott Williams & Wilkins (2005). Typically, an appropriate amount of a pharmaceutically-acceptable salt is used in the formulation to render the formulation isotonic, although the formulate can be hypertonic or hypotonic if desired. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the chimeric polypeptides or nucleic acid sequences encoding the chimeric polypeptides to humans or other subjects.

The pharmaceutical formulations or compositions are administered in a number of ways depending on whether local or systemic treatment is desired and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. In some embodiments, the compositions are administered locally (non-systemically), including intratumorally, intra-articularly, intrathecally, etc.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the chimeric polypeptides or nucleic acid sequences encoding the chimeric polypeptides are administered by a vector. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein. Such compositions and methods can be used to transfect or transduce cells in vitro or in vivo, for example, to produce cell lines that express and preferably secrete the encoded chimeric polypeptide or to therapeutically deliver nucleic acids to a subject. The components of the chimeric nucleic acids disclosed herein typically are operably linked in frame to encode a fusion protein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infectious viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Such vectors can also be used to make the chimeric polypeptides by expression is a suitable host cell, such as CHO cells.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g., β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Further-more, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g., chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the E. coli lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more. As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the chimeric polypeptides or chimeric nucleic acid sequences encoding the chimeric polypeptides described herein are administered to a subject prior to onset (e.g., before obvious signs of cancer or inflammation) or during early onset (e.g., upon initial signs and symptoms of cancer or inflammation). Prophylactic administration can occur for several days to years prior to the manifestation of symptoms of cancer or inflammation. Prophylactic administration can be used, for example, in the preventative treatment of subjects diagnosed with a genetic predisposition to cancer. Therapeutic treatment involves administering to a subject a therapeutically effective amount of the chimeric polypeptides or nucleic acid sequences encoding the chimeric polypeptides described herein after diagnosis or development of cancer or inflammation (e.g., an autoimmune disease). Prophylactic use may also apply when a patient is undergoing a treatment, e.g., a chemotherapy, in which inflammation is expected.

According to the methods taught herein, the subject is administered an effective amount of the agent (e.g., a chimeric polypeptide). The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus, in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

IL-2 variants have been developed that are selective for IL-2Rαβγ relative to IL-2Rβγ (Shanafelt, A. B., et al., 2000, Nat Biotechnol. 18:1197-202; Cassell, D. J., et. al., 2002, Curr Pharm Des., 8:2171-83). These variants have amino acid substitutions, which reduce their affinity for IL-2Rβ. Because IL-2 has undetectable affinity for IL-2Rγ, these variants consequently have reduced affinity for the IL-2Rβγ receptor complex and reduced ability to activate IL-2Rβγ-expressing cells, but retain the ability to bind IL-2Rα and the ability to bind and activate the IL-2Rαβγ receptor complex.

One of these variants, IL-2/N88R (Bay 50-4798), was clinically tested as a low-toxicity version of IL-2 as an immune system stimulator, based on the hypothesis that IL-2Rβγ-expressing NK cells are a major contributor to toxicity. Bay 50-4798 was shown to selectively stimulate the proliferation of activated T cells relative to NK cells, and was evaluated in phase I/II clinical trials in cancer patients (Margolin, K., et. al., 2007, Clin Cancer Res., 13:3312-9) and HIV patients (Davey, R. T., et. al., 2008, J Interferon Cytokine Res., 28:89-100). These clinical trials showed that Bay 50-4798 was considerably safer and more tolerable than aldesleukin, and also showed that it increased the levels of CD4+CD25+ T cells, a cell population enriched in Treg cells. Subsequent to these trials, research in the field more fully established the identity of Treg cells and demonstrated that Treg cells selectively express IL-2Rαβγ (reviewed in Malek, T. R., et al., 2010, Immunity, 33:153-65).

In addition, mutants can be made that selectively alter the affinity for the CD25 chain relative to native IL-2.

IL-2 can be engineered to produce mutants that bind the IL-2R complex generally or the IL-2Rα subunit specifically with an affinity that differs from that of the corresponding wild-type IL-2 or of a presently available mutant (referred to as C125S, as the cysteine residue at position 125 is replaced with a serine residue).

Accordingly, the present invention features mutant interleukin-2 (IL-2*) polypeptides that include an amino acid sequence that is at least 80% identical to wild-type IL-2 (e.g., 85, 87, 90, 95, 97, 98, or 99% identical) and that bind, as compared to WT IL-2, with higher to the IL-2 trimeric receptor relative to the dimeric IL-2 receptor. Typically, the muteins will also bind an IL-2 receptor a subunit (IL-2Rα) with an affinity that is greater than the affinity with which wild type IL-2 binds the IL-2Rα. The amino acid sequence within mutant IL-2 polypeptides can vary from SEQ ID NO: 1 (UniProtKB accession number P60568) by virtue of containing (or only containing) one or more amino acid substitutions, which may be considered conservative or non-conservative substitutions. Non-naturally occurring amino acids can also be incorporated. Alternatively, or in addition, the amino acid sequence can vary from SEQ ID NO: 1 (which may be considered the "reference" sequence) by virtue of containing and addition and/or deletion of one or more amino acid residues. More specifically, the amino acid sequence can differ from that of SEQ ID NO:1 by virtue of a mutation at least one of the following positions of SEQ ID NO:1: 1, 4, 8, 9, 10, 11, 13, 15, 26, 29, 30, 31, 35, 37, 46, 48, 49, 54, 61, 64, 67, 68, 69, 71, 73, 74, 75, 76, 79, 88, 89, 90, 92, 99, 101, 103, 114, 125, 128, or 133 (or combinations thereof). As noted, as few as one of these positions may be altered, as may two, three, four, five, six, seven, eight, nine, ten, or 11 or more (including up to all) of the positions. For example, the amino acid sequence can differ from SEQ ID NO: 1 at positions 69 and 74 and further at one or more of positions 30, 35, and 128. The amino acid sequence can also differ from SEQ ID NO:2 (as disclosed in U.S. Pat. No. 7,569,215, incorporated herein by reference) at one of the following sets of positions: (a) positions 64, 69, and 74; (b) positions 69, 74, and 101; (c) positions 69, 74, and 128; (d) positions 30, 69, 74, and 103; (e) positions 49, 69, 73, and 76; (f) positions 69, 74, 101, and 133; (g) positions 30, 69, 74, and 128; (h) positions 69, 74, 88, and 99; (i) positions 30, 69, 74, and 128; (j) positions 9, 11, 35, 69, and 74; (k) positions 1, 46, 49, 61, 69, and 79; (l) positions 48, 68, 71, 90, 103, and 114; (m) positions 4, 10, 11, 69, 74, 88, and 133; (n) positions 15, 30 31, 35, 48, 69, 74, and 92; (O) positions 30, 68, 69, 71, 74, 75, 76, and 90; (p) positions 30, 31, 37, 69, 73, 74, 79, and 128; (q) positions 26, 29, 30, 54, 67, 69, 74, and 92; (r) positions 8, 13, 26, 30, 35, 37, 69, 74, and 92; and (s) positions 29, 31, 35, 37, 48, 69, 71, 74, 88, and 89. Aside from mutations at these positions, the amino acid sequence of the mutant IL-2 polypeptide can otherwise be identical to SEQ ID NO: 1. With respect to specific substitutions, the amino acid sequence can differ from SEQ ID NO: 1 by virtue of having one or more of the following mutations: A1T, S4P, K8R, K9T, T10A, Q11R, Q13R, E15K, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P, 575P, K76E, K76R, H79R, N88D, I89V, N90H, I92T, S99P, T101A, F103S, I114V, I128T, I128A, T133A, or T133N. Our nomenclature is consistent with that of the scientific literature, where the single letter code of the amino acid in the wild-type or reference sequence is followed by its position within the sequence and then by the single letter code of the amino acid with which it is replaced. Thus, A1T designates a substitution of the alanine residue a position 1 with threonine. Other mutant polypeptides within the scope of the invention include those that include a mutant of SEQ ID NO: 2 having substitutions at V69 (e.g., A) and Q74 (e.g., P). For example, the amino acid sequence can include one of the following sets of mutations with respect to SEQ ID NO:2: (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (l) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54R, E67G, V69A, Q74P, and I92T;

(r) K8R, Q13R, N26D, N30T, K35R, T37R, V69A, Q74P, and I92T; and (s) N29S, Y31H, K35R, T37A, K48E, V69A, N71R, Q74P, N88D, and I89V. SEQ ID NO: 2 is disclosed in U.S. Pat. No. 7,569,215, which is incorporated herein by reference as an exemplary IL-2 polypeptide sequence that can be used in the invention.

As noted above, any of the mutant IL-2 polypeptides disclosed herein can include the sequences described; they can also be limited to the sequences described and otherwise identical to SEQ ID NO: 1. Moreover, any of the mutant IL-2 polypeptides described herein can optionally include a substitution of the cysteine residue at position 125 with another residue (e.g., serine) and/or can optionally include a deletion of the alanine residue at position 1 of SEQ ID NO: 1.

The mutant IL-2 polypeptides disclosed herein can bind to the IL-2Rα subunit with a $K_d$ of less than about 28 nM (e.g., less than about 25 nM; less than about 5 nM; about 1 nM; less than about 500 pM; or less than about 100 pM). More specifically, a mutant IL-2 polypeptide can have an affinity equilibrium constant less than 1.0 nM (e.g., about 0.8, 0.6, 0.4, or 0.2 nM). Affinity can also be expressed as a relative rate of dissociation from an IL-2Rα subunit or from an IL-2 receptor complex (e.g., a complex expressed on the surface of a cell or otherwise membrane bound). For example, the mutant IL-2 polypeptides can dissociate from, e.g., IL-2Rα, at a decreased rate relative to a wild-type polypeptide or to an IL-2 based therapeutic, e.g., IL-2*. Alternatively, affinity can be characterized as the time, or average time, an IL-2* polypeptide persists on, for example, the surface of a cell expressing an IL-2R. For example, an IL-2*polypeptide can persist on the receptor for at least about 2, 5, 10, 50, 100, or 250 times (or more).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following are examples of methods and compositions of the invention. It is understood that various other embodiments may be practiced, given the general description provided herein.

Example 1: Detection of IL-2, IL-2 Mutein, IL-2Rα and IL-2Rγ in Fusion Proteins by ELISA IL-2 or IL-2 mutein in a fusion protein is detected with a commercially available antibody, e.g., the anti-IL-2 monoclonal (JES6-1A12) (BD Pharmingen; San Jose, Calif.). A positive control is used to show whether the monoclonal antibody recognizes the cytokine or mutein. Antibodies against IL-2Rα and IL-2Rγ chain are also used. Wells of a 96-well plate are coated with an antibody (2.5 µg/ml) in PBS. Wells are blocked with 5% non-fat milk in PBS with 0.2% Tween®20 (PBS-M-Tw) and fusion proteins are added for 1-2 hours at 37° C. After washing, an anti-IL-2 biotin-labeled antibody, e.g., JES5H4 (BD Pharmingen) is added and binding is detected using Strepavidin HRP (Southern Biotechnology Associates; Birmingham, Ala.). The ELISA plate is developed by adding 50 µl O-phenylenediamine (OPD) (Sigma-Aldrich) in 0.1M Citrate pH 4.5 and 0.04% $H_2O_2$, stopped by adding 50 µl/well 2N $H_2SO_4$ and the absorbance was read at 490 nm.

Example 2: Protease Cleavage of IL-2 Fusion Protein by MMP9 Protease

Figure 10:
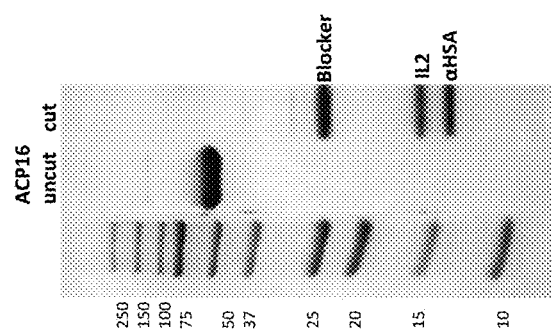
FIG. 10 shows results of protein cleavage assay, as described in Example 2. Fusion protein ACP16 was run on an SDS-PAGE gel in both cleaved and uncleaved form. As can be seen in the gel, cleavage was complete.

One of skill in the art would be familiar with methods of setting up protein cleavage assay. 100ug of protein in 1×PBS pH 7.4 were cleaved with 1 ug active MMP9 (Sigma catalog #SAE0078-50 or Enzo catalog BML-SE360) and incubated at room temperature for up to 16 hours. Digested protein is subsequently used in functional assays or stored at −80° C. prior to testing. Extent of cleavage was monitored by SD S PAGE using methods well known in the art. As shown in FIG. 10, the ACP16 fusion protein was cleaved by MMP9 protease.

Example 3: CTLL-2 Assay

CTLL2 cells (ATCC) were plated in suspension at a concentration of 500,000 cells/well in culture media with or without 40 mg/ml human serum albumin (HSA) and stimulated with a dilution series of recombinant hIL-2 or activatable hIL-2 for 72 hours at 37° C. and 5% $CO_2$. Activity of uncleaved and cleaved activatable hIL-2 was tested. Cleaved activatable hIL-2 was generated by incubation with active MMP9. Cell activity was assessed using a CellTiter-Glo (Promega) luminescence-based cell viability assay. Results are shown in FIGS. 7a-7h, 8a-8f, and 9a-9z.

Example 4: Protease Cleavage of the IL-2/IL-2Rα/IL-2Rγ Chimeric Polypeptide Results in Increased Accessibility to Antibodies and Biologically Active IL-2 Mutein The IL-2 mutein fusion proteins are biochemically characterized before and after cleavage with a protease, e.g., PSA Immunoblot analyses will show that the fusion proteins can be cleaved by PSA and that there is an increase in intensity of the predicted low molecular weight cleavage product of approximately 20 kDa reactive with an anti-IL-2 antibody after treatment of the samples with PSA. The degree of cleavage is dependent upon the amount of PSA as well as the time of incubation. Interestingly, when the fusion protein is analyzed before and after PSA treatment by ELISA, it was found that the apparent amount of IL-2 is increased after PSA cleavage. In this experiment, there is an approximately 2 or 4-fold increase in the apparent amount of IL-2 detected using this sandwich ELISA depending on the construct, suggesting that the antibody binding is partially hindered in the intact fusion protein. Aliquots of the same samples are also analyzed after PSA treatment using the CTLL-2 cell line that requires IL-2 for growth and survival and the viability of cells can be ascertained using the colorimetric MTT assay. In this assay, the more a supernatant can be diluted, the more biologically active IL-2 it contains, and there is an increase in the amount of biologically active IL-2 after PSA cleavage. The amount of IL-2 mutein increase will suggest that after PSA cleavage there is an increase in the predicted low molecular weight cleavage fragment of approximately 20 kDa reactive with an anti-IL-2 antibody, an increase in antibody accessibility, and most importantly, an increase in the amount of biologically active IL-2 mutein.

Example 5. In Vivo Delivery of a Protease Activated IL-2 Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IL-2 mutein fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 6: Construction of an Exemplary Activatable IL-2 Protein Targeting CD20 Generation of an Activatable IL-2 Domain An IL-2 polypeptide capable of binding to CD20 polypeptide present in a tumor or on a tumor cell is produced as follows. A nucleic acid is produced that contains nucleic acid sequences: (1) encoding an IL-2 polypeptide sequence and (2) one or more polypeptide linkers. Activatable IL-2 plasmid constructs can have optional Flag, His or other affinity tags, and are electroporated into HEK293 or other suitable human or mammalian cell lines and purified. Validation assays include T cell activation assays using T cells responsive to IL-2 stimulation in the presence of a protease.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable IL-2 protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" or "$G_4S$" subunit $(G_4S)_3$ connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.

Cloning of DNA Expression Constructs Encoding the Activatable IL-2 Protein

The activatable IL-2 construct with protease cleavage site domains are used to construct an activatable IL-2 protein in combination with an anti-CD20 scFv domain and a serum half-life extension element (e.g., a HSA binding peptide or VH domain) For expression of an activatable IL-2 protein in CHO cells, coding sequences of all protein domains are cloned into a mammalian expression vector system. In brief, gene sequences encoding the activatable IL-2 domain, serum half-life extension element, and CD20 binding domain along with peptide linkers L1 and L2 are separately synthesized and subcloned. The resulting constructs are then ligated together in the order of CD20 binding domain-L1-IL-2 subunit 1-L2-protease cleavage domain-L3-IL-2 subunit 2-L4-anti-CD20 scFv-L5-serum half-life extension element to yield a final construct. All expression constructs are designed to contain coding sequences for an N-terminal signal peptide and a C-terminal hexahistidine (6×His)-tag to facilitate protein secretion and purification, respectively.

Expression of Activatable IL-2 Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable IL-2 proteins are generated by transfection of suspension-adapted cells. During selection with the antibiotic Hygromycin B viable cell densities are measured twice a week, and cells are centrifuged and resuspended in fresh selection medium at a maximal density of $0.1 \times 10^6$ viable cells/mL. Cell pools stably expressing activatable IL-2 proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable IL-2 proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable IL-2 Proteins

Activatable IL-2 proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 7: Determination of Antigen Affinity by Flow Cytometry

The activatable IL-2 proteins are tested for their binding affinities to human $CD20^+$ cells and cynomolgus $CD20^+$ cells.

$CD20^+$ cells are incubated with 100 μL of serial dilutions of the activatable IL-2 proteins and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable IL-2 proteins. The cells were then washed again and resuspended in 0.2 mL of FACS buffer containing 2 μg/mL propidium iodide (PI) in order to exclude dead cells. The fluorescence of $1 \times 10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla Calif. USA).

CD20 binding and crossreactivity are assessed on the human $CD20^+$ tumor cell lines. The $K_D$ ratio of crossreactivity is calculated using the $K_D$ values determined on the CHO cell lines expressing either recombinant human or recombinant cynomolgus antigens.

Example 8: Cytotoxicity Assay

The activatable IL-2 protein is evaluated in vitro on its mediation of immune response to $CD20^+$ target cells.

Fluorescence labeled $CD20^+$ REC-1 cells (a Mantle cell lymphoma cell line, ATCC CRL-3004) are incubated with isolated PBMC of random donors or CB15 T-cells (standardized T-cell line) as effector cells in the presence of the activatable IL-2 protein and at least one protease. After incubation for 4 h at 37° C. in a humidified incubator, the release of the fluorescent dye from the target cells into the supernatant is determined in a spectrofluorimeter. Target cells incubated without the activatable IL-2 protein and target cells totally lysed by the addition of saponin at the end of the incubation serve as negative and positive controls, respectively.

Based on the measured remaining living target cells, the percentage of specific cell lysis is calculated according to the following formula: [1-(number of living targets$_{(sample)}$/number of living targets$_{(spontaneous)}$)]×100%. Sigmoidal dose response curves and $EC_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 9: Pharmacokinetics of Activatable IL-2 Proteins

The activatable IL-2 protein is evaluated for half-time elimination in animal studies.

The activatable IL-2 protein is administered to cynomolgus monkeys as a 0.5 mg/kg bolus injection into the saphenous vein. Another cynomolgus monkey group receives a comparable IL-2 construct in size, but lacking a serum half-life extension element. A third and fourth group receive an IL-2 construct with serum half-life extension element and a cytokine with CD20 and serum half-life extension elements respectively, and both comparable in size to the activatable IL-2 protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t) = Ae^{-\alpha t} + Be^{-\beta t}$, where c(t) is the plasma concentration at time t, A and B are intercepts on the Y-axis, and $\alpha$ and $\beta$ are the apparent first-order rate constants for the distribution and elimination phases, respectively. The $\alpha$-phase is the initial phase of the clearance and reflects distribution of the protein into all extracellular fluid of the animal, whereas the second or $\beta$-phase portion of the decay curve represents true plasma clearance. Methods for fitting such equations are well known in the art. For example, $A = D/V(\alpha - k21)/(\alpha - \beta)$, $B = D/V(\beta - k21)/(\alpha - \beta)$, and $\alpha$ and $\beta$ (for $\alpha > \beta$) are roots of the quadratic equation: $r^2 + (k12 + k21 + k10)r + k21k10 = 0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C.

It is expected that the activatable IL-2 protein has improved pharmacokinetic parameters such as an increase in elimination half-time as compared to proteins lacking a serum half-life extension element.

Example 10: Xenograft Tumor Model

The activatable IL-2 protein is evaluated in a xenograft model.

Female immune-deficient NOD/scid mice are sub-lethally irradiated (2 Gy) and subcutaneously inoculated with $4 \times 10^6$ Ramos RA1 cells into the right dorsal flank. When tumors reach 100 to 200 mm$^3$, animals are allocated into 3 treatment groups. Groups 2 and 3 (8 animals each) are intraperitoneally injected with $1.5 \times 10^7$ activated human T-cells. Three days later, animals from Group 3 are subsequently treated with a total of 9 intravenous doses of 50 µg activatable IL-2 protein (qdx9d). Groups 1 and 2 are only treated with vehicle. Body weight and tumor volume are determined for 30 days.

It is expected that animals treated with the activatable IL-2 protein have a statistically significant delay in tumor growth in comparison to the respective vehicle-treated control group.

Example 11: HEK Blue Assay

Figure 11A:
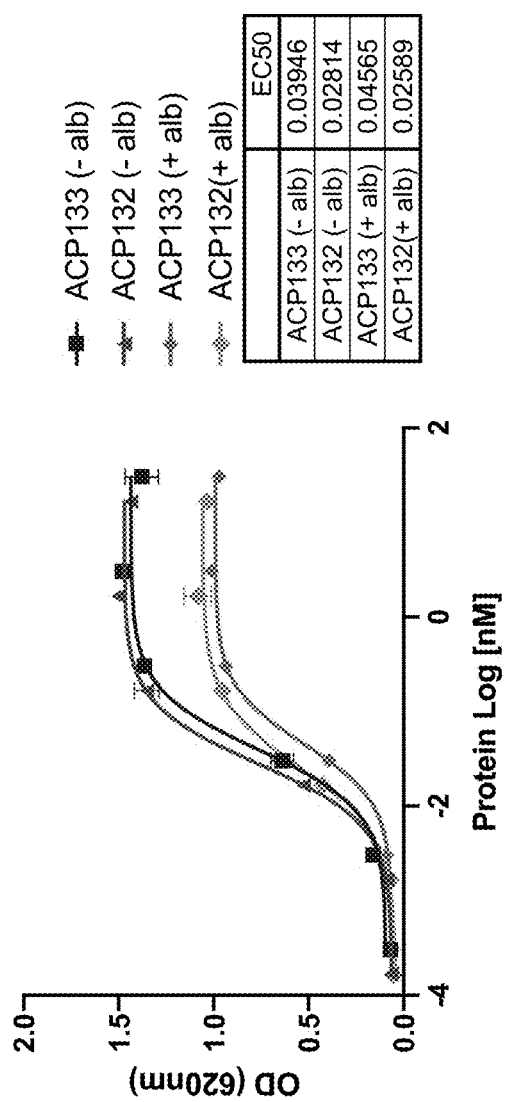
FIGS. 11a-11g is a series of graphs depicting results from a HEK-Blue IL-2 reporter assay performed on IL-2 fusion proteins and recombinant human IL-2 (Rec hIL-2) (FIGS. 11a, 11c, 11e, and 11f) or cleavage of the fusion proteins shown in SDS-PAGE gels (FIGS. 11b and 11d). Analysis was performed based on quantification of Secreted Alkaline Phosphatase (SEAP) activity using the reagent QUANTI-Blue (InvivoGen).
Figures 11B, 11C:
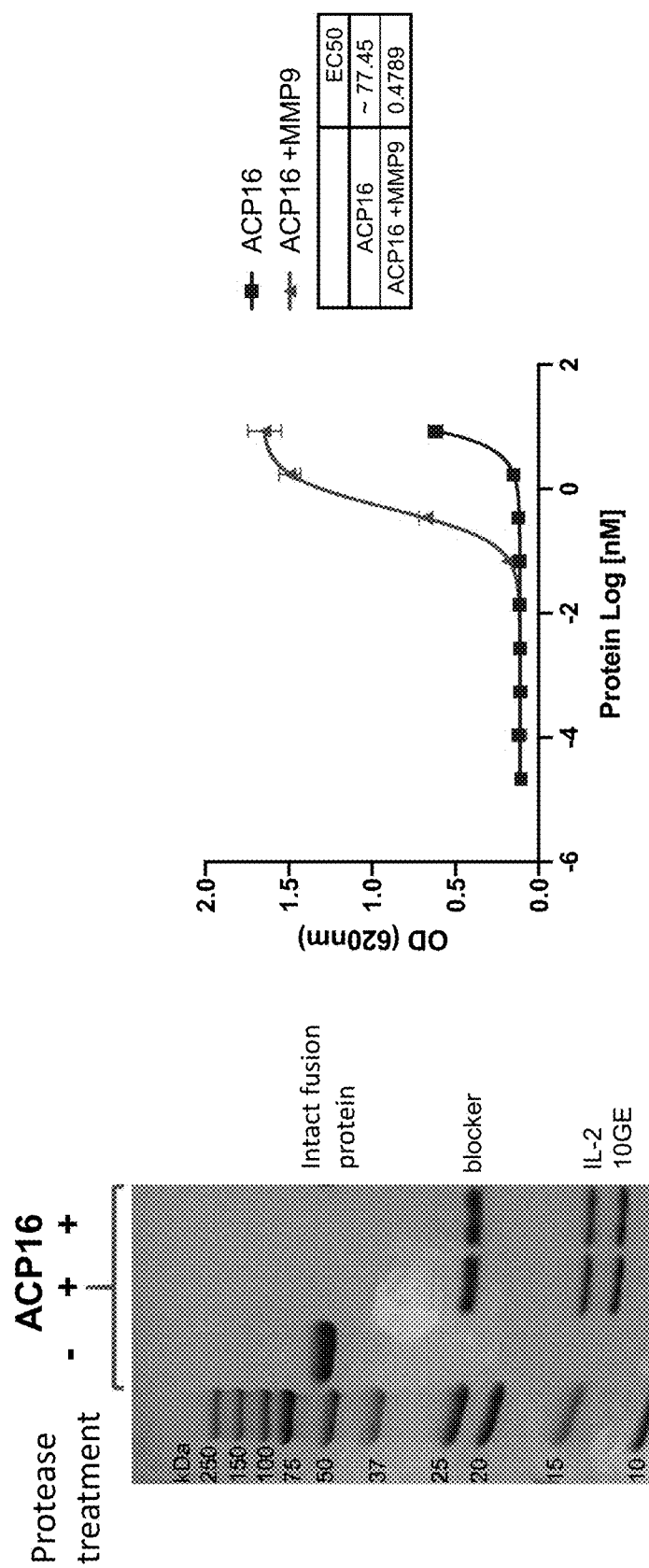
Figures 11D, 11E:
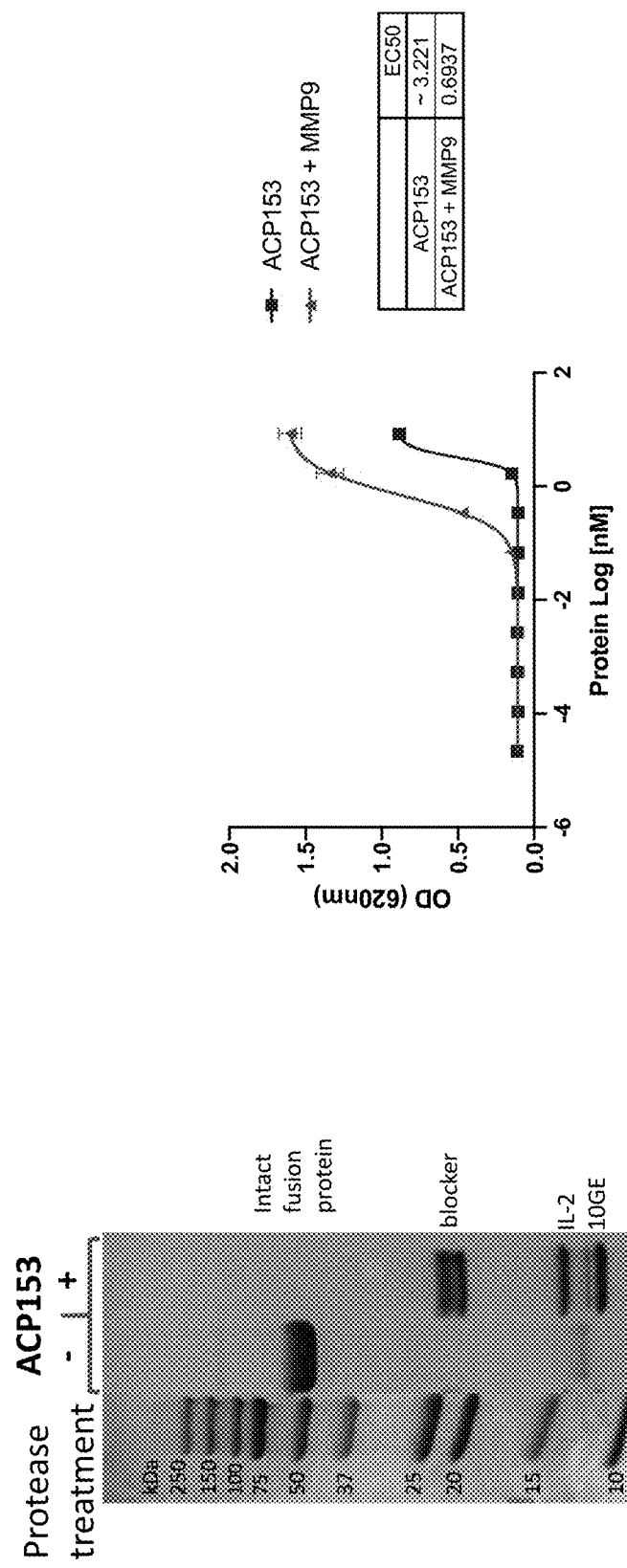
Figures 11F, 11G:
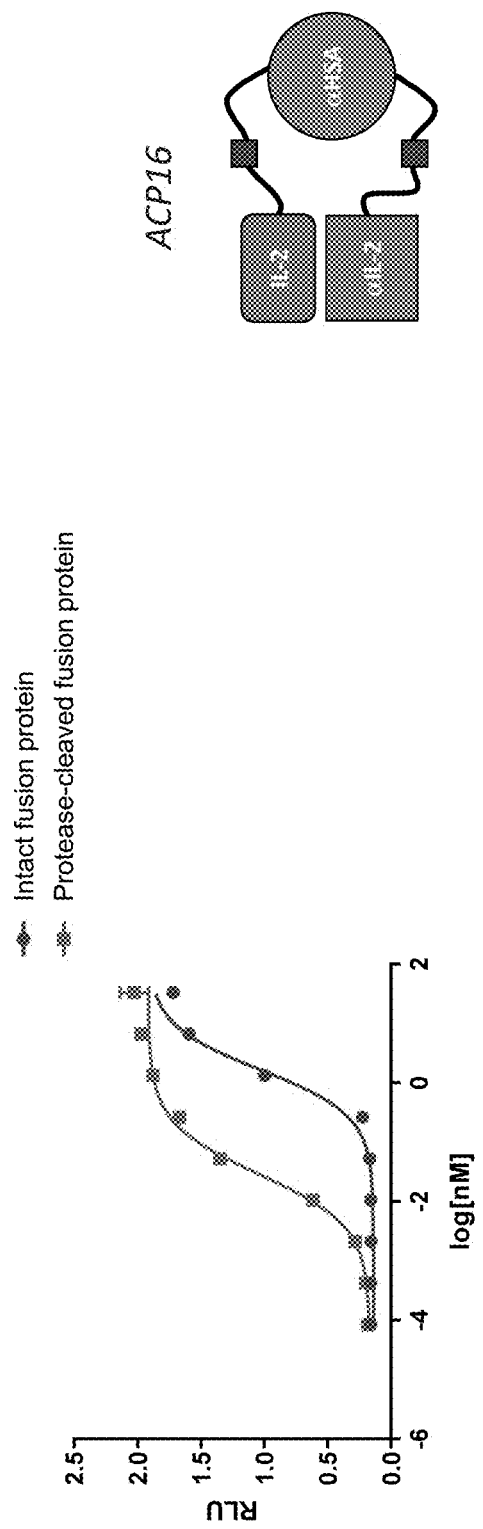
Figure 12B:
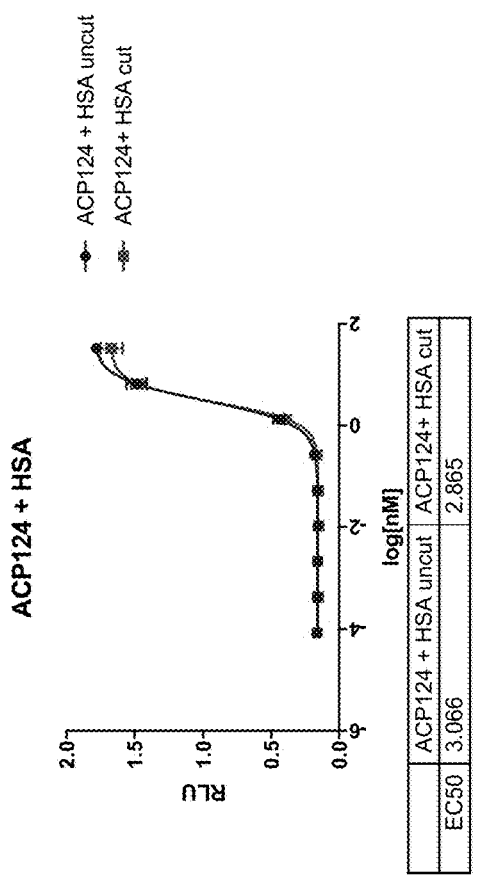
FIG. 12a and FIG. 12b are two graphs showing analysis of ACP16 (an IL-2 fusion protein) (FIG. 12a) and ACP124 (a non-cleavable IL-2 fusion protein) (FIG. 12b) in a HEK Blue IL-2 reporter assay in the presence of HSA. Circles depict the activity of the uncut polypeptide, squares depict activity of the cut polypeptide.
Figure 12A:
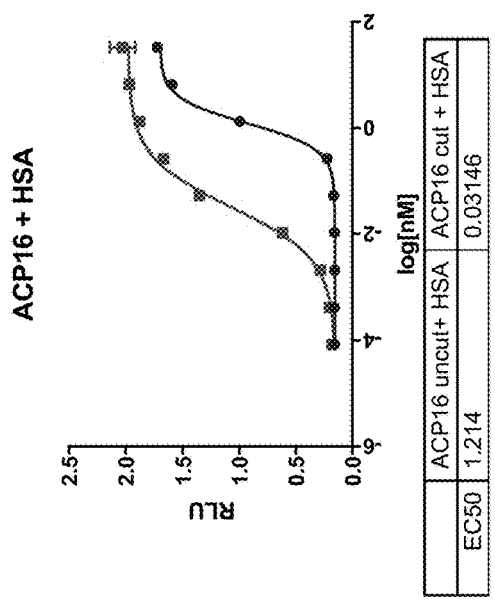
Figure 12C:
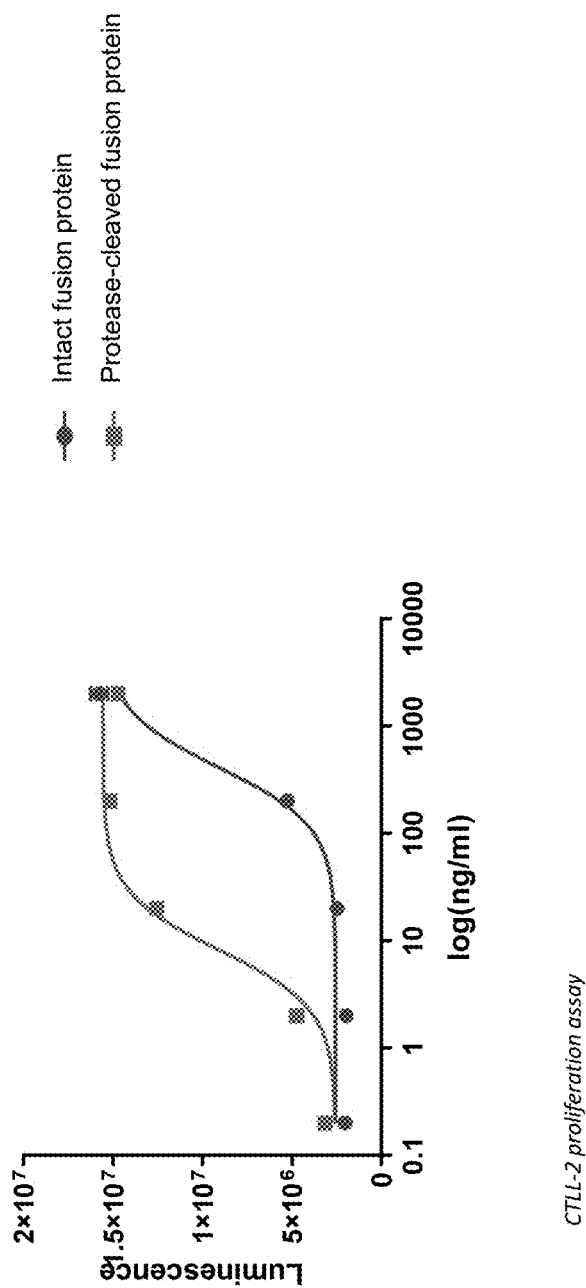
FIG. 12c is a graph showing results of a CTLL-2 proliferation assay. CTLL2 cells (ATCC) were plated in suspension at a concentration of 500,000 cells/well in culture media with or without 40 mg/ml human serum albumin (HSA) and stimulated with a dilution series of activatable hIL-2 for 72 hours at 37° C. and 5% $CO_2$. Activity of uncleaved and cleaved activatable ACP16 was tested. Cleaved activatable hIL-2 was generated by incubation with active MMP9. Cell activity was assessed using a CellTiter-Glo (Promega) luminescence-based cell viability assay. Circles depict intact fusion protein, and squares depict protease-cleaved fusion protein.

HEK-Blue IL-2 cells (InvivoGen) were plated in suspension at a concentration of 50,000 cells/well in culture media with or without 15-40 mg/ml human serum albumin (HSA) and stimulated with a dilution series of recombinant hIL-2 or activatable hIL-2 for 24 hours at 37° C. and 5% $CO_2$. Activity of uncleaved and cleaved activatable hIL-2 was tested. Cleaved inducible hIL-2 was generated by incubation with active MMP9. IL-2 activity was assessed by quantification of Secreted Alkaline Phosphatase (SEAP) activity using the reagent QUANTI-Blue (InvivoGen), a colorimetric based assay. Results are shown in FIGS. 11a, 11e, 11e and 11f.

Example 12: MC38 Experiments

The MC38 cell line, a rapidly growing colon adenocarcinoma cell line that expresses MMP9 in vitro, was used. Using this tumor model, the ability of fusion proteins to affect tumor growth was examined.

Example 12a: MC38 IL-2 Fusion Protein Treatment

Agents and Treatment:

| Gr. | N | Agent | Formulation dose | Route | Schedule |
|---|---|---|---|---|---|
| 1# | 10 | Vehicle | — | ip | biwk x 2 |
| 2 | 7 | ACP16 | 700 µg/animal | ip | biwk x 2 |
| 3 | 7 | ACP16 | 230 µg/animal | ip | biwk x 2 |
| 4 | 7 | ACP16 | 70 µg/animal | ip | biwk x 2 |
| 5 | 7 | ACP16 | 55 µg/animal | ip | biwk x 2 |
| 6 | 7 | ACP16 | 17 µg/animal | ip | biwk x 2 |
| 7 | 7 | ACP132 | 361 µg/animal | ip | biwk x 2 |
| 8 | 7 | ACP132 | 119 µg/animal | ip | biwk x 2 |
| 9 | 7 | ACP132 | 36 µg/animal | ip | biwk x 2 |
| 10 | 7 | ACP132 | 28 µg/animal | ip | biwk x 2 |
| 11 | 7 | ACP132 | 9 µg/animal | ip | biwk x 2 |
| 12 | 7 | ACP21 | 540 µg/animal | ip | biwk x 2 |
| 13 | 7 | ACP21 | 177 µg/animal | ip | biwk x 2 |
| 14 | 7 | ACP21 | 54 µg/animal | ip | biwk x 2 |
| 15 | 7 | ACP21 | 42 µg/animal | ip | biwk x 2 |
| 16 | 7 | ACP21 | 13 µg/animal | ip | biwk x 2 |
| 17 | 7 | ACP133 | 210 µg/animal | ip | bid x 5 then 2-day pause then bid x 5 then 2-day pause |
| 18 | 7 | ACP133 | 105 µg/animal | ip | bid x 5 then 2-day pause then bid x 5 then 2-day pause |
| 19 | 7 | ACP133 | 40 µg/animal | ip | bid x 5 then 2-day pause then bid x 5 then 2-day pause |
| 20 | 7 | ACP133 | 3 µg/animal | ip | bid x 5 then 2-day pause then bid x 5 then 2-day pause |

Control Group

Results are shown in FIGS. 17a-17m. The results show efficacy in tumor growth inhibition (TGI) with fusion protein treatments. Complete responses (CR) were observed in ACP16 groups 55 µg/animal (FIG. 17c), 70 µg/animal (FIG. 17d), and 230 µg/ml (FIG. 17e). Addition of an equivalent IL-2 molar amounts to ACP16 using ACP132 (IL-2 with half-life extension element and without a blocker) showed high toxicity in all groups except for the lowest dose, demonstrating the need for a blocker (FIGS. 17f-17l). Additionally, ACP21, a construct with the blocker only and no half-life extension element, was ineffective at equivalent doses to ACP16 (FIGS. 17j-17m). The data demonstrates the need for a blocker and half-life extension element in the design of an effective IL-2 fusion protein.

Example 12b: MC38 IL-2 Fusion Protein Treatment

Agents and Treatment:

| Gr. | N | Agent | Formulation dose | Route | Schedule |
|---|---|---|---|---|---|
| 1# | 12 | Vehicle | — | ip | biwk x 2 |
| 2 | 8 | ACP16 | 4.4 µg/animal | ip | biwk x 2 |
| 3 | 8 | ACP16 | 17 µg/animal | ip | biwk x 2 |
| 4 | 8 | ACP16 | 70 µg/animal | ip | biwk x 2 |
| 5 | 8 | ACP16 | 232 µg/animal | ip | biwk x 2 |
| 6 | 8 | ACP130 | 19 µg/animal | ip | biwk x 2 |
| 7 | 8 | ACP130 | 45 µg/animal | ip | biwk x 2 |
| 8 | 8 | ACP130 | 180 µg/animal | ip | biwk x 2 |
| 9 | 8 | ACP130 | 600 µg/animal | ip | biwk x 1 |
| 12 | 8 | ACP124 | 17 µg/animal | ip | biwk x 2 |
| 13 | 8 | ACP124 | 70 µg/animal | ip | biwk x 2 |
| 14 | 8 | ACP124 | 230 µg/animal | ip | biwk x 2 |
| 15 | 8 | ACP124 | 700 µg/animal | ip | biwk x 2 |
| 16 | 8 | IL-2-WTI | 12 µg/animal | ip | bid x 5 then 2-day pause then bid x 5 then 2-day pause |

| Gr. | N | Agent | Formulation dose | Route | Schedule |
|---|---|---|---|---|---|
| 17 | 8 | IL-2-WTI | 36 μg/animal | ip | bid x 5 then 2-day pause then bid x 5 then 2-day pause |

Control Group

Figure 13A:
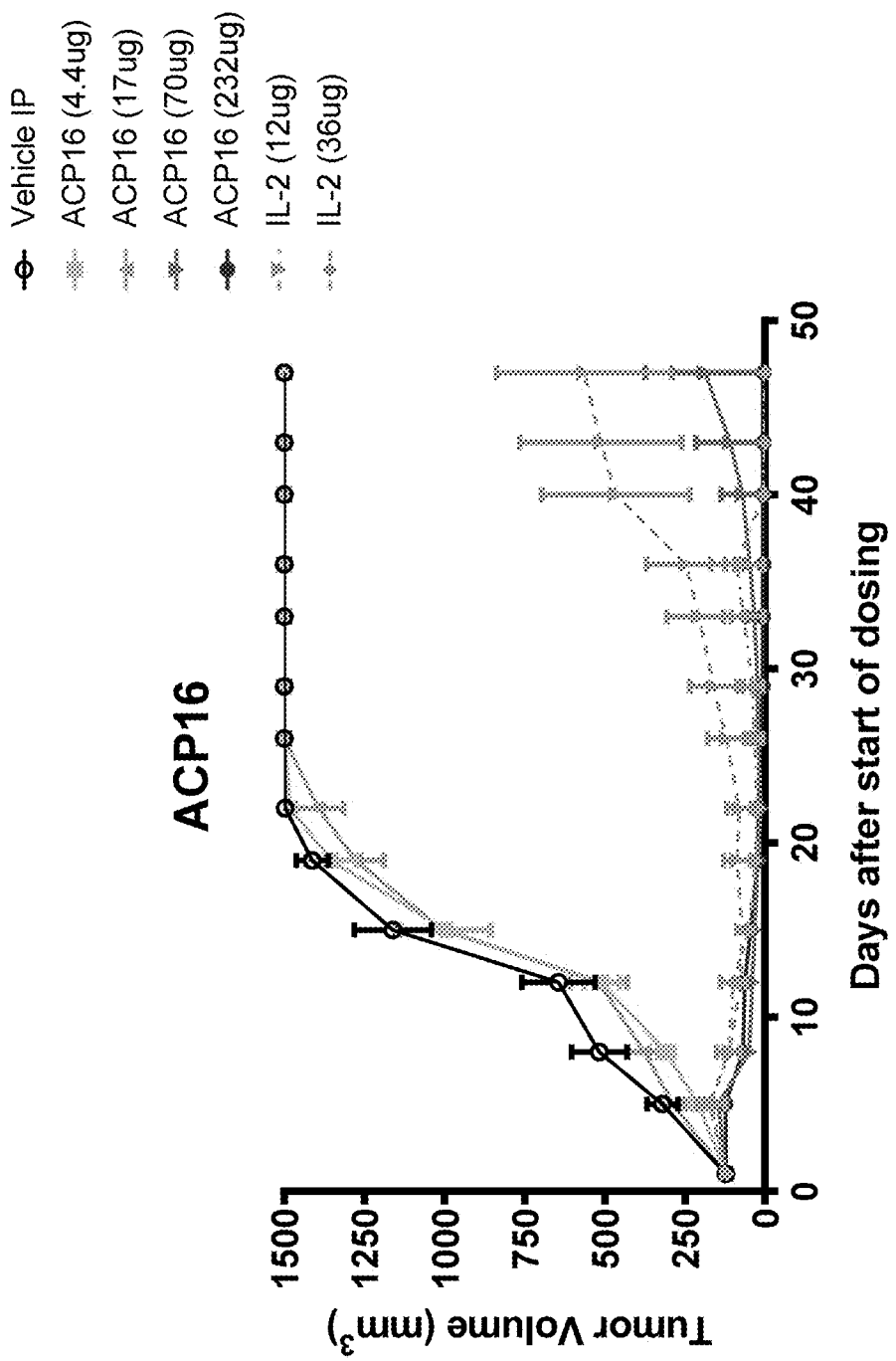
FIGS. 13a-13c are graphs showing results of analyzing ACP16 and ACP124 in a tumor xenograft model.
Figure 13B:
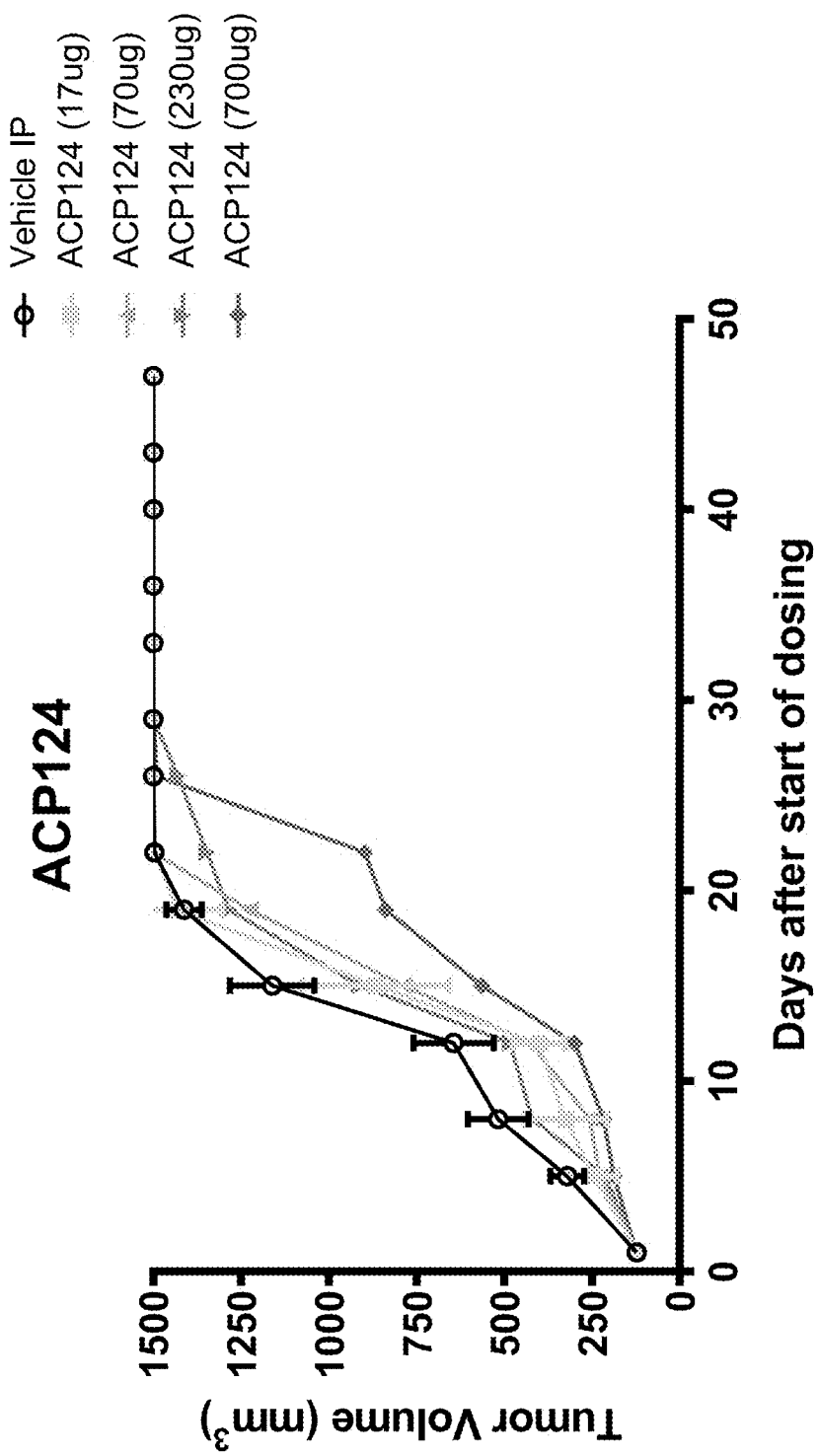
Figure 13C:
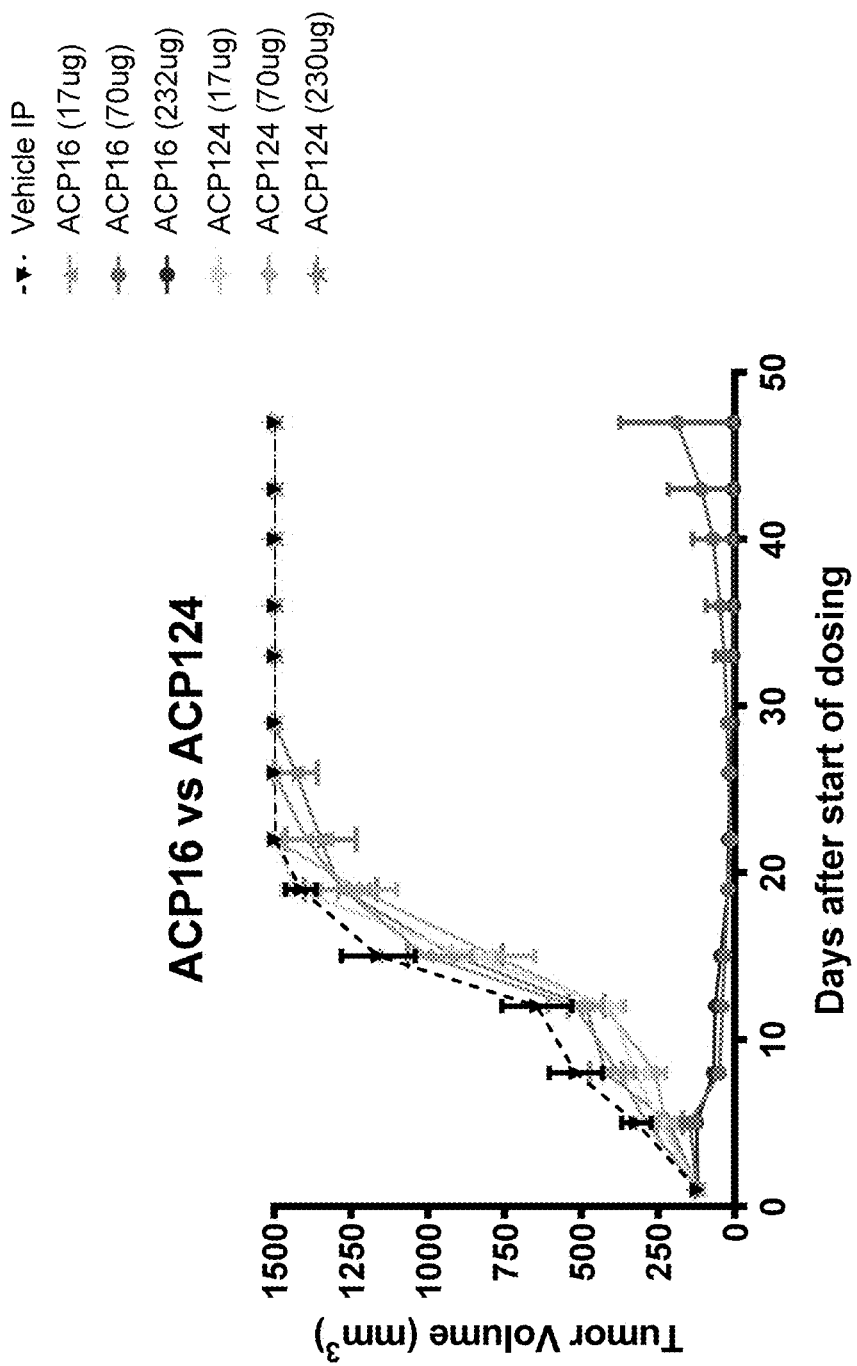

Results are shown in FIGS. 13, 14, and 16. The results show efficacy in tumor growth inhibition (TGI) with fusion protein treatments. Dosing with ACP16 at 70 μg/animal and 232 μg/animal showed TGI efficacy (FIG. 13a). Equivalent doses of a non-cleavable version of ACP16 (designated as ACP124) showed lack of TGI efficacy, demonstrating that a cleavable linker may be required for in vivo efficacy (FIGS. 13b and 13c).

Example 12c: Procedure for MC38 Experiments with Fusion Protein Treatment

Mice were anaesthetized with isoflurane for implant of cells to reduce the ulcerations. CR female C57BL/6 mice were set up with 5×10$^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment Animals were treated with agents and doses as indicated for Examples 12a and 12b above. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD) Animals were monitored individually. The endpoint of the experiment was a tumor volume of 1500 mm$^3$ or 45 days, whichever comes first. Responders were followed longer. When the endpoint was reached, the animals are to be euthanized.

Example 12c: MC38 Re-Challenge

Cured mice (ACP16-treated) from Example 12b were re-challenged with tumor implantation 60 days after initial inoculation with MC38 tumor cells to determine whether anti-tumor memory had been established from the initial treatments.
Agents and Treatment:

| Gr. | N | Agent | Formulation dose | Route | Schedule |
|---|---|---|---|---|---|
| 1# | 33 | No Treatment | — | — | — |
| 2 | 7 | ACP16 | 70 μg/animal | ip | (ACP16 biwkx2) |
| 3 | 8 | ACP16 | 232 μg/animal | ip | (ACP16 biwkx2) |
| 5 | 5 | IL-2-WTI | 12 μg/animal | ip | (IL-2-WTI bid x 5 then 2-day pause then bid x 5 then 2-day pause) |
| 6 | 7 | IL-2-WTI | 36 μg/animal | ip | (IL-2-WTI bid x 5 then 2-day pause then bid x 5 then 2-day pause) |

Control Group

Procedures:

Mice were anaesthetized with isoflurane for implant of cells to reduce the ulcerations. This portion of the study began on the day of implant (Day 1). Group 1 consisted of 33 CR female C57BL/6 mice set up with 5×10$^5$ MC38 tumor cells in 0% Matrigel subcutaneously in the flank. Groups 2-6 consisted of 33 CR female C57BL/6 mice set up with 5×10$^5$ MC38 tumor cells in 0% Matrigel sc in the left flank. The tumors from the previous MC38 experiment (Example 12b) were implanted in the right flank of each animal Cell Injection Volume was 0.1 mL/mouse. Age of control mice at initiation was 14 to 17 weeks. These mice were age matched to mice from the previous MC38 experiment (Example 12b). No dosing of active agent occurred during re-challenge. Body Weights were take biweekly until end, as were caliper measurements. Any adverse reactions or death were reported immediately. Any individual animal with a single observation of >than 30% body weight loss or three consecutive measurements of >25% body weight loss was euthanized Endpoint was tumor growth delay (TGD). Animals were monitored individually. The endpoint of the experiment was a tumor volume of 1000 mm$^3$ or 45 days, whichever comes first. Responders were followed longer when possible. When the endpoint was reached, the animals were euthanized.

Figure 15:
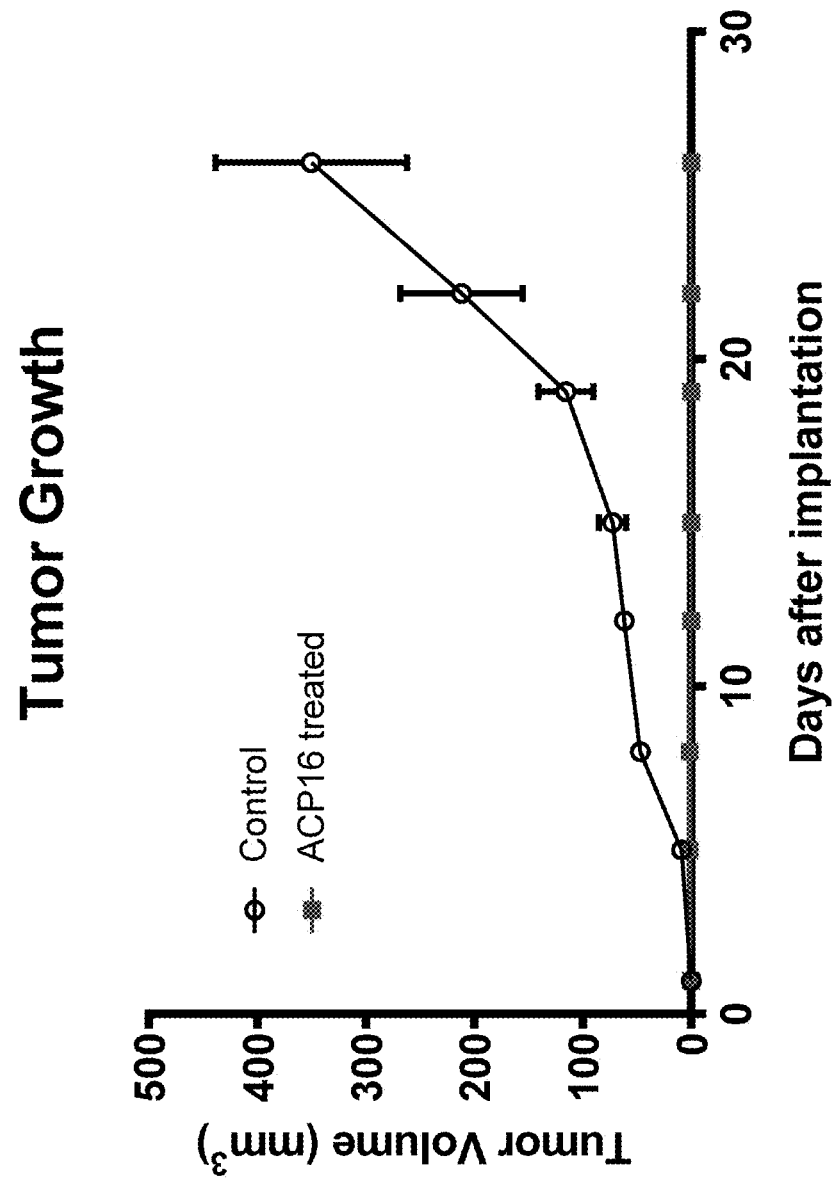
FIG. 15 is a graph showing tumor volume over time in a mouse xenograft model showing tumor growth in control mice (open circles) and AP16-treated mice (squares).
Figure 16A:
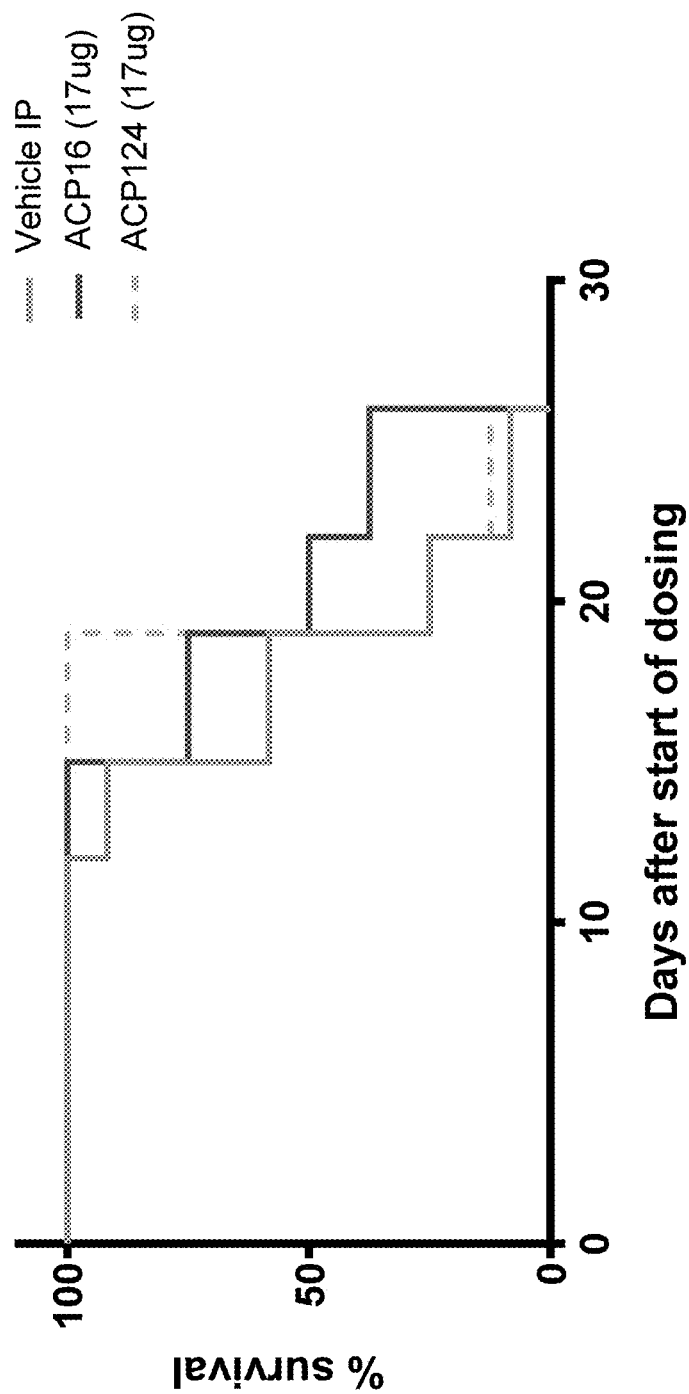
FIGS. 16a-16d are a series of survival plots showing survival of mice over time after treatment with cleavable fusion proteins.
Figure 16B:
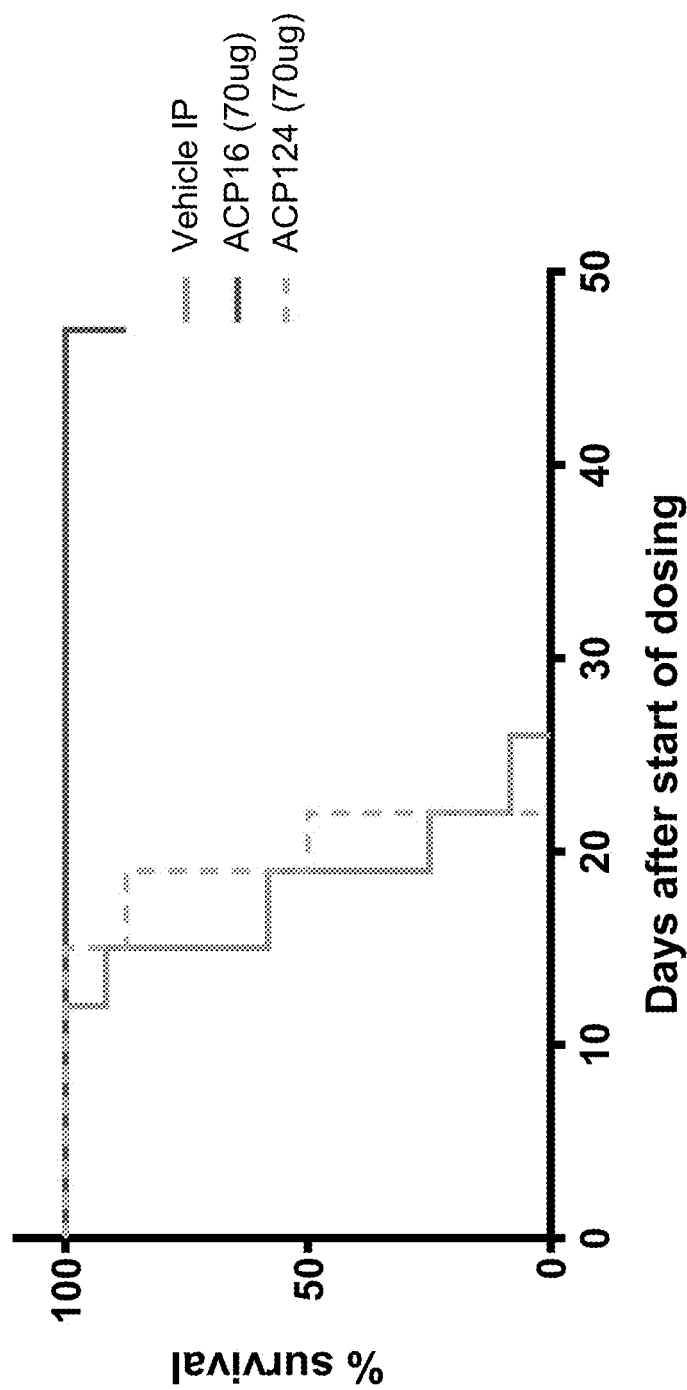
Figure 16C:
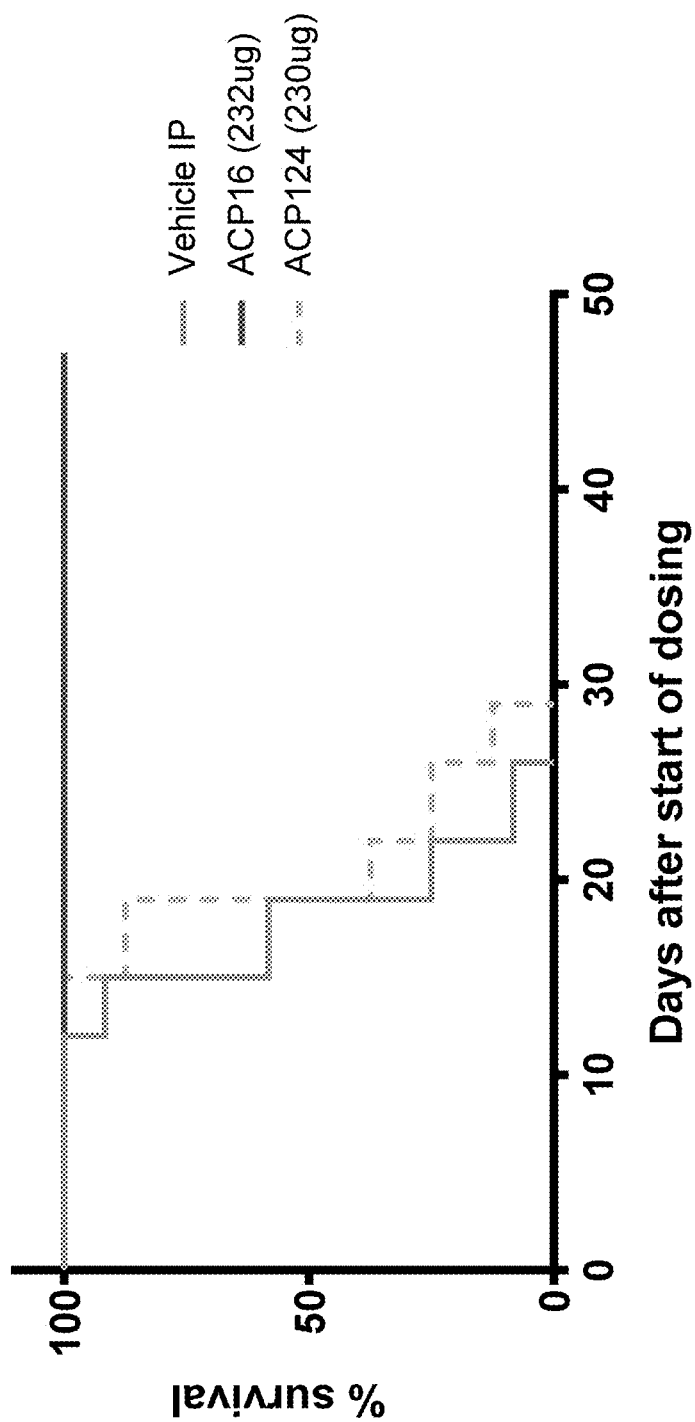
Figure 16D:
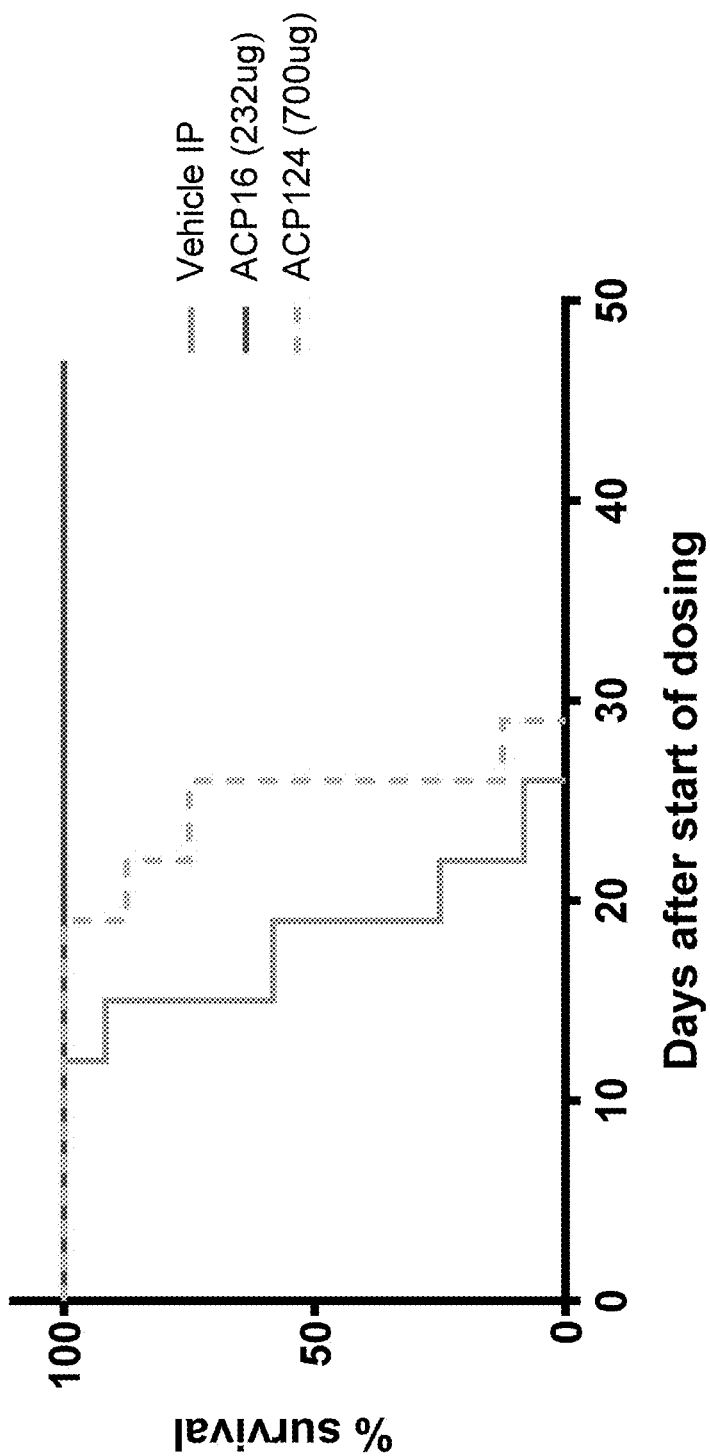
Figure 18:
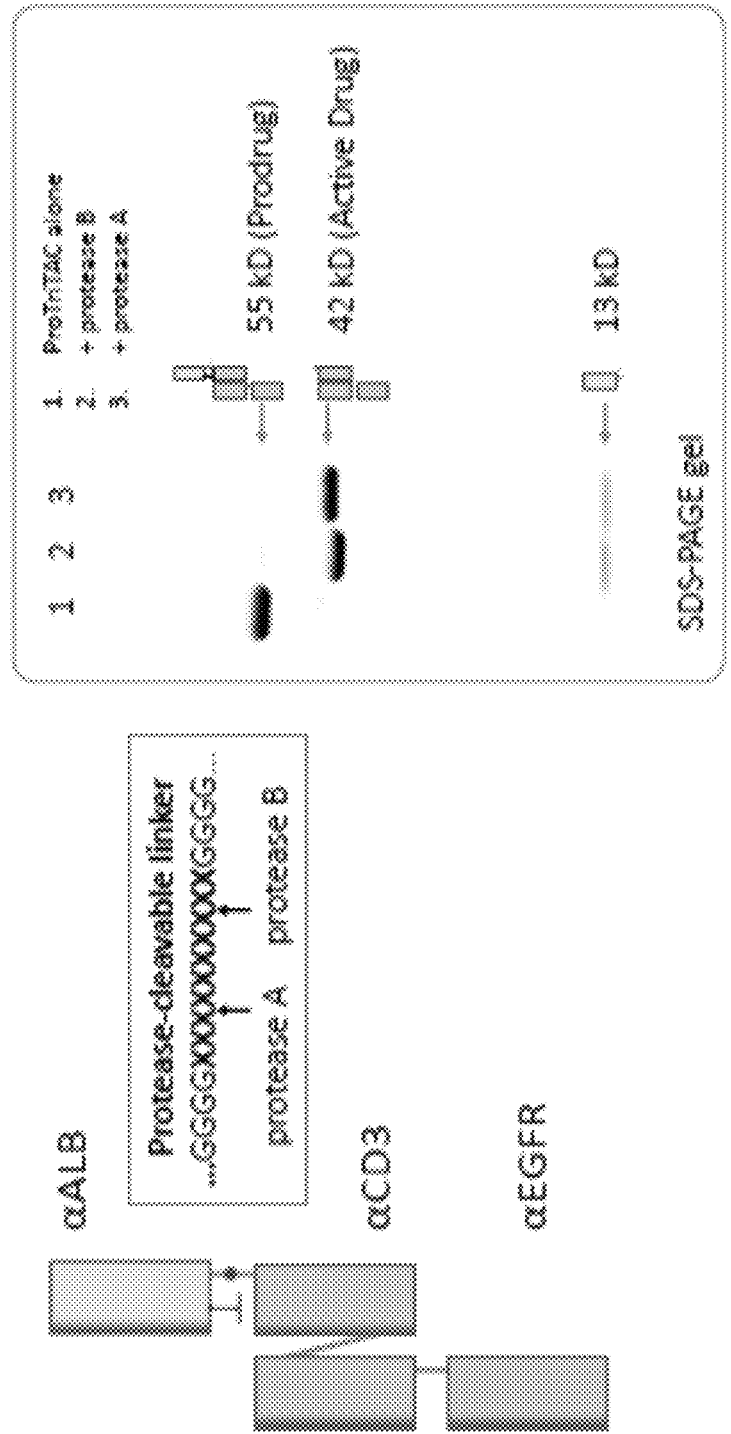
FIG. 18 illustrates the properties of ProTriTac polypeptides, which serve as exemplary protease cleavable fusion proteins.
Figure 20:
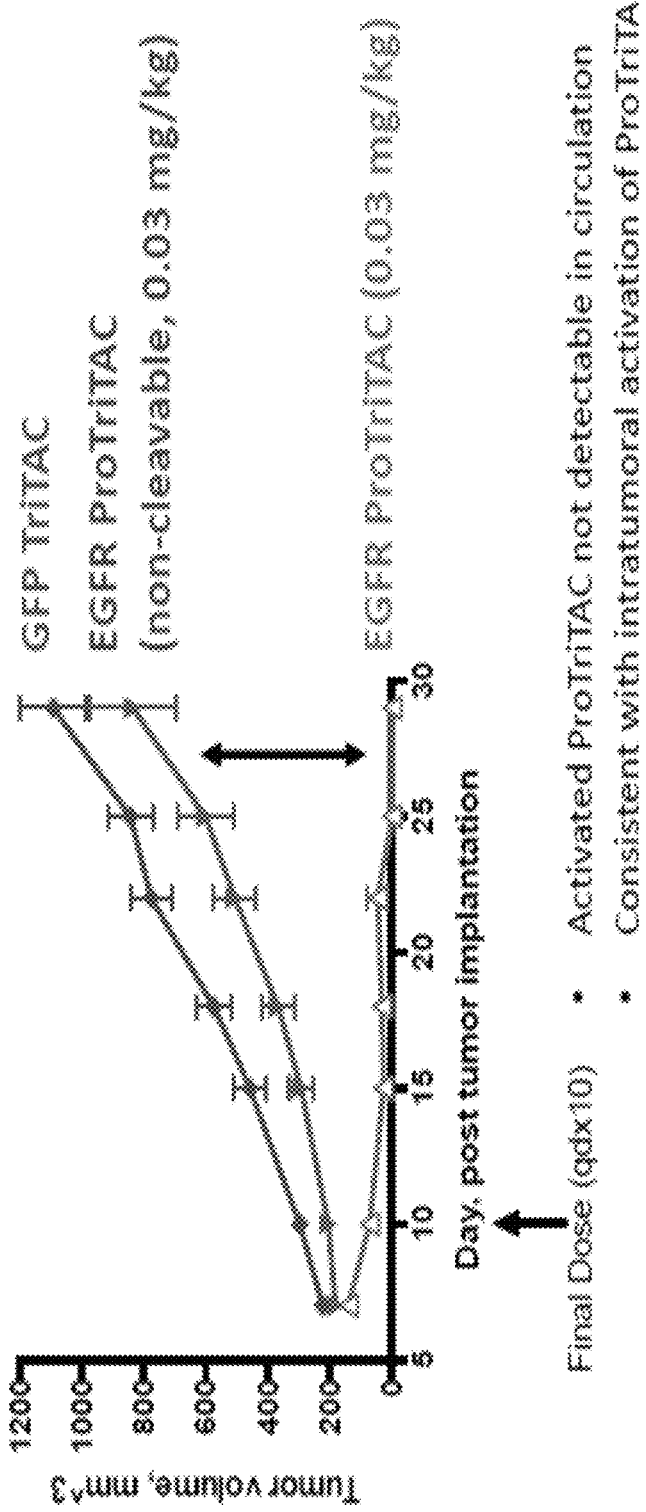
FIG. 20 illustrates ProTriTAC exhibits potent, protease-dependent, anti-tumor activity in a rodent tumor xenograft model.
Figure 21:
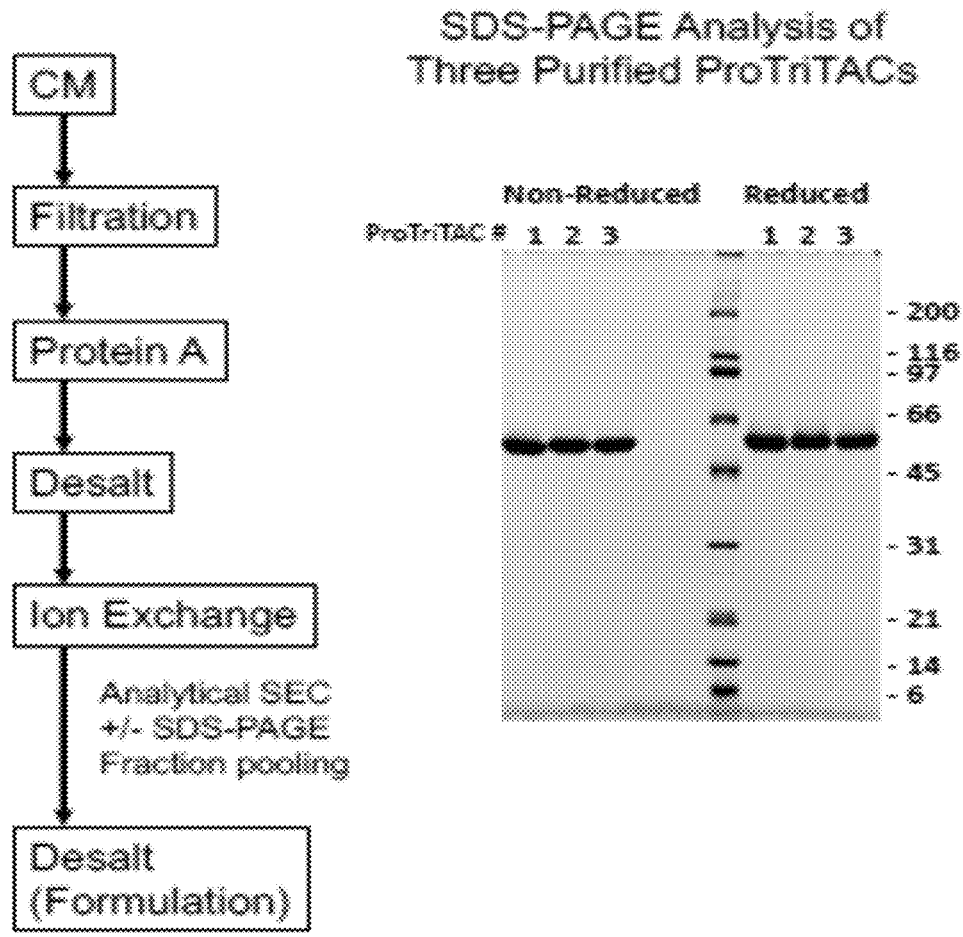
FIG. 21 illustrates SDS-PAGE analysis of purified ProTriTAC proteins.
Figure 22:
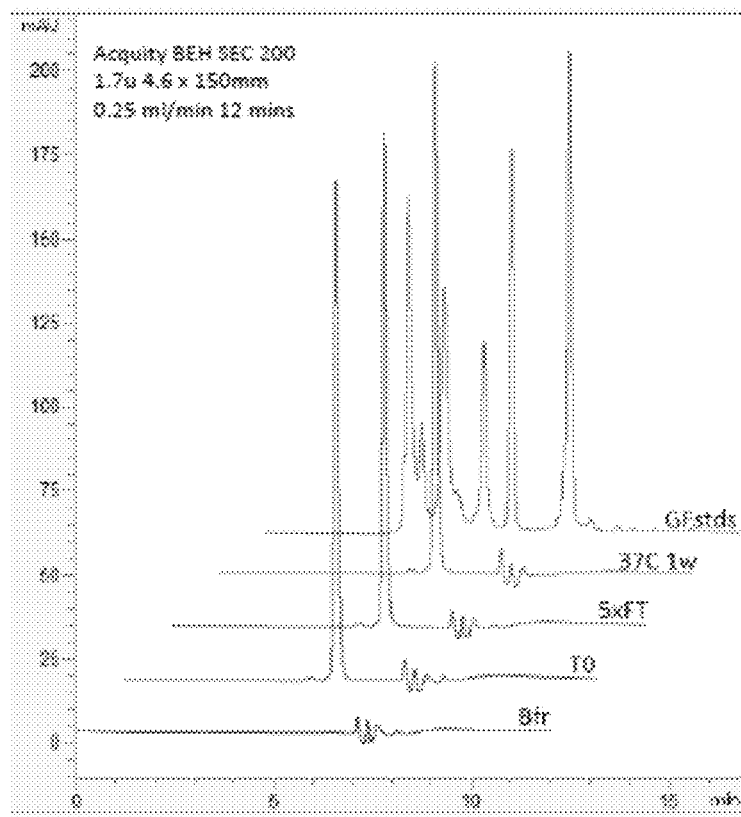
FIG. 22 illustrates analytical SEC of a ProTriTAC protein after different stress conditions.

All animals treated with ACP16 demonstrated development of immunological memory against the tumor as they did not develop any tumors upon re-challenge, while naïve C57B16 control animals developed tumors at a normal rate. Results are shown in FIG. 15.

Example 13. Conditionally Active Fusion Proteins that Contain a Blocking Moiety that is a Serum Albumin Binding Domain This example describes the production and activity of fusion proteins, preferably cytokines, that have inducible activity, i.e., they are inactive until induced, typically by separation of a blocking moiety from the active moiety upon cleavage of a linker between the blocking moiety and the active moiety. The fusion proteins contain a single antibody variable domain (a dAb) that binds serum albumin via the CDR loops, and binds to an active moiety (here an anti-CD3 scFV) via one or more non-CDR loops (e.g., the C loop). The serum albumin-binding blocking moiety is operably linked to the active moiety through a protease-cleavable linker, and active moiety is operably linked to a targeting domain (here an anti-epidermal growth factor receptor (EGFR) dAb or anti-prostate-specific membrane antigen (PSMA) dAb) through a linker that is not protease cleavable. These fusion proteins can be administered as inactive proteins that become activated upon cleavage of the protease-cleavable linker and subsequent release of the inhibitory albumin-binding domain. The anti-CD3 scFV in the fusion proteins is a surrogate for a desired cytokine in the fusion proteins described in this disclosure. Similar fusion proteins that contain a desired cytokine (e.g., IL-2, IL-12, an Interferon) or functional fragment or mutein thereof, a targeting domain and an albumin-binding dAb that also binds and inhibits the cytokine or functional fragment or mutein thereof can be prepared using the methods described and exemplified herein. Anti-serum albumin dAb that bind and inhibit the activity of a desired cytokine or functional fragment or mutein thereof can provide both steric masking of the cytokine (through the cytokines proximity to bound serum albumin) and specific masking of the cytokine (through binding to cytokine via the non-CDR loop (e.g., the C loop)). Anti-serum albumin dAb that bind and inhibit the activity of a desired cytokine or functional fragment or mutein thereof can be obtained using suitable methods, such as by introducing amino acid sequence diversity into the non-CDR loops (e.g., C loop) of an anti-serum albumin binding dAb and screening for binding to the desired cytokine. Any suitable methods can be used for the selection, such as phage display. For example, an exemplary anti-serum albumin dab that can be used has the following sequence, and the amino acid sequence in the C loop (Bold Underlined) can be diversified (e.g., randomized) and resulting dAbs screened for binding to serum albumin via CDR interaction and to cytokine via non-CDR loop interaction. If desired, the amino acid sequence of a known cytokine binding peptide can be grafted into the C loop.

(SEQ ID NO: 137)
EVQLVESGGGLVQPGNSLRLSCAASGFTFSKFGMSWVRQ
GGGGGLDGNEEPG
GLEWVSSISGSGRDTLYADSVKGRFTISRDNAKTTLYLQMNSLRPEDTAVYY
CTIGGSLSVSSQGTLVTVSS

A. Protease Activation of ProTriTAC Leads to Significantly Enhanced Activity In Vitro Purified ProTriTAC (prodrug), non-cleavable ProTriTAC [prodrug (non-cleavable)], and recombinant active drug fragment mimicking the protease-activated ProTriTAC (active drug) were tested for binding to recombinant human CD3 in an ELISA assay, binding to purified human primary T cells in a flow cytometry assay, and functional potency in a T cell-dependent cellular cytotoxicity assay.

For ELISA, soluble ProTriTAC proteins at the indication concentrations were incubated with immobilized recombinant human CD3e (R&D Systems) for 1 h at room temperature in PBS supplemented with 15 mg/ml human serum albumin. Plates were blocked using SuperBlock (Thermo Fisher), washed using PBS with 0.05% Tween-20, and detected using a non-competitive anti-CD3 idiotype monoclonal antibody 11D3 followed by peroxidase-labeled secondary antibody and TMB-ELISA substrate solution (Thermo Fisher).

For flow cytometry, soluble ProTriTAC proteins at the indicated concentrations were incubated with purified human primary T cells for 1 h at 4° C. in the presence of PBS with 2% fetal bovine serum and 15 mg/ml human serum albumin. Plates were washed with PBS with 2% fetal bovine serum, detected using AlexaFluor 647-labeled non-competitive anti-CD3 idiotype monoclonal antibody 11D3, and data was analyzed using FlowJo 10 (FlowJo, LLC).

For functional potency in a T cell-dependent cellular cytotoxicity assays, soluble ProTriTAC proteins at the indicated concentrations were incubated with purified resting human T cells (effector cell) and HCT116 cancer cell (target cell) at 10:1 effector:target cell ratio for 48 h at 37° C. The HCT116 target cell line has been stably transfected with a luciferase reporter gene to allow specific T cell-mediated cell killing measurement by ONE-Glo (Promega).

B. ProTriTAC Exhibits Potent, Protease-Dependent, Anti-Tumor Activity in a Rodent Tumor Xenograft Model ProTriTAC was evaluated for their anti-tumor activity in vivo in an HCT116 subcutaneous xenograft tumor admixed with expanded human T cells in immunocompromised NCG mice. Specifically, $5 \times 10^6$ HCT116 cells were admixed with $2.5 \times 10^6$ expanded T cells per mouse on day 0. Dosing of ProTriTACs were performed starting on the following day with a q.d.×10 schedule via intraperitoneal injection. Tumor volume measurements were determined using caliper measurements and calculated using the formula V=(length× width×width)/2 at the indicated times.

C. Expression, Purification and Stability of Exemplary Pro-TriTAC Trispecific Molecules Protein Production Sequences encoding inducible fusion protein molecules were cloned into mammalian expression vector pcDNA 3.4 (Invitrogen) preceded by a leader sequence and followed by a 6× Histidine Tag (SEQ ID NO: 136). Expi293F cells (Life Technologies A14527) were maintained in suspension in Optimum Growth Flasks (Thomson) between 0.2 to 8×1e6 cells/ml in Expi 293 media. Purified plasmid DNA was transfected into Expi293 cells in accordance with Expi293 Expression System Kit (Life Technologies, A14635) protocols, and maintained for 4-6 days post transfection. Alternatively sequences encoding the fusion protein molecules were cloned into mammalian expression vector pDEF38 (CMC ICOS) transfected into CHO-DG44 dhfr– cells, stable pools generated, and cultured in production media for up to 12 days prior to purification. The amount of the exemplary fusion proteins in conditioned media was quantified using an Octet RED 96 instrument with Protein A tips (ForteBio/Pall) using a control fusion protein for a standard curve. Conditioned media from either host cell was filtered and partially purified by affinity and desalting chromatography. Fusion proteins were subsequently polished by ion exchange and upon fraction pooling formulated in a neutral buffer containing excipients. Final purity was assessed by SDS-PAGE and analytical SEC using an Acquity BEH SEC 200 1.7u 4.6×150 mm column (Waters Corporation) resolved in an aqueous/organic mobile phase with excipients at neutral pH on a 1290 LC system and peaks integrated with Chemstation CDS software (Agilent). Fusion proteins purified from CHO host cells are shown in the SDS-PAGE depicted below.

Stability Assessment

Purified fusion proteins in two formulations were sub-aliquoted into sterile tubes and stressed by five freeze-thaw cycles each comprising greater than 1 hour at −80° C. and room temperature or by incubation at 37° C. for 1 week. Stressed samples were evaluated for concentration and turbidity by UV spectrometry using UV transparent 96 well plates (Corning 3635) with a SpectraMax M2 and SoftMax-Pro Software (Molecular Devices), SDS-PAGE, and analytical SEC and compared to the same analysis of control non-stressed samples. An overlay of chromatograms from analytical SEC of control and stressed samples for a single exemplary ProTriTAC molecule purified from 293 host cells is depicted below.

The results show that ProTriTACs were produced in comparable yields to regular TriTACs from CHO stable pools; and that the proteins were stable after repeated freeze-thaws and 37° C. for 1 week.

D. Demonstration of Functional Masking and Stability of ProTriTAC In Vivo in a Three-Week Cynomolgus Monkey Pharmacokinetic Study Single dose of PSMA-targeting ProTriTAC (SEQ ID NO: 119), non-cleavable ProTriTAC (SEQ ID NO: 120), non-masked/non-cleavable TriTAC (SEQ ID NO: 123), and active drug mimicking protease-activated ProTriTAC (SEQ ID NO: 121) was dosed into cynomolgus monkeys at 0.1 mg/kg via intravenous injection. Plasma samples were collected at the indicated time points. ProTriTAC concentrations were determined using ligand binding assays with biotinylated recombinant human PSMA (R&D systems) and sulfo-tagged anti-CD3 idiotype antibody cloned 11D3 in a MSD assay (Meso Scale Diagnostic, LLC). Pharmacokinetic parameters were estimated using Phoenix WinNonlin pharmacokinetic software using a non-compartmental approach consistent with the intravenous bolus route of administration.

To calculate the rate of in vivo prodrug conversion, the concentration of active drug in circulation was estimated by solving the following system of differential equations where P is the concentration of prodrug, A is the concentration of active drug, $k_a$ is the rate of prodrug activation in circulation, $k_{c,P}$ is the clearance rate of the prodrug, and $k_{c,A}$ is the clearance rate of the active drug.

$$\frac{dP}{dt} = -k_{c,P} P$$

$$\frac{dA}{dt} = k_a P - k_{c,A} A$$

The clearance rates of the prodrug, active drug, and a non-cleavable prodrug control ($k_{c,NCLV}$) were determined empirically in cynomolgus monkeys. To estimate the rate of prodrug activation in circulation, we assumed that the difference between the clearance rate of cleavable prodrug and non-cleavable prodrug arose solely from non-specific activation in circulation. Therefore, the rate of prodrug conversion to active drug in circulation was estimated by subtracting the clearance rate of the cleavable prodrug from the non-cleavable prodrug.

$$k_a = k_{c,NCLV} - k_{c,P}$$

The initial concentration of prodrug in circulation was determined empirically and the initial concentration of active drug was assumed to be zero.

Results and Discussion

The results of Example 13 show that fusion proteins that contain a polypeptide with desired therapeutic activity, such as a cytokine or functional fragment or mutein thereof or anti-CD3 scFV, can be prepared in which the therapeutic activity is masked by a masking domain that binds to both serum albumin and to the active polypeptide. The masking domain is operably linked to the active domain through a protease-cleavable linker. The results show that this type of fusion protein can be administered as an inactive protein that becomes activated upon protease cleavage at the desired location of therapeutic activity, such as, at a tumor.

Amino acid sequences of fusion proteins used in Example 13 are given SEQ ID NO: 116-123.

Sample fusion protein constructs are detailed in Table 3. In Table 3, "L" is an abbreviation of "linker", "cleav. link." and "LX" are abbreviations of different cleavable linkers, and "HSA" indicates human serum albumin (HSA).

TABLE 3

CONSTRUCT PERMUTATION TABLE

| Construct Name | Construct Description |
|---|---|
| ACP63 | anti-FN CGS-2 scFv (Vh/Vl)-6xHis |
| ACP12 | (anti-EpCAM)-IL2-(cleav. link.)-(anti-HSA)-blocker-6xHis |
| ACP13 | (anti-EpCAM)-Blocker2-(anti-HSA)-(cleav. link.)-IL2-6xHis |
| ACP14 | Blocker2-Linker-(cleav. link.)-IL2- (cleav. link.)-(anti-HSA)-6xHis |
| ACP15 | Blocker2-Linker-(anti-HSA)-Linker-(cleav. link.)- IL2 -6xHis |
| ACP16 | IL2-(cleav. link.)-(anti-HSA)-Linker-(cleav. link.)-Blocker2-6xHis |
| ACP17 | (anti-EpCAM)-Linker-IL2-(cleav. link.)-(anti-HSA)-Linker-(cleav. link.)-Blocker2-6xHis |
| ACP18 | (anti-EpCAM)-Linker-IL2-(cleav. link.)-(anti-HSA)-Linker-vh(cleav. link.)vl-6xHis |
| ACP19 | IL2-(cleav. link.)-Linker-Blocker2-Linker-(anti-HSA)-Linker-(anti-EpCAM) -6xHis |
| ACP20 | IL2-(cleav. link.)-Blocker2-6xHis |
| ACP21 | IL2-(cleav. link.)-Linker-Blocker2-6xHis |
| ACP22 | IL2-(cleav. link.)-Linker-blocker-(cleav. link.)-(anti-HSA)-Linker-(anti-EpCAM)-6xHis |
| ACP23 | (anti-FOLR1)-(cleav. link.)-Blocker2-Linker-(cleav. link.)-(anti-HSA)-(cleav. link.)-IL2-6xHis |
| ACP24 | (Blocker2)-(cleav. link.)-(IL2)-6xHis |
| ACP25 | Blocker2-Linker-(cleav. link.)-IL2-6xHis |
| ACP26 | (anti-EpCAM)-Linker-IL2-(cleav. link.)-(anti-HSA)-Linker-blocker(NARA1 Vh/Vl) |
| ACP27 | (anti-EpCAM)-Linker-IL2-(cleav. link.)-(anti-HSA)-Linker-blocker(NARA1 Vl/Vh) |
| ACP28 | IL2-(cleav. link.)-Linker-Blocker2-(NARA1 Vh/Vl)-Linker-(anti-HSA)-Linker-(anti-EpCAM) |
| ACP29 | IL2-(cleav. link.)-Linker-Blocker2-(NARA1 Vl/Vh)-Linker-(anti-HSA)-Linker-(anti-EpCAM) |
| ACP38 | IL2-(cleav. link.)-blocker-(anti-HSA)-(anti-EpCAM)-6xHis |
| ACP39 | (anti-EpCAM)-(cleav. link.)-(anti-HSA)-(cleav. link.)-Blocker2-(cleav. link.)-IL-2-6xHis |
| ACP40 | CD25ecd-Linker-(cleav. link.)-IL2-6xHis |
| ACP41 | IL2-(cleav. link.)-Linker-CD25ecd-6xHis |
| ACP42 | (anti-HSA)-Linker-CD25ecd-Linker-(cleav. link.)-IL2-6xHis |
| ACP43 | IL2-(cleav. link.)-Linker-CD25ecd-(anti-HSA)-6xHis |
| ACP44 | IL2-(cleav. link.)-Linker-CD25ecd-(cleav. link.)-(anti-HSA)-6xHis |
| ACP45 | (anti-HSA)-(cleav. link.)-Blocker2-Linker-(cleav. link.)-IL2-6xHis |
| ACP46 | IL2-(cleav. link.)-linker-vh(cleav. link.)vl-Linker-(anti-HSA)-L-(anti-EpCAM)-6xHis |
| ACP47 | (anti-EpCAM)-Linker-IL2-(Cleavable Linker)-(anti-HSA)-Linker-Blocker2-6xHis |
| ACP48 | IL2-(cleav. link.)-Blocker2-Linker-(anti-HSA)-6xHis |
| ACP49 | IL2-(cleav. link.)-Linker-Blocker2-Linker-(anti-HSA)-6xHis |
| ACP92 | (anti-HSA)-(16mer cleav. link.)-IL2-(16mer cleav. Link.)-(anti-HSA)-6XHis |
| ACP93 | (anti-EpCAM)-(anti-HSA)-(anti-EpCAM)-Blocker2-(cleav. link.)-IL2-6xHis |
| ACP94 | (anti-EpCAM)-(anti-HSA)-Blocker2-(cleav. link.)-IL2-6xHis |
| ACP95 | (anti-EpCAM)-(anti-HSA)-(cleav. link.)-IL2-6xHis |
| ACP96 | (anti-EpCAM)-(16mer cleav. link.)-IL2-(16mer cleav. link.)-(anti-HSA) |
| ACP97 | (anti-EpCAM)-(anti-HSA)-(cleav. link.)-IL2-(cleav. link.)-(anti-HSA)-6xHis |
| ACP99 | (anti-EpCAM)-Linker-IL2-(cleav. link.)-(anti-HSA)-6xHis |
| ACP100 | (anti-EpCAM)-Linker-IL2-6xHis |
| ACP101 | IL2-(cleav. link.)-(anti-HSA)-6xHis |
| ACP102 | (anti-EpCAM)-(cleav. link.)-IL2-(cleav. link.)-(anti-HSA)-Linker-blocker-6xHis |
| ACP103 | IL2-(cleav. link.)-Linker-Blocker2-Linker-(anti-HSA)-Linker-(antiI-FOLR1)-6xHis |
| ACP104 | (anti-FOLR1)-IL2-(cleav. link.)-(anti-HSA)-Linker-Blocker2-6xHis |
| ACP1O5 | Blocker2-Linker-(cleav. link.)-IL2-(cleav. link.)-(anti-HSA)-Linker-(anti-FOLR1)-6xHis |
| ACP106 | (anti-FOLR1)-Linker-(anti-HSA)-(cleav. link.)-blocker-Linker-(cleav. link.)-IL2 -6xHis |
| ACP107 | Blocker2-Linker-(anti-HSA)-(cleav. link.)-IL2-Linker-(anti-FOLR1)-6xHis |

TABLE 3-continued

CONSTRUCT PERMUTATION TABLE

| Construct Name | Construct Description |
|---|---|
| ACP108 | (anti-EpCAM)-IL2-(Dually cleav. link.)-(anti-HSA)-Linker-blocker-6xHis |
| ACP117 | anti-FN CGS-2 scFv (Vh/Vl)-6xHis |
| ACP118 | NARA1 Vh/Vl non-cleavable |
| ACP119 | NARA1 Vh/Vl cleavable |
| ACP120 | NARA1 Vl/Vh non-cleavable |
| ACP121 | NARA1 Vl/Vh cleavable |
| ACP124 | IL2-Linker-(anti-HSA)-Linker-Linker-blocker_(non-cleavable_control) |
| ACP132 | IL2-L-HSA |
| ACP141 | IL2-L-hAlb |
| ACP142 | IL2-(cleav. link.)-hAlb |
| ACP144 | IL2-(cleav. link.)-HSA-LX-blocker-L-FOLR1 |
| ACP145 | FOLR1 -L-IL2-(cleav. link.)-HSA-LX-blocker |
| ACP146 | FOLR1-(cleav. link.)-IL2-(cleav. link.)-HSA-LX-blocker |
| ACP133 | IL-2-6x His |
| ACP147 | IL2-(cleav. link.)-HSA-LX-blocker-L-TAA |
| ACP148 | TAA-L-IL2-(cleav. link.)-HSA-LX-blocker |
| ACP149 | TAA-(cleav. link.)-IL2-(cleav. link.)-HSA-LX-blocker |
| ACP153 | IL2-(cleav. link.)-(anti-HSA)-linker(cleav. link.)-Blocker2 |
| ACP154 | IL2-(cleav. link.)-(anti-HSA)-linker(cleav. link.)-Blocker2 |
| ACP155 | IL2-(cleav. link.)-(anti-HSA)-linker(cleav. link.)-Blocker2 |
| ACP156 | IL2-(cleav. link.)-(anti-HSA)-linker(cleav. link.)-Blocker2 |
| ACP157 | IL2-(cleav. link.)-(anti-HSA)-linker(cleav. link.)-Blocker2 |

TABLE 4

SEQUENCE TABLE

| SEQ ID NO. | Name | Sequence |
|---|---|---|
| 1 | Human IL-2 | MYRMQLLSCI ALSLALVTNS APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIISTLT |
| 2 | Human serum albumin | MKWVTFISLL FLFSSAYSRG VFRRDAHKSE VAHRFKDLGE ENFKALVLIA FAQYLQQCPF EDHVKLVNEV TEFAKTCVAD ESAENCDKSL HTLFGDKLCT VATLRETYGE MADCCAKQEP ERNECFLQHK DDNPNLPRLV RPEVDVMCTA FHDNEETFLK KYLYEIARRH PYFYAPELLF FAKRYKAAFT ECCQAADKAA CLLPKLDELR DEGKASSAKQ GLKCASLQKF GERAFKAWAV ARLSQRFPKA EFAEVSKLVT DLTKYHTECC HGDLLECADD RADLAKYICE NQDSISSKLK ECCEKPLLEK SHCIAEVEND EMPADLPSLA ADFVGSKDVC KNYAEAKDVF LGMFLYEYAR RHPDYSVVLL LRLAKTYETT LEKCCAAADP HECYAKVFDE FKPLVEEPQN LIKQNCELFE QLGEYKFQNA LLVRYTKKVP QVSTPTLVEV SRNLGKVGSK CCKHPEAKRM PCAEDCLSVF LNQLCVLHEK TPVSDRVTKC CTESLVNGRPCFSALEVDETYVPKEFNAETFTFHADICTLSEKERQIKK QTALV ELVKHK PKATKEQLKAVMDDFAAFVEKCCKADDKET CFAEEGKKLVAASQAALGL |
| 45 | ACP12 (IL-2 fusion protein) | QVQLQESGGGLVQAGGSLRLSCAASGRIFSIDIMSWYRQAPGKQREL VARITRGGTISYDDSVKGRFTISRDNAKNTVYLQMNSLKPEDTGVYY CNALYGTDYWGKGTQVTVSSggggsggggsggggsaptssstkktqlqlehllldlqmil nginnyknpkltrmltfkfympkkatelkhlqcleeelkpleevlnlaqsknfhlrprdlisninvivlelkgs ettfmceyadetativeflnrwitfcqsiistltSGGPGPAGMKGLPGSEVQLVESGGGL VQPGNSLRLSCAASGFTFSKFGMSWVRQAPGKGLEWVSSISGSGRDT LYAESVKGRFTISRDNAKTTLYLQMNSLRPEDTAVYYCTIGGSLSVSS QGTLVTVSSggggsggggsggggsEVQLVESGGGLVQPGGSLRLSCAASGFT FSSYTLAWVRQAPGKGLEWVAAIDSSSYTYSPDTVRGRFTISRDNAK NSLYLQMNSLRAEDTAVYYCARDSNWDALDYWGQTTVTVSSGGG GSGGGGSGGGGSDIQMTQSPSSLSASVGDRVTITCKASQNVGTNVGW YQQKPGKAPKALIYSASFRYSGVPSRFSGSGSGTDFTLTISSLQPEDFA TYYCQQYYTYPYTFGGGTKVEIKHHHHHH |
| 46 | ACP13 (IL-2 fusion protein) | QVQLQESGGGLVQAGGSLRLSCAASGRIFSIDIMSWYRQAPGKQREL VARITRGGTISYDDSVKGRFTISRDNAKNTVYLQMNSLKPEDTGVYY CNALYGTDYWGKGTQVTVSSggggsggggsggggsEVQLVESGGGLVQPG GSLRLSCAASGFTFSSYTLAWVRQAPGKGLEWVAAIDSSSYTYSPDT VRGRFTISRDNAKNSLYLQMNSLRAEDTAVYYCARDSNWDALDYW GQTTVTVSSGGGGSGGGGSGGGGSDIQMTQSPSSLSASVGDRVTIT CKASQNVGTNVGWYQQKPGKAPKALIYSASFRYSGVPSRFSGSGSGT DFTLTISSLQPEDFATYYCQQYYTYPYTFGGGTKVEIKggggsggggsggggs sEVQLVESGGGLVQPGNSLRLSCAASGFTFSKFGMSWVRQAPGKGLE WVSSISGSGRDTLYAESVKGRFTISRDNAKTTLYLQMNSLRPEDTAVY YCTIGGSLSVSSQGTLVTVSSGGGPGPAGMKGLPGSaptssstkktqlqlehllldl |

TABLE 4-continued

SEQUENCE TABLE

| SEQ ID NO. | Name | Sequence |
|---|---|---|
| | | qmilnginnyknpkltrmltfkfympkkatelkhlqcleeelkpleevlnlaqsknfhlrprdlisninvivl elkgsettfmceyadetativeflnrwitfcqsiistltHHHHHH |
| 47 | ACP14 (IL-2 fusion protein) | EVQLVESGGGLVQPGGSLRLSCAASGFTFSSYTLAWVRQAPGKGLEW VAAIDSSSYTYSPDTVRGRFTISRDNAKNSLYLQMNSLRAEDTAVYY CARDSNWDALDYWGQGTTVTVSSGGGGSGGGGSGGGGSDIQMTQS PSSLSASVGDRVTITCKASQNVGTNVGWYQQKPGKAPKALIYSASFR YSGVPSRFSGSGSGTDFTLTISSLQPEDFATYYCQQYYTYPYTFGGGT KVEIKggggsggggsggggsggggsggggsggggsSGGPGPAGMKGLPGSaptssstkk tqlqlehllldlqmilnginnyknpkltrmltfkfympkkatelkhlqcleeelkpleevlnlaqsknfhlrpr dlisninvivlelkgsettfmceyadetativeflnrwitfcqsiistltSGGPGPAGMKGLPGSEV QLVESGGGLVQPGNSLRLSCAASGFTFSKFGMSWVRQAPGKGLEWV SSISGSGRDTLYAESVKGRFTISRDNAKTTLYLQMNSLRPEDTAVYYC TIGGSLSVSSQGTLVTVSSHHHHHH |
| 48 | ACP15 (IL-2 fusion protein) | EVQLVESGGGLVQPGGSLRLSCAASGFTFSSYTLAWVRQAPGKGLEW VAAIDSSSYTYSPDTVRGRFTISRDNAKNSLYLQMNSLRAEDTAVYY CARDSNWDALDYWGQGTTVTVSSGGGGSGGGGSGGGGSDIQMTQS PSSLSASVGDRVTITCKASQNVGTNVGWYQQKPGKAPKALIYSASFR YSGVPSRFSGSGSGTDFTLTISSLQPEDFATYYCQQYYTYPYTFGGGT KVEIKggggsggggsggggsggggsggggsggggsEVQLVESGGGLVQPGNSLRLS CAASGFTFSKFGMSWVRQAPGKGLEWVSSISGSGRDTLYAESVKGRF TISRDNAKTTLYLQMNSLRPEDTAVYYCTIGGSLSVSSQGTLVTVSSgg ggsggggsggggsSGGPGPAGMKGLPGSaptssstkktqlqlehllldlqmilnginnyknpkl trmltfkfympkkatelkhlqcleeelkpleevlnlaqsknfhlrprdlisninvivlelkgsettfmceyadet ativeflnrwitfcqsiistltHHHHHH |
| 49 | ACP16 (IL-2 fusion protein) | aptssstkktqlqlehllldlqmilnginnyknpkltrmltfkfympkkatelkhlqcleeelkpleevlnlaq sknfhlrprdlisninvivlelkgsettfmceyadetativeflnrwitfcqsiistltSGGPGPAGMKG LPGSEVQLVESGGGLVQPGNSLRLSCAASGFTFSKFGMSWVRQAPGK GLEWVSSISGSGRDTLYAESVKGRFTISRDNAKTTLYLQMNSLRPEDT AVYYCTIGGSLSVSSQGTLVTVSSggggsggggsggggsggggsggggsggggsSG GPGPAGMKGLPGSEVQLVESGGGLVQPGGSLRLSCAASGFTFSSYTL AWVRQAPGKGLEWVAAIDSSSYTYSPDTVRGRFTISRDNAKNSLYLQ MNSLRAEDTAVYYCARDSNWDALDYWGQGTTVTVSSGGGGSGGGG SGGGGSDIQMTQSPSSLSASVGDRVTITCKASQNVGTNVGWYQQKPG KAPKALIYSASFRYSGVPSRFSGSGSGTDFTLTISSLQPEDFATYYCQQ YYTYPYTFGGGTKVEIKHHHHHH |
| 50 | ACP17 (IL-2 fusion protein) | QVQLQESGGGLVQAGGSLRLSCAASGRIFSIDIMSWYRQAPGKQREL VARITRGGTISYDDSVKGRFTISRDNAKNTVYLQMNSLKPEDTGVYY CNALYGTDYWGKGTQVTVSSggggsggggsggggsaptssstkktqlqlehllldlqmil nginnyknpkltrmltfkfympkkatelkhlqcleeelkpleevlnlaqsknfhlrprdlisninvivlelkgs ettfmceyadetativeflnrwitfcqsiistltSGGPGPAGMKGLPGSEVQLVESGGGL VQPGNSLRLSCAASGFTFSKFGMSWVRQAPGKGLEWVSSISGSGRDT LYAESVKGRFTISRDNAKTTLYLQMNSLRPEDTAVYYCTIGGSLSVSS QGTLVTVSSggggsggggsggggsggggsggggsggggsggggsSGGPGPAGMKGLPGSE VQLVESGGGLVQPGGSLRLSCAASGFTFSSYTLAWVRQAPGKGLEW VAAIDSSSYTYSPDTVRGRFTISRDNAKNSLYLQMNSLRAEDTAVYY CARDSNWDALDYWGQGTTVTVSSGGGGSGGGGSGGGGSDIQMTQS PSSLSASVGDRVTITCKASQNVGTNVGWYQQKPGKAPKALIYSASFR YSGVPSRFSGSGSGTDFTLTISSLQPEDFATYYCQQYYTYPYTFGGGT KVEIKHHHHHH |
| 51 | ACP18 (IL-2 fusion protein) | QVQLQESGGGLVQAGGSLRLSCAASGRIFSIDIMSWYRQAPGKQREL VARITRGGTISYDDSVKGRFTISRDNAKNTVYLQMNSLKPEDTGVYY CNALYGTDYWGKGTQVTVSSggggsggggsggggsaptssstkktqlqlehllldlqmil nginnyknpkltrmltfkfympkkatelkhlqcleeelkpleevlnlaqsknfhlrprdlisninvivlelkgs ettfmceyadetativeflnrwitfcqsiistltSGGPGPAGMKGLPGSEVQLVESGGGL VQPGNSLRLSCAASGFTFSKFGMSWVRQAPGKGLEWVSSISGSGRDT LYAESVKGRFTISRDNAKTTLYLQMNSLRPEDTAVYYCTIGGSLSVSS QGTLVTVSSggggsggggsggggsggggsggggsggggsggggsEVQLVESGGGLVQPGG SLRLSCAASGFTFSSYTLAWVRQAPGKGLEWVAAIDSSSYTYSPDTV RGRFTISRDNAKNSLYLQMNSLRAEDTAVYYCARDSNWDALDYWG QGTTVTVSSsggpgpagmkglpgsDIQMTQSPSSLSASVGDRVTITCKASQN VGTNVGWYQQKPGKAPKALIYSASFRYSGVPSRFSGSGSGTDFTLTIS SLQPEDFATYYCQQYYTYPYTFGGGTKVEIKHHHHHH |
| 52 | ACP19 (IL-2 fusion protein) | aptssstkktqlqlehllldlqmilnginnyknpkltrmltfkfympkkatelkhlqcleeelkpleevlnlaq sknfhlrprdlisninvivlelkgsettfmceyadetativeflnrwitfcqsiistltSGGPGPAGMKG LPGSggggsggggsggggsggggsggggsggggsggggsEVQLVESGGGLVQPGGSLRLSC AASGFTFSSYTLAWVRQAPGKGLEWVAAIDSSSYTYSPDTVRGRFTIS RDNAKNSLYLQMNSLRAEDTAVYYCARDSNWDALDYWGQGTTVT VSSGGGGSGGGGSGGGGSDIQMTQSPSSLSASVGDRVTITCKASQNV |

TABLE 4-continued

SEQUENCE TABLE

| SEQ ID NO. | Name | Sequence |
|---|---|---|
| | | GTNVGWYQQKPGKAPKALIYSASFRYSGVPSRFSGSGSGTDFTLTISS<br>LQPEDFATYYCQQYYTYPYTFGGGTKVEIKggggsggggsggggsEVQLVE<br>SGGGLVQPGNSLRLSCAASGFTFSKFGMSWVRQAPGKGLEWVSSISG<br>SGRDTLYAESVKGRFTISRDNAKTTLYLQMNSLRPEDTAVYYCTIGGS<br>LSVSSQGTLVTVSSggggsggggsggggsggggsQVQLQESGGGLVQAGGSLRLSC<br>AASGRIFSIDIMSWYRQAPGKQRELVARITRGGTISYDDSVKGRFTISR<br>DNAKNTVYLQMNSLKPEDTGVYYCNALYGTDYWGKGTQVTVSSHH<br>HHHH** |
| 53 | ACP20<br>(IL2 fusion protein) | aptssstkktqlqlehllldlqmilnginnyknpkltrmltfkfympkkatelkhlqcleeelkpleevlnlaq<br>sknfhlrprdlisninvivlelkgsettfmceyadetativeflnrwitfcqsiistltSGGPGPAGMKG<br>LPGSEVQLVESGGGLVQPGGSLRLSCAASGFTFSSYTLAWVRQAPGK<br>GLEWVAAIDSSSYTYSPDTVRGRFTISRDNAKNSLYLQMNSLRAEDT<br>AVYYCARDSNWDALDYWGQGTTVTVSSGGGGSGGGGSGGGGSDIQ<br>MTQSPSSLSASVGDRVTITCKASQNVGTNVGWYQQKPGKAPKALIYS<br>ASFRYSGVPSRFSGSGSGTDFTLTISSLQPEDFATYYCQQYYTYPYTFG<br>GGTKVEIKHHHHHH |
| 54 | ACP21<br>(IL-2 fusion protein) | aptssstkktqlqlehllldlqmilnginnyknpkltrmltfkfympkkatelkhlqcleeelkpleevlnlaq<br>sknfhlrprdlisninvivlelkgsettfmceyadetativeflnrwitfcqsiistltSGGPGPAGMKG<br>LPGSggggsggggsggggsggggsggggsggggsEVQLVESGGGLVQPGGSLRLSC<br>AASGFTFSSYTLAWVRQAPGKGLEWVAAIDSSSYTYSPDTVRGRFTIS<br>RDNAKNSLYLQMNSLRAEDTAVYYCARDSNWDALDYWGQGTTVT<br>VSSGGGGSGGGGSGGGGSDIQMTQSPSSLSASVGDRVTITCKASQNV<br>GTNVGWYQQKPGKAPKALIYSASFRYSGVPSRFSGSGSGTDFTLTISS<br>LQPEDFATYYCQQYYTYPYTFGGGTKVEIKHHHHHH |
| 55 | ACP22<br>(IL-2 fusion protein) | aptssstkktqlqlehllldlqmilnginnyknpkltrmltfkfympkkatelkhlqcleeelkpleevlnlaq<br>sknfhlrprdlisninvivlelkgsettfmceyadetativeflnrwitfcqsiistltSGGPGPAGMKG<br>LPGSggggsggggsggggsggggsggggsggggsEVQLVESGGGLVQPGGSLRLSC<br>AASGFTFSSYTLAWVRQAPGKGLEWVAAIDSSSYTYSPDTVRGRFTIS<br>RDNAKNSLYLQMNSLRAEDTAVYYCARDSNWDALDYWGQGTTVT<br>VSSGGGGSGGGGSGGGGSDIQMTQSPSSLSASVGDRVTITCKASQNV<br>GTNVGWYQQKPGKAPKALIYSASFRYSGVPSRFSGSGSGTDFTLTISS<br>LQPEDFATYYCQQYYTYPYTFGGGTKVEIKSGGPGPAGMKGLPGSEV<br>QLVESGGGLVQPGNSLRLSCAASGFTFSKFGMSWVRQAPGKGLEWV<br>SSISGSGRDTLYAESVKGRFTISRDNAKTTLYLQMNSLRPEDTAVYYC<br>TIGGSLSVSSQGTLVTVSSggggsggggsggggsggggsQVQLQESGGGLVQAGGSL<br>RLSCAASGRIFSIDIMSWYRQAPGKQRELVARITRGGTISYDDSVKGR<br>FTISRDNAKNTVYLQMNSLKPEDTGVYYCNALYGTDYWGKGTQVTV<br>SSHHHHHH |
| 56 | ACP23<br>(IL-2 fusion protein) | QVQLQESGGGLAQAGGSLSLSCAASGFTVSNSVMAWYRQTPGKQRE<br>FVAIINSVGSTNYADSVKGRFTISRDNAKNTVYLQMNNLKPEDTAVY<br>VCNRNFDRIYWGQGTQVTVSSSGGPGPAGMKGLPGSEVQLVESGGG<br>LVQPGGSLRLSCAASGFTFSSYTLAWVRQAPGKGLEWVAAIDSSSYT<br>YSPDTVRGRFTISRDNAKNSLYLQMNSLRAEDTAVYYCARDSNWDA<br>LDYWGQGTTVTVSSGGGGSGGGGSGGGGSDIQMTQSPSSLSASVGD<br>RVTITCKASQNVGTNVGWYQQKPGKAPKALIYSASFRYSGVPSRFSG<br>SGSGTDFTLTISSLQPEDFATYYCQQYYTYPYTFGGGTKVEIKggggsgg<br>ggsggggsggggsggggsggggsSGGPGPAGMKGLPGSEVQLVESGGGLVQPG<br>NSLRLSCAASGFTFSKFGMSWVRQAPGKGLEWVSSISGSGRDTLYAE<br>SVKGRFTISRDNAKTTLYLQMNSLRPEDTAVYYCTIGGSLSVSSQGTL<br>VTVSSSGGPGPAGMKGLPGSaptssstkktqlqlehllldlqmilnginnyknpkltrmltfkf<br>ympkkatelkhlqcleeelkpleevlnlaqsknfhlrprdlisninvivlelkgsettfmceyadetativefln<br>rwitfcqsiistltHHHHHH |
| 57 | ACP24<br>(IL-2 fusion protein) | EVQLVESGGGLVQPGGSLRLSCAASGFTFSSYTLAWVRQAPGKGLEW<br>VAAIDSSSYTYSPDTVRGRFTISRDNAKNSLYLQMNSLRAEDTAVYY<br>CARDSNWDALDYWGQGTTVTVSSGGGGSGGGGSGGGGSDIQMTQS<br>PSSLSASVGDRVTITCKASQNVGTNVGWYQQKPGKAPKALIYSASFR<br>YSGVPSRFSGSGSGTDFTLTISSLQPEDFATYYCQQYYTYPYTFGGGT<br>KVEIKSGGPGPAGMKGLPGSaptssstkktqlqlehllldlqmilnginnyknpkltrmltfkf<br>ympkkatelkhlqcleeelkpleevlnlaqsknfhlrprdlisninvivlelkgsettfmceyadetativefln<br>rwitfcqsiistltHHHHHH |
| 58 | ACP25<br>(IL-2 fusion protein) | EVQLVESGGGLVQPGGSLRLSCAASGFTFSSYTLAWVRQAPGKGLEW<br>VAAIDSSSYTYSPDTVRGRFTISRDNAKNSLYLQMNSLRAEDTAVYY<br>CARDSNWDALDYWGQGTTVTVSSGGGGSGGGGSGGGGSDIQMTQS<br>PSSLSASVGDRVTITCKASQNVGTNVGWYQQKPGKAPKALIYSASFR<br>YSGVPSRFSGSGSGTDFTLTISSLQPEDFATYYCQQYYTYPYTFGGGT<br>KVEIKggggsggggsggggsggggsggggsggggsSGGPGPAGMKGLPGSaptssstkk<br>tqlqlehllldlqmilnginnyknpkltrmltfkfympkkatelkhlqcleeelkpleevinlaqsknfhlrpr<br>dlisninvivlelkgsettfmceyadetativeflnrwitfcqsiistltHHHHHH |

TABLE 4-continued

SEQUENCE TABLE

| SEQ ID NO. | Name | Sequence |
|---|---|---|
| 59 | ACP26 (IL-2 fusion protein) | QVQLQESGGGLVQAGGSLRLSCAASGRIFSIDIMSWYRQAPGKQREL VARITRGGTISYDDSVKGRFTISRDNAKNTVYLQMNSLKPEDTGVYY CNALYGTDYWGKGTQVTVSSggggsggggsggggsaptssstkktqlqlehllldlqmil nginnyknpkltrmltfkfympkkatelkhlqcleeelkpleevlnlaqsknfhlrprdlisninvivlelkgs ettfmceyadetativeflnrwitfcqsiistltSGGPGPAGMKGLPGSEVQLVESGGGL VQPGNSLRLSCAASGFTFSKFGMSWVRQAPGKGLEWVSSISGSGRDT LYAESVKGRFTISRDNAKTTLYLQMNSLRPEDTAVYYCTIGGSLSVSS QGTLVTVSSggggsggggsggggsggggsQVQLQQSGAELVRPGTSVKVSCK ASGYAFTNYLIEWVKQRPGQGLEWIGVINPGSGGTNYNEKFKGKATL TADKSSSTAYMQLSSLTSDDSAVYFCARWRGDGYYAYFDVWGAGT TVTVSSggggsggggsggggsDIVLTQSPASLAVSLGQRATISCKASQSVDY DGDSYMNWYQQKPGQPPKLLIYAASNLESGIPARFSGSGSGTDFTLNI HPVEEEDAATYYCQQSNEDPYTFGGGTKLEIKHHHHHHEPEA |
| 60 | ACP27 (IL-2 fusion protein) | QVQLQESGGGLVQAGGSLRLSCAASGRIFSIDIMSWYRQAPGKQREL VARITRGGTISYDDSVKGRFTISRDNAKNTVYLQMNSLKPEDTGVYY CNALYGTDYWGKGTQVTVSSggggsggggsggggsaptssstkktqlqlehllldlqmil nginnyknpkltrmltfkfympkkatelkhlqcleeelkpleevlnlaqsknfhlrprdlisninvivlelkgs ettfmceyadetativeflnrwitfcqsiistltSGGPGPAGMKGLPGSEVQLVESGGGL VQPGNSLRLSCAASGFTFSKFGMSWVRQAPGKGLEWVSSISGSGRDT LYAESVKGRFTISRDNAKTTLYLQMNSLRPEDTAVYYCTIGGSLSVSS QGTLVTVSSggggsggggsggggsggggsDIVLTQSPASLAVSLGQRATISCKA SQSVDYDGDSYMNWYQQKPGQPPKLLIYAASNLESGIPARFSGSGSG TDFTLNIHPVEEEDAATYYCQQSNEDPYTFGGGTKLEIKggggsggggsgg ggsQVQLQQSGAELVRPGTSVKVSCKASGYAFTNYLIEWVKQRPGQG LEWIGVINPGSGGTNYNEKFKGKATLTADKSSSTAYMQLSSLTSDDS AVYFCARWRGDGYYAYFDVWGAGTTVTVSSHHHHHHEPEA |
| 61 | ACP28 (IL-2 fusion protein) | aptssstkktqlqlehllldlqmilnginnyknpkltrmltfkfympkkatelkhlqcleeelkpleevlnlaq sknfhlrprdlisninvivlelkgsettfmceyadetativeflnrwitfcqsiistltSGGPGPAGMKG LPGSggggsggggsggggsggggsggggsQVQLQQSGAELVRPGTSVKVSCKAS GYAFTNYLIEWVKQRPGQGLEWIGVINPGSGGTNYNEKFKGKATLTA DKSSSTAYMQLSSLTSDDSAVYFCARWRGDGYYAYFDVWGAGTTV TVSSggggsggggsggggsDIVLTQSPASLAVSLGQRATISCKASQSVDYDG DSYMNWYQQKPGQPPKLLIYAASNLESGIPARFSGSGSGTDFTLNIHP VEEEDAATYYCQQSNEDPYTFGGGTKLEIKggggsggggsggggsEVQLVE SGGGLVQPGNSLRLSCAASGFTFSKFGMSWVRQAPGKGLEWVSSISG SGRDTLYAESVKGRFTISRDNAKTTLYLQMNSLRPEDTAVYYCTIGGS LSVSSQGTLVTVSSggggsggggsggggsggggsQVQLQESGGGLVQAGGSLRLSC AASGRIFSIDIMSWYRQAPGKQRELVARITRGGTISYDDSVKGRFTISR DNAKNTVYLQMNSLKPEDTGVYYCNALYGTDYWGKGTQVTVSSHH HHHHEPEA |
| 62 | ACP29 (IL-2 fusion protein) | aptssstkktqlqlehllldlqmilnginnyknpkltrmltfkfympkkatelkhlqcleeelkpleevlnlaq sknfhlrprdlisninvivlelkgsettfmceyadetativeflnrwitfcqsiistltSGGPGPAGMKG LPGSggggsggggsggggsggggsggggsDIVLTQSPASLAVSLGQRATISCKAS QSVDYDGDSYMNWYQQKPGQPPKLLIYAASNLESGIPARFSGSGSGT DFTLNIHPVEEEDAATYYCQQSNEDPYTFGGGTKLEIKggggsggggsggggg sQVQLQQSGAELVRPGTSVKVSCKASGYAFTNYLIEWVKQRPGQGLE WIGVINPGSGGTNYNEKFKGKATLTADKSSSTAYMQLSSLTSDDSAV YFCARWRGDGYYAYFDVWGAGTTVTVSSggggsggggsggggsEVQLVES GGGLVQPGNSLRLSCAASGFTFSKFGMSWVRQAPGKGLEWVSSISGS GRDTLYAESVKGRFTISRDNAKTTLYLQMNSLRPEDTAVYYCTIGGSL SVSSQGTLVTVSSggggsggggsggggsQVQLQESGGGLVQAGGSLRLSCA ASGRIFSIDIMSWYRQAPGKQRELVARITRGGTISYDDSVKGRFTISRD NAKNTVYLQMNSLKPEDTGVYYCNALYGTDYWGKGTQVTVSSHHH HHEPEA |
| 63 | IL-2Ra |        10       20       30       40       50<br>MDSYLLMWGL LTFIMVPGCQ AELCDDDPPE IPHATFKAMA YKEGTMLNCE<br>       60       70       80       90      100<br>CKRGFRRIKS GSLYMLCTGN SSHSSWDNQC QCTSSATRNT TKQVTPQPEE<br>     110     120     130     140     150<br>QKERKTTEMQ SPMQPVDQAS LPGHCREPPP WENEATERIY HFVVGQMVYY<br>     160     170     180     190     200<br>QCVQGYRALH RGPAESVCKM THGKTRWTQP QLICTGEMET SQFPGEEKPQ<br>     210     220     230     240     250<br>ASPEGRPESE TSCLVTTTDF QIQTEMAATM ETSIFTTEYQ VAVAGCVFLL<br>     260     270<br>ISVLLLSGLT WQRRQRKSRR TI |

TABLE 4-continued

SEQUENCE TABLE

| SEQ ID NO. | Name | Sequence |
|---|---|---|
| 64 | IL-2Rb | MAAPALSWRL PLLILLLPLA TSWASAAVNG TSQFTCFYNS RANISCVWSQ DGALQDTSCQ VHAWPDRRRW NQTCELLPVS QASWACNLIL GAPDSQKLTT VDIVTLRVLC REGVRWRVMA IQDFKPFENL RLMAPISLQV VHVETHRCNI SWEISQASHY FERHLEFEAR TLSPGHTWEE APLLTLKQKQ EWICLETLTP DTQYEFQVRV KPLQGEFTTW SPWSQPLAFR TKPAALGKDT IPWLGHLLVG LSGAFGFIIL VYLLINCRNT GPWLKKVLKC NTPDPSKFFS QLSSEHGGDV QKWLSSPFPS SSFSPGGLAP EISPLEVLER DKVTQLLLQQ DKVPEPASLS SNHSLTSCFT NQGYFFFHLP DALEIEACQV YFTYDPYSEE DPDEVVAGAP TGSSPQPLQP LSGEDDAYCT FPSRDDLLLF SPSLLGGPSP PSTAPGGSGA GEERMPPSLQ ERVPRDWDPQ PLGPPTPGVP DLVDFQPPPE LVLREAGEEV PDAGPREGVS FPWSRPPGQG EFRALNARLP LNTDAYLSLQ ELQGQDPTHL V |
| 65 | IL-2Rg | MLKPSLPFTS LLFLQLPLLG VGLNTTILTP NGNEDTTADF FLTTMPTDSL SVSTLPLPEV QCFVFNVEYM NCTWNSSSEP QPTNLTLHYW YKNSDNDKVQ KCSHYLFSEE ITSGCQLQKK EIHLYQTFVV QLQDPREPRR QATQMLKLQN LVIPWAPENL TLHKLSESQL ELNWNNRFLN HCLEHLVQYR TDWDHSWTEQ SVDYRHKFSL PSVDGQKRYT FRVRSRFNPL CDSAQHWSEW SHPIHWGSNT SKENPFLFAL EAVVISVGSM GLIISLLCVY FWLERTMPRI PTLKNLEDLV TEYHGNFSAW SGVSKGLAES LQPDYSERLC LVSEIPPKGG ALGEGPGASP CNQHSPYWAP PCYTLKPET |
| 66 | ACP63 (Anti-FN CGS-2 scFv) | mdmrvpaqllglllllwlrgarcEVQLVESGGGLVQPGGSLRLSCAASGFTFSSYA MSWVRQAPGKGLEWVSAISGSGGSTYYADSVKGRFTISRDNSKNTLY LQMNSLRAEDTAVYYCARGVGAFRPYRKHEWGQGTLVTVSRggggsg gggsggggsSSELTQDPAVSVALGQTVRITCQGDSLRSYYASWYQQKPG QAPVLVIYGKNNRPSGIPDRFSGSSSGNTASLTTTGAQAEDEADYYCN SSPFEHNLVVFGGGTKLTVLHHHHHHEPEA |
| 67 | ACP38 (IL-2 fusion protein) | mdmrvpaqllglllllwlrgarcaptsssttkktqlqlehllldlqmilnginnyknpkltrmltfkfympkkat elkhlqcleeeelkpleevlnlaqsknfhlrprdlisninivlvlkgsettfmceyadetativeflnrwitfcqsi istltSGGPGPAGMKGLPGSEVQLVESGGGLVQPGGSLRLSCAASGFTFS SYTLAWVRQAPGKGLEWVAAIDSSSYTYSPDTVRGRFTISRDNAKNS LYLQMNSLRAEDTAVYYCARDSNWDALDYWGQGTTVTVSSGGGGS GGGGSGGGGSDIQMTQSPSSLSASVGDRVTITCKASQNVGTNVGWY QQKPGKAPKALIYSASFRYSGVPSRFSGSGSGTDFTLTISSLQPEDFAT YYCQQYYTYPYTFGGGTKVEIKggggsggggsggggsEVQLVESGGGLVQP GNSLRLSCAASGFTFSKFGMSWVRQAPGKGLEWVSSISGSGRDTLYA ESVKGRFTISRDNAKTTLYLQMNSLRPEDTAVYYCTIGGSLSVSSQGT LVTVSSggggsggggsggggsQVQLQESGGGLVQAGGSLRLSCAASGRIFSI DIMSWYRQAPGKQRELVARITRGGTISYDDSVKGRFTISRDNAKNTV YLQMNSLKPEDTGVYYCNALYGTDYWGKGTQVTVSSHHHHHH |
| 68 | ACP39 (IL-2 fusion protein) | mdmrvpaqllglllllwlrgarcQVQLQESGGGLVQAGGSLRLSCAASGRIFSIDI MSWYRQAPGKQRELVARITRGGTISYDDSVKGRFTISRDNAKNTVYL QMNSLKPEDTGVYYCNALYGTDYWGKGTQVTVSSSGGPGPAGMKG LPGSEVQLVESGGGLVQPGNSLRLSCAASGFTFSKFGMSWVRQAPGK GLEWVSSISGSGRDTLYAESVKGRFTISRDNAKTTLYLQMNSLRPEDT AVYYCTIGGSLSVSSQGTLVTVSSSGGPGPAGMKGLPGSEVQLVESG GGLVQPGGSLRLSCAASGFTFSSYTLAWVRQAPGKGLEWVAAIDSSS YTYSPDTVRGRFTISRDNAKNSLYLQMNSLRAEDTAVYYCARDSNW DALDYWGQGTTVTVSSGGGGSGGGGSGGGGSDIQMTQSPSSLSASV GDRVTITCKASQNVGTNVGWYQQKPGKAPKALIYSASFRYSGVPSRF SGSGSGTDFTLTISSLQPEDFATYYCQQYYTYPYTFGGGTKVEIKSGGP |

TABLE 4-continued

SEQUENCE TABLE

| SEQ ID NO. | Name | Sequence |
|---|---|---|
| | | GPAGMKGLPGSaptssstkktqlqlehllldlqmilnginnyknpkltrmltfkfympkkatelkhl qcleeelkpleevlnlaqsknfhlrprdlisninvivlelkgsettfmceyadetativeflnrwitfcqsiistlt HHHHHH** |
| 69 | ACP40 (IL-2 fusion protein) | mdmrvpaqllgllllwlrgarcelcdddppeiphatfkamaykegtmlnceckrgfrriksgslymlctgn sshsswdnqcqctssatrnttkqvtpqpeeqkerkttemqspmqpvdqaslpghcrepppweneateri yhfvvgqmvyyqcvqgyralhrgpaesvckmthgktrwtqpqlictgemetsqfpgeekpqaspegrp esetsclvtttdfqiqtemaatmetsiftteyqggggsggggsggggsggggsggggsggggsggggsSGGPG PAGMKGLPGSaptssstkktqlqlehllldlqmilnginnyknpkltrmltfkfympkkatelkhlqc leeelkpleevlnlaqsknfhlrprdlisninvivlelkgsettfmceyadetativeflnrwitfcqsiistltHH HHHH |
| 70 | ACP41 (IL-2 fusion protein) | mdmrvpaqllgllllwlrgarcaptssstkktqlqlehllldlqmilnginnyknpkltrmltfkfympkkat elkhlqcleeelkpleevlnlaqsknfhlrprdlisninvivlelkgsettfmceyadetativeflnrwitfcqsi istltSGGPGPAGMKGLPGSggggsggggsggggsggggsggggsggggsggggselcddddppeiph atfkamaykegtmlnceckrgfrriksgslymlctgnsshsswdnqcqctssatrnttkqvtpqpeeqker kttemqspmqpvdqaslpghcrepppweneateriyhfvvgqmvyyqcvqgyralhrgpaesvckm thgktrwtqpqlictgemetsqfpgeekpqaspegrpesetsclvtttdfqiqtemaatmetsiftteyqHH HHHH |
| 71 | ACP42 (IL-2 fusion protein) | mdmrvpaqllgllllwlrgarcEVQLVESGGGLVQPGNSLRLSCAASGFTFSKFG MSWVRQAPGKGLEWVSSISGSGRDTLYAESVKGRFTISRDNAKTTLY LQMNSLRPEDTAVYYCTIGGSLSVSSQGTLVTVSSggggsggggsggggsselc dddddppeiphatfkamaykegtmlnceckrgfrriksgslymlctgnsshsswdnqcqctssatrnttkqvt pqpeeqkerkttemqspmqpvdqaslpghcrepppweneateriyhfvvgqmvyyqcvqgyralhrg paesvckmthgktrwtqpqlictgemetsqfpgeekpqaspegrpesetsclvtttdfqiqtemaatmetsi ftteyqggggsggggsggggsggggsggggsggggsSGGPGPAGMKGLPGSaptssstkktq lqlehllldlqmilnginnyknpkltrmltfkfympkkatelkhlqcleeelkpleevlnlaqsknfhlrprdli sninvivlelkgsettfmceyadetativeflnrwitfcqsiistltHHHHHH |
| 72 | ACP43 (IL-2 fusion protein) | mdmrvpaqllgllllwlrgarcaptssstkktqlqlehllldlqmilnginnyknpkltrmltfkfympkkat elkhlqcleeelkpleevlnlaqsknfhlrprdlisninvivlelkgsettfmceyadetativeflnrwitfcqsi istltSGGPGPAGMKGLPGSggggsggggsggggsggggsggggsggggselcddddppeiph atfkamaykegtmlnceckrgfrriksgslymlctgnsshsswdnqcqctssatrnttkqvtpqpeeqker kttemqspmqpvdqaslpghcrepppweneateriyhfvvgqmvyyqcvqgyralhrgpaesvckm thgktrwtqpqlictgemetsqfpgeekpqaspegrpesetsclvtttdfqiqtemaatmetsiftteyqgggg gsggggsggggsEVQLVESGGGLVQPGNSLRLSCAASGFTFSKFGMSWVR QAPGKGLEWVSSISGSGRDTLYAESVKGRFTISRDNAKTTLYLQMNS LRPEDTAVYYCTIGGSLSVSSQGTLVTVSSHHHHHH |
| 73 | ACP44 (IL-2 fusion protein) | mdmrvpaqllgllllwlrgarcaptssstkktqlqlehllldlqmilnginnyknpkltrmltfkfympkkat elkhlqcleeelkpleevlnlaqsknfhlrprdlisninvivlelkgsettfmceyadetativeflnrwitfcqsi istltSGGPGPAGMKGLPGSggggsggggsggggsggggsggggsggggsggggselcddddppeiph atfkamaykegtmlnceckrgfrriksgslymlctgnsshsswdnqcqctssatrnttkqvtpqpeeqker kttemqspmqpvdqaslpghcrepppweneateriyhfvvgqmvyyqcvqgyralhrgpaesvckm thgktrwtqpqlictgemetsqfpgeekpqaspegrpesetsclvtttdfqiqtemaatmetsiftteyqSG GPGPAGMKGLPGSEVQLVESGGGLVQPGNSLRLSCAASGFTFSKFGM SWVRQAPGKGLEWVSSISGSGRDTLYAESVKGRFTISRDNAKTTLYL QMNSLRPEDTAVYYCTIGGSLSVSSQGTLVTVSSHHHHHH |
| 74 | ACP45 (IL-2 fusion protein) | mdmrvpaqllgllllwlrgarcEVQLVESGGGLVQPGNSLRLSCAASGFTFSKFG MSWVRQAPGKGLEWVSSISGSGRDTLYAESVKGRFTISRDNAKTTLY LQMNSLRPEDTAVYYCTIGGSLSVSSQGTLVTVSSSGGPGPAGMKGL PGSEVQLVESGGGLVQPGGSLRLSCAASGFTFSSYTLAWVRQAPGKG LEWVAAIDSSSYTYSPDTVRGRFTISRDNAKNSLYLQMNSLRAEDTA VYYCARDSNWDALDYWGQGTTVTVSSGGGGSGGGGSGGGGSDIQM TQSPSSLSASVGDRVTITCKASQNVGTNVGWYQQKPGKAPKALIYSA SFRYSGVPSRFSGSGSGTDFTLTISSLQPEDFATYYCQQYYTYPYTFGG GTKVEIKggggsggggsggggsggggsggggsggggsSGGPGPAGMKGLPGSaptsss tkktqlqlehllldlqmilnginnyknpkltrmltfkfympkkatelkhlqcleeelkpleevlnlaqsknfhl rprdlisninvivlelkgsettfmceyadetativeflnrwitfcqsiistltHHHHHH |
| 75 | ACP46 (IL-2 fusion protein) | mdmrvpaqllgllllwlrgarcaptssstkktqlqlehllldlqmilnginnyknpkltrmltfkfympkkat elkhlqcleeelkpleevlnlaqsknfhlrprdlisninvivlelkgsettfmceyadetativeflnrwitfcqsi istltSGGPGPAGMKGLPGSggggsggggsggggsggggsggggsggggsggggsEVQLVESG GGLVQPGGSLRLSCAASGFTFSSYTLAWVRQAPGKGLEWVAAIDSSS YTYSPDTVRGRFTISRDNAKNSLYLQMNSLRAEDTAVYYCARDSNW DALDYWGQGTTVTVSSsggpgpagmkglpgsDIQMTQSPSSLSASVGDRVT ITCKASQNVGTNVGWYQQKPGKAPKALIYSASFRYSGSGSGS GTDFTLTISSLQPEDFATYYCQQYYTYPYTFGGGTKVEIKggggsggggsg gggsEVQLVESGGGLVQPGNSLRLSCAASGFTFSKFGMSWVRQAPGKG LEWVSSISGSGRDTLYAESVKGRFTISRDNAKTTLYLQMNSLRPEDTA VYYCTIGGSLSVSSQGTLVTVSSggggsggggsggggsggggsqVQLQESGGGLVQ AGGSLRLSCAASGRIFSIDIMSWYRQAPGKQRELVARITRGGTISYDDS |

TABLE 4-continued

SEQUENCE TABLE

| SEQ ID NO. | Name | Sequence |
|---|---|---|
| | | VKGRFTISRDNAKNTVYLQMNSLKPEDTGVYYCNALYGTDYWGKG<br>TQVTVSSHHHHHH |
| 76 | ACP47<br>(IL-2<br>fusion<br>protein) | mdmrvpaqllglllllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSggggsggggsggggsa<br>ptssstkktqlqlehllldlqmilnginnyknpkltrmltfkfympkkatelkhlqcleeelkpleevmnlaqs<br>knfhlrprdlisninvivlelkgsettfmceyadetativeflnrwitfcqsiistltSGGPGPAGMKGL<br>PGSEVQLVESGGGLVQPGNSLRLSCAASGFTFSKFGMSWVRQAPGKG<br>LEWVSSISGSGRDTLYAESVKGRFTISRDNAKTTLYLQMNSLRPEDTA<br>VYYCTIGGSLSVSSQGTLVTVSSggggsggggsggggsggggsggggsggggsEVQ<br>LVESGGGLVQPGGSLRLSCAASGFTFSSYTLAWVRQAPGKGLEWVA<br>AIDSSSYTYSPDTVRGRFTISRDNAKNSLYLQMNSLRAEDTAVYYCA<br>RDSNWDALDYWGQGTTVTVSSGGGGSGGGGSGGGGSDIQMTQSPSS<br>LSASVGDRVTITCKASQNVGTNVGWYQQKPGKAPKALIYSASFRYSG<br>VPSRFSGSGSGTDFTLTISSLQPEDFATYYCQQYTYPYTFGGGTKVEI<br>KHHHHHH |
| 77 | ACP48<br>(IL-2<br>fusion<br>protein) | mdmrvpaqllglllllwlrgarcaptssstkktqlqlehllldlqmilnginnyknpkltrmltfkfympkkat<br>elkhlqcleeelkpleevlnlaqsknfhlrprdlisninvivlelkgsettfmceyadetativeflnrwitfcqsi<br>istltSGGPGPAGMKGLPGSEVQLVESGGGLVQPGGSLRLSCAASGFTFS<br>SYTLAWVRQAPGKGLEWVAAIDSSSYTYSPDTVRGRFTISRDNAKNS<br>LYLQMNSLRAEDTAVYYCARDSNWDALDYWGQGTTVTVSSGGGGS<br>GGGGSGGGGSDIQMTQSPSSLSASVGDRVTITCKASQNVGTNVGWY<br>QQKPGKAPKALIYSASFRYSGVPSRFSGSGSGTDFTLTISSLQPEDFAT<br>YYCQQYTYPYTFGGGTKVEIKggggsggggsggggsEVQLVESGGGLVQP<br>GNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGT<br>LVTVSSHHHHHH |
| 78 | ACP49<br>(IL-2<br>fusion<br>protein) | mdmrvpaqllglllllwlrgarcaptssstkktqlqlehllldlqmilnginnyknpkltrmltfkfympkkat<br>elkhlqcleeelkpleevlnlaqsknfhlrprdlisninvivlelkgsettfmceyadetativeflnrwitfcqsi<br>istltSGGPGPAGMKGLPGSggggsggggsggggsggggsggggsggggsggggsEVQLVESG<br>GGLVQPGGSLRLSCAASGFTFSSYTLAWVRQAPGKGLEWVAAIDSSS<br>YTYSPDTVRGRFTISRDNAKNSLYLQMNSLRAEDTAVYYCARDSNW<br>DALDYWGQGTTVTVSSGGGGSGGGGSGGGGSDIQMTQSPSSLSASV<br>GDRVTITCKASQNVGTNVGWYQQKPGKAPKALIYSASFRYSGVPSRF<br>SGSGSGTDFTLTISSLQPEDFATYYCQQYTYPYTFGGGTKVEIKggggs<br>ggggsggggsEVQLVESGGGLVQPGNSLRLSCAASGFTFSKFGMSWVRQ<br>APGKGLEWVSSISGSGRDTLYAESVKGRFTISRDNAKTTLYLQMNSLR<br>PEDTAVYYCTIGGSLSVSSQGTLVTVSSHHHHHH |
| 79 | ACP92<br>(IL-2<br>fusion<br>protein) | mdmrvpaqllglllllwlrgarcEVQLVESGGGLVQPGNSLRLSCAASGFTFSKFG<br>MSWVRQAPGKGLEWVSSISGSGRDTLYAESVKGRFTISRDNAKTTLY<br>LQMNSLRPEDTAVYYCTIGGSLSVSSQGTLVTVSSSGGPGPAGMKGL<br>PGSaptssstkktqlqlehllldlqmilnginnyknpkltrmltfkfympkkatelkhlqcleeelkpleevl<br>nlaqsknfhlrprdlisninvivlelkgsettfmceyadetativeflnrwitfcqsiistltSGGPGPAGM<br>KGLPGSEVQLVESGGGLVQPGNSLRLSCAASGFTFSKFGMSWVRQAP<br>GKGLEWVSSISGSGRDTLYAESVKGRFTISRDNAKTTLYLQMNSLRPE<br>DTAVYYCTIGGSLSVSSQGTLVTVSSHHHHHH |
| 80 | ACP93<br>(IL-2<br>fusion<br>protein) | mdmrvpaqllglllllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSgsgsgsgsgsgsgsE<br>VQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYY<br>CTIGGSLSVSSQGTLVTVSSgsgsgsgsgsgsgsQVQLQESGGGLVQAGGS<br>LRLSCAASGRIFSIDIMSWYRQAPGKQRELVARITRGGTISYDDSVKG<br>RFTISRDNAKNTVYLQMNSLKPEDTGVYYCNALYGTDYWGKGTQVT<br>VSSgsgsgsgsgsgsgsEVQLVESGGGLVQPGGSLRLSCAASGFTFSSYTL<br>AWVRQAPGKGLEWVAAIDSSSYTYSPDTVRGRFTISRDNAKNSLYLQ<br>MNSLRAEDTAVYYCARDSNWDALDYWGQGTTVTVSSGGGGSGGGG<br>SGGGGSDIQMTQSPSSLSASVGDRVTITCKASQNVGTNVGWYQQKPG<br>KAPKALIYSASFRYSGVPSRFSGSGSGTDFTLTISSLQPEDFATYYCQQ<br>YYTYPYTFGGGTKVEIKSGGPGPAGMKGLPGSaptssstkktqlqlehllldlqmil<br>nginnyknpkltrmltfkfympkkatelkhlqcleeelkpleevlnlaqsknfhlrprdlisninvivlelkgs<br>ettfmceyadetativeflnrwitfcqsiistltHHHHHH |
| 81 | ACP94<br>(IL-2<br>fusion<br>protein) | mdmrvpaqllglllllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSgsgsgsgsgsgsgsE<br>VQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYY<br>CTIGGSLSVSSQGTLVTVSSgsgsgsgsgsgsgsEVQLVESGGGLVQPGGS |

TABLE 4-continued

SEQUENCE TABLE

| SEQ ID NO. | Name | Sequence |
|---|---|---|
| | | LRLSCAASGFTFSSYTLAWVRQAPGKGLEWVAAIDSSSYTYSPDTVR<br>GRFTISRDNAKNSLYLQMNSLRAEDTAVYYCARDSNWDALDYWGQ<br>GTTVTVSSGGGGSGGGGSGGGGSDIQMTQSPSSLSASVGDRVTITCK<br>ASQNVGTNVGWYQQKPGKAPKALIYSASFRYSGVPSRFSGSGSGTDF<br>TLTISSLQPEDFATYYCQQYYTYPYTFGGGTKVEIKSGGPGPAGMKGL<br>PGSaptssstkktqlqlehllldlqmilnginnyknpkltrmltfkfympkkatelkhlqcleeelkpleevl<br>nlaqsknfhlrprdlisninvivlelkgsettfmceyadetativeflnrwitfcqsiistltHHHHHH |
| 82 | ACP95<br>(IL-2<br>fusion<br>protein) | mdmrvpaqllglllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSgsgsgsgsgsgsgsE<br>VQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYY<br>CTIGGSLSVSSQGTLVTVSSSGGPGPAGMKGLPGSaptssstkktqlqlehllldlq<br>milnginnyknpkltrmltfkfympkkatelkhlqcleeelkpleevlnlaqsknfhlrprdlisninvivlel<br>kgsettfmceyadetativeflnrwitfcqsiistltHHHHHH |
| 83 | ACP96<br>(IL-2<br>fusion<br>protein) | mdmrvpaqllglllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSSGGPGPAGMKG<br>LPGSaptssstkktqlqlehllldlqmilnginnyknpkltrmltfkfympkkatelkhlqcleeelkplee<br>vlnlaqsknfhlrprdlisninvivlelkgsettfmceyadetativeflnrwitfcqsiistltSGGPGPAG<br>MKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLR<br>PEDTAVYYCTIGGSLSVSSQGTLVTVSSHHHHHH |
| 84 | ACP97<br>(IL-2<br>fusion<br>protein) | mdmrvpaqllglllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSggggsggggsggggsE<br>VQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYY<br>CTIGGSLSVSSQGTLVTVSSSGGPGPAGMKGLPGSaptssstkktqlqlehllldlq<br>milnginnyknpkltrmltfkfympkkatelkhlqcleeelkpleevlnlaqsknfhlrprdlisninvivlel<br>kgsettfmceyadetativeflnrwitfcqsiistltSGGPGPAGMKGLPGSEVQLVESGG<br>GLVQPGNSLRLSCAASGFTFSKFGMSWVRQAPGKGLEWVSSISGSGR<br>DTLYAESVKGRFTISRDNAKTTLYLQMNSLRPEDTAVYYCTIGGSLSV<br>SSQGTLVTVSSHHHHHH |
| 85 | ACP99<br>(IL-2<br>fusion<br>protein) | mdmrvpaqllglllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSggggsggggsggggsa<br>ptssstkktqlqlehllldlqmilnginnyknpkltrmltfkfympkkatelkhlqcleeelkpleevlnlaqs<br>knfhlrprdlisninvivlelkgsettfmceyadetativeflnrwitfcqsiistltSGGPGPAGMKGL<br>PGSEVQLVESGGGLVQPGNSLRLSCAASGFTFSKFGMSWVRQAPGKG<br>LEWVSSISGSGRDTLYAESVKGRFTISRDNAKTTLYLQMNSLRPEDTA<br>VYYCTIGGSLSVSSQGTLVTVSSHHHHHH |
| 86 | ACP100<br>(IL-2<br>fusion<br>protein) | mdmrvpaqllglllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSggggsggggsggggsa<br>ptssstkktqlqlehllldlqmilnginnyknpkltrmltfkfympkkatelkhlqcleeelkpleevlnlaqs<br>knfhlrprdlisninvivlelkgsettfmceyadetativeflnrwitfcqsiistltHHHHHH |
| 87 | ACP101<br>(IL-2<br>fusion<br>protein) | mdmrvpaqllglllwlrgarcaptssstkktqlqlehllldlqmilnginnyknpkltrmltfkfympkkat<br>elkhlqcleeelkpleevlnlaqsknfhlrprdlisninvivlelkgsettfmceyadetativeflnrwitfcqsi<br>istltSGGPGPAGMKGLPGSEVQLVESGGGLVQPGNSLRLSCAASGFTFS<br>KFGMSWVRQAPGKGLEWVSSISGSGRDTLYAESVKGRFTISRDNAKT<br>TLYLQMNSLRPEDTAVYYCTIGGSLSVSSQGTLVTVSSHHHHHH |
| 88 | ACP102<br>(IL-2<br>fusion<br>protein) | mdmrvpaqllglllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSSGGPGPAGMKG<br>LPGSaptssstkktqlqlehllldlqmilnginnyknpkltrmltfkfympkkatelkhlqcleeelkplee<br>vlnlaqsknfhlrprdlisninvivlelkgsettfmceyadetativeflnrwitfcqsiistltSGGPGPAG<br>MKGLPGSEVQLVESGGGLVQPGNSLRLSCAASGFTFSKFGMSWVRQ<br>APGKGLEWVSSISGSGRDTLYAESVKGRFTISRDNAKTTLYLQMNSLR<br>PEDTAVYYCTIGGSLSVSSQGTLVTVSSggggsggggsggggsggggsggggsggg<br>gsEVQLVESGGGLVQPGGSLRLSCAASGFTFSSYTLAWVRQAPGKGLE<br>WVAAIDSSSYTYSPDTVRGRFTISRDNAKNSLYLQMNSLRAEDTAVY<br>YCARDSNWDALDYWGQGTTVTVSSGGGGSGGGGSGGGGSDIQMTQ<br>SPSSLSASVGDRVTITCKASQNVGTNVGWYQQKPGKAPKALIYSASF<br>RYSGVPSRFSGSGSGTDFTLTISSLQPEDFATYYCQQYYTYPYTFGGG<br>TKVEIKHHHHHH |

TABLE 4-continued

SEQUENCE TABLE

| SEQ ID NO. | Name | Sequence |
|---|---|---|
| 89 | ACP103 (IL-2 fusion protein) | mdmrvpaqllglllllwlrgarcaptssstkktqlqlehllldlqmilnginnyknpkltrmltfkfympkkat elkhlqcleeelkpleevlnlaqsknfhlrprdlisninvivlelkgsettfmceyadetativeflnrwitfcqsi istltSGGPGPAGMKGLPGSggggsggggsggggsggggsggggsEVQLVESG GGLVQPGGSLRLSCAASGFTSSYTLAWVRQAPGKGLEWVAAIDSSS YTYSPDTVRGRFTISRDNAKNSLYLQMNSLRAEDTAVYYCARDSNW DALDYWGQGTTVTVSSGGGGSGGGGSGGGGSDIQMTQSPSSLSASV GDRVTITCKASQNVGTNVGWYQQKPGKAPKALIYSASFRYSGVPSRF SGSGSGTDFTLTISSLQPEDFATYYCQQYYTYPYTFGGGTKVEIKggggs ggggsggggsEVQLVESGGGLVQPGNSLRLSCAASGFTFSKFGMSWVRQ APGKGLEWVSSISGSGRDTLYAESVKGRFTISRDNAKTTLYLQMNSLR PEDTAVYYCTIGGSLSVSSQGTLVTVSSggggsggggsggggsQVQLQESGG GLAQAGGSLSLSCAASGFTVSNSVMAWYRQTPGKQREFVAIINSVGS TNYADSVKGRFTISRDNAKNTVYLQMNNLKPEDTAVYVCNRNFDRI YWGQGTQVTVSSHHHHHH |
| 90 | ACP104 (IL-2 fusion protein) | mdmrvpaqllglllllwlrgarcQVQLQESGGGLAQAGGSLSLSCAASGFTVSNSV MAWYRQTPGKQREFVAIINSVGSTNYADSVKGRFTISRDNAKNTVYL QMNNLKPEDTAVYVCNRNFDRIYWGQGTQVTVSSaptssstkktqlqlehllldl qmilnginnyknpkltrmltfkfympkkatelkhlqcleeelkpleevlnlaqsknfhlrprdlisninvivl elkgsettfmceyadetativeflnrwitfcqsiistltSGGPGPAGMKGLPGSEVQLVESG GGLVQPGNSLRLSCAASGFTFSKFGMSWVRQAPGKGLEWVSSISGSG RDTLYAESVKGRFTISRDNAKTTLYLQMNSLRPEDTAVYYCTIGGSLS VSSQGTLVTVSSggggsggggsggggsggggsggggsggggsEVQLVESGGGLVQP GGSLRLSCAASGFTFSSYTLAWVRQAPGKGLEWVAAIDSSSYTYSPD TVRGRFTISRDNAKNSLYLQMNSLRAEDTAVYYCARDSNWDALDY WGQGTTVTVSSGGGGSGGGGSGGGGSDIQMTQSPSSLSASVGDRVTI TCKASQNVGTNVGWYQQKPGKAPKALIYSASFRYSGVPSRFSGSGSG TDFTLTISSLQPEDFATYYCQQYYTYPYTFGGGTKVEIKHHHHHH |
| 91 | ACP105 (IL-2 fusion protein) | mdmrvpaqllglllllwlrgarcEVQLVESGGGLVQPGGSLRLSCAASGFTFSSYT LAWVRQAPGKGLEWVAAIDSSSYTYSPDTVRGRFTISRDNAKNSLYL QMNSLRAEDTAVYYCARDSNWDALDYWGQGTTVTVSSGGGGSGGG GSGGGGSDIQMTQSPSSLSASVGDRVTITCKASQNVGTNVGWYQQKP GKAPKALIYSASFRYSGVPSRFSGSGSGTDFTLTISSLQPEDFATYYCQ QYYTYPYTFGGGTKVEIKggggsggggsggggsggggsggggsggggsSGGPGPA GMKGLPGSaptssstkktqlqlehllldlqmilnginnyknpkltrmltfkfympkkatelkhlqclee elkpleevlnlaqsknfhlrprdlisninvivlelkgsettfmceyadetativeflnrwitfcqsiistltSGGP GPAGMKGLPGSEVQLVESGGGLVQPGNSLRLSCAASGFTFSKFGMS WVRQAPGKGLEWVSSISGSGRDTLYAESVKGRFTISRDNAKTTLYLQ MNSLRPEDTAVYYCTIGGSLSVSSQGTLVTVSSggggsggggsggggsQVQL QESGGGLAQAGGSLSLSCAASGFTVSNSVMAWYRQTPGKQREFVAII NSVGSTNYADSVKGRFTISRDNAKNTVYLQMNNLKPEDTAVYVCNR NFDRIYWGQGTQVTVSSHHHHHH |
| 92 | ACP106 (IL-2 fusion protein) | mdmrvpaqllglllllwlrgarcQVQLQESGGGLAQAGGSLSLSCAASGFTVSNSV MAWYRQTPGKQREFVAIINSVGSTNYADSVKGRFTISRDNAKNTVYL QMNNLKPEDTAVYVCNRNFDRIYWGQGTQVTVSSggggsggggsggggsE VQLVESGGGLVQPGNSLRLSCAASGFTFSKFGMSWVRQAPGKGLEW VSSISGSGRDTLYAESVKGRFTISRDNAKTTLYLQMNSLRPEDTAVYY CTIGGSLSVSSQGTLVTVSSSGGPGPAGMKGLPGSEVQLVESGGGLVQ PGGSLRLSCAASGFTFSSYTLAWVRQAPGKGLEWVAAIDSSSYTYSP DTVRGRFTISRDNAKNSLYLQMNSLRAEDTAVYYCARDSNWDALDY WGQGTTVTVSSGGGGSGGGGSGGGGSDIQMTQSPSSLSASVGDRVTI TCKASQNVGTNVGWYQQKPGKAPKALIYSASFRYSGVPSRFSGSGSG TDFTLTISSLQPEDFATYYCQQYYTYPYTFGGGTKVEIKggggsggggsggg gsggggsggggsggggsSGGPGPAGMKGLPGSaptssstkktqlqlehllldlqmilnginnyk npkltrmltfkfympkkatelkhlqcleeelkpleevlnlaqsknfhlrprdlisninvivlelkgsettfmce yadetativeflnrwitfcqsiistltHHHHHH |
| 93 | ACP107 (IL-2 fusion protein) | mdmrvpaqllglllllwlrgarcEVQLVESGGGLVQPGGSLRLSCAASGFTFSSYT LAWVRQAPGKGLEWVAAIDSSSYTYSPDTVRGRFTISRDNAKNSLYL QMNSLRAEDTAVYYCARDSNWDALDYWGQGTTVTVSSGGGGSGGG GSGGGGSDIQMTQSPSSLSASVGDRVTITCKASQNVGTNVGWYQQKP GKAPKALIYSASFRYSGVPSRFSGSGSGTDFTLTISSLQPEDFATYYCQ QYYTYPYTFGGGTKVEIKggggsggggsggggsggggsggggsggggsEVQLVES GGGLVQPGNSLRLSCAASGFTFSKFGMSWVRQAPGKGLEWVSSISGS GRDTLYAESVKGRFTISRDNAKTTLYLQMNSLRPEDTAVYYCTIGGSL SVSSQGTLVTVSSSGGPGPAGMKGLPGSaptssstkktqlqlehllldlqmilnginny knpkltrmltfkfympkkatelkhlqcleeelkpleevlnlaqsknfhlrprdlisninvlvlelkgsettfmc eyadetativeflnrwitfcqsiistltggggsggggsggggsQVQLQESGGGLAQAGGSLSL SCAASGFTVSNSVMAWYRQTPGKQREFVAIINSVGSTNYADSVKGRF TISRDNAKNTVYLQMNNLKPEDTAVYVCNRNFDRIYWGQGTQVTVS SHHHHHH |

TABLE 4-continued

SEQUENCE TABLE

| SEQ ID NO. | Name | Sequence |
|---|---|---|
| 94 | ACP108 (IL-2 fusion protein) | mdmrvpaqllglllllwlrgarcQVQLQESGGGLVQAGGSLRLSCAASGRIFSIDI<br>MSWYRQAPGKQRELVARITRGGTISYDDSVKGRFTISRDNAKNTVYL<br>QMNSLKPEDTGVYYCNALYGTDYWGKGTQVTVSSggggsggggsggggsa<br>ptssstkktqlqlehllldlqmilnginnyknpkktrmltfkfympkkatelkhlqcleeelkpleevlnlaqs<br>knfhlrprdlisninvivlelkgsettfmceyadetativeflnrwitfcqsiiistltSGGPGPAGMKGL<br>PGSrgetgpaaPGSEVQLVESGGGLVQPGNSLRLSCAASGFTFSKFGMSW<br>VRQAPGKGLEWVSSISGSGRDTLYAESVKGRFTISRDNAKTTLYLQM<br>NSLRPEDTAVYYCTIGGSLSVSSQGTLVTVSSggggsggggsggggsggggsgg<br>ggsggggsEVQLVESGGGLVQPGGSLRLSCAASGFTFSSYTLAWVRQAP<br>GKGLEWVAAIDSSSYTYSPDTVRGRFTISRDNAKNSLYLQMNSLRAE<br>DTAVYYCARDSNWDALDYWGQGTTVTVSSGGGGSGGGGSGGGGSD<br>IQMTQSPSSLSASVGDRVTITCKASQNVGTNVGWYQQKPGKAPKALI<br>YSASFRYSGVPSRFSGSGSGTDFTLTISSLQPEDFATYYCQQYYTYPYT<br>FGGGTKVEIKHHHHHH |
| 95 | ACP117 (Anti-FN CGS-2 scFv) | mdmrvpaqllglllllwlrgarcEVQLVESGGGLVQPGGSLRLSCAASGFTFSSYA<br>MSWVRQAPGKGLEWVSAISGSGGSTYYADSVKGRFTISRDNSKNTLY<br>LQMNSLRAEDTAVYYCARGVGAFRPYRKHEWGQGTLVTVSRggggsg<br>gggsggggsSSELTQDPAVSVALGQTVRITCQGDSLRSYYASWYQQKPG<br>QAPVLVIYGKNNRPSGIPDRFSGSSSGNTASLTTTGAQAEDEADYYCN<br>SSPPFEHNLVVFGGGTKLTVLHHHHHHEPEA |
| 96 | ACP118 (NARA1 Vh/Vl non-cleavable) | mdmrvpaqllglllllwlrgarcQVQLQQSGAELVRPGTSVKVSCKASGYAFTNY<br>LIEWVKQRPGQGLEWIGVINPGSGGTNYNEKFKGKATLTADKSSSTA<br>YMQLSSLTSDDSAVYFCARWRGDGYYAYFDVWGAGTTVTVSSggggs<br>ggggsggggsDIVLTQSPASLAVSLGQRATISCKASQSVDYDGDSYMNWY<br>QQKPGQPPKLLIYAASNLESGIPARFSGSGSGTDFTLNIHPVEEEDAAT<br>YYCQQSNEDPYTFGGGTKLEIKHHHHHHEPEA |
| 97 | ACP119 (NARA1 Vh/Vl cleavable) | mdmrvpaqllglllllwlrgarcQVQLQQSGAELVRPGTSVKVSCKASGYAFTNY<br>LIEWVKQRPGQGLEWIGVINPGSGGTNYNEKFKGKATLTADKSSSTA<br>YMQLSSLTSDDSAVYFCARWRGDGYYAYFDVWGAGTTVTVSSSGG<br>PGPAGMKGLPGSDIVLTQSPASLAVSLGQRATISCKASQSVDYDGDSY<br>MNWYQQKPGQPPKLLIYAASNLESGIPARFSGSGSGTDFTLNIHPVEE<br>EDAATYYCQQSNEDPYTFGGGTKLEIKHHHHHHEPEA |
| 98 | ACP120 (NARA1 Vl/Vh non-cleavable) | mdmrvpaqllglllllwlrgarcDIVLTQSPASLAVSLGQRATISCKASQSVDYDG<br>DSYMNWYQQKPGQPPKLLIYAASNLESGIPARFSGSGSGTDFTLNIHP<br>VEEEDAATYYCQQSNEDPYTFGGGTKLEIKggggsggggsggggsQVQLQQ<br>SGAELVRPGTSVKVSCKASGYAFTNYLIEWVKQRPGQGLEWIGVINP<br>GSGGTNYNEKFKGKATLTADKSSSTAYMQLSSLTSDDSAVYFCARW<br>RGDGYYAYFDVWGAGTTVTVSSHHHHHHEPEA |
| 99 | ACP121 (NARA1 Vl/Vh cleavable) | mdmrvpaqllglllllwlrgarcDIVLTQSPASLAVSLGQRATISCKASQSVDYDG<br>DSYMNWYQQKPGQPPKLLIYAASNLESGIPARFSGSGSGTDFTLNIHP<br>VEEEDAATYYCQQSNEDPYTFGGGTKLEIKSGGPGPAGMKGLPGSQV<br>QLQQSGAELVRPGTSVKVSCKASGYAFTNYLIEWVKQRPGQGLEWIG<br>VINPGSGGTNYNEKFKGKATLTADKSSSTAYMQLSSLTSDDSAVYFC<br>ARWRGDGYYAYFDVWGAGTTVTVSSHHHHHHEPEA |
| 100 | ACP124 (IL-2 fusion protein) | mdmrvpaqllglllllwlrgarcaptssstkktqlqlehllldlqmilnginnyknpkltrmltfkfympkkat<br>elkhlqcleeelkpleevlnlaqsknfhlrprdlisninvivlelkgsettfmceyadetativeflnrwitfcqsi<br>istltggggsggggsggggsEVQLVESGGGLVQPGNSLRLSCAASGFTFSKFGM<br>SWVRQAPGKGLEWVSSISGSGRDTLYAESVKGRFTISRDNAKTTLYL<br>QMNSLRPEDTAVYYCTIGGSLSVSSQGTLVTVSSHHHHHHEPEA |
| 101 | ACP132 (IL-2 fusion protein) | mdmrvpaqllglllllwlrgarcaptssstkktqlqlehllldlqmilnginnyknpkltrmltfkfympkkat<br>elkhlqcleeelkpleevlnlaqsknfhlrprdlisninvivlelkgsettfmceyadetativeflnrwitfcqsi<br>istltggggsggggsggggsdahksevahrfkdlgeenfkalvliafaqylqqcpfedhvklvnevtefakt<br>cvadesaencdkslhtlfgdklctvatlretygemadccakqepernecflqhkddnpnlprlvrpevdvm<br>ctafhdneetflkkylyeiarrhpyfyapellfffakrykaafteccqaadkaacllpkldelrdegkassakqrl<br>kcaslqkfgerafkawavarlsqrfpkaefaevsklvtdltkvhtecchgdllecaddradlakyicenqdsi<br>sskkleccekpllekshciaevendempadlpslaadfveskdvcknyaeakdvflgmflyeyarrhpdy<br>svvlllrlaktyettlekccaaadphecyakvfdefkplveepqnlikqncelfeqlgeykfqnallvrytkkv<br>pqvstptlvevsrnlgkvgskcchhpeakrmpcaedylsvvlnqlcvlhektpvsdrvtkcccteslvnapc<br>fsalevdetyvpkefnaetftfhadictlsekerqikkqtalvelvkhkpkatkeqlkavmdclfaafvekcc<br>kaddketcfaeegkklvaasqaalglHHHHHHEPEA |
| 102 | ACP141 (IL-2 fusion protein) | mdmrvpaqllglllllwlrgarcaptssstkktqlqlehllldlqmilnginnyknpkltrmltfkfympkkat<br>elkhlqcleeelkpleevlnlaqsknfhlrprdlisninvivlelkgsettfmceyadetativeflnrwitfcqsi<br>istltggggsggggsggggsdahksevahrfkdlgeenfkalvliafaqylqqcpfedhvklvnevtefakt<br>cvadesaencdkslhtlfgdklctvatlretygemadccakqepernecflqhkddnpnlprlvrpevdvm<br>ctafhdneetflkkylyeiarrhpyfyapellfffakrykaafteccqaadkaacllpkldelrdegkassakqrl<br>kcaslqkfgerafkawavarlsqrfpkaefaevsklvtdltkvhtecchgdllecaddradlakyicenqdsi |

TABLE 4-continued

SEQUENCE TABLE

| SEQ ID NO. | Name | Sequence |
|---|---|---|
| | | ssklkeccekpllekshciaevendempadlpslaadfveskdvcknyaeakdvflgmflyeyarrhpdy svvlllrlaktyettlekccaaadphecyakvfdefkplveepqnlikqncelfeqlgeykfqnallvrytkkv pqvstptlvevsrnlgkvgskcckhpeakrmpcaedylsvvlnqlcvlhektpvsdrvtkccteslvnapc fsalevdetyvpkefnaetftfhadictlsekerqikkqtalvelvkhhkpkatkeqlkavmdclfaafvekcc kaddketcfaeegkklvaasqaalglHHHHHHEPEA |
| 103 | ACP142 (IL-2 fusion protein) | mdmrvpaqllglllllwlrgarcaptssstkktqlqlehllldlqmilnginnyknpkltrmltfkfympkkat elkhlqcleeeelkpleevlnlaqsknfhlrprdlisninvivlelkgsettfmceyadetativeflnrwitfcqsi istltSGGPGPAGMKGLPGSdahksevahrfkdlgeenfkalvliafaqylqqcpfedhvklvne vtefaktcvadesaencdkslhtlfgdklctvatlretygemadccakqepernecflqhkddnpnlprivr pevdvmctafhdneetflkkylyeiarrhpyfyapellffakrykaafteccqaadkaacllpkldelrdegk assakqrlkcaslqkfgerafkawavarlsqrfpkaefaevsklvtdltkvhtecchgdllecaddradlakyi cenqdsissklkeccekpllekshciaevendempadlpslaadfveskdvcknyaeakdvflgmflyey arrhpdysvvlllrlaktyettlekccaaadphecyakvfdefkplveepqnlikqncelfeqlgeykfqnall vrytkkvpqvstptlvevsrnlgkvgskcckhpeakrmpcaedylsvvlnqlcvlhektpvsdrvtkccte slvnapcfsalevdetyvpkefnaetftfhadictlsekerqikkqtalvelvkhhkpkatkeqlkavmdclfa afvekcckaddketcfaeegkklvaasqaalglHHHHHHEPEA |
| 104 | ACP144 (IL-2 fusion protein) | mdmrvpaqllglllllwlrgarcaptssstkktqlqlehllldlqmilnginnyknpkltrmltfkfympkkat elkhlqcleeeelkpleevlnlaqsknfhlrprdlisninvivlelkgsettfmceyadetativeflnrwitfcqsi istltSGGPGPAGMKGLPGSEVQLVESGGGLVQPGNSLRLSCAASGFTFS KFGMSWVRQAPGKGLEWVSSISGSGRDTLYAESVKGRFTISRDNAKT TLYLQMNSLRPEDTAVYYCTIGGSLSVSSQGTLVTVSSggggsggggsgggg sggggsggggsggggsSGGPGPAGMKGLPGSEVQLVESGGGLVQPGGSLRL SCAASGFTFSSYTLAWVRQAPGKGLEWVAAIDSSSYTYSPDTVRGRF TISRDNAKNSLYLQMNSLRAEDTAVYYCARDSNWDALDYWGQTT VTVSSGGGGSGGGGSGGGGSDIQMTQSPSSLSASVGDRVTITCKASQ NVGTNVGWYQQKPGKAPKALIYSASFRYSGVPSRFSGSGSGTDFTLTI SSLQPEDFATYYCQQYYTYPYTFGGGTKVEIKggggsggggsggggsQVQL QESGGGLAQAGGSLSLSCAASGFTVSNSVMAWYRQTPGKQREFVAII NSVGSTNYADSVKGRFTISRDNAKNTVYLQMNNLKPEDTAVYVCNR NFDRIYWGQGTQVTVSSHHHHHHEPEA |
| 105 | ACP145 (IL-2 fusion protein) | mdmrvpaqllglllllwlrgarcQVQLQESGGGLAQAGGSLSLSCAASGFTVSNSV MAWYRQTPGKQREFVAIINSVGSTNYADSVKGRFTISRDNAKNTVYL QMNNLKPEDTAVYVCNRNFDRIYWGQGTQVTVSSggggsggggsggggsap tssstkktqlqlehllldlqmilnginnyknpkltrmltfkfympkkatelkhlqcleeeelkpleevlnlaqsk nfhlrprdlisninvivlelkgsettfmceyadetativeflnrwitfcqsiistltSGGPGPAGMKGLP GSEVQLVESGGGLVQPGNSLRLSCAASGFTFSKFGMSWVRQAPGKGL EWVSSISGSGRDTLYAESVKGRFTISRDNAKTTLYLQMNSLRPEDTAV YYCTIGGSLSVSSQGTLVTVSSggggsggggsggggsggggsggggsggggsSGGP GPAGMKGLPGSEVQLVESGGGLVQPGGSLRLSCAASGFTFSSYTLAW VRQAPGKGLEWVAAIDSSSYTYSPDTVRGRFTISRDNAKNSLYLQMN SLRAEDTAVYYCARDSNWDALDYWGQGTTVTVSSGGGGSGGGGSG GGGSDIQMTQSPSSLSASVGDRVTITCKASQNVGTNVGWYQQKPGK APKALIYSASFRYSGVPSRFSGSGSGTDFTLTISSLQPEDFATYYCQQY YTYPYTFGGGTKVEIKHHHHHHEPEA |
| 106 | ACP146 (IL-2 fusion protein) | mdmrvpaqllglllllwlrgarcQVQLQESGGGLAQAGGSLSLSCAASGFTVSNSV MAWYRQTPGKQREFVAIINSVGSTNYADSVKGRFTISRDNAKNTVYL QMNNLKPEDTAVYVCNRNFDRIYWGQGTQVTVSSSGGPGPAGMKG LPGSaptssstkktqlqlehllldlqmilnginnyknpkltrmltfkfympkkatelkhlqcleeeelkplee vlnlaqsknfhlrprdlisninvivlelkgsettfmceyadetativeflnrwitfcqsiistltSGGPGPAGPAG MKGLPGSEVQLVESGGGLVQPGNSLRLSCAASGFTFSKFGMSWVRQ APGKGLEWVSSISGSGRDTLYAESVKGRFTISRDNAKTTLYLQMNSLR PEDTAVYYCTIGGSLSVSSQGTLVTVSSggggsggggsggggsggggsggggsggg gsSGGPGPAGMKGLPGSEVQLVESGGGLVQPGGSLRLSCAASGFTFSS YTLAWVRQAPGKGLEWVAAIDSSSYTYSPDTVRGRFTISRDNAKNSL YLQMNSLRAEDTAVYYCARDSNWDALDYWGQGTTVTVSSGGGGSG GGGSGGGGSDIQMTQSPSSLSASVGDRVTITCKASQNVGTNVGWYQ QKPGKAPKALIYSASFRYSGVPSRFSGSGSGTDFTLTISSLQPEDFATY YCQQYYTYPYTFGGGTKVEIKHHHHHHEPEA |
| 107 | ACP133 (IL-2-6xHis) ("6xHis" disclosed as SEQ ID NO: 136) | mdmrvpaqllglllllwlrgarcaptssstkktqlqlehllldlqmilnginnyknpkltrmltikfympkkat elkhlqcleeeelkpleevinlaqsknfhlrprdlisninvivlelkgsettfmceyadetativeflnrwitfcqsi istltHHHHHH |

TABLE 4-continued

SEQUENCE TABLE

| SEQ ID NO. | Name | Sequence |
|---|---|---|
| 108 | ACP147 (IL-2 fusion protein) | mdmrvpaqllglllllwlrgarcaptssstkktqlqlehllldlqmilnginnyknpkltrmltttkfympkkat elkhlqcleeelkpleevlnlaqsknfhlrprdlisninvivlelkgsettfmceyadetativeflnrwitfcqsi istltSGGPGPAGMKGLPGSEVQLVESGGGLVQPGNSLRLSCAASGFTFS KFGMSWVRQAPGKGLEWVSSISGSGRDTLYAESVKGRFTISRDNAKT TLYLQMNSLRPEDTAVYYCTIGGSLSVSSQGTLVTVSSggggsggggsggggs sggggsggggsggggsSGGPGPAGMKGLPGSEVQLVESGGGLVQPGGSLRL SCAASGFTFSSYTLAWVRQAPGKGLEWVAAIDSSSYTYSPDTVRGRF TISRDNAKNSLYLQMNSLRAEDTAVYYCARDSNWDALDYWGQGTT VTVSSGGGGSGGGGSGGGGSDIQMTQSPSSLSASVGDRVTITCKASQ NVGTNVGWYQQKPGKAPKALIYSASFRYSGVPSRFSGSGSGTDFTLTI SSLQPEDFATYYCQQYYTYPYTFGGGTKVEIKggggsggggsggggsQVQL QESGGGLVQAGGSLRLSCAASGRIFSIDIMSWYRQAPGKQRELVARIT RGGTISYDDSVKGRFTISRDNAKNTVYLQMNSLKPEDTGVYYCNALY GTDYWGKGTQVTVSSHHHHHHEPEA |
| 109 | ACP148 (IL-2 fusion protein) | mdmrvpaqllglllllwlrgarcQVQLQESGGGLVQAGGSLRLSCAASGRIFSIDI MSWYRQAPGKQRELVARITRGGTISYDDSVKGRFTISRDNAKNTVYL QMNSLKPEDTGVYYCNALYGTDYWGKGTQVTVSSggggsggggsggggsa ptssstkktqlqlehllldlqmilnginnyknpkltrmltfkfympkkatelkhlqcleeelkpleevlnlaqs knfhlrprdlisninvivlelkgsettfmceyadetativeflnrwitfcqsiistltSGGPGPAGMKGL PGSEVQLVESGGGLVQPGNSLRLSCAASGFTFSKFGMSWVRQAPGKG LEWVSSISGSGRDTLYAESVKGRFTISRDNAKTTLYLQMNSLRPEDTA VYYCTIGGSLSVSSQGTLVTVSSggggsggggsggggsggggsggggsggggsSGG PGPAGMKGLPGSEVQLVESGGGLVQPGGSLRLSCAASGFTFSSYTLA WVRQAPGKGLEWVAAIDSSSYTYSPDTVRGRFTISRDNAKNSLYLQM NSLRAEDTAVYYCARDSNWDALDYWGQGTTVTVSSGGGGSGGGGS GGGGSDIQMTQSPSSLSASVGDRVTITCKASQNVGTNVGWYQQKPG KAPKALIYSASFRYSGVPSRFSGSGSGTDFTLTISSLQPEDFATYYCQQ YYTYPYTFGGGTKVEIKHHHHHHEPEA |
| 110 | ACP149 (IL-2 fusion protein) | mdmrvpaqllglllllwlrgarcQVQLQESGGGLVQAGGSLRLSCAASGRIFSIDI MSWYRQAPGKQRELVARITRGGTISYDDSVKGRFTISRDNAKNTVYL QMNSLKPEDTGVYYCNALYGTDYWGKGTQVTVSSSGGPGPAGMKG LPGSaptssstkktqlqlehllldlqmilnginnyknpkltrmltfkfympkkatelkhlqcleeelkplee vlnlaqsknfhlrprdlisninvivlelkgsettfmceyadetativeflnrwitfcqsiistltSGGPGPAG MKGLPGSEVQLVESGGGLVQPGNSLRLSCAASGFTFSKFGMSWVRQ APGKGLEWVSSISGSGRDTLYAESVKGRFTISRDNAKTTLYLQMNSLR PEDTAVYYCTIGGSLSVSSQGTLVTVSSggggsggggsggggsggggsggggsggg gsSGGPGPAGMKGLPGSEVQLVESGGGLVQPGGSLRLSCAASGFTFSS YTLAWVRQAPGKGLEWVAAIDSSSYTYSPDTVRGRFTISRDNAKNSL YLQMNSLRAEDTAVYYCARDSNWDALDYWGQGTTVTVSSGGGGSG GGGSGGGGSDIQMTQSPSSLSASVGDRVTITCKASQNVGTNVGWYQ QKPGKAPKALIYSASFRYSGVPSRFSGSGSGTDFTLTISSLQPEDFATY YCQQYYTYPYTFGGGTKVEIKHHHHHHEPEA |
| 111 | ACP153 (IL-2 Conjugate) | mdmrvpaqllglllllwlrgarcaptssstkktqlqlehllldlqmilnginnyknpkltrmltfkfympkkat elkhlqcleeelkpleevlnlaqsknfhlrprdlisninvivlelkgsettfmceyadetativeflnrwitfcqsi istltsggpGPAGLYAQpgsEVQLVESGGGLVQPGNSLRLSCAASGFTFSKF GMSWVRQAPGKGLEWVSSISGSGRDTLYAESVKGRFTISRDNAKTTL YLQMNSLRPEDTAVYYCTIGGSLSVSSQGTLVTVSSggggsggggsggggsg gggsggggsggggsggggssgpGPAGLYAQpgsEVQLVESGGGLVQPGGSLRLSCAA SGFTFSSYTLAWVRQAPGKGLEWVAAIDSSSYTYSPDTVRGRFTISRD NAKNSLYLQMNSLRAEDTAVYYCARDSNWDALDYWGQGTTVTVSS GGGGSGGGGSGGGGSDIQMTQSPSSLSASVGDRVTITCKASQNVGTN VGWYQQKPGKAPKALIYSASFRYSGVPSRFSGSGSGTDFTLTISSLQPE DFATYYCQQYYTYPYTFGGGTKVEIKHHHHHHEPEA |
| 112 | ACP154 (IL-2 Conjugate) | mdmrvpaqllglllllwlrgarcaptssstkktqlqlehllldlqmilnginnyknpkltrmltfkfympkkat elkhlqcleeelkpleevlnlaqsknfhlrprdlisninvivlelkgsettfmceyadetativeflnrwitfcqsi istltsggpPGGPAGIGpgsEVQLVESGGGLVQPGNSLRLSCAASGFTFSKFG MSWVRQAPGKGLEWVSSISGSGRDTLYAESVKGRFTISRDNAKTTLY LQMNSLRPEDTAVYYCTIGGSLSVSSQGTLVTVSSggggsggggsggggsggg gsggggsggggsggggssgpPGGPAGIGpgsEVQLVESGGGLVQPGGSLRLSCAASG FTFSSYTLAWVRQAPGKGLEWVAAIDSSSYTYSPDTVRGRFTISRDNA KNSLYLQMNSLRAEDTAVYYCARDSNWDALDYWGQGTTVTVSSGG GGSGGGGSGGGGSDIQMTQSPSSLSASVGDRVTITCKASQNVGTNVG WYQQKPGKAPKALIYSASFRYSGVPSRFSGSGSGTDFTLTISSLQPEDF ATYYCQQYYTYPYTFGGGTKVEIKHHHHHHEPEA |
| 113 | ACP155 (IL-2 Conjugate) | mdmrvpaqllglllllwlrgarcaptssstkktqlqlehllldlqmilnginnyknpkltrmltfkfympkkat elkhlqcleeelkpleevlnlaqsknfhlrprdlisninvivlelkgsettfmceyadetativeflnrwitfcqsi istltsggpALFKSSFPpgsEVQLVESGGGLVQPGNSLRLSCAASGFTFSKFG MSWVRQAPGKGLEWVSSISGSGRDTLYAESVKGRFTISRDNAKTTLY |

TABLE 4-continued

SEQUENCE TABLE

| SEQ ID NO. | Name | Sequence |
|---|---|---|
| | | LQMNSLRPEDTAVYYCTIGGSLSVSSQGTLVTVSSggggsggggsggggsggg<br>gsggggsggggssggpALFKSSFPpgsEVQLVESGGGLVQPGGSLRLSCAASG<br>FTFSSYTLAWVRQAPGKGLEWVAAIDSSSYTYSPDTVRGRFTISRDNA<br>KNSLYLQMNSLRAEDTAVYYCARDSNWDALDYWGQGTTVTVSSGG<br>GGSGGGGSGGGGSDIQMTQSPSSLSASVGDRVTITCKASQNVGTNVG<br>WYQQKPGKAPKALIYSASFRYSGVPSRFSGSGSGTDFTLTISSLQPEDF<br>ATYYCQQYYTYPYTFGGGTKVEIKHHHHHHEPEA |
| 114 | ACP156<br>(IL-2<br>Conjugate) | mdmrvpaqllglllllwlrgarcaptsssstkktqlqlehllldlqmilnginnyknpkltrmltfkfympkkat<br>elkhlqcleeelkpleevlnlaqsknfhlrprdlisninvivlelkgsettfmceyadetativeflnrwitfcqsi<br>istltsggpPLAQKLKSSpgsEVQLVESGGGLVQPGNSLRLSCAASGFTFSKF<br>GMSWVRQAPGKGLEWVSSISGSGRDTLYAESVKGRFTISRDNAKTTL<br>YLQMNSLRPEDTAVYYCTIGGSLSVSSQGTLVTVSSggggsggggsggggsg<br>gggsggggsggggssggpPLAQKLKSSpgsEVQLVESGGGLVQPGGSLRLSCA<br>ASGFTFSSYTLAWVRQAPGKGLEWVAAIDSSSYTYSPDTVRGRFTISR<br>DNAKNSLYLQMNSLRAEDTAVYYCARDSNWDALDYWGQGTTVTVS<br>SGGGGSGGGGSGGGGSDIQMTQSPSSLSASVGDRVTITCKASQNVGT<br>NVGWYQQKPGKAPKALIYSASFRYSGVPSRFSGSGSGTDFTLTISSLQ<br>PEDFATYYCQQYYTYPYTFGGGTKVEIKHHHHHHEPEA |
| 115 | ACP157<br>(IL-2<br>Conjugate) | mdmrvpaqllglllllwlrgarcaptsssstkktqlqlehllldlqmilnginnyknpkltrmltfkfympkkat<br>elkhlqcleeelkpleevlnlaqsknfhlrprdlisninvivlelkgsettfmceyadetativeflnrwitfcqsi<br>istltsggpPGGPAGIGalfkssfpPLAQKLKSSpgsEVQLVESGGGLVQPGNSL<br>RLSCAASGFTFSKFGMSWVRQAPGKGLEWVSSISGSGRDTLYAESVK<br>GRFTISRDNAKTTLYLQMNSLRPEDTAVYYCTIGGSLSVSSQGTLVTV<br>SSggggsggggsggggsggggsggggsggggssggpPGGPAGIGalfkssfpPLAQKLKS<br>SpgsEVQLVESGGGLVQPGGSLRLSCAASGFTFSSYTLAWVRQAPGKG<br>LEWVAAIDSSSYTYSPDTVRGRFTISRDNAKNSLYLQMNSLRAEDTA<br>VYYCARDSNWDALDYWGQGTTVTVSSGGGGSGGGGSGGGGSDIQM<br>TQSPSSLSASVGDRVTITCKASQNVGTNVGWYQQKPGKAPKALIYSA<br>SFRYSGVPSRFSGSGSGTDFTLTISSLQPEDFATYYCQQYYTYPYTFGG<br>GTKVEIKHHHHHHEPEA |
| 116 | EGFR<br>(G8)<br>Prodrug<br>C1486 | EVQLVESGGGLVQPGNSLRLSCAASGFTFSKFGMSWVRQ<u>GGGGGLD</u><br><u>GNEEPGG</u>LEWVSSISGSGRDTLYADSVKGRFTISRDNAKTTLYLQMN<br>SLRPEDTAVYYCTIGGSLSVSSQGTLVTVSS<u>GGGGKPLGLQARV</u>VGG<br><u>GGT</u>QTVVTQEPSLTVSPGGTVTLTCASSTGAVTSGNYPNWVQQKPGQ<br>APRGLIGGTKFLVPGTPARFSGSLLGGKAALTLSGVQPEDEAEYYCTL<br>WYSNRWVFGGGTKLTVLGGGGSGGGGSGGGGSEVQLVESGGGLVQ<br>PGGSLKLSCAASGFTFNKYAINWVRQAPGKGLEWVARIRSKYNNYA<br>TYYADQVKDRFTISRDDSKNTAYLQMNNLKTEDTAVYYCVRHANFG<br>NSYISYWAYWGQGTLVTVSSGGGGSGGGS*EVQLVESGGGLVQPGGSL*<br>*TLSCAASGRTESSYAMGWERQAPGKEREFVVAINWASGSTYYADSVKGRFT*<br>*ISRDNSKNTLYLQMNSLRAEDTAVYYCAAGYQINSGNYNEKDYEYDWGQ*<br>*GTLVTVSSHHHHHH* |
| 117 | EGFR<br>(G8) Non-<br>cleavable<br>Prodrug<br>C1756 | EVQLVESGGGLVQPGNSLRLSCAASGFTFSKFGMSWVRQ<u>GGGGGLD</u><br><u>GNEEPGG</u>LEWVSSISGSGRDTLYADSVKGRFTISRDNAKTTLYLQMN<br>SLRPEDTAVYYCTIGGSLSVSSQGTLVTVSSGGGGSGGGGSGGVVGG<br><u>GGT</u>QTVVTQEPSLTVSPGGTVTLTCASSTGAVTSGNYPNWVQQKPGQ<br>APRGLIGGTKFLVPGTPARFSGSLLGGKAALTLSGVQPEDEAEYYCTL<br>WYSNRWVFGGGTKLTVLGGGGSGGGGSGGGGSEVQLVESGGGLVQ<br>PGGSLKLSCAASGFTFNKYAINWVRQAPGKGLEWVARIRSKYNNYA<br>TYYADQVKDRFTISRDDSKNTAYLQMNNLKTEDTAVYYCVRHANFG<br>NSYISYWAYWGQGTLVTVSSGGGGSGGGS*EVQLVESGGGLVQPGGSL*<br>*TLSCAASGRTESSYAMGWERQAPGKEREFVVAINWASGSTYYADSVKGRFT*<br>*ISRDNSKNTLYLQMNSLRAEDTAVYYCAAGYQINSGNYNEKDYEYDWGQ*<br>*GTLVTVSSHHHHHH* |
| 118 | EGFR<br>(G8)<br>Active<br>Drug<br>C1300 | <u>VVGGGGT</u>QTVVTQEPSLTVSPGGTVTLTCASSTGAVTSGNYPNWVQ<br>QKPGQAPRGLIGGTKFLVPGTPARFSGSLLGGKAALTLSGVQPEDEAE<br>YYCTLWYSNRWVFGGGTKLTVLGGGGSGGGGSGGGGSEVQLVESG<br>GGLVQPGGSLKLSCAASGFTFNKYAINWVRQAPGKGLEWVARIRSK<br>YNNYATYYADQVKDRFTISRDDSKNTAYLQMNNLKTEDTAVYYCV<br>RHANFGNSYISYWAYWGQGTLVTVSSGGGGSGGGS*EVQLVESGGGLV*<br>*QPGGSLTLSCAASGRTFSSYAMGWFRQAPGKEREFVVAINWASGSTYYAD*<br>*SVKGRFTISRDNSKNTLYLQMNSLRAEDTAVYYCAAGYQINSGNYNEKDYE*<br>*YDYWGQGTLVTVSSHHHHHH* |
| 119 | PSMA<br>Prodrug<br>C1872 | EVQLVESGGGLVQPGNSLRLSCAASGFTFSKFGMSWVRQ<u>GGGGGLD</u><br><u>GNEEPGG</u>LEWVSSISGSGRDTLYADSVKGRFTISRDNAKTTLYLQMN<br>SLRPEDTAVYYCTIGGSLSVSSQGTLVTVSS<u>GGGGKPLGLQARV</u>VGG<br><u>GGT</u>QTVVTQEPSLTVSPGGTVTLTCASSTGAVTSGNYPNWVQQKPGQ<br>APRGLIGGTKFLVPGTPARFSGSLLGGKAALTLSGVQPEDEAEYYCTL |

TABLE 4-continued

SEQUENCE TABLE

| SEQ ID NO. | Name | Sequence |
|---|---|---|
| | | WYSNRWVFGGGTKLTVLGGGGSGGGGSGGGGSEVQLVESGGGLVQ<br>PGGSLKLSCAASGFTFNKYAINWVRQAPGKGLEWVARIRSKYNNYA<br>TYYADQVKDRFTISRDDSKNTAYLQMNNLKTEDTAVYYCVRHANFG<br>NSYISYWAYWGQGTLVTVSSGGGGSGGGS*EVQLVESGGGLVQPGGSL*<br>*TLSCAASREVIISEYHMHWVRQAPGKGLEWVSTINPAGIIDYAESVKGRFTI*<br>*SRDNAKNTLYLQMNSLKPEDTAVYYCDSYGYRGQGTQVTVSS*HHHHHH |
| 120 | PSMA Non-cleavable Prodrug C1873 | EVQLVESGGGLVQPGNSLRLSCAASGFTFSKFGMSWVRQ<u>GGGGGLD</u><br><u>GNEEPGG</u>LEWVSSISGSGRDTLYADSVKGRFTISRDNAKTTLYLQMN<br>SLRPEDTAVYYCTIGGSLSVSSQGTLVTVSS<u>GGGGSGGGGSGGVVGG</u><br><u>GGT</u>QTVVTQEPSLTVSPGGTVTLTCASSTGAVTSGNYPNWVQQKPGQ<br>APRGLIGGTKFLVPGTPARFSGSLLGGKAALTLSGVQPEDEAEYYCTL<br>WYSNRWVFGGGTKLTVLGGGGSGGGGSGGGGSEVQLVESGGGLVQ<br>PGGSLKLSCAASGFTFNKYAINWVRQAPGKGLEWVARIRSKYNNYA<br>TYYADQVKDRFTISRDDSKNTAYLQMNNLKTEDTAVYYCVRHANFG<br>NSYISYWAYWGQGTLVTVSSGGGGSGGGS*EVQLVESGGGLVQPGGSL*<br>*TLSCAASREVIISEYHMHWVRQAPGKGLEWVSTINPAGTTDYAESVKGRFTI*<br>*SRDNAKNTLYLQMNSLKPEDTAVYYCDSYGYRGQGTQVTVSS*HHHHHH |
| 121 | PSMA Active Drug C1875 | <u>VVGGGGT</u>QTVVTQEPSLTVSPGGTVTLTCASSTGAVTSGNYPNWVQ<br>QKPGQAPRGLIGGTKFLVPGTPARFSGSLLGGKAALTLSGVQPEDEAE<br>YYCTLWYSNRWVFGGGTKLTVLGGGGSGGGGSGGGGSEVQLVESG<br>GGLVQPGGSLKLSCAASGFTFNKYAINWVRQAPGKGLEWVARIRSK<br>YNNYATYYADQVKDRFTISRDDSKNTAYLQMNNLKTEDTAVYYCV<br>RHANFGNSYISYWAYWGQGTLVTVSSGGGGSGGGS*EVQLVESGGGLV*<br>*QPGGSLTLSCAASRFMISEYHMHWVRQAPGKGLEWVSTINPAGTTDYAES*<br>*VKGRFTISRDNAKNTLYLQMNSLKPEDTAVYYCDSYGYRGQGTQVTVSS*H<br>HHHHH |
| 122 | GFP TriTAC C646 | *QVQLVESGGALVQPGGSLRLSCAASGFPVNRYSMRWYRQAPGKEREWVA*<br>*GMSSAGDRSSYEDSVKGRFTISRDDARNTVYLQMNSLKPEDTAVYYCNVN*<br>*VGFEYWGQGTQVTVSS*GGGGSGGGSEVQLVESGGGLVQPGNSLRLSC<br>AASGFTFSKFGMSWVRQAPGKGLEWVSSISGSGRDTLYADSVKGRFT<br>ISRDNAKTTLYLQMNSLRPEDTAVYYCTIGGSLSVSSQGTLVTVSSGG<br>GGSGGGGSEVQLVESGGGLVQPGGSLKLSCAASGFTFNKYAINWVRQ<br>APGKGLEWVARIRSKYNNYATYYADQVKDRFTISRDDSKNTAYLQM<br>NNLKTEDTAVYYCVRHANFGNSYISYWAYWGQGTLVTVSSGGGGS<br>GGGGSGGGGSQTVVTQEPSLTVSPGGTVTLTCASSTGAVTSGNYPNW<br>VQQKPGQAPRGLIGGTKFLVPGTPARFSGSLLGGKAALTLSGVQPEDE<br>AEYYCTLWYSNRWVFGGGTKLTVLHHHHHH |
| 123 | non-masked/non-cleavable TriTAC C1874 | EVQLVESGGGLVQPGNSLRLSCAASGFTFSKFGMSWVRQAPGKGLE<br>WVSSISGSGRDTLYADSVKGRFTISRDNAKTTLYLQMNSLRPEDTAV<br>YYCTIGGSLSVSSQGTLVTVSSGGGGSGGGGSGGVVGGGGTQTVTQ<br>EPSLTVSPGGTVTLTCASSTGAVTSGNYPNWVQQKPGQAPRGLIGGT<br>KFLVPGTPARFSGSLLGGKAALTLSGVQPEDEAEYYCTLWYSNRWVF<br>GGGTKLTVLGGGGSGGGGSGGGGSEVQLVESGGGLVQPGGSLKLSC<br>AASGFTFNKYAINWVRQAPGKGLEWVARIRSKYNNYATYYADQVK<br>DRFTISRDDSKNTAYLQMNNLKTEDTAVYYCVRHANFGNSYISYWA<br>YWGQGTLVTVSSGGGGSGGGSEVQLVESGGGLVQPGGSLTLSCAAS<br>RFMISEYHMHWVRQAPGKGLEWVSTINPAGTTDYAESVKGRFTISRD<br>NAKNTLYLQMNSLKPEDTAVYYCDSYGYRGQGTQVTVSSHHHHHH |
| 124 | Blocker 2 (IL-2 blocker) | mdmrvpaqllglllllwlrgarcEVQLVESGGGLVQPGGSLRLSCAASGFTFSSYT<br>LAWVRQAPGKGLEWVAAIDSSSYTYSPDTVRGRFTISRDNAKNSLYL<br>QMNSLRAEDTAVYYCARDSNWDALDYWGQGTTVTVSSggggsggggsg<br>gggsDIQMTQSPSSLSASVGDRVTITCKASQNVGTNVGWYQQKPGKAP<br>KALIYSASFRYSGVPSRFSGSGSGTDFTLTISSLQPEDFATYYCQQYYT<br>YPYTFGGGTKVEIKHHHHHH |

INCORPORATION BY REFERENCE

The entire disclosures of all patent and non-patent publications cited herein are each incorporated by reference in their entireties for all purposes.

OTHER EMBODIMENTS

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

The invention claimed is:

1. A pharmaceutical composition comprising at least one of each of:
   a) a human interleukin 2 (IL-2) polypeptide [A];
   b) a half-life extension element [B], wherein the half-life extension element is human serum albumin, an antigen-binding polypeptide that binds human serum albumin, or an immunoglobulin Fc;
   c) an IL-2 blocking moiety [D], wherein the IL-2 blocking moiety comprises a ligand-binding domain or fragment of a cognate receptor for the IL-2 polypeptide, an antibody or antigen-binding fragment of an antibody that binds the IL-2 polypeptide; and
   d) a protease-cleavable polypeptide linker [L];
   wherein the IL-2 polypeptide and the IL-2 blocking moiety are operably linked by the protease-cleavable polypeptide linker and the IL-2 polypeptide has attenuated IL-2-receptor activating activity at least about 10 fold less than the IL-2-receptor activating activity of the polypeptide that comprises the IL-2 polypeptide that is produced by cleavage of the protease-cleavable polypeptide linker, and wherein the IL-2 receptor activating activity is assessed using a CTLL-2 proliferation assay, a phospho STAT ELISA, or HEK Blue reporter cell assay and using equal amounts, on a mole basis, of the IL-2 polypeptide and the pharmaceutical composition.

2. The pharmaceutical composition of claim 1, wherein the serum half-life of the IL-2 polypeptide that is produced by cleavage of the protease-cleavable polypeptide linker is comparable to the half-life of naturally occurring IL-2.

3. The pharmaceutical composition of claim 1, wherein the IL-2 polypeptide comprises an IL-2 variant or mutein.

4. The pharmaceutical composition of claim 1, further comprising a tumor-specific antigen binding peptide, wherein the tumor-specific antigen binding peptide is linked to any one of [A], [B], or [D] by a cleavable linker.

5. The pharmaceutical composition of claim 4, wherein the tumor-specific antigen binding peptide is linked to the IL-2 polypeptide by a non-cleavable linker and wherein the IL-2 polypeptide is linked to the half-life extension element or the IL-2 blocking moiety by a cleavable linker.

6. The pharmaceutical composition of claim 1, comprising a plurality of protease-cleavable polypeptide linkers, wherein each protease-cleavable polypeptide linker independently comprises at least one sequence that is capable of being cleaved by a protease selected from the group consisting of a kallikrein, thrombin, chymase, carboxypeptidase A, cathepsin G, cathepsin L, an elastase, PR-3, granzyme M, a calpain, a matrix metalloproteinase (MMP), a fibroblast activation protein (FAP), an ADAM metalloproteinase, a plasminogen activator, a cathepsin, a caspase, a tryptase, and a tumor cell surface protease.

7. The pharmaceutical composition of claim 1, wherein IL-2 blocking moiety inhibits activation of the IL-2 receptor by the human IL-2 polypeptide.

8. The pharmaceutical composition of claim 1, wherein the antibody fragment that binds to the IL-2 polypeptide is a single domain antibody, Fab or scFv.

9. The pharmaceutical composition of claim 1, wherein the IL-2 polypeptide comprises a naturally-occurring IL-2 polypeptide sequence or a functional fragment thereof.

10. The pharmaceutical composition of claim 1, wherein the protease cleavable polypeptide linker comprises a sequence that is cleaved by cathepsin selected from the group consisting of cathepsin B, cathepsin C, cathepsin D, cathepsin E, cathepsin K, cathepsin L, and cathepsin G.

11. The pharmaceutical composition of claim 1, wherein the protease cleavable polypeptide linker comprises a sequence that is cleaved by a matrix metalloprotease (MMP) selected from the group consisting of MMP1, MMP2, MMP3, MMP8, MMP9, MMP10, MMP11, MMP12, MMP13, and MMP14.

12. The pharmaceutical composition of claim 1, wherein the IL-2 polypeptide that is produced by cleavage of the protease-cleavable polypeptide linker does not comprise the half-life extension element or IL-2 blocking moiety.

13. The pharmaceutical composition of claim 1, wherein the cognate receptor for the IL-2 is a alpha chain of the IL-2 receptor (IL-2Rα), beta chain of the IL-2 receptor (IL-2Rβ) or the gamma chain of the IL-2 receptor (IL-2Rγ).

* * * * *

SEQUENCE LISTING

```
<160> NUMBER OF SEQ ID NOS: 137

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150

<210> SEQ ID NO 2
<211> LENGTH: 609
<212> TYPE: PRT
<213> ORGANISM: Homo sapiens

<400> SEQUENCE: 2

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
```

```
                100             105             110
Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
            130                 135             140

Asp Val Met Cys Thr Ala Phe His Asp Asn Glu Thr Phe Leu Lys
145             150                 155                     160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Gly Leu Lys Cys
            210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
                275                 280                 285

Cys Glu Asn Gln Asp Ser Ile Ser Ser Lys Leu Lys Glu Cys Cys Glu
            290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Gly Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
            370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Cys Leu Ser Val Phe
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Gly Arg Pro Cys Phe
                500                 505                 510

Ser Ala Leu Glu Val Asp Glu Thr Tyr Val Pro Lys Glu Phe Asn Ala
            515                 520                 525
```

```
Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 3
<211> LENGTH: 8
<212> TYPE: PRT
<213> ORGANISM: Unknown
<220> FEATURE:
<223> OTHER INFORMATION: Description of Unknown:
      MMP7 cleavage domain sequence

<400> SEQUENCE: 3

Lys Arg Ala Leu Gly Leu Pro Gly
1               5

<210> SEQ ID NO 4
<211> LENGTH: 40
<212> TYPE: PRT
<213> ORGANISM: Unknown
<220> FEATURE:
<223> OTHER INFORMATION: Description of Unknown:
      MMP7 cleavage domain sequence

<400> SEQUENCE: 4

Asp Glu Asp Glu Asp Glu Asp Glu Asp Glu Asp Glu Asp Glu Asp Glu
1               5                   10                  15

Arg Pro Leu Ala Leu Trp Arg Ser Asp Arg Asp Arg Asp Arg Asp Arg
            20                  25                  30

Asp Arg Asp Arg Asp Arg Asp Arg
            35                  40

<210> SEQ ID NO 5
<211> LENGTH: 5
<212> TYPE: PRT
<213> ORGANISM: Unknown
<220> FEATURE:
<223> OTHER INFORMATION: Description of Unknown:
      MMP9 cleavage domain sequence
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Ile or Leu
<220> FEATURE:
<221> NAME/KEY: MOD_RES
<222> LOCATION: (5)..(5)
<223> OTHER INFORMATION: Ser or Thr

<400> SEQUENCE: 5

Pro Arg Xaa Xaa Xaa
1               5
```

-continued

```
<210> SEQ ID NO 6
<211> LENGTH: 5
<212> TYPE: PRT
<213> ORGANISM: Unknown
<220> FEATURE:
<223> OTHER INFORMATION: Description of Unknown:
      MMP9 cleavage domain sequence

<400> SEQUENCE: 6

Leu Glu Ala Thr Ala
1               5

<210> SEQ ID NO 7
<211> LENGTH: 10
<212> TYPE: PRT
<213> ORGANISM: Unknown
<220> FEATURE:
<223> OTHER INFORMATION: Description of Unknown:
      MMP11 cleavage domain sequence

<400> SEQUENCE: 7

Gly Gly Ala Ala Asn Leu Val Arg Gly Gly
1               5                   10

<210> SEQ ID NO 8
<211> LENGTH: 10
<212> TYPE: PRT
<213> ORGANISM: Unknown
<220> FEATURE:
<223> OTHER INFORMATION: Description of Unknown:
      MMP14 cleavage domain sequence

<400> SEQUENCE: 8

Ser Gly Arg Ile Gly Phe Leu Arg Thr Ala
1               5                   10

<210> SEQ ID NO 9
<211> LENGTH: 6
<212> TYPE: PRT
<213> ORGANISM: Unknown
<220> FEATURE:
<223> OTHER INFORMATION: Description of Unknown:
      MMP cleavage domain sequence

<400> SEQUENCE: 9

Pro Leu Gly Leu Ala Gly
1               5

<210> SEQ ID NO 10
<211> LENGTH: 6
<212> TYPE: PRT
<213> ORGANISM: Unknown
<220> FEATURE:
<223> OTHER INFORMATION: Description of Unknown:
      MMP cleavage domain sequence
<220> FEATURE:
<221> NAME/KEY: MOD_RES
<222> LOCATION: (6)..(6)
<223> OTHER INFORMATION: Any amino acid

<400> SEQUENCE: 10

Pro Leu Gly Leu Ala Xaa
1               5

<210> SEQ ID NO 11
<211> LENGTH: 6
<212> TYPE: PRT
<213> ORGANISM: Unknown
<220> FEATURE:
```

```
<223> OTHER INFORMATION: Description of Unknown:
      MMP cleavage domain sequence
<220> FEATURE:
<221> NAME/KEY: MOD_RES
<222> LOCATION: (4)..(4)
<223> OTHER INFORMATION: Cys(me)

<400> SEQUENCE: 11

Pro Leu Gly Cys Ala Gly
1               5

<210> SEQ ID NO 12
<211> LENGTH: 8
<212> TYPE: PRT
<213> ORGANISM: Unknown
<220> FEATURE:
<223> OTHER INFORMATION: Description of Unknown:
      MMP cleavage domain sequence

<400> SEQUENCE: 12

Glu Ser Pro Ala Tyr Tyr Thr Ala
1               5

<210> SEQ ID NO 13
<211> LENGTH: 6
<212> TYPE: PRT
<213> ORGANISM: Unknown
<220> FEATURE:
<223> OTHER INFORMATION: Description of Unknown:
      MMP cleavage domain sequence

<400> SEQUENCE: 13

Arg Leu Gln Leu Lys Leu
1               5

<210> SEQ ID NO 14
<211> LENGTH: 7
<212> TYPE: PRT
<213> ORGANISM: Unknown
<220> FEATURE:
<223> OTHER INFORMATION: Description of Unknown:
      MMP cleavage domain sequence

<400> SEQUENCE: 14

Arg Leu Gln Leu Lys Ala Cys
1               5

<210> SEQ ID NO 15
<211> LENGTH: 7
<212> TYPE: PRT
<213> ORGANISM: Unknown
<220> FEATURE:
<223> OTHER INFORMATION: Description of Unknown:
      MMP2, MMP9, MMP14 cleavage domain sequence
<220> FEATURE:
<221> NAME/KEY: MOD_RES
<222> LOCATION: (3)..(3)
<223> OTHER INFORMATION: Cit
<220> FEATURE:
<221> NAME/KEY: MOD_RES
<222> LOCATION: (5)..(5)
<223> OTHER INFORMATION: Hof

<400> SEQUENCE: 15

Glu Pro Xaa Gly Xaa Tyr Leu
1               5

<210> SEQ ID NO 16
<211> LENGTH: 5
```

```
<212> TYPE: PRT
<213> ORGANISM: Unknown
<220> FEATURE:
<223> OTHER INFORMATION: Description of Unknown:
      Urokinase plasminogen activator (uPA) cleavage domain
      sequence

<400> SEQUENCE: 16

Ser Gly Arg Ser Ala
1               5

<210> SEQ ID NO 17
<211> LENGTH: 4
<212> TYPE: PRT
<213> ORGANISM: Unknown
<220> FEATURE:
<223> OTHER INFORMATION: Description of Unknown:
      Urokinase plasminogen activator (uPA) cleavage domain
      sequence

<400> SEQUENCE: 17

Asp Ala Phe Lys
1

<210> SEQ ID NO 18
<211> LENGTH: 5
<212> TYPE: PRT
<213> ORGANISM: Unknown
<220> FEATURE:
<223> OTHER INFORMATION: Description of Unknown:
      Urokinase plasminogen activator (uPA) cleavage domain
      sequence

<400> SEQUENCE: 18

Gly Gly Gly Arg Arg
1               5

<210> SEQ ID NO 19
<211> LENGTH: 4
<212> TYPE: PRT
<213> ORGANISM: Unknown
<220> FEATURE:
<223> OTHER INFORMATION: Description of Unknown:
      Lysosomal Enzyme cleavage domain sequence

<400> SEQUENCE: 19

Gly Phe Leu Gly
1

<210> SEQ ID NO 20
<211> LENGTH: 4
<212> TYPE: PRT
<213> ORGANISM: Unknown
<220> FEATURE:
<223> OTHER INFORMATION: Description of Unknown:
      Lysosomal Enzyme cleavage domain sequence

<400> SEQUENCE: 20

Ala Leu Ala Leu
1

<210> SEQ ID NO 21
<211> LENGTH: 2
<212> TYPE: PRT
<213> ORGANISM: Unknown
<220> FEATURE:
<223> OTHER INFORMATION: Description of Unknown:
      Lysosomal Enzyme cleavage domain sequence
```

```
<400> SEQUENCE: 21

Phe Lys
1

<210> SEQ ID NO 22
<211> LENGTH: 3
<212> TYPE: PRT
<213> ORGANISM: Unknown
<220> FEATURE:
<223> OTHER INFORMATION: Description of Unknown:
      Cathepsin B cleavage domain sequence

<400> SEQUENCE: 22

Asn Leu Leu
1

<210> SEQ ID NO 23
<211> LENGTH: 5
<212> TYPE: PRT
<213> ORGANISM: Unknown
<220> FEATURE:
<223> OTHER INFORMATION: Description of Unknown:
      Cathepsin D cleavage domain sequence
<220> FEATURE:
<221> NAME/KEY: MOD_RES
<222> LOCATION: (3)..(3)
<223> OTHER INFORMATION: Cys(et)

<400> SEQUENCE: 23

Pro Ile Cys Phe Phe
1               5

<210> SEQ ID NO 24
<211> LENGTH: 8
<212> TYPE: PRT
<213> ORGANISM: Unknown
<220> FEATURE:
<223> OTHER INFORMATION: Description of Unknown:
      Cathepsin K cleavage domain sequence

<400> SEQUENCE: 24

Gly Gly Pro Arg Gly Leu Pro Gly
1               5

<210> SEQ ID NO 25
<211> LENGTH: 6
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 25

His Ser Ser Lys Leu Gln
1               5

<210> SEQ ID NO 26
<211> LENGTH: 7
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 26

His Ser Ser Lys Leu Gln Leu
1               5
```

<210> SEQ ID NO 27
<211> LENGTH: 9
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 27

His Ser Ser Lys Leu Gln Glu Asp Ala
1               5

<210> SEQ ID NO 28
<211> LENGTH: 10
<212> TYPE: PRT
<213> ORGANISM: Unknown
<220> FEATURE:
<223> OTHER INFORMATION: Description of Unknown:
      Herpes Simplex Virus Protease cleavage domain
      sequence

<400> SEQUENCE: 28

Leu Val Leu Ala Ser Ser Ser Phe Gly Tyr
1               5                   10

<210> SEQ ID NO 29
<211> LENGTH: 10
<212> TYPE: PRT
<213> ORGANISM: Unknown
<220> FEATURE:
<223> OTHER INFORMATION: Description of Unknown:
      HIV Protease cleavage domain sequence

<400> SEQUENCE: 29

Gly Val Ser Gln Asn Tyr Pro Ile Val Gly
1               5                   10

<210> SEQ ID NO 30
<211> LENGTH: 10
<212> TYPE: PRT
<213> ORGANISM: Unknown
<220> FEATURE:
<223> OTHER INFORMATION: Description of Unknown:
      CMV Protease cleavage domain sequence

<400> SEQUENCE: 30

Gly Val Val Gln Ala Ser Cys Arg Leu Ala
1               5                   10

<210> SEQ ID NO 31
<211> LENGTH: 4
<212> TYPE: PRT
<213> ORGANISM: Unknown
<220> FEATURE:
<223> OTHER INFORMATION: Description of Unknown:
      Thrombin cleavage domain sequence
<220> FEATURE:
<221> NAME/KEY: MOD_RES
<222> LOCATION: (2)..(2)
<223> OTHER INFORMATION: 2-carboxy piperdine

<400> SEQUENCE: 31

Phe Xaa Arg Ser
1

<210> SEQ ID NO 32
<211> LENGTH: 6
<212> TYPE: PRT

```
<213> ORGANISM: Unknown
<220> FEATURE:
<223> OTHER INFORMATION: Description of Unknown:
      Thrombin cleavage domain sequence

<400> SEQUENCE: 32

Asp Pro Arg Ser Phe Leu
1               5

<210> SEQ ID NO 33
<211> LENGTH: 6
<212> TYPE: PRT
<213> ORGANISM: Unknown
<220> FEATURE:
<223> OTHER INFORMATION: Description of Unknown:
      Thrombin cleavage domain sequence

<400> SEQUENCE: 33

Pro Pro Arg Ser Phe Leu
1               5

<210> SEQ ID NO 34
<211> LENGTH: 4
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 34

Asp Glu Val Asp
1

<210> SEQ ID NO 35
<211> LENGTH: 5
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 35

Asp Glu Val Asp Pro
1               5

<210> SEQ ID NO 36
<211> LENGTH: 8
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 36

Lys Gly Ser Gly Asp Val Glu Gly
1               5

<210> SEQ ID NO 37
<211> LENGTH: 6
<212> TYPE: PRT
<213> ORGANISM: Unknown
<220> FEATURE:
<223> OTHER INFORMATION: Description of Unknown:
      Interleukin 1-Beta converting enzyme cleavage domain
      sequence

<400> SEQUENCE: 37

Gly Trp Glu His Asp Gly
```

```
1               5

<210> SEQ ID NO 38
<211> LENGTH: 7
<212> TYPE: PRT
<213> ORGANISM: Unknown
<220> FEATURE:
<223> OTHER INFORMATION: Description of Unknown:
      Enterokinase cleavage domain sequence

<400> SEQUENCE: 38

Glu Asp Asp Asp Asp Lys Ala
1               5

<210> SEQ ID NO 39
<211> LENGTH: 9
<212> TYPE: PRT
<213> ORGANISM: Unknown
<220> FEATURE:
<223> OTHER INFORMATION: Description of Unknown:
      FAP cleavage domain sequence

<400> SEQUENCE: 39

Lys Gln Glu Gln Asn Pro Gly Ser Thr
1               5

<210> SEQ ID NO 40
<211> LENGTH: 6
<212> TYPE: PRT
<213> ORGANISM: Unknown
<220> FEATURE:
<223> OTHER INFORMATION: Description of Unknown:
      Kallikrein 2 cleavage domain sequence

<400> SEQUENCE: 40

Gly Lys Ala Phe Arg Arg
1               5

<210> SEQ ID NO 41
<211> LENGTH: 4
<212> TYPE: PRT
<213> ORGANISM: Unknown
<220> FEATURE:
<223> OTHER INFORMATION: Description of Unknown:
      Plasmin cleavage domain sequence

<400> SEQUENCE: 41

Asp Ala Phe Lys
1

<210> SEQ ID NO 42
<211> LENGTH: 4
<212> TYPE: PRT
<213> ORGANISM: Unknown
<220> FEATURE:
<223> OTHER INFORMATION: Description of Unknown:
      Plasmin cleavage domain sequence

<400> SEQUENCE: 42

Asp Val Leu Lys
1

<210> SEQ ID NO 43
<211> LENGTH: 4
<212> TYPE: PRT
<213> ORGANISM: Unknown
<220> FEATURE:
<223> OTHER INFORMATION: Description of Unknown:
```

Plasmin cleavage domain sequence

<400> SEQUENCE: 43

Asp Ala Phe Lys
1

<210> SEQ ID NO 44
<211> LENGTH: 7
<212> TYPE: PRT
<213> ORGANISM: Unknown
<220> FEATURE:
<223> OTHER INFORMATION: Description of Unknown:
      TOP cleavage domain sequence

<400> SEQUENCE: 44

Ala Leu Leu Leu Ala Leu Leu
1               5

<210> SEQ ID NO 45
<211> LENGTH: 652
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asp
            20                  25                  30

Ile Met Ser Trp Tyr Arg Gln Ala Pro Gly Lys Gln Arg Glu Leu Val
        35                  40                  45

Ala Arg Ile Thr Arg Gly Gly Thr Ile Ser Tyr Asp Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Leu Tyr Gly Thr Asp Tyr Trp Gly Lys Gly Thr Gln Val Thr Val
            100                 105                 110

Ser Ser Gly Gly Gly Gly Ser Gly Gly Gly Gly Ser Gly Gly Gly Gly
        115                 120                 125

Ser Ala Pro Thr Ser Ser Ser Thr Lys Lys Thr Gln Leu Gln Leu Glu
    130                 135                 140

His Leu Leu Leu Asp Leu Gln Met Ile Leu Asn Gly Ile Asn Asn Tyr
145                 150                 155                 160

Lys Asn Pro Lys Leu Thr Arg Met Leu Thr Phe Lys Phe Tyr Met Pro
                165                 170                 175

Lys Lys Ala Thr Glu Leu Lys His Leu Gln Cys Leu Glu Glu Glu Leu
            180                 185                 190

Lys Pro Leu Glu Glu Val Leu Asn Leu Ala Gln Ser Lys Asn Phe His
        195                 200                 205

Leu Arg Pro Arg Asp Leu Ile Ser Asn Ile Asn Val Ile Val Leu Glu
    210                 215                 220

Leu Lys Gly Ser Glu Thr Thr Phe Met Cys Glu Tyr Ala Asp Glu Thr
225                 230                 235                 240

Ala Thr Ile Val Glu Phe Leu Asn Arg Trp Ile Thr Phe Cys Gln Ser
                245                 250                 255

```
Ile Ile Ser Thr Leu Thr Ser Gly Gly Pro Gly Pro Ala Gly Met Lys
                260                 265                 270

Gly Leu Pro Gly Ser Glu Val Gln Leu Val Glu Ser Gly Gly Gly Leu
            275                 280                 285

Val Gln Pro Gly Asn Ser Leu Arg Leu Ser Cys Ala Ala Ser Gly Phe
290                 295                 300

Thr Phe Ser Lys Phe Gly Met Ser Trp Val Arg Gln Ala Pro Gly Lys
305                 310                 315                 320

Gly Leu Glu Trp Val Ser Ser Ile Ser Gly Ser Gly Arg Asp Thr Leu
                325                 330                 335

Tyr Ala Glu Ser Val Lys Gly Arg Phe Thr Ile Ser Arg Asp Asn Ala
            340                 345                 350

Lys Thr Thr Leu Tyr Leu Gln Met Asn Ser Leu Arg Pro Glu Asp Thr
        355                 360                 365

Ala Val Tyr Tyr Cys Thr Ile Gly Gly Ser Leu Ser Val Ser Ser Gln
        370                 375                 380

Gly Thr Leu Val Thr Val Ser Ser Gly Gly Gly Ser Gly Gly Gly
385                 390                 395                 400

Gly Ser Gly Gly Gly Gly Ser Glu Val Gln Leu Val Glu Ser Gly Gly
                405                 410                 415

Gly Leu Val Gln Pro Gly Gly Ser Leu Arg Leu Ser Cys Ala Ala Ser
            420                 425                 430

Gly Phe Thr Phe Ser Ser Tyr Thr Leu Ala Trp Val Arg Gln Ala Pro
        435                 440                 445

Gly Lys Gly Leu Glu Trp Val Ala Ala Ile Asp Ser Ser Ser Tyr Thr
    450                 455                 460

Tyr Ser Pro Asp Thr Val Arg Gly Arg Phe Thr Ile Ser Arg Asp Asn
465                 470                 475                 480

Ala Lys Asn Ser Leu Tyr Leu Gln Met Asn Ser Leu Arg Ala Glu Asp
                485                 490                 495

Thr Ala Val Tyr Tyr Cys Ala Arg Asp Ser Asn Trp Asp Ala Leu Asp
            500                 505                 510

Tyr Trp Gly Gln Gly Thr Thr Val Thr Val Ser Ser Gly Gly Gly Gly
        515                 520                 525

Ser Gly Gly Gly Gly Ser Gly Gly Gly Gly Ser Asp Ile Gln Met Thr
    530                 535                 540

Gln Ser Pro Ser Ser Leu Ser Ala Ser Val Gly Asp Arg Val Thr Ile
545                 550                 555                 560

Thr Cys Lys Ala Ser Gln Asn Val Gly Thr Asn Val Gly Trp Tyr Gln
                565                 570                 575

Gln Lys Pro Gly Lys Ala Pro Lys Ala Leu Ile Tyr Ser Ala Ser Phe
            580                 585                 590

Arg Tyr Ser Gly Val Pro Ser Arg Phe Ser Gly Ser Gly Ser Gly Thr
        595                 600                 605

Asp Phe Thr Leu Thr Ile Ser Ser Leu Gln Pro Glu Asp Phe Ala Thr
        610                 615                 620

Tyr Tyr Cys Gln Gln Tyr Tyr Thr Tyr Pro Tyr Thr Phe Gly Gly Gly
625                 630                 635                 640

Thr Lys Val Glu Ile Lys His His His His His His
                645                 650

<210> SEQ ID NO 46
<211> LENGTH: 652
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asp
            20                  25                  30

Ile Met Ser Trp Tyr Arg Gln Ala Pro Gly Lys Gln Arg Glu Leu Val
        35                  40                  45

Ala Arg Ile Thr Arg Gly Gly Thr Ile Ser Tyr Asp Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Leu Tyr Gly Thr Asp Tyr Trp Gly Lys Gly Thr Gln Val Thr Val
            100                 105                 110

Ser Ser Gly Gly Gly Gly Ser Gly Gly Gly Ser Gly Gly Gly Gly
        115                 120                 125

Ser Glu Val Gln Leu Val Glu Ser Gly Gly Leu Val Gln Pro Gly
130                 135                 140

Gly Ser Leu Arg Leu Ser Cys Ala Ala Ser Gly Phe Thr Phe Ser Ser
145                 150                 155                 160

Tyr Thr Leu Ala Trp Val Arg Gln Ala Pro Gly Lys Gly Leu Glu Trp
            165                 170                 175

Val Ala Ala Ile Asp Ser Ser Tyr Thr Tyr Ser Pro Asp Thr Val
            180                 185                 190

Arg Gly Arg Phe Thr Ile Ser Arg Asp Asn Ala Lys Asn Ser Leu Tyr
            195                 200                 205

Leu Gln Met Asn Ser Leu Arg Ala Glu Asp Thr Ala Val Tyr Tyr Cys
    210                 215                 220

Ala Arg Asp Ser Asn Trp Asp Ala Leu Asp Tyr Trp Gly Gln Gly Thr
225                 230                 235                 240

Thr Val Thr Val Ser Ser Gly Gly Gly Ser Gly Gly Gly Gly Ser
                245                 250                 255

Gly Gly Gly Gly Ser Asp Ile Gln Met Thr Gln Ser Pro Ser Ser Leu
            260                 265                 270

Ser Ala Ser Val Gly Asp Arg Val Thr Ile Thr Cys Lys Ala Ser Gln
            275                 280                 285

Asn Val Gly Thr Asn Val Gly Trp Tyr Gln Gln Lys Pro Gly Lys Ala
            290                 295                 300

Pro Lys Ala Leu Ile Tyr Ser Ala Ser Phe Arg Tyr Ser Gly Val Pro
305                 310                 315                 320

Ser Arg Phe Ser Gly Ser Gly Ser Gly Thr Asp Phe Thr Leu Thr Ile
                325                 330                 335

Ser Ser Leu Gln Pro Glu Asp Phe Ala Thr Tyr Tyr Cys Gln Gln Tyr
            340                 345                 350

Tyr Thr Tyr Pro Tyr Thr Phe Gly Gly Gly Thr Lys Val Glu Ile Lys
            355                 360                 365

Gly Gly Gly Gly Ser Gly Gly Gly Ser Gly Gly Gly Gly Ser Glu
            370                 375                 380
```

```
Val Gln Leu Val Glu Ser Gly Gly Leu Val Gln Pro Gly Asn Ser
385                 390                 395                 400

Leu Arg Leu Ser Cys Ala Ala Ser Gly Phe Thr Phe Ser Lys Phe Gly
                405                 410                 415

Met Ser Trp Val Arg Gln Ala Pro Gly Lys Gly Leu Glu Trp Val Ser
            420                 425                 430

Ser Ile Ser Gly Ser Gly Arg Asp Thr Leu Tyr Ala Glu Ser Val Lys
            435                 440                 445

Gly Arg Phe Thr Ile Ser Arg Asp Asn Ala Lys Thr Thr Leu Tyr Leu
        450                 455                 460

Gln Met Asn Ser Leu Arg Pro Glu Asp Thr Ala Val Tyr Tyr Cys Thr
465                 470                 475                 480

Ile Gly Gly Ser Leu Ser Val Ser Ser Gln Gly Thr Leu Val Thr Val
                485                 490                 495

Ser Ser Ser Gly Gly Pro Gly Pro Ala Gly Met Lys Gly Leu Pro Gly
            500                 505                 510

Ser Ala Pro Thr Ser Ser Ser Thr Lys Lys Thr Gln Leu Gln Leu Glu
        515                 520                 525

His Leu Leu Leu Asp Leu Gln Met Ile Leu Asn Gly Ile Asn Asn Tyr
            530                 535                 540

Lys Asn Pro Lys Leu Thr Arg Met Leu Thr Phe Lys Phe Tyr Met Pro
545                 550                 555                 560

Lys Lys Ala Thr Glu Leu Lys His Leu Gln Cys Leu Glu Glu Glu Leu
                565                 570                 575

Lys Pro Leu Glu Glu Val Leu Asn Leu Ala Gln Ser Lys Asn Phe His
            580                 585                 590

Leu Arg Pro Arg Asp Leu Ile Ser Asn Ile Asn Val Ile Val Leu Glu
        595                 600                 605

Leu Lys Gly Ser Glu Thr Thr Phe Met Cys Glu Tyr Ala Asp Glu Thr
610                 615                 620

Ala Thr Ile Val Glu Phe Leu Asn Arg Trp Ile Thr Phe Cys Gln Ser
625                 630                 635                 640

Ile Ile Ser Thr Leu Thr His His His His His
                645                 650

<210> SEQ ID NO 47
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Leu Ala Trp Val Arg Gln Ala Pro Gly Lys Gly Leu Glu Trp Val
        35                  40                  45

Ala Ala Ile Asp Ser Ser Ser Tyr Thr Tyr Ser Pro Asp Thr Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
```

```
            85                  90                  95
Arg Asp Ser Asn Trp Asp Ala Leu Asp Tyr Trp Gly Gln Gly Thr Thr
            100                 105                 110

Val Thr Val Ser Ser Gly Gly Gly Gly Ser Gly Gly Gly Ser Gly
            115                 120                 125

Gly Gly Gly Ser Asp Ile Gln Met Thr Gln Ser Pro Ser Ser Leu Ser
            130                 135                 140

Ala Ser Val Gly Asp Arg Val Thr Ile Thr Cys Lys Ala Ser Gln Asn
145                 150                 155                 160

Val Gly Thr Asn Val Gly Trp Tyr Gln Gln Lys Pro Gly Lys Ala Pro
            165                 170                 175

Lys Ala Leu Ile Tyr Ser Ala Ser Phe Arg Tyr Ser Gly Val Pro Ser
            180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Tyr Tyr
            210                 215                 220

Thr Tyr Pro Tyr Thr Phe Gly Gly Gly Thr Lys Val Glu Ile Lys Gly
225                 230                 235                 240

Gly Gly Gly Ser Gly Gly Gly Gly Ser Gly Gly Gly Ser Gly Gly
            245                 250                 255

Gly Gly Ser Gly Gly Gly Ser Gly Gly Gly Ser Ser Gly Gly
            260                 265                 270

Pro Gly Pro Ala Gly Met Lys Gly Leu Pro Gly Ser Ala Pro Thr Ser
            275                 280                 285

Ser Ser Thr Lys Lys Thr Gln Leu Gln Leu Glu His Leu Leu Leu Asp
            290                 295                 300

Leu Gln Met Ile Leu Asn Gly Ile Asn Asn Tyr Lys Asn Pro Lys Leu
305                 310                 315                 320

Thr Arg Met Leu Thr Phe Lys Phe Tyr Met Pro Lys Lys Ala Thr Glu
            325                 330                 335

Leu Lys His Leu Gln Cys Leu Glu Glu Glu Leu Lys Pro Leu Glu Glu
            340                 345                 350

Val Leu Asn Leu Ala Gln Ser Lys Asn Phe His Leu Arg Pro Arg Asp
            355                 360                 365

Leu Ile Ser Asn Ile Asn Val Ile Val Leu Glu Leu Lys Gly Ser Glu
            370                 375                 380

Thr Thr Phe Met Cys Glu Tyr Ala Asp Glu Thr Ala Thr Ile Val Glu
385                 390                 395                 400

Phe Leu Asn Arg Trp Ile Thr Phe Cys Gln Ser Ile Ile Ser Thr Leu
            405                 410                 415

Thr Ser Gly Gly Pro Gly Pro Ala Gly Met Lys Gly Leu Pro Gly Ser
            420                 425                 430

Glu Val Gln Leu Val Glu Ser Gly Gly Leu Val Gln Pro Gly Asn
            435                 440                 445

Ser Leu Arg Leu Ser Cys Ala Ala Ser Gly Phe Thr Phe Ser Lys Phe
            450                 455                 460

Gly Met Ser Trp Val Arg Gln Ala Pro Gly Lys Gly Leu Glu Trp Val
465                 470                 475                 480

Ser Ser Ile Ser Gly Ser Gly Arg Asp Thr Leu Tyr Ala Glu Ser Val
            485                 490                 495

Lys Gly Arg Phe Thr Ile Ser Arg Asp Asn Ala Lys Thr Thr Leu Tyr
            500                 505                 510
```

```
Leu Gln Met Asn Ser Leu Arg Pro Glu Asp Thr Ala Val Tyr Tyr Cys
            515                 520                 525

Thr Ile Gly Gly Ser Leu Ser Val Ser Ser Gln Gly Thr Leu Val Thr
        530                 535                 540

Val Ser Ser His His His His His His
545                 550

<210> SEQ ID NO 48
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Leu Ala Trp Val Arg Gln Ala Pro Gly Lys Gly Leu Glu Trp Val
        35                  40                  45

Ala Ala Ile Asp Ser Ser Tyr Thr Tyr Ser Pro Asp Thr Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Asn Trp Asp Ala Leu Asp Tyr Trp Gly Gln Gly Thr Thr
            100                 105                 110

Val Thr Val Ser Ser Gly Gly Gly Ser Gly Gly Gly Gly Ser Gly
        115                 120                 125

Gly Gly Gly Ser Asp Ile Gln Met Thr Gln Ser Pro Ser Ser Leu Ser
130                 135                 140

Ala Ser Val Gly Asp Arg Val Thr Ile Thr Cys Lys Ala Ser Gln Asn
145                 150                 155                 160

Val Gly Thr Asn Val Gly Trp Tyr Gln Gln Lys Pro Gly Lys Ala Pro
                165                 170                 175

Lys Ala Leu Ile Tyr Ser Ala Ser Phe Arg Tyr Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Tyr Tyr
    210                 215                 220

Thr Tyr Pro Tyr Thr Phe Gly Gly Thr Lys Val Glu Ile Lys Gly
225                 230                 235                 240

Gly Gly Gly Ser Gly Gly Gly Gly Ser Gly Gly Gly Gly Ser Gly Gly
                245                 250                 255

Gly Gly Ser Gly Gly Gly Gly Ser Gly Gly Gly Gly Ser Glu Val Gln
            260                 265                 270

Leu Val Glu Ser Gly Gly Gly Leu Val Gln Pro Gly Asn Ser Leu Arg
        275                 280                 285

Leu Ser Cys Ala Ala Ser Gly Phe Thr Phe Ser Lys Phe Gly Met Ser
    290                 295                 300

Trp Val Arg Gln Ala Pro Gly Lys Gly Leu Glu Trp Val Ser Ser Ile
```

```
                305                 310                 315                 320
Ser Gly Ser Gly Arg Asp Thr Leu Tyr Ala Glu Ser Val Lys Gly Arg
                    325                 330                 335

Phe Thr Ile Ser Arg Asp Asn Ala Lys Thr Thr Leu Tyr Leu Gln Met
                340                 345                 350

Asn Ser Leu Arg Pro Glu Asp Thr Ala Val Tyr Tyr Cys Thr Ile Gly
            355                 360                 365

Gly Ser Leu Ser Val Ser Ser Gln Gly Thr Leu Val Thr Val Ser Ser
        370                 375                 380

Gly Gly Gly Gly Ser Gly Gly Gly Ser Gly Gly Gly Gly Ser Ser
385                 390                 395                 400

Gly Gly Pro Gly Pro Ala Gly Met Lys Gly Leu Pro Gly Ser Ala Pro
                405                 410                 415

Thr Ser Ser Thr Lys Lys Thr Gln Leu Gln Leu Glu His Leu Leu
            420                 425                 430

Leu Asp Leu Gln Met Ile Leu Asn Gly Ile Asn Asn Tyr Lys Asn Pro
        435                 440                 445

Lys Leu Thr Arg Met Leu Thr Phe Lys Phe Tyr Met Pro Lys Lys Ala
    450                 455                 460

Thr Glu Leu Lys His Leu Gln Cys Leu Glu Glu Leu Lys Pro Leu
465                 470                 475                 480

Glu Glu Val Leu Asn Leu Ala Gln Ser Lys Asn Phe His Leu Arg Pro
                485                 490                 495

Arg Asp Leu Ile Ser Asn Ile Asn Val Ile Val Leu Glu Leu Lys Gly
            500                 505                 510

Ser Glu Thr Thr Phe Met Cys Glu Tyr Ala Asp Glu Thr Ala Thr Ile
        515                 520                 525

Val Glu Phe Leu Asn Arg Trp Ile Thr Phe Cys Gln Ser Ile Ile Ser
    530                 535                 540

Thr Leu Thr His His His His His His
545                 550

<210> SEQ ID NO 49
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

Thr Ile Val Glu Phe Leu Asn Arg Trp Ile Thr Phe Cys Gln Ser Ile
            115                 120                 125

Ile Ser Thr Leu Thr Ser Gly Gly Pro Gly Pro Ala Gly Met Lys Gly
        130                 135                 140

Leu Pro Gly Ser Glu Val Gln Leu Val Glu Ser Gly Gly Gly Leu Val
145                 150                 155                 160

Gln Pro Gly Asn Ser Leu Arg Leu Ser Cys Ala Ala Ser Gly Phe Thr
                165                 170                 175

Phe Ser Lys Phe Gly Met Ser Trp Val Arg Gln Ala Pro Gly Lys Gly
            180                 185                 190

Leu Glu Trp Val Ser Ser Ile Ser Gly Ser Gly Arg Asp Thr Leu Tyr
        195                 200                 205

Ala Glu Ser Val Lys Gly Arg Phe Thr Ile Ser Arg Asp Asn Ala Lys
    210                 215                 220

Thr Thr Leu Tyr Leu Gln Met Asn Ser Leu Arg Pro Glu Asp Thr Ala
225                 230                 235                 240

Val Tyr Tyr Cys Thr Ile Gly Gly Ser Leu Ser Val Ser Ser Gln Gly
                245                 250                 255

Thr Leu Val Thr Val Ser Ser Gly Gly Gly Gly Ser Gly Gly Gly Gly
            260                 265                 270

Ser Gly Gly Gly Gly Ser Gly Gly Gly Ser Gly Gly Gly Gly Ser
        275                 280                 285

Gly Gly Gly Ser Ser Gly Gly Pro Gly Pro Ala Gly Met Lys Gly
    290                 295                 300

Leu Pro Gly Ser Glu Val Gln Leu Val Glu Ser Gly Gly Gly Leu Val
305                 310                 315                 320

Gln Pro Gly Gly Ser Leu Arg Leu Ser Cys Ala Ala Ser Gly Phe Thr
                325                 330                 335

Phe Ser Ser Tyr Thr Leu Ala Trp Val Arg Gln Ala Pro Gly Lys Gly
            340                 345                 350

Leu Glu Trp Val Ala Ala Ile Asp Ser Ser Ser Tyr Thr Tyr Ser Pro
        355                 360                 365

Asp Thr Val Arg Gly Arg Phe Thr Ile Ser Arg Asp Asn Ala Lys Asn
    370                 375                 380

Ser Leu Tyr Leu Gln Met Asn Ser Leu Arg Ala Glu Asp Thr Ala Val
385                 390                 395                 400

Tyr Tyr Cys Ala Arg Asp Ser Asn Trp Asp Ala Leu Asp Tyr Trp Gly
                405                 410                 415

Gln Gly Thr Thr Val Thr Val Ser Ser Gly Gly Gly Ser Gly Gly
            420                 425                 430

Gly Gly Ser Gly Gly Gly Gly Ser Asp Ile Gln Met Thr Gln Ser Pro
        435                 440                 445

Ser Ser Leu Ser Ala Ser Val Gly Asp Arg Val Thr Ile Thr Cys Lys
    450                 455                 460

Ala Ser Gln Asn Val Gly Thr Asn Val Gly Trp Tyr Gln Gln Lys Pro
465                 470                 475                 480

Gly Lys Ala Pro Lys Ala Leu Ile Tyr Ser Ala Ser Phe Arg Tyr Ser
                485                 490                 495

Gly Val Pro Ser Arg Phe Ser Gly Ser Gly Ser Gly Thr Asp Phe Thr
            500                 505                 510

Leu Thr Ile Ser Ser Leu Gln Pro Glu Asp Phe Ala Thr Tyr Tyr Cys
        515                 520                 525

Gln Gln Tyr Tyr Thr Tyr Pro Tyr Thr Phe Gly Gly Gly Thr Lys Val

```
                    530                 535                 540
Glu Ile Lys His His His His His
545                 550

<210> SEQ ID NO 50
<211> LENGTH: 682
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asp
                20                  25                  30

Ile Met Ser Trp Tyr Arg Gln Ala Pro Gly Lys Gln Arg Glu Leu Val
            35                  40                  45

Ala Arg Ile Thr Arg Gly Gly Thr Ile Ser Tyr Asp Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Leu Tyr Gly Thr Asp Tyr Trp Gly Lys Gly Thr Gln Val Thr Val
            100                 105                 110

Ser Ser Gly Gly Gly Gly Ser Gly Gly Gly Ser Gly Gly Gly Gly
        115                 120                 125

Ser Ala Pro Thr Ser Ser Thr Lys Lys Thr Gln Leu Gln Leu Glu
130                 135                 140

His Leu Leu Leu Asp Leu Gln Met Ile Leu Asn Gly Ile Asn Asn Tyr
145                 150                 155                 160

Lys Asn Pro Lys Leu Thr Arg Met Leu Thr Phe Lys Phe Tyr Met Pro
                165                 170                 175

Lys Lys Ala Thr Glu Leu Lys His Leu Gln Cys Leu Glu Glu Glu Leu
            180                 185                 190

Lys Pro Leu Glu Glu Val Leu Asn Leu Ala Gln Ser Lys Asn Phe His
        195                 200                 205

Leu Arg Pro Arg Asp Leu Ile Ser Asn Ile Asn Val Ile Val Leu Glu
210                 215                 220

Leu Lys Gly Ser Glu Thr Thr Phe Met Cys Glu Tyr Ala Asp Glu Thr
225                 230                 235                 240

Ala Thr Ile Val Glu Phe Leu Asn Arg Trp Ile Thr Phe Cys Gln Ser
                245                 250                 255

Ile Ile Ser Thr Leu Thr Ser Gly Gly Pro Gly Pro Ala Gly Met Lys
            260                 265                 270

Gly Leu Pro Gly Ser Glu Val Gln Leu Val Glu Ser Gly Gly Gly Leu
        275                 280                 285

Val Gln Pro Gly Asn Ser Leu Arg Leu Ser Cys Ala Ala Ser Gly Phe
290                 295                 300

Thr Phe Ser Lys Phe Gly Met Ser Trp Val Arg Gln Ala Pro Gly Lys
305                 310                 315                 320

Gly Leu Glu Trp Val Ser Ser Ile Ser Gly Ser Gly Arg Asp Thr Leu
                325                 330                 335
```

Tyr Ala Glu Ser Val Lys Gly Arg Phe Thr Ile Ser Arg Asp Asn Ala
               340                 345                 350

Lys Thr Thr Leu Tyr Leu Gln Met Asn Ser Leu Arg Pro Glu Asp Thr
            355                 360                 365

Ala Val Tyr Tyr Cys Thr Ile Gly Gly Ser Leu Ser Val Ser Ser Gln
        370                 375                 380

Gly Thr Leu Val Thr Val Ser Ser Gly Gly Gly Ser Gly Gly Gly Gly
385                 390                 395                 400

Gly Ser Gly Gly Gly Gly Ser Gly Gly Gly Ser Gly Gly Gly Gly Gly
                405                 410                 415

Ser Gly Gly Gly Gly Ser Ser Gly Gly Pro Gly Pro Ala Gly Met Lys
            420                 425                 430

Gly Leu Pro Gly Ser Glu Val Gln Leu Val Glu Ser Gly Gly Gly Leu
        435                 440                 445

Val Gln Pro Gly Gly Ser Leu Arg Leu Ser Cys Ala Ala Ser Gly Phe
    450                 455                 460

Thr Phe Ser Ser Tyr Thr Leu Ala Trp Val Arg Gln Ala Pro Gly Lys
465                 470                 475                 480

Gly Leu Glu Trp Val Ala Ala Ile Asp Ser Ser Ser Tyr Thr Tyr Ser
                485                 490                 495

Pro Asp Thr Val Arg Gly Arg Phe Thr Ile Ser Arg Asp Asn Ala Lys
            500                 505                 510

Asn Ser Leu Tyr Leu Gln Met Asn Ser Leu Arg Ala Glu Asp Thr Ala
        515                 520                 525

Val Tyr Tyr Cys Ala Arg Asp Ser Asn Trp Asp Ala Leu Asp Tyr Trp
    530                 535                 540

Gly Gln Gly Thr Thr Val Thr Val Ser Ser Gly Gly Gly Gly Ser Gly
545                 550                 555                 560

Gly Gly Gly Ser Gly Gly Gly Gly Ser Asp Ile Gln Met Thr Gln Ser
                565                 570                 575

Pro Ser Ser Leu Ser Ala Ser Val Gly Asp Arg Val Thr Ile Thr Cys
            580                 585                 590

Lys Ala Ser Gln Asn Val Gly Thr Asn Val Gly Trp Tyr Gln Gln Lys
        595                 600                 605

Pro Gly Lys Ala Pro Lys Ala Leu Ile Tyr Ser Ala Ser Phe Arg Tyr
    610                 615                 620

Ser Gly Val Pro Ser Arg Phe Ser Gly Ser Gly Ser Gly Thr Asp Phe
625                 630                 635                 640

Thr Leu Thr Ile Ser Ser Leu Gln Pro Glu Asp Phe Ala Thr Tyr Tyr
                645                 650                 655

Cys Gln Gln Tyr Tyr Thr Tyr Pro Tyr Thr Phe Gly Gly Gly Thr Lys
            660                 665                 670

Val Glu Ile Lys His His His His His His
        675                 680

<210> SEQ ID NO 51
<211> LENGTH: 667
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asp
            20                  25                  30

Ile Met Ser Trp Tyr Arg Gln Ala Pro Gly Lys Gln Arg Glu Leu Val
            35                  40                  45

Ala Arg Ile Thr Arg Gly Gly Thr Ile Ser Tyr Asp Asp Ser Val Lys
 50                      55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Gly Val Tyr Tyr Cys Asn
                 85                  90                  95

Ala Leu Tyr Gly Thr Asp Tyr Trp Gly Lys Gly Thr Gln Val Thr Val
             100                 105                 110

Ser Ser Gly Gly Gly Ser Gly Gly Gly Ser Gly Gly Gly Gly
             115                 120                 125

Ser Ala Pro Thr Ser Ser Ser Thr Lys Lys Thr Gln Leu Gln Leu Glu
 130                     135                 140

His Leu Leu Leu Asp Leu Gln Met Ile Leu Asn Gly Ile Asn Asn Tyr
145                 150                 155                 160

Lys Asn Pro Lys Leu Thr Arg Met Leu Thr Phe Lys Phe Tyr Met Pro
                 165                 170                 175

Lys Lys Ala Thr Glu Leu Lys His Leu Gln Cys Leu Glu Glu Glu Leu
             180                 185                 190

Lys Pro Leu Glu Glu Val Leu Asn Leu Ala Gln Ser Lys Asn Phe His
         195                 200                 205

Leu Arg Pro Arg Asp Leu Ile Ser Asn Ile Asn Val Ile Val Leu Glu
     210                 215                 220

Leu Lys Gly Ser Glu Thr Thr Phe Met Cys Glu Tyr Ala Asp Glu Thr
225                 230                 235                 240

Ala Thr Ile Val Glu Phe Leu Asn Arg Trp Ile Thr Phe Cys Gln Ser
                 245                 250                 255

Ile Ile Ser Thr Leu Thr Ser Gly Gly Pro Gly Pro Ala Gly Met Lys
             260                 265                 270

Gly Leu Pro Gly Ser Glu Val Gln Leu Val Glu Ser Gly Gly Gly Leu
         275                 280                 285

Val Gln Pro Gly Asn Ser Leu Arg Leu Ser Cys Ala Ala Ser Gly Phe
 290                     295                 300

Thr Phe Ser Lys Phe Gly Met Ser Trp Val Arg Gln Ala Pro Gly Lys
305                 310                 315                 320

Gly Leu Glu Trp Val Ser Ser Ile Ser Gly Ser Gly Arg Asp Thr Leu
                 325                 330                 335

Tyr Ala Glu Ser Val Lys Gly Arg Phe Thr Ile Ser Arg Asp Asn Ala
             340                 345                 350

Lys Thr Thr Leu Tyr Leu Gln Met Asn Ser Leu Arg Pro Glu Asp Thr
         355                 360                 365

Ala Val Tyr Tyr Cys Thr Ile Gly Gly Ser Leu Ser Val Ser Ser Gln
     370                 375                 380

Gly Thr Leu Val Thr Val Ser Ser Gly Gly Gly Gly Ser Gly Gly Gly
385                 390                 395                 400

Gly Ser Gly Gly Gly Gly Ser Gly Gly Gly Ser Gly Gly Gly Gly
                 405                 410                 415

Ser Gly Gly Gly Gly Ser Glu Val Gln Leu Val Glu Ser Gly Gly Gly
             420                 425                 430

Leu Val Gln Pro Gly Gly Ser Leu Arg Leu Ser Cys Ala Ala Ser Gly
            435                 440                 445

Phe Thr Phe Ser Ser Tyr Thr Leu Ala Trp Val Arg Gln Ala Pro Gly
    450                 455                 460

Lys Gly Leu Glu Trp Val Ala Ala Ile Asp Ser Ser Ser Tyr Thr Tyr
465                 470                 475                 480

Ser Pro Asp Thr Val Arg Gly Arg Phe Thr Ile Ser Arg Asp Asn Ala
                485                 490                 495

Lys Asn Ser Leu Tyr Leu Gln Met Asn Ser Leu Arg Ala Glu Asp Thr
            500                 505                 510

Ala Val Tyr Tyr Cys Ala Arg Asp Ser Asn Trp Asp Ala Leu Asp Tyr
            515                 520                 525

Trp Gly Gln Gly Thr Thr Val Thr Val Ser Ser Gly Gly Pro Gly
            530                 535                 540

Pro Ala Gly Met Lys Gly Leu Pro Gly Ser Asp Ile Gln Met Thr Gln
545                 550                 555                 560

Ser Pro Ser Ser Leu Ser Ala Ser Val Gly Asp Arg Val Thr Ile Thr
                565                 570                 575

Cys Lys Ala Ser Gln Asn Val Gly Thr Asn Val Gly Trp Tyr Gln Gln
            580                 585                 590

Lys Pro Gly Lys Ala Pro Lys Ala Leu Ile Tyr Ser Ala Ser Phe Arg
            595                 600                 605

Tyr Ser Gly Val Pro Ser Arg Phe Ser Gly Ser Gly Ser Gly Thr Asp
            610                 615                 620

Phe Thr Leu Thr Ile Ser Ser Leu Gln Pro Glu Asp Phe Ala Thr Tyr
625                 630                 635                 640

Tyr Cys Gln Gln Tyr Tyr Thr Tyr Pro Tyr Thr Phe Gly Gly Gly Thr
                645                 650                 655

Lys Val Glu Ile Lys His His His His His His
            660                 665

<210> SEQ ID NO 52
<211> LENGTH: 682
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

```
Ile Ser Thr Leu Thr Ser Gly Gly Pro Gly Ala Gly Met Lys Gly
    130                 135                 140

Leu Pro Gly Ser Gly Gly Gly Ser Gly Gly Gly Ser Gly Gly
145                 150                 155                 160

Gly Gly Ser Gly Gly Gly Ser Gly Gly Gly Ser Gly Gly Gly
                165                 170                 175

Gly Ser Glu Val Gln Leu Val Glu Ser Gly Gly Leu Val Gln Pro
        180                 185                 190

Gly Gly Ser Leu Arg Leu Ser Cys Ala Ala Ser Gly Phe Thr Phe Ser
        195                 200                 205

Ser Tyr Thr Leu Ala Trp Val Arg Gln Ala Pro Gly Lys Gly Leu Glu
    210                 215                 220

Trp Val Ala Ala Ile Asp Ser Ser Ser Tyr Thr Tyr Ser Pro Asp Thr
225                 230                 235                 240

Val Arg Gly Arg Phe Thr Ile Ser Arg Asp Asn Ala Lys Asn Ser Leu
                245                 250                 255

Tyr Leu Gln Met Asn Ser Leu Arg Ala Glu Asp Thr Ala Val Tyr Tyr
            260                 265                 270

Cys Ala Arg Asp Ser Asn Trp Asp Ala Leu Asp Tyr Trp Gly Gln Gly
            275                 280                 285

Thr Thr Val Thr Val Ser Ser Gly Gly Gly Gly Ser Gly Gly Gly Gly
        290                 295                 300

Ser Gly Gly Gly Gly Ser Asp Ile Gln Met Thr Gln Ser Pro Ser Ser
305                 310                 315                 320

Leu Ser Ala Ser Val Gly Asp Arg Val Thr Ile Thr Cys Lys Ala Ser
                325                 330                 335

Gln Asn Val Gly Thr Asn Val Gly Trp Tyr Gln Gln Lys Pro Gly Lys
            340                 345                 350

Ala Pro Lys Ala Leu Ile Tyr Ser Ala Ser Phe Arg Tyr Ser Gly Val
            355                 360                 365

Pro Ser Arg Phe Ser Gly Ser Gly Ser Gly Thr Asp Phe Thr Leu Thr
        370                 375                 380

Ile Ser Ser Leu Gln Pro Glu Asp Phe Ala Thr Tyr Tyr Cys Gln Gln
385                 390                 395                 400

Tyr Tyr Thr Tyr Pro Tyr Thr Phe Gly Gly Gly Thr Lys Val Glu Ile
                405                 410                 415

Lys Gly Gly Gly Gly Ser Gly Gly Gly Gly Ser Gly Gly Gly Gly Ser
            420                 425                 430

Glu Val Gln Leu Val Glu Ser Gly Gly Gly Leu Val Gln Pro Gly Asn
        435                 440                 445

Ser Leu Arg Leu Ser Cys Ala Ala Ser Gly Phe Thr Phe Ser Lys Phe
    450                 455                 460

Gly Met Ser Trp Val Arg Gln Ala Pro Gly Lys Gly Leu Glu Trp Val
465                 470                 475                 480

Ser Ser Ile Ser Gly Ser Gly Arg Asp Thr Leu Tyr Ala Glu Ser Val
                485                 490                 495

Lys Gly Arg Phe Thr Ile Ser Arg Asp Asn Ala Lys Thr Thr Leu Tyr
            500                 505                 510

Leu Gln Met Asn Ser Leu Arg Pro Glu Asp Thr Ala Val Tyr Tyr Cys
            515                 520                 525

Thr Ile Gly Gly Ser Leu Ser Val Ser Ser Gln Gly Thr Leu Val Thr
        530                 535                 540
```

Val Ser Ser Gly Gly Gly Ser Gly Gly Gly Ser Gly Gly Gly
545                 550                 555                 560

Gly Ser Gln Val Gln Leu Gln Glu Ser Gly Gly Leu Val Gln Ala
            565                 570                 575

Gly Gly Ser Leu Arg Leu Ser Cys Ala Ala Ser Gly Arg Ile Phe Ser
            580                 585                 590

Ile Asp Ile Met Ser Trp Tyr Arg Gln Ala Pro Gly Lys Gln Arg Glu
            595                 600                 605

Leu Val Ala Arg Ile Thr Arg Gly Gly Thr Ile Ser Tyr Asp Asp Ser
            610                 615                 620

Val Lys Gly Arg Phe Thr Ile Ser Arg Asp Asn Ala Lys Asn Thr Val
625                 630                 635                 640

Tyr Leu Gln Met Asn Ser Leu Lys Pro Glu Asp Thr Gly Val Tyr Tyr
            645                 650                 655

Cys Asn Ala Leu Tyr Gly Thr Asp Tyr Trp Gly Lys Gly Thr Gln Val
            660                 665                 670

Thr Val Ser Ser His His His His His His
            675                 680

<210> SEQ ID NO 53
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Ser Gly Gly Pro Gly Pro Ala Gly Met Lys Gly
            130                 135                 140

Leu Pro Gly Ser Glu Val Gln Leu Val Glu Ser Gly Gly Gly Leu Val
145                 150                 155                 160

Gln Pro Gly Gly Ser Leu Arg Leu Ser Cys Ala Ala Ser Gly Phe Thr
            165                 170                 175

Phe Ser Ser Tyr Thr Leu Ala Trp Val Arg Gln Ala Pro Gly Lys Gly
            180                 185                 190

Leu Glu Trp Val Ala Ala Ile Asp Ser Ser Ser Tyr Thr Tyr Ser Pro
            195                 200                 205

Asp Thr Val Arg Gly Arg Phe Thr Ile Ser Arg Asp Asn Ala Lys Asn
            210                 215                 220

```
Ser Leu Tyr Leu Gln Met Asn Ser Leu Arg Ala Glu Asp Thr Ala Val
225                 230                 235                 240

Tyr Tyr Cys Ala Arg Asp Ser Asn Trp Asp Ala Leu Asp Tyr Trp Gly
                245                 250                 255

Gln Gly Thr Thr Val Thr Val Ser Ser Gly Gly Gly Ser Gly Gly
            260                 265                 270

Gly Gly Ser Gly Gly Gly Gly Ser Asp Ile Gln Met Thr Gln Ser Pro
        275                 280                 285

Ser Ser Leu Ser Ala Ser Val Gly Asp Arg Val Thr Ile Thr Cys Lys
        290                 295                 300

Ala Ser Gln Asn Val Gly Thr Asn Val Gly Trp Tyr Gln Gln Lys Pro
305                 310                 315                 320

Gly Lys Ala Pro Lys Ala Leu Ile Tyr Ser Ala Ser Phe Arg Tyr Ser
                325                 330                 335

Gly Val Pro Ser Arg Phe Ser Gly Ser Gly Ser Gly Thr Asp Phe Thr
            340                 345                 350

Leu Thr Ile Ser Ser Leu Gln Pro Glu Asp Phe Ala Thr Tyr Tyr Cys
        355                 360                 365

Gln Gln Tyr Tyr Thr Tyr Pro Tyr Thr Phe Gly Gly Gly Thr Lys Val
    370                 375                 380

Glu Ile Lys His His His His His His
385                 390
```

<210> SEQ ID NO 54
<211> LENGTH: 423
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Ser Gly Gly Pro Gly Pro Ala Gly Met Lys Gly
    130                 135                 140

Leu Pro Gly Ser Gly Gly Gly Gly Ser Gly Gly Gly Gly Ser Gly Gly
145                 150                 155                 160

Gly Gly Ser Gly Gly Gly Gly Ser Gly Gly Gly Gly Ser Gly Gly Gly
                165                 170                 175

Gly Ser Glu Val Gln Leu Val Glu Ser Gly Gly Gly Leu Val Gln Pro
```

```
            180                 185                 190
Gly Gly Ser Leu Arg Leu Ser Cys Ala Ala Ser Gly Phe Thr Phe Ser
            195                 200                 205

Ser Tyr Thr Leu Ala Trp Val Arg Gln Ala Pro Gly Lys Gly Leu Glu
        210                 215                 220

Trp Val Ala Ala Ile Asp Ser Ser Tyr Thr Tyr Ser Pro Asp Thr
225                 230                 235                 240

Val Arg Gly Arg Phe Thr Ile Ser Arg Asp Asn Ala Lys Asn Ser Leu
                245                 250                 255

Tyr Leu Gln Met Asn Ser Leu Arg Ala Glu Asp Thr Ala Val Tyr Tyr
            260                 265                 270

Cys Ala Arg Asp Ser Asn Trp Asp Ala Leu Asp Tyr Trp Gly Gln Gly
            275                 280                 285

Thr Thr Val Thr Val Ser Gly Gly Gly Ser Gly Gly Gly Gly
        290                 295                 300

Ser Gly Gly Gly Gly Ser Asp Ile Gln Met Thr Gln Ser Pro Ser Ser
305                 310                 315                 320

Leu Ser Ala Ser Val Gly Asp Arg Val Thr Ile Thr Cys Lys Ala Ser
                325                 330                 335

Gln Asn Val Gly Thr Asn Val Gly Trp Tyr Gln Lys Pro Gly Lys
            340                 345                 350

Ala Pro Lys Ala Leu Ile Tyr Ser Ala Ser Phe Arg Tyr Ser Gly Val
            355                 360                 365

Pro Ser Arg Phe Ser Gly Ser Gly Ser Gly Thr Asp Phe Thr Leu Thr
        370                 375                 380

Ile Ser Ser Leu Gln Pro Glu Asp Phe Ala Thr Tyr Tyr Cys Gln Gln
385                 390                 395                 400

Tyr Tyr Thr Tyr Pro Tyr Thr Phe Gly Gly Gly Thr Lys Val Glu Ile
                405                 410                 415

Lys His His His His His His
            420

<210> SEQ ID NO 55
<211> LENGTH: 682
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Cys Gln Ser Ile
        115                 120                 125
Ile Ser Thr Leu Thr Ser Gly Gly Pro Gly Pro Ala Gly Met Lys Gly
130                 135                 140
Leu Pro Gly Ser Gly Gly Gly Ser Gly Gly Gly Ser Gly Gly
145                 150                 155                 160
Gly Gly Ser Gly Gly Gly Ser Gly Gly Gly Ser Gly Gly
                165                 170                 175
Gly Ser Glu Val Gln Leu Val Glu Ser Gly Gly Leu Val Gln Pro
            180                 185                 190
Gly Gly Ser Leu Arg Leu Ser Cys Ala Ala Ser Gly Phe Thr Phe Ser
        195                 200                 205
Ser Tyr Thr Leu Ala Trp Val Arg Gln Ala Pro Gly Lys Gly Leu Glu
        210                 215                 220
Trp Val Ala Ala Ile Asp Ser Ser Tyr Thr Tyr Ser Pro Asp Thr
225                 230                 235                 240
Val Arg Gly Arg Phe Thr Ile Ser Arg Asp Asn Ala Lys Asn Ser Leu
            245                 250                 255
Tyr Leu Gln Met Asn Ser Leu Arg Ala Glu Asp Thr Ala Val Tyr Tyr
        260                 265                 270
Cys Ala Arg Asp Ser Asn Trp Asp Ala Leu Asp Tyr Trp Gly Gln Gly
        275                 280                 285
Thr Thr Val Thr Val Ser Ser Gly Gly Gly Gly Ser Gly Gly Gly Gly
        290                 295                 300
Ser Gly Gly Gly Gly Ser Asp Ile Gln Met Thr Gln Ser Pro Ser Ser
305                 310                 315                 320
Leu Ser Ala Ser Val Gly Asp Arg Val Thr Ile Thr Cys Lys Ala Ser
            325                 330                 335
Gln Asn Val Gly Thr Asn Val Gly Trp Tyr Gln Gln Lys Pro Gly Lys
        340                 345                 350
Ala Pro Lys Ala Leu Ile Tyr Ser Ala Ser Phe Arg Tyr Ser Gly Val
        355                 360                 365
Pro Ser Arg Phe Ser Gly Ser Gly Ser Gly Thr Asp Phe Thr Leu Thr
370                 375                 380
Ile Ser Ser Leu Gln Pro Glu Asp Phe Ala Thr Tyr Tyr Cys Gln Gln
385                 390                 395                 400
Tyr Tyr Thr Tyr Pro Tyr Thr Phe Gly Gly Thr Lys Val Glu Ile
            405                 410                 415
Lys Ser Gly Gly Pro Gly Pro Ala Gly Met Lys Gly Leu Pro Gly Ser
        420                 425                 430
Glu Val Gln Leu Val Glu Ser Gly Gly Leu Val Gln Pro Gly Asn
        435                 440                 445
Ser Leu Arg Leu Ser Cys Ala Ala Ser Gly Phe Thr Phe Ser Lys Phe
        450                 455                 460
Gly Met Ser Trp Val Arg Gln Ala Pro Lys Gly Leu Glu Trp Val
465                 470                 475                 480
Ser Ser Ile Ser Gly Ser Gly Arg Asp Thr Leu Tyr Ala Glu Ser Val
            485                 490                 495
Lys Gly Arg Phe Thr Ile Ser Arg Asp Asn Ala Lys Thr Thr Leu Tyr
            500                 505                 510
Leu Gln Met Asn Ser Leu Arg Pro Glu Asp Thr Ala Val Tyr Tyr Cys
        515                 520                 525
Thr Ile Gly Gly Ser Leu Ser Val Ser Ser Gln Gly Thr Leu Val Thr
```

```
                    530                 535                 540
Val Ser Ser Gly Gly Gly Ser Gly Gly Gly Ser Gly Gly
545                 550                 555                 560

Gly Ser Gln Val Gln Leu Gln Glu Ser Gly Gly Leu Val Gln Ala
                565                 570                 575

Gly Gly Ser Leu Arg Leu Ser Cys Ala Ala Ser Gly Arg Ile Phe Ser
            580                 585                 590

Ile Asp Ile Met Ser Trp Tyr Arg Gln Ala Pro Gly Lys Gln Arg Glu
        595                 600                 605

Leu Val Ala Arg Ile Thr Arg Gly Gly Thr Ile Ser Tyr Asp Asp Ser
            610                 615                 620

Val Lys Gly Arg Phe Thr Ile Ser Arg Asp Asn Ala Lys Asn Thr Val
625                 630                 635                 640

Tyr Leu Gln Met Asn Ser Leu Lys Pro Glu Asp Thr Gly Val Tyr Tyr
                645                 650                 655

Cys Asn Ala Leu Tyr Gly Thr Asp Tyr Trp Gly Lys Gly Thr Gln Val
            660                 665                 670

Thr Val Ser Ser His His His His His His
            675                 680

<210> SEQ ID NO 56
<211> LENGTH: 682
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Glu Ser Gly Gly Gly Leu Ala Gln Ala Gly Gly
1               5                   10                  15

Ser Leu Ser Leu Ser Cys Ala Ala Ser Gly Phe Thr Val Ser Asn Ser
            20                  25                  30

Val Met Ala Trp Tyr Arg Gln Thr Pro Gly Lys Gln Arg Glu Phe Val
        35                  40                  45

Ala Ile Ile Asn Ser Val Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Val Cys Asn
                85                  90                  95

Arg Asn Phe Asp Arg Ile Tyr Trp Gly Gln Gly Thr Gln Val Thr Val
            100                 105                 110

Ser Ser Ser Gly Gly Pro Gly Pro Ala Gly Met Lys Gly Leu Pro Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Phe Ser Ser
145                 150                 155                 160

Tyr Thr Leu Ala Trp Val Arg Gln Ala Pro Gly Lys Gly Leu Glu Trp
                165                 170                 175

Val Ala Ala Ile Asp Ser Ser Ser Tyr Thr Tyr Ser Pro Asp Thr Val
            180                 185                 190

Arg Gly Arg Phe Thr Ile Ser Arg Asp Asn Ala Lys Asn Ser Leu Tyr
        195                 200                 205
```

-continued

Leu Gln Met Asn Ser Leu Arg Ala Glu Asp Thr Ala Val Tyr Tyr Cys
210                 215                 220

Ala Arg Asp Ser Asn Trp Asp Ala Leu Asp Tyr Trp Gly Gln Gly Thr
225                 230                 235                 240

Thr Val Thr Val Ser Ser Gly Gly Gly Gly Ser Gly Gly Gly Gly Ser
        245                 250                 255

Gly Gly Gly Gly Ser Asp Ile Gln Met Thr Gln Ser Pro Ser Ser Leu
        260                 265                 270

Ser Ala Ser Val Gly Asp Arg Val Thr Ile Thr Cys Lys Ala Ser Gln
        275                 280                 285

Asn Val Gly Thr Asn Val Gly Trp Tyr Gln Gln Lys Pro Gly Lys Ala
290                 295                 300

Pro Lys Ala Leu Ile Tyr Ser Ala Ser Phe Arg Tyr Ser Gly Val Pro
305                 310                 315                 320

Ser Arg Phe Ser Gly Ser Gly Ser Gly Thr Asp Phe Thr Leu Thr Ile
            325                 330                 335

Ser Ser Leu Gln Pro Glu Asp Phe Ala Thr Tyr Tyr Cys Gln Gln Tyr
            340                 345                 350

Tyr Thr Tyr Pro Tyr Thr Phe Gly Gly Gly Thr Lys Val Glu Ile Lys
        355                 360                 365

Gly Gly Gly Gly Ser Gly Gly Gly Gly Ser Gly Gly Gly Gly Ser Gly
        370                 375                 380

Gly Gly Gly Ser Gly Gly Gly Gly Ser Gly Gly Gly Gly Ser Ser Gly
385                 390                 395                 400

Gly Pro Gly Pro Ala Gly Met Lys Gly Leu Pro Gly Ser Glu Val Gln
            405                 410                 415

Leu Val Glu Ser Gly Gly Gly Leu Val Gln Pro Gly Asn Ser Leu Arg
            420                 425                 430

Leu Ser Cys Ala Ala Ser Gly Phe Thr Phe Ser Lys Phe Gly Met Ser
            435                 440                 445

Trp Val Arg Gln Ala Pro Gly Lys Gly Leu Glu Trp Val Ser Ser Ile
450                 455                 460

Ser Gly Ser Gly Arg Asp Thr Leu Tyr Ala Glu Ser Val Lys Gly Arg
465                 470                 475                 480

Phe Thr Ile Ser Arg Asp Asn Ala Lys Thr Thr Leu Tyr Leu Gln Met
            485                 490                 495

Asn Ser Leu Arg Pro Glu Asp Thr Ala Val Tyr Tyr Cys Thr Ile Gly
            500                 505                 510

Gly Ser Leu Ser Val Ser Ser Gln Gly Thr Leu Val Thr Val Ser Ser
            515                 520                 525

Ser Gly Gly Pro Gly Pro Ala Gly Met Lys Gly Leu Pro Gly Ser Ala
        530                 535                 540

Pro Thr Ser Ser Ser Thr Lys Lys Thr Gln Leu Gln Leu Glu His Leu
545                 550                 555                 560

Leu Leu Asp Leu Gln Met Ile Leu Asn Gly Ile Asn Asn Tyr Lys Asn
            565                 570                 575

Pro Lys Leu Thr Arg Met Leu Thr Phe Lys Phe Tyr Met Pro Lys Lys
            580                 585                 590

Ala Thr Glu Leu Lys His Leu Gln Cys Leu Glu Glu Leu Lys Pro
            595                 600                 605

Leu Glu Glu Val Leu Asn Leu Ala Gln Ser Lys Asn Phe His Leu Arg
610                 615                 620

Pro Arg Asp Leu Ile Ser Asn Ile Asn Val Ile Val Leu Glu Leu Lys

```
                625                 630                 635                 640
Gly Ser Glu Thr Thr Phe Met Cys Glu Tyr Ala Asp Glu Thr Ala Thr
                    645                 650                 655

Ile Val Glu Phe Leu Asn Arg Trp Ile Thr Phe Cys Gln Ser Ile Ile
                660                 665                 670

Ser Thr Leu Thr His His His His His His
            675                 680

<210> SEQ ID NO 57
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Leu Ala Trp Val Arg Gln Ala Pro Gly Lys Gly Leu Glu Trp Val
        35                  40                  45

Ala Ala Ile Asp Ser Ser Ser Tyr Thr Tyr Ser Pro Asp Thr Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Asn Trp Asp Ala Leu Asp Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
    130                 135                 140

Ala Ser Val Gly Asp Arg Val Thr Ile Thr Cys Lys Ala Ser Gln Asn
145                 150                 155                 160

Val Gly Thr Asn Val Gly Trp Tyr Gln Gln Lys Pro Gly Lys Ala Pro
                165                 170                 175

Lys Ala Leu Ile Tyr Ser Ala Ser Phe Arg Tyr Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Tyr Tyr
    210                 215                 220

Thr Tyr Pro Tyr Thr Phe Gly Gly Gly Thr Lys Val Glu Ile Lys Ser
225                 230                 235                 240

Gly Gly Pro Gly Pro Ala Gly Met Lys Gly Leu Pro Gly Ser Ala Pro
                245                 250                 255

Thr Ser Ser Ser Thr Lys Lys Thr Gln Leu Gln Leu Glu His Leu Leu
            260                 265                 270

Leu Asp Leu Gln Met Ile Leu Asn Gly Ile Asn Asn Tyr Lys Asn Pro
        275                 280                 285

Lys Leu Thr Arg Met Leu Thr Phe Lys Phe Tyr Met Pro Lys Lys Ala
    290                 295                 300
```

```
Thr Glu Leu Lys His Leu Gln Cys Leu Glu Glu Leu Lys Pro Leu
305                 310                 315                 320

Glu Glu Val Leu Asn Leu Ala Gln Ser Lys Asn Phe His Leu Arg Pro
            325                 330                 335

Arg Asp Leu Ile Ser Asn Ile Asn Val Ile Val Leu Glu Leu Lys Gly
        340                 345                 350

Ser Glu Thr Thr Phe Met Cys Glu Tyr Ala Asp Glu Thr Ala Thr Ile
        355                 360                 365

Val Glu Phe Leu Asn Arg Trp Ile Thr Phe Cys Gln Ser Ile Ile Ser
    370                 375                 380

Thr Leu Thr His His His His His His
385                 390

<210> SEQ ID NO 58
<211> LENGTH: 423
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Leu Ala Trp Val Arg Gln Ala Pro Gly Lys Gly Leu Glu Trp Val
        35                  40                  45

Ala Ala Ile Asp Ser Ser Ser Tyr Thr Tyr Ser Pro Asp Thr Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Asn Trp Asp Ala Leu Asp Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
    130                 135                 140

Ala Ser Val Gly Asp Arg Val Thr Ile Thr Cys Lys Ala Ser Gln Asn
145                 150                 155                 160

Val Gly Thr Asn Val Gly Trp Tyr Gln Gln Lys Pro Gly Lys Ala Pro
                165                 170                 175

Lys Ala Leu Ile Tyr Ser Ala Ser Phe Arg Tyr Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Tyr Tyr
    210                 215                 220

Thr Tyr Pro Tyr Thr Phe Gly Gly Gly Thr Lys Val Glu Ile Lys Gly
225                 230                 235                 240

Gly Gly Gly Ser Gly Gly Gly Gly Ser Gly Gly Gly Gly Ser Gly Gly
                245                 250                 255

Gly Gly Ser Gly Gly Gly Gly Ser Gly Gly Gly Gly Ser Ser Gly Gly
            260                 265                 270
```

```
Pro Gly Pro Ala Gly Met Lys Gly Leu Pro Gly Ser Ala Pro Thr Ser
        275                 280                 285

Ser Ser Thr Lys Lys Thr Gln Leu Gln Leu Glu His Leu Leu Leu Asp
    290                 295                 300

Leu Gln Met Ile Leu Asn Gly Ile Asn Asn Tyr Lys Asn Pro Lys Leu
305                 310                 315                 320

Thr Arg Met Leu Thr Phe Lys Phe Tyr Met Pro Lys Lys Ala Thr Glu
                325                 330                 335

Leu Lys His Leu Gln Cys Leu Glu Glu Leu Lys Pro Leu Glu Glu
                340                 345                 350

Val Leu Asn Leu Ala Gln Ser Lys Asn Phe His Leu Arg Pro Arg Asp
            355                 360                 365

Leu Ile Ser Asn Ile Asn Val Ile Val Leu Glu Leu Lys Gly Ser Glu
370                 375                 380

Thr Thr Phe Met Cys Glu Tyr Ala Asp Glu Thr Ala Thr Ile Val Glu
385                 390                 395                 400

Phe Leu Asn Arg Trp Ile Thr Phe Cys Gln Ser Ile Ile Ser Thr Leu
                405                 410                 415

Thr His His His His His His
            420

<210> SEQ ID NO 59
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asp
            20                  25                  30

Ile Met Ser Trp Tyr Arg Gln Ala Pro Gly Lys Gln Arg Glu Leu Val
        35                  40                  45

Ala Arg Ile Thr Arg Gly Gly Thr Ile Ser Tyr Asp Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Leu Tyr Gly Thr Asp Tyr Trp Gly Lys Gly Thr Gln Val Thr Val
                100                 105                 110

Ser Ser Gly Gly Gly Gly Ser Gly Gly Gly Gly Ser Gly Gly Gly Gly
            115                 120                 125

Ser Ala Pro Thr Ser Ser Thr Lys Lys Thr Gln Leu Gln Leu Glu
            130                 135                 140

His Leu Leu Leu Asp Leu Gln Met Ile Leu Asn Gly Ile Asn Asn Tyr
145                 150                 155                 160

Lys Asn Pro Lys Leu Thr Arg Met Leu Thr Phe Lys Phe Tyr Met Pro
                165                 170                 175

Lys Lys Ala Thr Glu Leu Lys His Leu Gln Cys Leu Glu Glu Glu Leu
            180                 185                 190

Lys Pro Leu Glu Glu Val Leu Asn Leu Ala Gln Ser Lys Asn Phe His
```

```
            195                 200                 205
Leu Arg Pro Arg Asp Leu Ile Ser Asn Ile Asn Val Ile Val Leu Glu
            210                 215                 220

Leu Lys Gly Ser Glu Thr Thr Phe Met Cys Glu Tyr Ala Asp Glu Thr
225                 230                 235                 240

Ala Thr Ile Val Glu Phe Leu Asn Arg Trp Ile Thr Phe Cys Gln Ser
            245                 250                 255

Ile Ile Ser Thr Leu Thr Ser Gly Gly Pro Gly Pro Ala Gly Met Lys
            260                 265                 270

Gly Leu Pro Gly Ser Glu Val Gln Leu Val Glu Ser Gly Gly Gly Leu
            275                 280                 285

Val Gln Pro Gly Asn Ser Leu Arg Leu Ser Cys Ala Ala Ser Gly Phe
            290                 295                 300

Thr Phe Ser Lys Phe Gly Met Ser Trp Val Arg Gln Ala Pro Gly Lys
305                 310                 315                 320

Gly Leu Glu Trp Val Ser Ser Ile Ser Gly Ser Gly Arg Asp Thr Leu
            325                 330                 335

Tyr Ala Glu Ser Val Lys Gly Arg Phe Thr Ile Ser Arg Asp Asn Ala
            340                 345                 350

Lys Thr Thr Leu Tyr Leu Gln Met Asn Ser Leu Arg Pro Glu Asp Thr
            355                 360                 365

Ala Val Tyr Tyr Cys Thr Ile Gly Gly Ser Leu Ser Val Ser Ser Gln
            370                 375                 380

Gly Thr Leu Val Thr Val Ser Ser Gly Gly Gly Gly Ser Gly Gly Gly
385                 390                 395                 400

Gly Ser Gly Gly Gly Gly Ser Gly Gly Gly Gly Ser Gln Val Gln Leu
            405                 410                 415

Gln Gln Ser Gly Ala Glu Leu Val Arg Pro Gly Thr Ser Val Lys Val
            420                 425                 430

Ser Cys Lys Ala Ser Gly Tyr Ala Phe Thr Asn Tyr Leu Ile Glu Trp
            435                 440                 445

Val Lys Gln Arg Pro Gly Gln Gly Leu Glu Trp Ile Gly Val Ile Asn
450                 455                 460

Pro Gly Ser Gly Gly Thr Asn Tyr Asn Glu Lys Phe Lys Gly Lys Ala
465                 470                 475                 480

Thr Leu Thr Ala Asp Lys Ser Ser Thr Ala Tyr Met Gln Leu Ser
            485                 490                 495

Ser Leu Thr Ser Asp Asp Ser Ala Val Tyr Phe Cys Ala Arg Trp Arg
            500                 505                 510

Gly Asp Gly Tyr Tyr Ala Tyr Phe Asp Val Trp Gly Ala Gly Thr Thr
            515                 520                 525

Val Thr Val Ser Ser Gly Gly Gly Gly Ser Gly Gly Gly Gly Ser Gly
            530                 535                 540

Gly Gly Gly Ser Asp Ile Val Leu Thr Gln Ser Pro Ala Ser Leu Ala
545                 550                 555                 560

Val Ser Leu Gly Gln Arg Ala Thr Ile Ser Cys Lys Ala Ser Gln Ser
            565                 570                 575

Val Asp Tyr Asp Gly Asp Ser Tyr Met Asn Trp Tyr Gln Gln Lys Pro
            580                 585                 590

Gly Gln Pro Pro Lys Leu Leu Ile Tyr Ala Ala Ser Asn Leu Glu Ser
            595                 600                 605

Gly Ile Pro Ala Arg Phe Ser Gly Ser Gly Ser Gly Thr Asp Phe Thr
            610                 615                 620
```

```
Leu Asn Ile His Pro Val Glu Glu Asp Ala Ala Thr Tyr Tyr Cys
625                 630                 635                 640

Gln Gln Ser Asn Glu Asp Pro Tyr Thr Phe Gly Gly Gly Thr Lys Leu
            645                 650                 655

Glu Ile Lys His His His His His His Glu Pro Glu Ala
        660                 665
```

<210> SEQ ID NO 60
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asp
            20                  25                  30

Ile Met Ser Trp Tyr Arg Gln Ala Pro Gly Lys Gln Arg Glu Leu Val
        35                  40                  45

Ala Arg Ile Thr Arg Gly Gly Thr Ile Ser Tyr Asp Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Leu Tyr Gly Thr Asp Tyr Trp Gly Lys Gly Thr Gln Val Thr Val
            100                 105                 110

Ser Ser Gly Gly Gly Gly Ser Gly Gly Gly Gly Ser Gly Gly Gly Gly
        115                 120                 125

Ser Ala Pro Thr Ser Ser Ser Thr Lys Lys Thr Gln Leu Gln Leu Glu
    130                 135                 140

His Leu Leu Leu Asp Leu Gln Met Ile Leu Asn Gly Ile Asn Asn Tyr
145                 150                 155                 160

Lys Asn Pro Lys Leu Thr Arg Met Leu Thr Phe Lys Phe Tyr Met Pro
                165                 170                 175

Lys Lys Ala Thr Glu Leu Lys His Leu Gln Cys Leu Glu Glu Glu Leu
            180                 185                 190

Lys Pro Leu Glu Glu Val Leu Asn Leu Ala Gln Ser Lys Asn Phe His
        195                 200                 205

Leu Arg Pro Arg Asp Leu Ile Ser Asn Ile Asn Val Ile Val Leu Glu
    210                 215                 220

Leu Lys Gly Ser Glu Thr Thr Phe Met Cys Glu Tyr Ala Asp Glu Thr
225                 230                 235                 240

Ala Thr Ile Val Glu Phe Leu Asn Arg Trp Ile Thr Phe Cys Gln Ser
                245                 250                 255

Ile Ile Ser Thr Leu Thr Ser Gly Gly Pro Gly Pro Ala Gly Met Lys
            260                 265                 270

Gly Leu Pro Gly Ser Glu Val Gln Leu Val Glu Ser Gly Gly Gly Leu
        275                 280                 285

Val Gln Pro Gly Asn Ser Leu Arg Leu Ser Cys Ala Ala Ser Gly Phe
    290                 295                 300

Thr Phe Ser Lys Phe Gly Met Ser Trp Val Arg Gln Ala Pro Gly Lys
```

```
            305                 310                 315                 320
Gly Leu Glu Trp Val Ser Ser Ile Ser Gly Ser Gly Arg Asp Thr Leu
                325                 330                 335

Tyr Ala Glu Ser Val Lys Gly Arg Phe Thr Ile Ser Arg Asp Asn Ala
            340                 345                 350

Lys Thr Thr Leu Tyr Leu Gln Met Asn Ser Leu Arg Pro Glu Asp Thr
        355                 360                 365

Ala Val Tyr Tyr Cys Thr Ile Gly Gly Ser Leu Ser Val Ser Ser Gln
    370                 375                 380

Gly Thr Leu Val Thr Val Ser Ser Gly Gly Gly Ser Gly Gly Gly
385                 390                 395                 400

Gly Ser Gly Gly Gly Ser Gly Gly Gly Ser Asp Ile Val Leu
                405                 410                 415

Thr Gln Ser Pro Ala Ser Leu Ala Val Ser Leu Gly Gln Arg Ala Thr
            420                 425                 430

Ile Ser Cys Lys Ala Ser Gln Ser Val Asp Tyr Asp Gly Asp Ser Tyr
        435                 440                 445

Met Asn Trp Tyr Gln Gln Lys Pro Gly Gln Pro Lys Leu Leu Ile
    450                 455                 460

Tyr Ala Ala Ser Asn Leu Glu Ser Gly Ile Pro Ala Arg Phe Ser Gly
465                 470                 475                 480

Ser Gly Ser Gly Thr Asp Phe Thr Leu Asn Ile His Pro Val Glu Glu
                485                 490                 495

Glu Asp Ala Ala Thr Tyr Tyr Cys Gln Gln Ser Asn Glu Asp Pro Tyr
            500                 505                 510

Thr Phe Gly Gly Gly Thr Lys Leu Glu Ile Lys Gly Gly Gly Gly Ser
        515                 520                 525

Gly Gly Gly Gly Ser Gly Gly Gly Ser Gln Val Gln Leu Gln Gln
    530                 535                 540

Ser Gly Ala Glu Leu Val Arg Pro Gly Thr Ser Val Lys Val Ser Cys
545                 550                 555                 560

Lys Ala Ser Gly Tyr Ala Phe Thr Asn Tyr Leu Ile Glu Trp Val Lys
                565                 570                 575

Gln Arg Pro Gly Gln Gly Leu Glu Trp Ile Gly Val Ile Asn Pro Gly
            580                 585                 590

Ser Gly Gly Thr Asn Tyr Asn Glu Lys Phe Lys Gly Lys Ala Thr Leu
        595                 600                 605

Thr Ala Asp Lys Ser Ser Thr Ala Tyr Met Gln Leu Ser Ser Leu
    610                 615                 620

Thr Ser Asp Asp Ser Ala Val Tyr Phe Cys Ala Arg Trp Arg Gly Asp
625                 630                 635                 640

Gly Tyr Tyr Ala Tyr Phe Asp Val Trp Gly Ala Gly Thr Thr Val Thr
                645                 650                 655

Val Ser Ser His His His His His His Glu Pro Glu Ala
            660                 665
```

<210> SEQ ID NO 61
<211> LENGTH: 689
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

-continued

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Ser Gly Gly Pro Gly Pro Ala Gly Met Lys Gly
            130                 135                 140

Leu Pro Gly Ser Gly Gly Gly Ser Gly Gly Gly Ser Gly Gly Gly Gly
145                 150                 155                 160

Gly Gly Ser Gly Gly Gly Ser Gly Gly Gly Ser Gln Val Gln
            165                 170                 175

Leu Gln Gln Ser Gly Ala Glu Leu Val Arg Pro Gly Thr Ser Val Lys
            180                 185                 190

Val Ser Cys Lys Ala Ser Gly Tyr Ala Phe Thr Asn Tyr Leu Ile Glu
            195                 200                 205

Trp Val Lys Gln Arg Pro Gly Gln Gly Leu Glu Trp Ile Gly Val Ile
210                 215                 220

Asn Pro Gly Ser Gly Gly Thr Asn Tyr Asn Glu Lys Phe Lys Gly Lys
225                 230                 235                 240

Ala Thr Leu Thr Ala Asp Lys Ser Ser Ser Thr Ala Tyr Met Gln Leu
            245                 250                 255

Ser Ser Leu Thr Ser Asp Asp Ser Ala Val Tyr Phe Cys Ala Arg Trp
            260                 265                 270

Arg Gly Asp Gly Tyr Tyr Ala Tyr Phe Asp Val Trp Gly Ala Gly Thr
            275                 280                 285

Thr Val Thr Val Ser Ser Gly Gly Gly Ser Gly Gly Gly Gly Ser
            290                 295                 300

Gly Gly Gly Gly Ser Asp Ile Val Leu Thr Gln Ser Pro Ala Ser Leu
305                 310                 315                 320

Ala Val Ser Leu Gly Gln Arg Ala Thr Ile Ser Cys Lys Ala Ser Gln
            325                 330                 335

Ser Val Asp Tyr Asp Gly Asp Ser Tyr Met Asn Trp Tyr Gln Gln Lys
            340                 345                 350

Pro Gly Gln Pro Pro Lys Leu Leu Ile Tyr Ala Ala Ser Asn Leu Glu
            355                 360                 365

Ser Gly Ile Pro Ala Arg Phe Ser Gly Ser Gly Ser Gly Thr Asp Phe
            370                 375                 380

Thr Leu Asn Ile His Pro Val Glu Glu Glu Asp Ala Ala Thr Tyr Tyr
385                 390                 395                 400

Cys Gln Gln Ser Asn Glu Asp Pro Tyr Thr Phe Gly Gly Gly Thr Lys
            405                 410                 415

Leu Glu Ile Lys Gly Gly Gly Gly Ser Gly Gly Gly Gly Ser Gly Gly
```

```
            420                 425                 430
Gly Gly Ser Glu Val Gln Leu Val Glu Ser Gly Gly Gly Leu Val Gln
        435                 440                 445
Pro Gly Asn Ser Leu Arg Leu Ser Cys Ala Ala Ser Gly Phe Thr Phe
    450                 455                 460
Ser Lys Phe Gly Met Ser Trp Val Arg Gln Ala Pro Gly Lys Gly Leu
465                 470                 475                 480
Glu Trp Val Ser Ile Ser Gly Ser Gly Arg Asp Thr Leu Tyr Ala
                485                 490                 495
Glu Ser Val Lys Gly Arg Phe Thr Ile Ser Arg Asp Asn Ala Lys Thr
            500                 505                 510
Thr Leu Tyr Leu Gln Met Asn Ser Leu Arg Pro Glu Asp Thr Ala Val
        515                 520                 525
Tyr Tyr Cys Thr Ile Gly Gly Ser Leu Ser Val Ser Ser Gln Gly Thr
    530                 535                 540
Leu Val Thr Val Ser Ser Gly Gly Gly Ser Gly Gly Gly Ser
545                 550                 555                 560
Gly Gly Gly Gly Ser Gln Val Gln Leu Gln Glu Ser Gly Gly Gly Leu
                565                 570                 575
Val Gln Ala Gly Gly Ser Leu Arg Leu Ser Cys Ala Ala Ser Gly Arg
            580                 585                 590
Ile Phe Ser Ile Asp Ile Met Ser Trp Tyr Arg Gln Ala Pro Gly Lys
        595                 600                 605
Gln Arg Glu Leu Val Ala Arg Ile Thr Arg Gly Gly Thr Ile Ser Tyr
    610                 615                 620
Asp Asp Ser Val Lys Gly Arg Phe Thr Ile Ser Arg Asp Asn Ala Lys
625                 630                 635                 640
Asn Thr Val Tyr Leu Gln Met Asn Ser Leu Lys Pro Glu Asp Thr Gly
                645                 650                 655
Val Tyr Tyr Cys Asn Ala Leu Tyr Gly Thr Asp Tyr Trp Gly Lys Gly
            660                 665                 670
Thr Gln Val Thr Val Ser Ser His His His His His Glu Pro Glu
        675                 680                 685
Ala

<210> SEQ ID NO 62
<211> LENGTH: 689
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
```

```
                85                  90                  95
Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Ser Gly Gly Pro Gly Pro Ala Gly Met Lys Gly
        130                 135                 140

Leu Pro Gly Ser Gly Gly Gly Ser Gly Gly Gly Ser Gly Gly
145                 150                 155                 160

Gly Gly Ser Gly Gly Gly Ser Gly Gly Gly Ser Asp Ile Val
                165                 170                 175

Leu Thr Gln Ser Pro Ala Ser Leu Ala Val Ser Leu Gly Gln Arg Ala
            180                 185                 190

Thr Ile Ser Cys Lys Ala Ser Gln Ser Val Asp Tyr Asp Gly Asp Ser
            195                 200                 205

Tyr Met Asn Trp Tyr Gln Gln Lys Pro Gly Gln Pro Pro Lys Leu Leu
        210                 215                 220

Ile Tyr Ala Ala Ser Asn Leu Glu Ser Gly Ile Pro Ala Arg Phe Ser
225                 230                 235                 240

Gly Ser Gly Ser Gly Thr Asp Phe Thr Leu Asn Ile His Pro Val Glu
                245                 250                 255

Glu Glu Asp Ala Ala Thr Tyr Tyr Cys Gln Gln Ser Asn Glu Asp Pro
            260                 265                 270

Tyr Thr Phe Gly Gly Gly Thr Lys Leu Glu Ile Lys Gly Gly Gly Gly
        275                 280                 285

Ser Gly Gly Gly Gly Ser Gly Gly Gly Gly Ser Gln Val Gln Leu Gln
290                 295                 300

Gln Ser Gly Ala Glu Leu Val Arg Pro Gly Thr Ser Val Lys Val Ser
305                 310                 315                 320

Cys Lys Ala Ser Gly Tyr Ala Phe Thr Asn Tyr Leu Ile Glu Trp Val
                325                 330                 335

Lys Gln Arg Pro Gly Gln Gly Leu Glu Trp Ile Gly Val Ile Asn Pro
            340                 345                 350

Gly Ser Gly Gly Thr Asn Tyr Asn Glu Lys Phe Lys Gly Lys Ala Thr
        355                 360                 365

Leu Thr Ala Asp Lys Ser Ser Ser Thr Ala Tyr Met Gln Leu Ser Ser
    370                 375                 380

Leu Thr Ser Asp Asp Ser Ala Val Tyr Phe Cys Ala Arg Trp Arg Gly
385                 390                 395                 400

Asp Gly Tyr Tyr Ala Tyr Phe Asp Val Trp Gly Ala Gly Thr Thr Val
                405                 410                 415

Thr Val Ser Ser Gly Gly Gly Gly Ser Gly Gly Gly Gly Ser Gly Gly
            420                 425                 430

Gly Gly Ser Glu Val Gln Leu Val Glu Ser Gly Gly Gly Leu Val Gln
        435                 440                 445

Pro Gly Asn Ser Leu Arg Leu Ser Cys Ala Ala Ser Gly Phe Thr Phe
    450                 455                 460

Ser Lys Phe Gly Met Ser Trp Val Arg Gln Ala Pro Gly Lys Gly Leu
465                 470                 475                 480

Glu Trp Val Ser Ser Ile Ser Gly Ser Gly Arg Asp Thr Leu Tyr Ala
                485                 490                 495

Glu Ser Val Lys Gly Arg Phe Thr Ile Ser Arg Asp Asn Ala Lys Thr
            500                 505                 510
```

```
Thr Leu Tyr Leu Gln Met Asn Ser Leu Arg Pro Glu Asp Thr Ala Val
            515                 520                 525

Tyr Tyr Cys Thr Ile Gly Gly Ser Leu Ser Val Ser Ser Gln Gly Thr
        530                 535                 540

Leu Val Thr Val Ser Ser Gly Gly Gly Ser Gly Gly Gly Gly Ser
545                 550                 555                 560

Gly Gly Gly Gly Ser Gln Val Gln Leu Gln Glu Ser Gly Gly Gly Leu
                565                 570                 575

Val Gln Ala Gly Gly Ser Leu Arg Leu Ser Cys Ala Ala Ser Gly Arg
                580                 585                 590

Ile Phe Ser Ile Asp Ile Met Ser Trp Tyr Arg Gln Ala Pro Gly Lys
            595                 600                 605

Gln Arg Glu Leu Val Ala Arg Ile Thr Arg Gly Gly Thr Ile Ser Tyr
        610                 615                 620

Asp Asp Ser Val Lys Gly Arg Phe Thr Ile Ser Arg Asp Asn Ala Lys
625                 630                 635                 640

Asn Thr Val Tyr Leu Gln Met Asn Ser Leu Lys Pro Glu Asp Thr Gly
                645                 650                 655

Val Tyr Tyr Cys Asn Ala Leu Tyr Gly Thr Asp Tyr Trp Gly Lys Gly
                660                 665                 670

Thr Gln Val Thr Val Ser Ser His His His His His Glu Pro Glu
        675                 680                 685

Ala
```

<210> SEQ ID NO 63
<211> LENGTH: 272
<212> TYPE: PRT
<213> ORGANISM: Unknown
<220> FEATURE:
<223> OTHER INFORMATION: Description of Unknown:
      IL2Ra sequence

<400> SEQUENCE: 63

```
Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175
```

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 64
<211> LENGTH: 551
<212> TYPE: PRT
<213> ORGANISM: Unknown
<220> FEATURE:
<223> OTHER INFORMATION: Description of Unknown:
      IL2Rb sequence

<400> SEQUENCE: 64

Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro

-continued

```
                260                 265                 270
Trp Leu Lys Lys Val Leu Lys Cys Asn Thr Pro Asp Pro Ser Lys Phe
            275                 280                 285

Phe Ser Gln Leu Ser Ser Glu His Gly Gly Asp Val Gln Lys Trp Leu
            290                 295                 300

Ser Ser Pro Phe Pro Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe Phe His
            355                 360                 365

Leu Pro Asp Ala Leu Glu Ile Glu Ala Cys Gln Val Tyr Phe Thr Tyr
        370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Pro Ser Thr Ala Pro Gly Gly Ser
            435                 440                 445

Gly Ala Gly Glu Glu Arg Met Pro Pro Ser Leu Gln Glu Arg Val Pro
        450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Pro Glu Leu Val Leu Arg Glu Ala
                485                 490                 495

Gly Glu Glu Val Pro Asp Ala Gly Pro Arg Glu Gly Val Ser Phe Pro
            500                 505                 510

Trp Ser Arg Pro Pro Gly Gln Gly Glu Phe Arg Ala Leu Asn Ala Arg
            515                 520                 525

Leu Pro Leu Asn Thr Asp Ala Tyr Leu Ser Leu Gln Glu Leu Gln Gly
        530                 535                 540

Gln Asp Pro Thr His Leu Val
545                 550

<210> SEQ ID NO 65
<211> LENGTH: 369
<212> TYPE: PRT
<213> ORGANISM: Unknown
<220> FEATURE:
<223> OTHER INFORMATION: Description of Unknown:
      IL2Rg sequence

<400> SEQUENCE: 65

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60
```

Phe Asn Val Glu Tyr Met Asn Cys Thr Trp Asn Ser Ser Glu Pro
65                  70                  75                  80

Gln Pro Thr Asn Leu Thr Leu His Tyr Trp Tyr Lys Asn Ser Asp Asn
            85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
            115                 120                 125

Val Val Gln Leu Gln Asp Pro Arg Glu Pro Arg Arg Gln Ala Thr Gln
130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
            165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
            195                 200                 205

Ser Leu Pro Ser Val Asp Gly Gln Lys Arg Tyr Thr Phe Arg Val Arg
210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
            245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
            275                 280                 285

Arg Ile Pro Thr Leu Lys Asn Leu Glu Asp Leu Val Thr Glu Tyr His
            290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
            325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
            355                 360                 365

Thr

<210> SEQ ID NO 66
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
            35                  40                  45

```
Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
                100                 105                 110

Thr Ala Val Tyr Tyr Cys Ala Arg Gly Val Gly Ala Phe Arg Pro Tyr
                115                 120                 125

Arg Lys His Glu Trp Gly Gln Gly Thr Leu Val Thr Val Ser Arg Gly
            130                 135                 140

Gly Gly Gly Ser Gly Gly Gly Ser Gly Gly Gly Ser Ser
145                 150                 155                 160

Glu Leu Thr Gln Asp Pro Ala Val Ser Val Ala Leu Gly Gln Thr Val
                165                 170                 175

Arg Ile Thr Cys Gln Gly Asp Ser Leu Arg Ser Tyr Tyr Ala Ser Trp
            180                 185                 190

Tyr Gln Gln Lys Pro Gly Gln Ala Pro Val Leu Val Ile Tyr Gly Lys
        195                 200                 205

Asn Asn Arg Pro Ser Gly Ile Pro Asp Arg Phe Ser Gly Ser Ser Ser
    210                 215                 220

Gly Asn Thr Ala Ser Leu Thr Thr Thr Gly Ala Gln Ala Glu Asp Glu
225                 230                 235                 240

Ala Asp Tyr Tyr Cys Asn Ser Ser Pro Phe Glu His Asn Leu Val Val
                245                 250                 255

Phe Gly Gly Gly Thr Lys Leu Thr Val Leu His His His His His His
            260                 265                 270

Glu Pro Glu Ala
        275

<210> SEQ ID NO 67
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
                20                  25                  30

Gln Leu Gln Leu Glu His Leu Leu Leu Asp Leu Gln Met Ile Leu Asn
            35                  40                  45

Gly Ile Asn Asn Tyr Lys Asn Pro Lys Leu Thr Arg Met Leu Thr Phe
        50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
                100                 105                 110

Val Ile Val Leu Glu Leu Lys Gly Ser Glu Thr Thr Phe Met Cys Glu
                115                 120                 125
```

```
Tyr Ala Asp Glu Thr Ala Thr Ile Val Glu Phe Leu Asn Arg Trp Ile
    130                 135                 140
Thr Phe Cys Gln Ser Ile Ile Ser Thr Leu Thr Ser Gly Gly Pro Gly
145                 150                 155                 160
Pro Ala Gly Met Lys Gly Leu Pro Gly Ser Glu Val Gln Leu Val Glu
                165                 170                 175
Ser Gly Gly Gly Leu Val Gln Pro Gly Gly Ser Leu Arg Leu Ser Cys
            180                 185                 190
Ala Ala Ser Gly Phe Thr Phe Ser Ser Tyr Thr Leu Ala Trp Val Arg
        195                 200                 205
Gln Ala Pro Gly Lys Gly Leu Glu Trp Val Ala Ala Ile Asp Ser Ser
    210                 215                 220
Ser Tyr Thr Tyr Ser Pro Asp Thr Val Arg Gly Arg Phe Thr Ile Ser
225                 230                 235                 240
Arg Asp Asn Ala Lys Asn Ser Leu Tyr Leu Gln Met Asn Ser Leu Arg
                245                 250                 255
Ala Glu Asp Thr Ala Val Tyr Tyr Cys Ala Arg Asp Ser Asn Trp Asp
            260                 265                 270
Ala Leu Asp Tyr Trp Gly Gln Gly Thr Thr Val Thr Val Ser Ser Gly
        275                 280                 285
Gly Gly Gly Ser Gly Gly Gly Ser Gly Gly Gly Ser Asp Ile
    290                 295                 300
Gln Met Thr Gln Ser Pro Ser Ser Leu Ser Ala Ser Val Gly Asp Arg
305                 310                 315                 320
Val Thr Ile Thr Cys Lys Ala Ser Gln Asn Val Gly Thr Asn Val Gly
                325                 330                 335
Trp Tyr Gln Gln Lys Pro Gly Lys Ala Pro Lys Ala Leu Ile Tyr Ser
            340                 345                 350
Ala Ser Phe Arg Tyr Ser Gly Val Pro Ser Arg Phe Ser Gly Ser Gly
        355                 360                 365
Ser Gly Thr Asp Phe Thr Leu Thr Ile Ser Ser Leu Gln Pro Glu Asp
    370                 375                 380
Phe Ala Thr Tyr Tyr Cys Gln Gln Tyr Thr Tyr Pro Tyr Thr Phe
385                 390                 395                 400
Gly Gly Gly Thr Lys Val Glu Ile Lys Gly Gly Gly Ser Gly Gly
                405                 410                 415
Gly Gly Ser Gly Gly Gly Ser Glu Val Gln Leu Val Glu Ser Gly
            420                 425                 430
Gly Gly Leu Val Gln Pro Gly Asn Ser Leu Arg Leu Ser Cys Ala Ala
        435                 440                 445
Ser Gly Phe Thr Phe Ser Lys Phe Gly Met Ser Trp Val Arg Gln Ala
    450                 455                 460
Pro Gly Lys Gly Leu Glu Trp Val Ser Ser Ile Ser Gly Ser Gly Arg
465                 470                 475                 480
Asp Thr Leu Tyr Ala Glu Ser Val Lys Gly Arg Phe Thr Ile Ser Arg
                485                 490                 495
Asp Asn Ala Lys Thr Thr Leu Tyr Leu Gln Met Asn Ser Leu Arg Pro
            500                 505                 510
Glu Asp Thr Ala Val Tyr Tyr Cys Thr Ile Gly Gly Ser Leu Ser Val
        515                 520                 525
Ser Ser Gln Gly Thr Leu Val Thr Val Ser Ser Gly Gly Gly Gly Ser
    530                 535                 540
```

Gly Gly Gly Ser Gly Gly Gly Ser Gln Val Gln Leu Gln Glu
545                 550                 555                 560

Ser Gly Gly Gly Leu Val Gln Ala Gly Gly Ser Leu Arg Leu Ser Cys
                565                 570                 575

Ala Ala Ser Gly Arg Ile Phe Ser Ile Asp Ile Met Ser Trp Tyr Arg
            580                 585                 590

Gln Ala Pro Gly Lys Gln Arg Glu Leu Val Ala Arg Ile Thr Arg Gly
        595                 600                 605

Gly Thr Ile Ser Tyr Asp Asp Ser Val Lys Gly Arg Phe Thr Ile Ser
        610                 615                 620

Arg Asp Asn Ala Lys Asn Thr Val Tyr Leu Gln Met Asn Ser Leu Lys
625                 630                 635                 640

Pro Glu Asp Thr Gly Val Tyr Tyr Cys Asn Ala Leu Tyr Gly Thr Asp
                645                 650                 655

Tyr Trp Gly Lys Gly Thr Gln Val Thr Val Ser Ser His His His
            660                 665                 670

His His

<210> SEQ ID NO 68
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Pro Gly Pro Ala Gly
    130                 135                 140

Met Lys Gly Leu Pro Gly Ser Glu Val Gln Leu Val Glu Ser Gly Gly
145                 150                 155                 160

Gly Leu Val Gln Pro Gly Asn Ser Leu Arg Leu Ser Cys Ala Ala Ser
                165                 170                 175

Gly Phe Thr Phe Ser Lys Phe Gly Met Ser Trp Val Arg Gln Ala Pro
            180                 185                 190

Gly Lys Gly Leu Glu Trp Val Ser Ser Ile Ser Gly Ser Gly Arg Asp
        195                 200                 205

Thr Leu Tyr Ala Glu Ser Val Lys Gly Arg Phe Thr Ile Ser Arg Asp
    210                 215                 220

```
Asn Ala Lys Thr Thr Leu Tyr Leu Gln Met Asn Ser Leu Arg Pro Glu
225                 230                 235                 240

Asp Thr Ala Val Tyr Tyr Cys Thr Ile Gly Gly Ser Leu Ser Val Ser
            245                 250                 255

Ser Gln Gly Thr Leu Val Thr Val Ser Ser Gly Gly Pro Gly Pro
        260                 265                 270

Ala Gly Met Lys Gly Leu Pro Gly Ser Glu Val Gln Leu Val Glu Ser
        275                 280                 285

Gly Gly Gly Leu Val Gln Pro Gly Gly Ser Leu Arg Leu Ser Cys Ala
290                 295                 300

Ala Ser Gly Phe Thr Phe Ser Ser Tyr Thr Leu Ala Trp Val Arg Gln
305                 310                 315                 320

Ala Pro Gly Lys Gly Leu Glu Trp Val Ala Ala Ile Asp Ser Ser Ser
            325                 330                 335

Tyr Thr Tyr Ser Pro Asp Thr Val Arg Gly Arg Phe Thr Ile Ser Arg
            340                 345                 350

Asp Asn Ala Lys Asn Ser Leu Tyr Leu Gln Met Asn Ser Leu Arg Ala
            355                 360                 365

Glu Asp Thr Ala Val Tyr Tyr Cys Ala Arg Asp Ser Asn Trp Asp Ala
370                 375                 380

Leu Asp Tyr Trp Gly Gln Gly Thr Thr Val Thr Val Ser Ser Gly Gly
385                 390                 395                 400

Gly Gly Ser Gly Gly Gly Ser Gly Gly Gly Ser Asp Ile Gln
            405                 410                 415

Met Thr Gln Ser Pro Ser Ser Leu Ser Ala Ser Val Gly Asp Arg Val
            420                 425                 430

Thr Ile Thr Cys Lys Ala Ser Gln Asn Val Gly Thr Asn Val Gly Trp
            435                 440                 445

Tyr Gln Gln Lys Pro Gly Lys Ala Pro Lys Ala Leu Ile Tyr Ser Ala
450                 455                 460

Ser Phe Arg Tyr Ser Gly Val Pro Ser Arg Phe Ser Gly Ser Gly Ser
465                 470                 475                 480

Gly Thr Asp Phe Thr Leu Thr Ile Ser Ser Leu Gln Pro Glu Asp Phe
            485                 490                 495

Ala Thr Tyr Tyr Cys Gln Gln Tyr Tyr Thr Tyr Pro Tyr Thr Phe Gly
            500                 505                 510

Gly Gly Thr Lys Val Glu Ile Lys Ser Gly Gly Pro Gly Pro Ala Gly
        515                 520                 525

Met Lys Gly Leu Pro Gly Ser Ala Pro Thr Ser Ser Ser Thr Lys Lys
        530                 535                 540

Thr Gln Leu Gln Leu Glu His Leu Leu Leu Asp Leu Gln Met Ile Leu
545                 550                 555                 560

Asn Gly Ile Asn Asn Tyr Lys Asn Pro Lys Leu Thr Arg Met Leu Thr
            565                 570                 575

Phe Lys Phe Tyr Met Pro Lys Lys Ala Thr Glu Leu Lys His Leu Gln
            580                 585                 590

Cys Leu Glu Glu Glu Leu Lys Pro Leu Glu Glu Val Leu Asn Leu Ala
            595                 600                 605

Gln Ser Lys Asn Phe His Leu Arg Pro Arg Asp Leu Ile Ser Asn Ile
            610                 615                 620

Asn Val Ile Val Leu Glu Leu Lys Gly Ser Glu Thr Thr Phe Met Cys
625                 630                 635                 640

Glu Tyr Ala Asp Glu Thr Ala Thr Ile Val Glu Phe Leu Asn Arg Trp
```

```
                    645                 650                 655
Ile Thr Phe Cys Gln Ser Ile Ile Ser Thr Leu Thr His His His His
            660                 665                 670

His His
```

```
<210> SEQ ID NO 69
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Asp Met Arg Val Pro Ala Gln Leu Leu Gly Leu Leu Leu Leu Trp
1               5                   10                  15

Leu Arg Gly Ala Arg Cys Glu Leu Cys Asp Asp Pro Pro Glu Ile
            20                  25                  30

Pro His Ala Thr Phe Lys Ala Met Ala Tyr Lys Glu Gly Thr Met Leu
        35                  40                  45

Asn Cys Glu Cys Lys Arg Gly Phe Arg Arg Ile Lys Ser Gly Ser Leu
50                  55                  60

Tyr Met Leu Cys Thr Gly Asn Ser Ser His Ser Ser Trp Asp Asn Gln
65                  70                  75                  80

Cys Gln Cys Thr Ser Ser Ala Thr Arg Asn Thr Thr Lys Gln Val Thr
                85                  90                  95

Pro Gln Pro Glu Glu Gln Lys Glu Arg Lys Thr Thr Glu Met Gln Ser
            100                 105                 110

Pro Met Gln Pro Val Asp Gln Ala Ser Leu Pro Gly His Cys Arg Glu
        115                 120                 125

Pro Pro Pro Trp Glu Asn Glu Ala Thr Glu Arg Ile Tyr His Phe Val
130                 135                 140

Val Gly Gln Met Val Tyr Tyr Gln Cys Val Gln Gly Tyr Arg Ala Leu
145                 150                 155                 160

His Arg Gly Pro Ala Glu Ser Val Cys Lys Met Thr His Gly Lys Thr
                165                 170                 175

Arg Trp Thr Gln Pro Gln Leu Ile Cys Thr Gly Glu Met Glu Thr Ser
            180                 185                 190

Gln Phe Pro Gly Glu Glu Lys Pro Gln Ala Ser Pro Glu Gly Arg Pro
        195                 200                 205

Glu Ser Glu Thr Ser Cys Leu Val Thr Thr Asp Phe Gln Ile Gln
    210                 215                 220

Thr Glu Met Ala Ala Thr Met Glu Thr Ser Ile Phe Thr Thr Glu Tyr
225                 230                 235                 240

Gln Gly Gly Gly Ser Gly Gly Gly Ser Gly Gly Gly Ser
                245                 250                 255

Gly Gly Gly Gly Ser Gly Gly Gly Ser Gly Gly Gly Ser Ser
            260                 265                 270

Gly Gly Pro Gly Pro Ala Gly Met Lys Gly Leu Pro Gly Ser Ala Pro
        275                 280                 285

Thr Ser Ser Thr Lys Lys Thr Gln Leu Gln Glu His Leu Leu
    290                 295                 300

Leu Asp Leu Gln Met Ile Leu Asn Gly Ile Asn Asn Tyr Lys Asn Pro
305                 310                 315                 320

Lys Leu Thr Arg Met Leu Thr Phe Lys Phe Tyr Met Pro Lys Lys Ala
```

```
                    325                 330                 335

Thr Glu Leu Lys His Leu Gln Cys Leu Glu Glu Leu Lys Pro Leu
            340                 345                 350

Glu Glu Val Leu Asn Leu Ala Gln Ser Lys Asn Phe His Leu Arg Pro
                355                 360                 365

Arg Asp Leu Ile Ser Asn Ile Asn Val Ile Val Leu Glu Leu Lys Gly
    370                 375                 380

Ser Glu Thr Thr Phe Met Cys Glu Tyr Ala Asp Glu Thr Ala Thr Ile
385                 390                 395                 400

Val Glu Phe Leu Asn Arg Trp Ile Thr Phe Cys Gln Ser Ile Ile Ser
                405                 410                 415

Thr Leu Thr His His His His His His
            420                 425

<210> SEQ ID NO 70
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65              70                  75                  80

Leu Glu Glu Glu Leu Lys Pro Leu Glu Glu Val Leu Asn Leu Ala Gln
            85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
            115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Gly Gly Gly Ser Gly
            165                 170                 175

Gly Gly Gly Ser Gly Gly Gly Ser Gly Gly Gly Ser Gly Gly
            180                 185                 190

Gly Gly Ser Gly Gly Gly Ser Glu Leu Cys Asp Asp Pro Pro
        195                 200                 205

Glu Ile Pro His Ala Thr Phe Lys Ala Met Ala Tyr Lys Glu Gly Thr
    210                 215                 220

Met Leu Asn Cys Glu Cys Lys Arg Gly Phe Arg Arg Ile Lys Ser Gly
225                 230                 235                 240

Ser Leu Tyr Met Leu Cys Thr Gly Asn Ser Ser His Ser Ser Trp Asp
            245                 250                 255
```

-continued

```
Asn Gln Cys Gln Cys Thr Ser Ser Ala Thr Arg Asn Thr Thr Lys Gln
                260                 265                 270

Val Thr Pro Gln Pro Glu Glu Gln Lys Glu Arg Lys Thr Thr Glu Met
            275                 280                 285

Gln Ser Pro Met Gln Pro Val Asp Gln Ala Ser Leu Pro Gly His Cys
        290                 295                 300

Arg Glu Pro Pro Trp Glu Asn Glu Ala Thr Glu Arg Ile Tyr His
305                 310                 315                 320

Phe Val Val Gly Gln Met Val Tyr Tyr Gln Cys Val Gln Gly Tyr Arg
                325                 330                 335

Ala Leu His Arg Gly Pro Ala Glu Ser Val Cys Lys Met Thr His Gly
            340                 345                 350

Lys Thr Arg Trp Thr Gln Pro Gln Leu Ile Cys Thr Gly Glu Met Glu
        355                 360                 365

Thr Ser Gln Phe Pro Gly Glu Lys Pro Gln Ala Ser Pro Glu Gly
    370                 375                 380

Arg Pro Glu Ser Glu Thr Ser Cys Leu Val Thr Thr Asp Phe Gln
385                 390                 395                 400

Ile Gln Thr Glu Met Ala Ala Thr Met Glu Thr Ser Ile Phe Thr Thr
                405                 410                 415

Glu Tyr Gln His His His His His His
            420                 425

<210> SEQ ID NO 71
<211> LENGTH: 555
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
                20                  25                  30

Leu Val Gln Pro Gly Asn Ser Leu Arg Leu Ser Cys Ala Ala Ser Gly
            35                  40                  45

Phe Thr Phe Ser Lys Phe Gly Met Ser Trp Val Arg Gln Ala Pro Gly
        50                  55                  60

Lys Gly Leu Glu Trp Val Ser Ser Ile Ser Gly Ser Gly Arg Asp Thr
65                  70                  75                  80

Leu Tyr Ala Glu Ser Val Lys Gly Arg Phe Thr Ile Ser Arg Asp Asn
                85                  90                  95

Ala Lys Thr Thr Leu Tyr Leu Gln Met Asn Ser Leu Arg Pro Glu Asp
                100                 105                 110

Thr Ala Val Tyr Tyr Cys Thr Ile Gly Gly Ser Leu Ser Val Ser Ser
            115                 120                 125

Gln Gly Thr Leu Val Thr Val Ser Ser Gly Gly Gly Gly Ser Gly Gly
        130                 135                 140

Gly Gly Ser Gly Gly Gly Gly Ser Glu Leu Cys Asp Asp Asp Pro Pro
145                 150                 155                 160

Glu Ile Pro His Ala Thr Phe Lys Ala Met Ala Tyr Lys Glu Gly Thr
                165                 170                 175

Met Leu Asn Cys Glu Cys Lys Arg Gly Phe Arg Arg Ile Lys Ser Gly
                180                 185                 190
```

Ser Leu Tyr Met Leu Cys Thr Gly Asn Ser Ser His Ser Ser Trp Asp
                195                 200                 205

Asn Gln Cys Gln Cys Thr Ser Ser Ala Thr Arg Asn Thr Thr Lys Gln
    210                 215                 220

Val Thr Pro Gln Pro Glu Glu Gln Lys Glu Arg Lys Thr Thr Glu Met
225                 230                 235                 240

Gln Ser Pro Met Gln Pro Val Asp Gln Ala Ser Leu Pro Gly His Cys
                245                 250                 255

Arg Glu Pro Pro Pro Trp Glu Asn Glu Ala Thr Glu Arg Ile Tyr His
                260                 265                 270

Phe Val Val Gly Gln Met Val Tyr Tyr Gln Cys Val Gln Gly Tyr Arg
            275                 280                 285

Ala Leu His Arg Gly Pro Ala Glu Ser Val Cys Lys Met Thr His Gly
        290                 295                 300

Lys Thr Arg Trp Thr Gln Pro Gln Leu Ile Cys Thr Gly Glu Met Glu
305                 310                 315                 320

Thr Ser Gln Phe Pro Gly Glu Glu Lys Pro Gln Ala Ser Pro Glu Gly
                325                 330                 335

Arg Pro Glu Ser Glu Thr Ser Cys Leu Val Thr Thr Thr Asp Phe Gln
                340                 345                 350

Ile Gln Thr Glu Met Ala Ala Thr Met Glu Thr Ser Ile Phe Thr Thr
            355                 360                 365

Glu Tyr Gln Gly Gly Gly Gly Ser Gly Gly Gly Ser Gly Gly Gly
        370                 375                 380

Gly Ser Gly Gly Gly Ser Gly Gly Gly Ser Gly Gly Gly Gly
385                 390                 395                 400

Ser Ser Gly Gly Pro Gly Pro Ala Gly Met Lys Gly Leu Pro Gly Ser
                405                 410                 415

Ala Pro Thr Ser Ser Thr Lys Lys Thr Gln Leu Gln Leu Glu His
            420                 425                 430

Leu Leu Leu Asp Leu Gln Met Ile Leu Asn Gly Ile Asn Asn Tyr Lys
        435                 440                 445

Asn Pro Lys Leu Thr Arg Met Leu Thr Phe Lys Phe Tyr Met Pro Lys
        450                 455                 460

Lys Ala Thr Glu Leu Lys His Leu Gln Cys Leu Glu Glu Leu Lys
465                 470                 475                 480

Pro Leu Glu Glu Val Leu Asn Leu Ala Gln Ser Lys Asn Phe His Leu
                485                 490                 495

Arg Pro Arg Asp Leu Ile Ser Asn Ile Asn Val Ile Val Leu Glu Leu
            500                 505                 510

Lys Gly Ser Glu Thr Thr Phe Met Cys Glu Tyr Ala Asp Glu Thr Ala
        515                 520                 525

Thr Ile Val Glu Phe Leu Asn Arg Trp Ile Thr Phe Cys Gln Ser Ile
        530                 535                 540

Ile Ser Thr Leu Thr His His His His His
545                 550                 555

<210> SEQ ID NO 72
<211> LENGTH: 555
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Met Asp Met Arg Val Pro Ala Gln Leu Leu Gly Leu Leu Leu Trp
1               5                   10                  15

Leu Arg Gly Ala Arg Cys Ala Pro Thr Ser Ser Thr Lys Lys Thr
            20                  25                  30

Gln Leu Gln Leu Glu His Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65              70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Gly
145             150                 155                 160

Pro Ala Gly Met Lys Gly Leu Pro Gly Ser Gly Gly Gly Ser Gly
                165                 170                 175

Gly Gly Gly Ser Gly Gly Gly Ser Gly Gly Gly Ser Gly Gly
            180                 185                 190

Gly Gly Ser Gly Gly Gly Ser Glu Leu Cys Asp Asp Pro Pro
        195                 200                 205

Glu Ile Pro His Ala Thr Phe Lys Ala Met Ala Tyr Lys Glu Gly Thr
    210                 215                 220

Met Leu Asn Cys Glu Cys Lys Arg Gly Phe Arg Arg Ile Lys Ser Gly
225             230                 235                 240

Ser Leu Tyr Met Leu Cys Thr Gly Asn Ser Ser His Ser Ser Trp Asp
            245                 250                 255

Asn Gln Cys Gln Cys Thr Ser Ser Ala Thr Arg Asn Thr Thr Lys Gln
            260                 265                 270

Val Thr Pro Gln Pro Glu Glu Gln Lys Glu Arg Lys Thr Thr Glu Met
            275                 280                 285

Gln Ser Pro Met Gln Pro Val Asp Gln Ala Ser Leu Pro Gly His Cys
    290                 295                 300

Arg Glu Pro Pro Pro Trp Glu Asn Glu Ala Thr Glu Arg Ile Tyr His
305             310                 315                 320

Phe Val Val Gly Gln Met Val Tyr Tyr Gln Cys Val Gln Gly Tyr Arg
                325                 330                 335

Ala Leu His Arg Gly Pro Ala Glu Ser Val Cys Lys Met Thr His Gly
            340                 345                 350

Lys Thr Arg Trp Thr Gln Pro Gln Leu Ile Cys Thr Gly Glu Met Glu
        355                 360                 365

Thr Ser Gln Phe Pro Gly Glu Glu Lys Pro Gln Ala Ser Pro Glu Gly
    370                 375                 380

Arg Pro Glu Ser Glu Thr Ser Cys Leu Val Thr Thr Asp Phe Gln
385             390                 395                 400

Ile Gln Thr Glu Met Ala Ala Thr Met Glu Thr Ser Ile Phe Thr Thr
                405                 410                 415
```

Glu Tyr Gln Gly Gly Gly Ser Gly Gly Gly Ser Gly Gly
                420             425             430

Gly Ser Glu Val Gln Leu Val Glu Ser Gly Gly Leu Val Gln Pro
        435                 440                 445

Gly Asn Ser Leu Arg Leu Ser Cys Ala Ala Ser Gly Phe Thr Phe Ser
    450                 455                 460

Lys Phe Gly Met Ser Trp Val Arg Gln Ala Pro Gly Lys Gly Leu Glu
465                 470                 475                 480

Trp Val Ser Ser Ile Ser Gly Ser Gly Arg Asp Thr Leu Tyr Ala Glu
                485                 490                 495

Ser Val Lys Gly Arg Phe Thr Ile Ser Arg Asp Asn Ala Lys Thr Thr
            500                 505                 510

Leu Tyr Leu Gln Met Asn Ser Leu Arg Pro Glu Asp Thr Ala Val Tyr
        515                 520                 525

Tyr Cys Thr Ile Gly Gly Ser Leu Ser Val Ser Gln Gly Thr Leu
    530                 535                 540

Val Thr Val Ser Ser His His His His His
545                 550                 555

<210> SEQ ID NO 73
<211> LENGTH: 555
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Gly Gly Gly Ser Gly
                165                 170                 175

Gly Gly Gly Ser Gly Gly Gly Gly Ser Gly Gly Gly Ser Gly Gly
                180                 185                 190

Gly Gly Ser Gly Gly Gly Ser Glu Leu Cys Asp Asp Pro Pro
            195                 200                 205

Glu Ile Pro His Ala Thr Phe Lys Ala Met Ala Tyr Lys Glu Gly Thr

```
                210                 215                 220
Met Leu Asn Cys Glu Cys Lys Arg Gly Phe Arg Arg Ile Lys Ser Gly
225                 230                 235                 240

Ser Leu Tyr Met Leu Cys Thr Gly Asn Ser Ser His Ser Ser Trp Asp
                245                 250                 255

Asn Gln Cys Gln Cys Thr Ser Ser Ala Thr Arg Asn Thr Thr Lys Gln
                260                 265                 270

Val Thr Pro Gln Pro Glu Glu Gln Lys Glu Arg Lys Thr Thr Glu Met
            275                 280                 285

Gln Ser Pro Met Gln Pro Val Asp Gln Ala Ser Leu Pro Gly His Cys
        290                 295                 300

Arg Glu Pro Pro Pro Trp Glu Asn Glu Ala Thr Glu Arg Ile Tyr His
305                 310                 315                 320

Phe Val Val Gly Gln Met Val Tyr Tyr Gln Cys Val Gln Gly Tyr Arg
                325                 330                 335

Ala Leu His Arg Gly Pro Ala Glu Ser Val Cys Lys Met Thr His Gly
                340                 345                 350

Lys Thr Arg Trp Thr Gln Pro Gln Leu Ile Cys Thr Gly Glu Met Glu
            355                 360                 365

Thr Ser Gln Phe Pro Gly Glu Glu Lys Pro Gln Ala Ser Pro Glu Gly
370                 375                 380

Arg Pro Glu Ser Glu Thr Ser Cys Leu Val Thr Thr Thr Asp Phe Gln
385                 390                 395                 400

Ile Gln Thr Glu Met Ala Ala Thr Met Glu Thr Ser Ile Phe Thr Thr
                405                 410                 415

Glu Tyr Gln Ser Gly Gly Pro Gly Pro Ala Gly Met Lys Gly Leu Pro
                420                 425                 430

Gly Ser Glu Val Gln Leu Val Glu Ser Gly Gly Leu Val Gln Pro
            435                 440                 445

Gly Asn Ser Leu Arg Leu Ser Cys Ala Ala Ser Gly Phe Thr Phe Ser
        450                 455                 460

Lys Phe Gly Met Ser Trp Val Arg Gln Ala Pro Gly Lys Gly Leu Glu
465                 470                 475                 480

Trp Val Ser Ser Ile Ser Gly Ser Gly Arg Asp Thr Leu Tyr Ala Glu
                485                 490                 495

Ser Val Lys Gly Arg Phe Thr Ile Ser Arg Asp Asn Ala Lys Thr Thr
                500                 505                 510

Leu Tyr Leu Gln Met Asn Ser Leu Arg Pro Glu Asp Thr Ala Val Tyr
            515                 520                 525

Tyr Cys Thr Ile Gly Gly Ser Leu Ser Val Ser Ser Gln Gly Thr Leu
        530                 535                 540

Val Thr Val Ser Ser His His His His His
545                 550                 555

<210> SEQ ID NO 74
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Asp Met Arg Val Pro Ala Gln Leu Leu Gly Leu Leu Leu Leu Trp
1               5                   10                  15
```

```
Leu Arg Gly Ala Arg Cys Glu Val Gln Leu Val Glu Ser Gly Gly
            20                  25                  30

Leu Val Gln Pro Gly Asn Ser Leu Arg Leu Ser Cys Ala Ala Ser Gly
        35                  40                  45

Phe Thr Phe Ser Lys Phe Gly Met Ser Trp Val Arg Gln Ala Pro Gly
    50                  55                  60

Lys Gly Leu Glu Trp Val Ser Ser Ile Ser Gly Ser Gly Arg Asp Thr
65                  70                  75                  80

Leu Tyr Ala Glu Ser Val Lys Gly Arg Phe Thr Ile Ser Arg Asp Asn
                85                  90                  95

Ala Lys Thr Thr Leu Tyr Leu Gln Met Asn Ser Leu Arg Pro Glu Asp
            100                 105                 110

Thr Ala Val Tyr Tyr Cys Thr Ile Gly Gly Ser Leu Ser Val Ser Ser
        115                 120                 125

Gln Gly Thr Leu Val Thr Val Ser Ser Gly Gly Pro Gly Pro Ala
130                 135                 140

Gly Met Lys Gly Leu Pro Gly Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Phe Thr Phe Ser Ser Tyr Thr Leu Ala Trp Val Arg Gln Ala
            180                 185                 190

Pro Gly Lys Gly Leu Glu Trp Val Ala Ala Ile Asp Ser Ser Ser Tyr
        195                 200                 205

Thr Tyr Ser Pro Asp Thr Val Arg Gly Arg Phe Thr Ile Ser Arg Asp
    210                 215                 220

Asn Ala Lys Asn Ser Leu Tyr Leu Gln Met Asn Ser Leu Arg Ala Glu
225                 230                 235                 240

Asp Thr Ala Val Tyr Tyr Cys Ala Arg Asp Ser Asn Trp Asp Ala Leu
                245                 250                 255

Asp Tyr Trp Gly Gln Gly Thr Thr Val Thr Val Ser Ser Gly Gly Gly
            260                 265                 270

Gly Ser Gly Gly Gly Gly Ser Gly Gly Gly Ser Asp Ile Gln Met
        275                 280                 285

Thr Gln Ser Pro Ser Ser Leu Ser Ala Ser Val Gly Asp Arg Val Thr
    290                 295                 300

Ile Thr Cys Lys Ala Ser Gln Asn Val Gly Thr Asn Val Gly Trp Tyr
305                 310                 315                 320

Gln Gln Lys Pro Gly Lys Ala Pro Lys Ala Leu Ile Tyr Ser Ala Ser
                325                 330                 335

Phe Arg Tyr Ser Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Tyr Cys Gln Gln Tyr Tyr Thr Tyr Pro Tyr Thr Phe Gly Gly
    370                 375                 380

Gly Thr Lys Val Glu Ile Lys Gly Gly Gly Gly Ser Gly Gly Gly Gly
385                 390                 395                 400

Ser Gly Gly Gly Gly Ser Gly Gly Gly Ser Gly Gly Gly Gly Ser
                405                 410                 415

Gly Gly Gly Gly Ser Ser Gly Gly Pro Gly Pro Ala Gly Met Lys Gly
            420                 425                 430

Leu Pro Gly Ser Ala Pro Thr Ser Ser Ser Thr Lys Lys Thr Gln Leu
```

```
            435                 440                 445
Gln Leu Glu His Leu Leu Leu Asp Leu Gln Met Ile Leu Asn Gly Ile
    450                 455                 460

Asn Asn Tyr Lys Asn Pro Lys Leu Thr Arg Met Leu Thr Phe Lys Phe
465                 470                 475                 480

Tyr Met Pro Lys Lys Ala Thr Glu Leu Lys His Leu Gln Cys Leu Glu
                485                 490                 495

Glu Glu Leu Lys Pro Leu Glu Glu Val Leu Asn Leu Ala Gln Ser Lys
            500                 505                 510

Asn Phe His Leu Arg Pro Arg Asp Leu Ile Ser Asn Ile Asn Val Ile
            515                 520                 525

Val Leu Glu Leu Lys Gly Ser Glu Thr Thr Phe Met Cys Glu Tyr Ala
            530                 535                 540

Asp Glu Thr Ala Thr Ile Val Glu Phe Leu Asn Arg Trp Ile Thr Phe
545                 550                 555                 560

Cys Gln Ser Ile Ile Ser Thr Leu Thr His His His His His His
                565                 570                 575

<210> SEQ ID NO 75
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Gly Gly Gly Ser Gly
                165                 170                 175

Gly Gly Gly Ser Gly Gly Gly Ser Gly Gly Gly Ser Gly Gly
            180                 185                 190

Gly Gly Ser Gly Gly Gly Gly Ser Glu Val Gln Leu Val Glu Ser Gly
        195                 200                 205

Gly Gly Leu Val Gln Pro Gly Gly Ser Leu Arg Leu Ser Cys Ala Ala
    210                 215                 220
```

```
Ser Gly Phe Thr Phe Ser Ser Tyr Thr Leu Ala Trp Val Arg Gln Ala
225                 230                 235                 240

Pro Gly Lys Gly Leu Glu Trp Val Ala Ala Ile Asp Ser Ser Ser Tyr
            245                 250                 255

Thr Tyr Ser Pro Asp Thr Val Arg Gly Arg Phe Thr Ile Ser Arg Asp
                260                 265                 270

Asn Ala Lys Asn Ser Leu Tyr Leu Gln Met Asn Ser Leu Arg Ala Glu
            275                 280                 285

Asp Thr Ala Val Tyr Tyr Cys Ala Arg Asp Ser Asn Trp Asp Ala Leu
290                 295                 300

Asp Tyr Trp Gly Gln Gly Thr Thr Val Thr Val Ser Ser Ser Gly Gly
305                 310                 315                 320

Pro Gly Pro Ala Gly Met Lys Gly Leu Pro Gly Ser Asp Ile Gln Met
                325                 330                 335

Thr Gln Ser Pro Ser Ser Leu Ser Ala Ser Val Gly Asp Arg Val Thr
                340                 345                 350

Ile Thr Cys Lys Ala Ser Gln Asn Val Gly Thr Asn Val Gly Trp Tyr
            355                 360                 365

Gln Gln Lys Pro Gly Lys Ala Pro Lys Ala Leu Ile Tyr Ser Ala Ser
370                 375                 380

Phe Arg Tyr Ser Gly Val Pro Ser Arg Phe Ser Gly Ser Gly Ser Gly
385                 390                 395                 400

Thr Asp Phe Thr Leu Thr Ile Ser Ser Leu Gln Pro Glu Asp Phe Ala
                405                 410                 415

Thr Tyr Tyr Cys Gln Gln Tyr Tyr Thr Tyr Pro Tyr Thr Phe Gly Gly
            420                 425                 430

Gly Thr Lys Val Glu Ile Lys Gly Gly Gly Ser Gly Gly Gly Gly
            435                 440                 445

Ser Gly Gly Gly Gly Ser Glu Val Gln Leu Val Glu Ser Gly Gly Gly
            450                 455                 460

Leu Val Gln Pro Gly Asn Ser Leu Arg Leu Ser Cys Ala Ala Ser Gly
465                 470                 475                 480

Phe Thr Phe Ser Lys Phe Gly Met Ser Trp Val Arg Gln Ala Pro Gly
                485                 490                 495

Lys Gly Leu Glu Trp Val Ser Ser Ile Ser Gly Ser Gly Arg Asp Thr
            500                 505                 510

Leu Tyr Ala Glu Ser Val Lys Gly Arg Phe Thr Ile Ser Arg Asp Asn
            515                 520                 525

Ala Lys Thr Thr Leu Tyr Leu Gln Met Asn Ser Leu Arg Pro Glu Asp
            530                 535                 540

Thr Ala Val Tyr Tyr Cys Thr Ile Gly Gly Ser Leu Ser Val Ser Ser
545                 550                 555                 560

Gln Gly Thr Leu Val Thr Val Ser Ser Gly Gly Gly Gly Ser Gly Gly
                565                 570                 575

Gly Gly Ser Gly Gly Gly Gly Ser Gln Val Gln Leu Gln Glu Ser Gly
            580                 585                 590

Gly Gly Leu Val Gln Ala Gly Gly Ser Leu Arg Leu Ser Cys Ala Ala
            595                 600                 605

Ser Gly Arg Ile Phe Ser Ile Asp Ile Met Ser Trp Tyr Arg Gln Ala
            610                 615                 620

Pro Gly Lys Gln Arg Glu Leu Val Ala Arg Ile Thr Arg Gly Gly Thr
625                 630                 635                 640

Ile Ser Tyr Asp Asp Ser Val Lys Gly Arg Phe Thr Ile Ser Arg Asp
```

-continued

```
                    645                 650                 655
Asn Ala Lys Asn Thr Val Tyr Leu Gln Met Asn Ser Leu Lys Pro Glu
                660                 665                 670

Asp Thr Gly Val Tyr Tyr Cys Asn Ala Leu Tyr Gly Thr Asp Tyr Trp
            675                 680                 685

Gly Lys Gly Thr Gln Val Thr Val Ser Ser His His His His His
        690                 695                 700

<210> SEQ ID NO 76
<211> LENGTH: 689
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Asp Met Arg Val Pro Ala Gln Leu Leu Gly Leu Leu Leu Leu Trp
1               5                  10                  15

Leu Arg Gly Ala Arg Cys Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Gly Gly Ser Gly Gly Gly
    130                 135                 140

Gly Ser Gly Gly Gly Ser Ala Pro Thr Ser Ser Ser Thr Lys Lys
145                 150                 155                 160

Thr Gln Leu Gln Leu Glu His Leu Leu Leu Asp Leu Gln Met Ile Leu
                165                 170                 175

Asn Gly Ile Asn Asn Tyr Lys Asn Pro Lys Leu Thr Arg Met Leu Thr
            180                 185                 190

Phe Lys Phe Tyr Met Pro Lys Lys Ala Thr Glu Leu Lys His Leu Gln
        195                 200                 205

Cys Leu Glu Glu Glu Leu Lys Pro Leu Glu Glu Val Leu Asn Leu Ala
    210                 215                 220

Gln Ser Lys Asn Phe His Leu Arg Pro Arg Asp Leu Ile Ser Asn Ile
225                 230                 235                 240

Asn Val Ile Val Leu Glu Leu Lys Gly Ser Glu Thr Thr Phe Met Cys
                245                 250                 255

Glu Tyr Ala Asp Glu Thr Ala Thr Ile Val Glu Phe Leu Asn Arg Trp
            260                 265                 270

Ile Thr Phe Cys Gln Ser Ile Ile Ser Thr Leu Thr Ser Gly Gly Pro
        275                 280                 285

Gly Pro Ala Gly Met Lys Gly Leu Pro Gly Ser Glu Val Gln Leu Val
    290                 295                 300
```

Glu Ser Gly Gly Gly Leu Val Gln Pro Gly Asn Ser Leu Arg Leu Ser
305                 310                 315                 320

Cys Ala Ala Ser Gly Phe Thr Phe Ser Lys Phe Gly Met Ser Trp Val
            325                 330                 335

Arg Gln Ala Pro Gly Lys Gly Leu Glu Trp Val Ser Ser Ile Ser Gly
            340                 345                 350

Ser Gly Arg Asp Thr Leu Tyr Ala Glu Ser Val Lys Gly Arg Phe Thr
            355                 360                 365

Ile Ser Arg Asp Asn Ala Lys Thr Thr Leu Tyr Leu Gln Met Asn Ser
370                 375                 380

Leu Arg Pro Glu Asp Thr Ala Val Tyr Tyr Cys Thr Ile Gly Gly Ser
385                 390                 395                 400

Leu Ser Val Ser Ser Gln Gly Thr Leu Val Thr Val Ser Ser Gly Gly
            405                 410                 415

Gly Gly Ser Gly Gly Gly Gly Ser Gly Gly Gly Ser Gly Gly Gly
            420                 425                 430

Gly Ser Gly Gly Gly Gly Ser Gly Gly Gly Gly Ser Glu Val Gln Leu
            435                 440                 445

Val Glu Ser Gly Gly Gly Leu Val Gln Pro Gly Gly Ser Leu Arg Leu
450                 455                 460

Ser Cys Ala Ala Ser Gly Phe Thr Phe Ser Ser Tyr Thr Leu Ala Trp
465                 470                 475                 480

Val Arg Gln Ala Pro Gly Lys Gly Leu Glu Trp Val Ala Ala Ile Asp
            485                 490                 495

Ser Ser Ser Tyr Thr Tyr Ser Pro Asp Thr Val Arg Gly Arg Phe Thr
            500                 505                 510

Ile Ser Arg Asp Asn Ala Lys Asn Ser Leu Tyr Leu Gln Met Asn Ser
515                 520                 525

Leu Arg Ala Glu Asp Thr Ala Val Tyr Tyr Cys Ala Arg Asp Ser Asn
530                 535                 540

Trp Asp Ala Leu Asp Tyr Trp Gly Gln Gly Thr Val Thr Val Ser
545                 550                 555                 560

Ser Gly Gly Gly Gly Ser Gly Gly Gly Gly Ser Gly Gly Gly Gly Ser
            565                 570                 575

Asp Ile Gln Met Thr Gln Ser Pro Ser Ser Leu Ser Ala Ser Val Gly
            580                 585                 590

Asp Arg Val Thr Ile Thr Cys Lys Ala Ser Gln Asn Val Gly Thr Asn
            595                 600                 605

Val Gly Trp Tyr Gln Gln Lys Pro Gly Lys Ala Pro Lys Ala Leu Ile
            610                 615                 620

Tyr Ser Ala Ser Phe Arg Tyr Ser Gly Val Pro Ser Arg Phe Ser Gly
625                 630                 635                 640

Ser Gly Ser Gly Thr Asp Phe Thr Leu Thr Ile Ser Ser Leu Gln Pro
            645                 650                 655

Glu Asp Phe Ala Thr Tyr Tyr Cys Gln Gln Tyr Tyr Thr Tyr Pro Tyr
            660                 665                 670

Thr Phe Gly Gly Gly Thr Lys Val Glu Ile Lys His His His His His
            675                 680                 685

His

<210> SEQ ID NO 77
<211> LENGTH: 545
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Thr Lys Lys Thr
            20                  25                  30

Gln Leu Gln Leu Glu His Leu Leu Leu Asp Leu Gln Met Ile Leu Asn
            35                  40                  45

Gly Ile Asn Asn Tyr Lys Asn Pro Lys Leu Thr Arg Met Leu Thr Phe
        50                  55                  60

Lys Phe Tyr Met Pro Lys Lys Ala Thr Glu Leu Lys His Leu Gln Cys
65              70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Glu Val Gln Leu Val Glu
                165                 170                 175

Ser Gly Gly Gly Leu Val Gln Pro Gly Gly Ser Leu Arg Leu Ser Cys
            180                 185                 190

Ala Ala Ser Gly Phe Thr Phe Ser Ser Tyr Thr Leu Ala Trp Val Arg
        195                 200                 205

Gln Ala Pro Gly Lys Gly Leu Glu Trp Val Ala Ala Ile Asp Ser Ser
    210                 215                 220

Ser Tyr Thr Tyr Ser Pro Asp Thr Val Arg Gly Arg Phe Thr Ile Ser
225                 230                 235                 240

Arg Asp Asn Ala Lys Asn Ser Leu Tyr Leu Gln Met Asn Ser Leu Arg
                245                 250                 255

Ala Glu Asp Thr Ala Val Tyr Tyr Cys Ala Arg Asp Ser Asn Trp Asp
            260                 265                 270

Ala Leu Asp Tyr Trp Gly Gln Gly Thr Thr Val Thr Val Ser Ser Gly
        275                 280                 285

Gly Gly Gly Ser Gly Gly Gly Gly Ser Gly Gly Gly Gly Ser Asp Ile
    290                 295                 300

Gln Met Thr Gln Ser Pro Ser Ser Leu Ser Ala Ser Val Gly Asp Arg
305                 310                 315                 320

Val Thr Ile Thr Cys Lys Ala Ser Gln Asn Val Gly Thr Asn Val Gly
                325                 330                 335

Trp Tyr Gln Gln Lys Pro Gly Lys Ala Pro Lys Ala Leu Ile Tyr Ser
            340                 345                 350

Ala Ser Phe Arg Tyr Ser Gly Val Pro Ser Arg Phe Ser Gly Ser Gly
        355                 360                 365

Ser Gly Thr Asp Phe Thr Leu Thr Ile Ser Ser Leu Gln Pro Glu Asp
    370                 375                 380

Phe Ala Thr Tyr Tyr Cys Gln Gln Tyr Tyr Thr Tyr Pro Tyr Thr Phe
```

```
              385                 390                 395                 400
    Gly Gly Gly Thr Lys Val Glu Ile Lys Gly Gly Gly Ser Gly Gly
                    405                 410                 415

Gly Gly Ser Gly Gly Gly Ser Glu Val Gln Leu Val Glu Ser Gly
                    420                 425                 430

Gly Gly Leu Val Gln Pro Gly Asn Ser Leu Arg Leu Ser Cys Ala Ala
                    435                 440                 445

Ser Gly Phe Thr Phe Ser Lys Phe Gly Met Ser Trp Val Arg Gln Ala
                    450                 455                 460

Pro Gly Lys Gly Leu Glu Trp Val Ser Ser Ile Ser Gly Ser Gly Arg
    465                 470                 475                 480

Asp Thr Leu Tyr Ala Glu Ser Val Lys Gly Arg Phe Thr Ile Ser Arg
                    485                 490                 495

Asp Asn Ala Lys Thr Thr Leu Tyr Leu Gln Met Asn Ser Leu Arg Pro
                    500                 505                 510

Glu Asp Thr Ala Val Tyr Tyr Cys Thr Ile Gly Gly Ser Leu Ser Val
                    515                 520                 525

Ser Ser Gln Gly Thr Leu Val Thr Val Ser Ser His His His His
                    530                 535                 540

His
    545

<210> SEQ ID NO 78
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Asp Met Arg Val Pro Ala Gln Leu Leu Gly Leu Leu Leu Leu Trp
    1               5                   10                  15

Leu Arg Gly Ala Arg Cys Ala Pro Thr Ser Ser Ser Thr Lys Lys Thr
                    20                  25                  30

Gln Leu Gln Leu Glu His Leu Leu Leu Asp Leu Gln Met Ile Leu Asn
                    35                  40                  45

Gly Ile Asn Asn Tyr Lys Asn Pro Lys Leu Thr Arg Met Leu Thr Phe
                50                  55                  60

Lys Phe Tyr Met Pro Lys Lys Ala Thr Glu Leu Lys His Leu Gln Cys
    65                  70                  75                  80

Leu Glu Glu Glu Leu Lys Pro Leu Glu Glu Val Leu Asn Leu Ala Gln
                    85                  90                  95

Ser Lys Asn Phe His Leu Arg Pro Arg Asp Leu Ile Ser Asn Ile Asn
                    100                 105                 110

Val Ile Val Leu Glu Leu Lys Gly Ser Glu Thr Thr Phe Met Cys Glu
                    115                 120                 125

Tyr Ala Asp Glu Thr Ala Thr Ile Val Glu Phe Leu Asn Arg Trp Ile
                    130                 135                 140

Thr Phe Cys Gln Ser Ile Ile Ser Thr Leu Thr Ser Gly Gly Pro Gly
    145                 150                 155                 160

Pro Ala Gly Met Lys Gly Leu Pro Gly Ser Gly Gly Gly Ser Gly
                    165                 170                 175

Gly Gly Gly Ser Gly Gly Gly Ser Gly Gly Gly Ser Gly Gly
                    180                 185                 190
```

```
Gly Gly Ser Gly Gly Gly Ser Glu Val Gln Leu Val Glu Ser Gly
            195                 200                 205
Gly Gly Leu Val Gln Pro Gly Gly Ser Leu Arg Leu Ser Cys Ala Ala
210                 215                 220
Ser Gly Phe Thr Phe Ser Ser Tyr Thr Leu Ala Trp Val Arg Gln Ala
225                 230                 235                 240
Pro Gly Lys Gly Leu Glu Trp Val Ala Ala Ile Asp Ser Ser Ser Tyr
                245                 250                 255
Thr Tyr Ser Pro Asp Thr Val Arg Gly Arg Phe Thr Ile Ser Arg Asp
            260                 265                 270
Asn Ala Lys Asn Ser Leu Tyr Leu Gln Met Asn Ser Leu Arg Ala Glu
        275                 280                 285
Asp Thr Ala Val Tyr Tyr Cys Ala Arg Asp Ser Asn Trp Asp Ala Leu
290                 295                 300
Asp Tyr Trp Gly Gln Gly Thr Thr Val Thr Val Ser Ser Gly Gly Gly
305                 310                 315                 320
Gly Ser Gly Gly Gly Gly Ser Gly Gly Gly Gly Ser Asp Ile Gln Met
                325                 330                 335
Thr Gln Ser Pro Ser Ser Leu Ser Ala Ser Val Gly Asp Arg Val Thr
            340                 345                 350
Ile Thr Cys Lys Ala Ser Gln Asn Val Gly Thr Asn Val Gly Trp Tyr
        355                 360                 365
Gln Gln Lys Pro Gly Lys Ala Pro Lys Ala Leu Ile Tyr Ser Ala Ser
370                 375                 380
Phe Arg Tyr Ser Gly Val Pro Ser Arg Phe Ser Gly Ser Gly Ser Gly
385                 390                 395                 400
Thr Asp Phe Thr Leu Thr Ile Ser Ser Leu Gln Pro Glu Asp Phe Ala
                405                 410                 415
Thr Tyr Tyr Cys Gln Gln Tyr Tyr Thr Tyr Pro Tyr Thr Phe Gly Gly
            420                 425                 430
Gly Thr Lys Val Glu Ile Lys Gly Gly Gly Gly Ser Gly Gly Gly Gly
        435                 440                 445
Ser Gly Gly Gly Gly Ser Glu Val Gln Leu Val Glu Ser Gly Gly Gly
450                 455                 460
Leu Val Gln Pro Gly Asn Ser Leu Arg Leu Ser Cys Ala Ala Ser Gly
465                 470                 475                 480
Phe Thr Phe Ser Lys Phe Gly Met Ser Trp Val Arg Gln Ala Pro Gly
                485                 490                 495
Lys Gly Leu Glu Trp Val Ser Ser Ile Ser Gly Ser Gly Arg Asp Thr
            500                 505                 510
Leu Tyr Ala Glu Ser Val Lys Gly Arg Phe Thr Ile Ser Arg Asp Asn
        515                 520                 525
Ala Lys Thr Thr Leu Tyr Leu Gln Met Asn Ser Leu Arg Pro Glu Asp
530                 535                 540
Thr Ala Val Tyr Tyr Cys Thr Ile Gly Gly Ser Leu Ser Val Ser Ser
545                 550                 555                 560
Gln Gly Thr Leu Val Thr Val Ser Ser His His His His His His
                565                 570                 575
```

<210> SEQ ID NO 79
<211> LENGTH: 421
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Asn Ser Leu Arg Leu Ser Cys Ala Ala Ser Gly
        35                  40                  45

Phe Thr Phe Ser Lys Phe Gly Met Ser Trp Val Arg Gln Ala Pro Gly
    50                  55                  60

Lys Gly Leu Glu Trp Val Ser Ser Ile Ser Gly Ser Gly Arg Asp Thr
65                  70                  75                  80

Leu Tyr Ala Glu Ser Val Lys Gly Arg Phe Thr Ile Ser Arg Asp Asn
                85                  90                  95

Ala Lys Thr Thr Leu Tyr Leu Gln Met Asn Ser Leu Arg Pro Glu Asp
            100                 105                 110

Thr Ala Val Tyr Tyr Cys Thr Ile Gly Gly Ser Leu Ser Val Ser Ser
        115                 120                 125

Gln Gly Thr Leu Val Thr Val Ser Ser Ser Gly Gly Pro Gly Pro Ala
    130                 135                 140

Gly Met Lys Gly Leu Pro Gly Ser Ala Pro Thr Ser Ser Ser Thr Lys
145                 150                 155                 160

Lys Thr Gln Leu Gln Leu Glu His Leu Leu Leu Asp Leu Gln Met Ile
                165                 170                 175

Leu Asn Gly Ile Asn Asn Tyr Lys Asn Pro Lys Leu Thr Arg Met Leu
            180                 185                 190

Thr Phe Lys Phe Tyr Met Pro Lys Lys Ala Thr Glu Leu Lys His Leu
        195                 200                 205

Gln Cys Leu Glu Glu Glu Leu Lys Pro Leu Glu Glu Val Leu Asn Leu
    210                 215                 220

Ala Gln Ser Lys Asn Phe His Leu Arg Pro Arg Asp Leu Ile Ser Asn
225                 230                 235                 240

Ile Asn Val Ile Val Leu Glu Leu Lys Gly Ser Glu Thr Thr Phe Met
                245                 250                 255

Cys Glu Tyr Ala Asp Glu Thr Ala Thr Ile Val Glu Phe Leu Asn Arg
            260                 265                 270

Trp Ile Thr Phe Cys Gln Ser Ile Ile Ser Thr Leu Thr Ser Gly Gly
        275                 280                 285

Pro Gly Pro Ala Gly Met Lys Gly Leu Pro Gly Ser Glu Val Gln Leu
    290                 295                 300

Val Glu Ser Gly Gly Gly Leu Val Gln Pro Gly Asn Ser Leu Arg Leu
305                 310                 315                 320

Ser Cys Ala Ala Ser Gly Phe Thr Phe Ser Lys Phe Gly Met Ser Trp
                325                 330                 335

Val Arg Gln Ala Pro Gly Lys Gly Leu Glu Trp Val Ser Ser Ile Ser
            340                 345                 350

Gly Ser Gly Arg Asp Thr Leu Tyr Ala Glu Ser Val Lys Gly Arg Phe
        355                 360                 365

Thr Ile Ser Arg Asp Asn Ala Lys Thr Thr Leu Tyr Leu Gln Met Asn
    370                 375                 380

Ser Leu Arg Pro Glu Asp Thr Ala Val Tyr Tyr Cys Thr Ile Gly Gly
385                 390                 395                 400
```

```
Ser Leu Ser Val Ser Ser Gln Gly Thr Leu Val Thr Val Ser Ser His
                405                 410                 415
His His His His His
            420

<210> SEQ ID NO 80
<211> LENGTH: 806
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
                20                  25                  30

Leu Val Gln Ala Gly Gly Ser Leu Arg Leu Ser Cys Ala Ala Ser Gly
            35                  40                  45

Arg Ile Phe Ser Ile Asp Ile Met Ser Trp Tyr Arg Gln Ala Pro Gly
        50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Ser Gly Ser Gly Ser Gly Ser
    130                 135                 140

Gly Ser Gly Ser Gly Ser Gly Ser Glu Val Gln Leu Val Glu Ser Gly
145                 150                 155                 160

Gly Gly Leu Val Gln Pro Gly Asn Ser Leu Arg Leu Ser Cys Ala Ala
                165                 170                 175

Ser Gly Phe Thr Phe Ser Lys Phe Gly Met Ser Trp Val Arg Gln Ala
            180                 185                 190

Pro Gly Lys Gly Leu Glu Trp Val Ser Ser Ile Ser Gly Ser Gly Arg
        195                 200                 205

Asp Thr Leu Tyr Ala Glu Ser Val Lys Gly Arg Phe Thr Ile Ser Arg
    210                 215                 220

Asp Asn Ala Lys Thr Thr Leu Tyr Leu Gln Met Asn Ser Leu Arg Pro
225                 230                 235                 240

Glu Asp Thr Ala Val Tyr Tyr Cys Thr Ile Gly Gly Ser Leu Ser Val
                245                 250                 255

Ser Ser Gln Gly Thr Leu Val Thr Val Ser Ser Gly Ser Gly Ser Gly
            260                 265                 270

Ser Gly Ser Gly Ser Gly Ser Gly Ser Gln Val Gln Leu Gln
    275                 280                 285

Glu Ser Gly Gly Gly Leu Val Gln Ala Gly Gly Ser Leu Arg Leu Ser
    290                 295                 300

Cys Ala Ala Ser Gly Arg Ile Phe Ser Ile Asp Ile Met Ser Trp Tyr
305                 310                 315                 320

Arg Gln Ala Pro Gly Lys Gln Arg Glu Leu Val Ala Arg Ile Thr Arg
                325                 330                 335
```

```
Gly Gly Thr Ile Ser Tyr Asp Ser Val Lys Gly Arg Phe Thr Ile
            340                 345                 350

Ser Arg Asp Asn Ala Lys Asn Thr Val Tyr Leu Gln Met Asn Ser Leu
        355                 360                 365

Lys Pro Glu Asp Thr Gly Val Tyr Tyr Cys Asn Ala Leu Tyr Gly Thr
    370                 375                 380

Asp Tyr Trp Gly Lys Gly Thr Gln Val Thr Val Ser Ser Gly Ser Gly
385                 390                 395                 400

Ser Gly Ser Gly Ser Gly Ser Gly Ser Gly Ser Glu Val Gln
            405                 410                 415

Leu Val Glu Ser Gly Gly Leu Val Gln Pro Gly Gly Ser Leu Arg
        420                 425                 430

Leu Ser Cys Ala Ala Ser Gly Phe Thr Phe Ser Ser Tyr Thr Leu Ala
            435                 440                 445

Trp Val Arg Gln Ala Pro Gly Lys Gly Leu Glu Trp Val Ala Ala Ile
    450                 455                 460

Asp Ser Ser Ser Tyr Thr Tyr Ser Pro Asp Thr Val Arg Gly Arg Phe
465                 470                 475                 480

Thr Ile Ser Arg Asp Asn Ala Lys Asn Ser Leu Tyr Leu Gln Met Asn
            485                 490                 495

Ser Leu Arg Ala Glu Asp Thr Ala Val Tyr Tyr Cys Ala Arg Asp Ser
        500                 505                 510

Asn Trp Asp Ala Leu Asp Tyr Trp Gly Gln Gly Thr Val Thr Val
    515                 520                 525

Ser Ser Gly Gly Gly Gly Ser Gly Gly Gly Gly Ser Gly Gly Gly Gly
            530                 535                 540

Ser Asp Ile Gln Met Thr Gln Ser Pro Ser Ser Leu Ser Ala Ser Val
545                 550                 555                 560

Gly Asp Arg Val Thr Ile Thr Cys Lys Ala Ser Gln Asn Val Gly Thr
            565                 570                 575

Asn Val Gly Trp Tyr Gln Gln Lys Pro Gly Lys Ala Pro Lys Ala Leu
        580                 585                 590

Ile Tyr Ser Ala Ser Phe Arg Tyr Ser Gly Val Pro Ser Arg Phe Ser
    595                 600                 605

Gly Ser Gly Ser Gly Thr Asp Phe Thr Leu Thr Ile Ser Ser Leu Gln
            610                 615                 620

Pro Glu Asp Phe Ala Thr Tyr Tyr Cys Gln Gln Tyr Thr Tyr Pro
625                 630                 635                 640

Tyr Thr Phe Gly Gly Gly Thr Lys Val Glu Ile Lys Ser Gly Gly Pro
            645                 650                 655

Gly Pro Ala Gly Met Lys Gly Leu Pro Gly Ser Ala Pro Thr Ser Ser
        660                 665                 670

Ser Thr Lys Lys Thr Gln Leu Gln Leu Glu His Leu Leu Asp Leu
    675                 680                 685

Gln Met Ile Leu Asn Gly Ile Asn Asn Tyr Lys Asn Pro Lys Leu Thr
            690                 695                 700

Arg Met Leu Thr Phe Lys Phe Tyr Met Pro Lys Lys Ala Thr Glu Leu
705                 710                 715                 720

Lys His Leu Gln Cys Leu Glu Glu Glu Leu Lys Pro Leu Glu Glu Val
            725                 730                 735

Leu Asn Leu Ala Gln Ser Lys Asn Phe His Leu Arg Pro Arg Asp Leu
        740                 745                 750
```

Ile Ser Asn Ile Asn Val Ile Val Leu Glu Leu Lys Gly Ser Glu Thr
            755                 760                 765

Thr Phe Met Cys Glu Tyr Ala Asp Glu Thr Ala Thr Ile Val Glu Phe
    770                 775                 780

Leu Asn Arg Trp Ile Thr Phe Cys Gln Ser Ile Ile Ser Thr Leu Thr
785                 790                 795                 800

His His His His His His
            805

<210> SEQ ID NO 81
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Ser Gly Ser Gly Ser Gly Ser
    130                 135                 140

Gly Ser Gly Ser Gly Ser Gly Ser Glu Val Gln Leu Val Glu Ser Gly
145                 150                 155                 160

Gly Gly Leu Val Gln Pro Gly Asn Ser Leu Arg Leu Ser Cys Ala Ala
                165                 170                 175

Ser Gly Phe Thr Phe Ser Lys Phe Gly Met Ser Trp Val Arg Gln Ala
            180                 185                 190

Pro Gly Lys Gly Leu Glu Trp Val Ser Ser Ile Ser Gly Ser Gly Arg
        195                 200                 205

Asp Thr Leu Tyr Ala Glu Ser Val Lys Gly Arg Phe Thr Ile Ser Arg
    210                 215                 220

Asp Asn Ala Lys Thr Thr Leu Tyr Leu Gln Met Asn Ser Leu Arg Pro
225                 230                 235                 240

Glu Asp Thr Ala Val Tyr Tyr Cys Thr Ile Gly Gly Ser Leu Ser Val
                245                 250                 255

Ser Ser Gln Gly Thr Leu Val Thr Val Ser Ser Gly Gly Ser Gly Gly
            260                 265                 270

Ser Gly Ser Gly Ser Gly Ser Gly Ser Glu Val Gln Leu Val
        275                 280                 285

Glu Ser Gly Gly Gly Leu Val Gln Pro Gly Gly Ser Leu Arg Leu Ser
290                 295                 300

Cys Ala Ala Ser Gly Phe Thr Phe Ser Ser Tyr Thr Leu Ala Trp Val
305                 310                 315                 320

Arg Gln Ala Pro Gly Lys Gly Leu Glu Trp Val Ala Ala Ile Asp Ser
            325                 330                 335

Ser Ser Tyr Thr Tyr Ser Pro Asp Thr Val Arg Gly Arg Phe Thr Ile
        340                 345                 350

Ser Arg Asp Asn Ala Lys Asn Ser Leu Tyr Leu Gln Met Asn Ser Leu
    355                 360                 365

Arg Ala Glu Asp Thr Ala Val Tyr Tyr Cys Ala Arg Asp Ser Asn Trp
370                 375                 380

Asp Ala Leu Asp Tyr Trp Gly Gln Gly Thr Thr Val Thr Val Ser Ser
385                 390                 395                 400

Gly Gly Gly Gly Ser Gly Gly Gly Ser Gly Gly Gly Gly Ser Gly Asp
                405                 410                 415

Ile Gln Met Thr Gln Ser Pro Ser Ser Leu Ser Ala Ser Val Gly Asp
            420                 425                 430

Arg Val Thr Ile Thr Cys Lys Ala Ser Gln Asn Val Gly Thr Asn Val
    435                 440                 445

Gly Trp Tyr Gln Gln Lys Pro Gly Lys Ala Pro Lys Ala Leu Ile Tyr
450                 455                 460

Ser Ala Ser Phe Arg Tyr Ser Gly Val Pro Ser Arg Phe Ser Gly Ser
465                 470                 475                 480

Gly Ser Gly Thr Asp Phe Thr Leu Thr Ile Ser Ser Leu Gln Pro Glu
                485                 490                 495

Asp Phe Ala Thr Tyr Tyr Cys Gln Gln Tyr Tyr Thr Tyr Pro Tyr Thr
            500                 505                 510

Phe Gly Gly Gly Thr Lys Val Glu Ile Lys Ser Gly Gly Pro Gly Pro
    515                 520                 525

Ala Gly Met Lys Gly Leu Pro Gly Ser Ala Pro Thr Ser Ser Ser Thr
530                 535                 540

Lys Lys Thr Gln Leu Gln Leu Glu His Leu Leu Leu Asp Leu Gln Met
545                 550                 555                 560

Ile Leu Asn Gly Ile Asn Asn Tyr Lys Asn Pro Lys Leu Thr Arg Met
                565                 570                 575

Leu Thr Phe Lys Phe Tyr Met Pro Lys Lys Ala Thr Glu Leu Lys His
            580                 585                 590

Leu Gln Cys Leu Glu Glu Glu Leu Lys Pro Leu Glu Glu Val Leu Asn
    595                 600                 605

Leu Ala Gln Ser Lys Asn Phe His Leu Arg Pro Arg Asp Leu Ile Ser
610                 615                 620

Asn Ile Asn Val Ile Val Leu Glu Leu Lys Gly Ser Glu Thr Thr Phe
625                 630                 635                 640

Met Cys Glu Tyr Ala Asp Glu Thr Ala Thr Ile Val Glu Phe Leu Asn
                645                 650                 655

Arg Trp Ile Thr Phe Cys Gln Ser Ile Ile Ser Thr Leu Thr His His
            660                 665                 670

His His His His
        675

<210> SEQ ID NO 82
<211> LENGTH: 421
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 82

```
Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Ser Gly Ser Gly Ser Gly Ser
    130                 135                 140

Gly Ser Gly Ser Gly Ser Glu Val Gln Leu Val Glu Ser Gly
145                 150                 155                 160

Gly Gly Leu Val Gln Pro Gly Asn Ser Leu Arg Leu Ser Cys Ala Ala
                165                 170                 175

Ser Gly Phe Thr Phe Ser Lys Phe Gly Met Ser Trp Val Arg Gln Ala
            180                 185                 190

Pro Gly Lys Gly Leu Glu Trp Val Ser Ser Ile Ser Gly Ser Gly Arg
        195                 200                 205

Asp Thr Leu Tyr Ala Glu Ser Val Lys Gly Arg Phe Thr Ile Ser Arg
    210                 215                 220

Asp Asn Ala Lys Thr Thr Leu Tyr Leu Gln Met Asn Ser Leu Arg Pro
225                 230                 235                 240

Glu Asp Thr Ala Val Tyr Tyr Cys Thr Ile Gly Gly Ser Leu Ser Val
                245                 250                 255

Ser Ser Gln Gly Thr Leu Val Thr Val Ser Ser Gly Gly Pro Gly
            260                 265                 270

Pro Ala Gly Met Lys Gly Leu Pro Gly Ser Ala Pro Thr Ser Ser Ser
        275                 280                 285

Thr Lys Lys Thr Gln Leu Gln Leu Glu His Leu Leu Leu Asp Leu Gln
    290                 295                 300

Met Ile Leu Asn Gly Ile Asn Asn Tyr Lys Asn Pro Lys Leu Thr Arg
305                 310                 315                 320

Met Leu Thr Phe Lys Phe Tyr Met Pro Lys Lys Ala Thr Glu Leu Lys
                325                 330                 335

His Leu Gln Cys Leu Glu Glu Glu Leu Lys Pro Leu Glu Glu Val Leu
            340                 345                 350

Asn Leu Ala Gln Ser Lys Asn Phe His Leu Arg Pro Arg Asp Leu Ile
        355                 360                 365

Ser Asn Ile Asn Val Ile Val Leu Glu Leu Lys Gly Ser Glu Thr Thr
    370                 375                 380

Phe Met Cys Glu Tyr Ala Asp Glu Thr Ala Thr Ile Val Glu Phe Leu
385                 390                 395                 400
```

```
Asn Arg Trp Ile Thr Phe Cys Gln Ser Ile Ile Ser Thr Leu Thr His
                405                 410                 415

His His His His His
            420

<210> SEQ ID NO 83
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
                20                  25                  30

Leu Val Gln Ala Gly Gly Ser Leu Arg Leu Ser Cys Ala Ala Ser Gly
            35                  40                  45

Arg Ile Phe Ser Ile Asp Ile Met Ser Trp Tyr Arg Gln Ala Pro Gly
        50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Pro Gly Pro Ala Gly
130                 135                 140

Met Lys Gly Leu Pro Gly Ser Ala Pro Thr Ser Ser Thr Lys Lys
145                 150                 155                 160

Thr Gln Leu Gln Leu Glu His Leu Leu Leu Asp Leu Gln Met Ile Leu
                165                 170                 175

Asn Gly Ile Asn Asn Tyr Lys Asn Pro Lys Leu Thr Arg Met Leu Thr
            180                 185                 190

Phe Lys Phe Tyr Met Pro Lys Lys Ala Thr Glu Leu Lys His Leu Gln
        195                 200                 205

Cys Leu Glu Glu Glu Leu Lys Pro Leu Glu Glu Val Leu Asn Leu Ala
210                 215                 220

Gln Ser Lys Asn Phe His Leu Arg Pro Arg Asp Leu Ile Ser Asn Ile
225                 230                 235                 240

Asn Val Ile Val Leu Glu Leu Lys Gly Ser Glu Thr Thr Phe Met Cys
                245                 250                 255

Glu Tyr Ala Asp Glu Thr Ala Thr Ile Val Glu Phe Leu Asn Arg Trp
            260                 265                 270

Ile Thr Phe Cys Gln Ser Ile Ile Ser Thr Leu Thr Ser Gly Gly Pro
        275                 280                 285

Gly Pro Ala Gly Met Lys Gly Leu Pro Gly Ser Glu Val Gln Leu Val
        290                 295                 300

Glu Ser Gly Gly Gly Leu Val Gln Pro Gly Asn Ser Leu Arg Leu Ser
305                 310                 315                 320

Cys Ala Ala Ser Gly Phe Thr Phe Ser Lys Phe Gly Met Ser Trp Val
```

```
                    325                 330                 335
Arg Gln Ala Pro Gly Lys Gly Leu Glu Trp Val Ser Ile Ser Gly
                340                 345                 350

Ser Gly Arg Asp Thr Leu Tyr Ala Glu Ser Val Lys Gly Arg Phe Thr
                355                 360                 365

Ile Ser Arg Asp Asn Ala Lys Thr Thr Leu Tyr Leu Gln Met Asn Ser
            370                 375                 380

Leu Arg Pro Glu Asp Thr Ala Val Tyr Tyr Cys Thr Ile Gly Gly Ser
385                 390                 395                 400

Leu Ser Val Ser Gln Gly Thr Leu Val Thr Val Ser Ser His His
                405                 410                 415

His His His His
        420

<210> SEQ ID NO 84
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
                20                  25                  30

Leu Val Gln Ala Gly Gly Ser Leu Arg Leu Ser Cys Ala Ala Ser Gly
            35                  40                  45

Arg Ile Phe Ser Ile Asp Ile Met Ser Trp Tyr Arg Gln Ala Pro Gly
        50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Gly Gly Ser Gly Gly Gly
    130                 135                 140

Gly Ser Gly Gly Gly Gly Ser Glu Val Gln Leu Val Glu Ser Gly Gly
145                 150                 155                 160

Gly Leu Val Gln Pro Gly Asn Ser Leu Arg Leu Ser Cys Ala Ala Ser
                165                 170                 175

Gly Phe Thr Phe Ser Lys Phe Gly Met Ser Trp Val Arg Gln Ala Pro
            180                 185                 190

Gly Lys Gly Leu Glu Trp Val Ser Ile Ser Gly Ser Gly Arg Asp
        195                 200                 205

Thr Leu Tyr Ala Glu Ser Val Lys Gly Arg Phe Thr Ile Ser Arg Asp
    210                 215                 220

Asn Ala Lys Thr Thr Leu Tyr Leu Gln Met Asn Ser Leu Arg Pro Glu
225                 230                 235                 240

Asp Thr Ala Val Tyr Tyr Cys Thr Ile Gly Gly Ser Leu Ser Val Ser
                245                 250                 255
```

Ser Gln Gly Thr Leu Val Thr Val Ser Ser Gly Gly Pro Gly Pro
            260                 265                 270

Ala Gly Met Lys Gly Leu Pro Gly Ser Ala Pro Thr Ser Ser Thr
        275                 280                 285

Lys Lys Thr Gln Leu Gln Leu Glu His Leu Leu Leu Asp Leu Gln Met
290                 295                 300

Ile Leu Asn Gly Ile Asn Asn Tyr Lys Asn Pro Lys Leu Thr Arg Met
305                 310                 315                 320

Leu Thr Phe Lys Phe Tyr Met Pro Lys Lys Ala Thr Glu Leu Lys His
                325                 330                 335

Leu Gln Cys Leu Glu Glu Glu Leu Lys Pro Leu Glu Glu Val Leu Asn
            340                 345                 350

Leu Ala Gln Ser Lys Asn Phe His Leu Arg Pro Arg Asp Leu Ile Ser
            355                 360                 365

Asn Ile Asn Val Ile Val Leu Glu Leu Lys Gly Ser Glu Thr Thr Phe
            370                 375                 380

Met Cys Glu Tyr Ala Asp Glu Thr Ala Thr Ile Val Glu Phe Leu Asn
385                 390                 395                 400

Arg Trp Ile Thr Phe Cys Gln Ser Ile Ile Ser Thr Leu Thr Ser Gly
                405                 410                 415

Gly Pro Gly Pro Ala Gly Met Lys Gly Leu Pro Gly Ser Glu Val Gln
            420                 425                 430

Leu Val Glu Ser Gly Gly Gly Leu Val Gln Pro Gly Asn Ser Leu Arg
            435                 440                 445

Leu Ser Cys Ala Ala Ser Gly Phe Thr Phe Ser Lys Phe Gly Met Ser
450                 455                 460

Trp Val Arg Gln Ala Pro Gly Lys Gly Leu Glu Trp Val Ser Ser Ile
465                 470                 475                 480

Ser Gly Ser Gly Arg Asp Thr Leu Tyr Ala Glu Ser Val Lys Gly Arg
                485                 490                 495

Phe Thr Ile Ser Arg Asp Asn Ala Lys Thr Thr Leu Tyr Leu Gln Met
            500                 505                 510

Asn Ser Leu Arg Pro Glu Asp Thr Ala Val Tyr Tyr Cys Thr Ile Gly
            515                 520                 525

Gly Ser Leu Ser Val Ser Ser Gln Gly Thr Leu Val Thr Val Ser Ser
        530                 535                 540

His His His His His His
545                 550

<210> SEQ ID NO 85
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Arg Ile Phe Ser Ile Asp Ile Met Ser Trp Tyr Arg Gln Ala Pro Gly
    50                  55                  60

```
Lys Gln Arg Glu Leu Val Ala Arg Ile Thr Arg Gly Thr Ile Ser
 65                  70                  75                  80

Tyr Asp Asp Ser Val Lys Gly Arg Phe Thr Ile Ser Arg Asp Asn Ala
                 85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Gly Ser Gly Gly Gly
    130                 135                 140

Gly Ser Gly Gly Gly Ser Ala Pro Thr Ser Ser Thr Lys Lys
145                 150                 155                 160

Thr Gln Leu Gln Leu Glu His Leu Leu Leu Asp Leu Gln Met Ile Leu
                165                 170                 175

Asn Gly Ile Asn Asn Tyr Lys Asn Pro Lys Leu Thr Arg Met Leu Thr
            180                 185                 190

Phe Lys Phe Tyr Met Pro Lys Lys Ala Thr Glu Leu Lys His Leu Gln
        195                 200                 205

Cys Leu Glu Glu Glu Leu Lys Pro Leu Glu Glu Val Leu Asn Leu Ala
    210                 215                 220

Gln Ser Lys Asn Phe His Leu Arg Pro Arg Asp Leu Ile Ser Asn Ile
225                 230                 235                 240

Asn Val Ile Val Leu Glu Leu Lys Gly Ser Glu Thr Thr Phe Met Cys
                245                 250                 255

Glu Tyr Ala Asp Glu Thr Ala Thr Ile Val Glu Phe Leu Asn Arg Trp
            260                 265                 270

Ile Thr Phe Cys Gln Ser Ile Ile Ser Thr Leu Thr Ser Gly Gly Pro
        275                 280                 285

Gly Pro Ala Gly Met Lys Gly Leu Pro Gly Ser Glu Val Gln Leu Val
    290                 295                 300

Glu Ser Gly Gly Gly Leu Val Gln Pro Gly Asn Ser Leu Arg Leu Ser
305                 310                 315                 320

Cys Ala Ala Ser Gly Phe Thr Phe Ser Lys Phe Gly Met Ser Trp Val
                325                 330                 335

Arg Gln Ala Pro Gly Lys Gly Leu Glu Trp Val Ser Ser Ile Ser Gly
            340                 345                 350

Ser Gly Arg Asp Thr Leu Tyr Ala Glu Ser Val Lys Gly Arg Phe Thr
        355                 360                 365

Ile Ser Arg Asp Asn Ala Lys Thr Thr Leu Tyr Leu Gln Met Asn Ser
    370                 375                 380

Leu Arg Pro Glu Asp Thr Ala Val Tyr Tyr Cys Thr Ile Gly Gly Ser
385                 390                 395                 400

Leu Ser Val Ser Ser Gln Gly Thr Leu Val Thr Val Ser Ser His His
                405                 410                 415

His His His His
        420

<210> SEQ ID NO 86
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 86

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Gly Ser Gly Gly Gly
    130                 135                 140

Gly Ser Gly Gly Gly Gly Ser Ala Pro Thr Ser Ser Ser Thr Lys Lys
145                 150                 155                 160

Thr Gln Leu Gln Leu Glu His Leu Leu Leu Asp Leu Gln Met Ile Leu
                165                 170                 175

Asn Gly Ile Asn Asn Tyr Lys Asn Pro Lys Leu Thr Arg Met Leu Thr
            180                 185                 190

Phe Lys Phe Tyr Met Pro Lys Lys Ala Thr Glu Leu Lys His Leu Gln
        195                 200                 205

Cys Leu Glu Glu Glu Leu Lys Pro Leu Glu Glu Val Leu Asn Leu Ala
    210                 215                 220

Gln Ser Lys Asn Phe His Leu Arg Pro Arg Asp Leu Ile Ser Asn Ile
225                 230                 235                 240

Asn Val Ile Val Leu Glu Leu Lys Gly Ser Glu Thr Thr Phe Met Cys
                245                 250                 255

Glu Tyr Ala Asp Glu Thr Ala Thr Ile Val Glu Phe Leu Asn Arg Trp
            260                 265                 270

Ile Thr Phe Cys Gln Ser Ile Ile Ser Thr Leu Thr His His His His
        275                 280                 285

His His
    290

<210> SEQ ID NO 87
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

```
Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
 65                  70                  75                  80

Leu Glu Glu Glu Leu Lys Pro Leu Glu Val Leu Asn Leu Ala Gln
                 85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
                115                 120                 125

Tyr Ala Asp Glu Thr Ala Thr Ile Val Glu Phe Leu Asn Arg Trp Ile
            130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Glu Val Gln Leu Val Glu
                165                 170                 175

Ser Gly Gly Gly Leu Val Gln Pro Gly Asn Ser Leu Arg Leu Ser Cys
            180                 185                 190

Ala Ala Ser Gly Phe Thr Phe Ser Lys Phe Gly Met Ser Trp Val Arg
            195                 200                 205

Gln Ala Pro Gly Lys Gly Leu Glu Trp Val Ser Ser Ile Ser Gly Ser
    210                 215                 220

Gly Arg Asp Thr Leu Tyr Ala Glu Ser Val Lys Gly Arg Phe Thr Ile
225                 230                 235                 240

Ser Arg Asp Asn Ala Lys Thr Thr Leu Tyr Leu Gln Met Asn Ser Leu
                245                 250                 255

Arg Pro Glu Asp Thr Ala Val Tyr Tyr Cys Thr Ile Gly Gly Ser Leu
            260                 265                 270

Ser Val Ser Ser Gln Gly Thr Leu Val Thr Val Ser Ser His His His
        275                 280                 285

His His His
    290

<210> SEQ ID NO 88
<211> LENGTH: 689
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Asp Met Arg Val Pro Ala Gln Leu Leu Gly Leu Leu Leu Leu Trp
 1               5                  10                  15

Leu Arg Gly Ala Arg Cys Gln Val Gln Leu Gln Glu Ser Gly Gly Gly
                20                  25                  30

Leu Val Gln Ala Gly Gly Ser Leu Arg Leu Ser Cys Ala Ala Ser Gly
            35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
 65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110
```

```
Gly Val Tyr Tyr Cys Asn Ala Leu Tyr Gly Thr Asp Tyr Trp Gly Lys
            115                 120                 125
Gly Thr Gln Val Thr Val Ser Ser Gly Gly Pro Gly Pro Ala Gly
    130                 135                 140
Met Lys Gly Leu Pro Gly Ser Ala Pro Thr Ser Ser Ser Thr Lys Lys
145                 150                 155                 160
Thr Gln Leu Gln Leu Glu His Leu Leu Leu Asp Leu Gln Met Ile Leu
                165                 170                 175
Asn Gly Ile Asn Asn Tyr Lys Asn Pro Lys Leu Thr Arg Met Leu Thr
            180                 185                 190
Phe Lys Phe Tyr Met Pro Lys Lys Ala Thr Glu Leu Lys His Leu Gln
        195                 200                 205
Cys Leu Glu Glu Glu Leu Lys Pro Leu Glu Glu Val Leu Asn Leu Ala
    210                 215                 220
Gln Ser Lys Asn Phe His Leu Arg Pro Arg Asp Leu Ile Ser Asn Ile
225                 230                 235                 240
Asn Val Ile Val Leu Glu Leu Lys Gly Ser Glu Thr Thr Phe Met Cys
                245                 250                 255
Glu Tyr Ala Asp Glu Thr Ala Thr Ile Val Glu Phe Leu Asn Arg Trp
            260                 265                 270
Ile Thr Phe Cys Gln Ser Ile Ile Ser Thr Leu Thr Ser Gly Gly Pro
        275                 280                 285
Gly Pro Ala Gly Met Lys Gly Leu Pro Gly Ser Glu Val Gln Leu Val
    290                 295                 300
Glu Ser Gly Gly Gly Leu Val Gln Pro Gly Asn Ser Leu Arg Leu Ser
305                 310                 315                 320
Cys Ala Ala Ser Gly Phe Thr Phe Ser Lys Phe Gly Met Ser Trp Val
                325                 330                 335
Arg Gln Ala Pro Gly Lys Gly Leu Glu Trp Val Ser Ser Ile Ser Gly
            340                 345                 350
Ser Gly Arg Asp Thr Leu Tyr Ala Glu Ser Val Lys Gly Arg Phe Thr
        355                 360                 365
Ile Ser Arg Asp Asn Ala Lys Thr Thr Leu Tyr Leu Gln Met Asn Ser
    370                 375                 380
Leu Arg Pro Glu Asp Thr Ala Val Tyr Tyr Cys Thr Ile Gly Gly Ser
385                 390                 395                 400
Leu Ser Val Ser Ser Gln Gly Thr Leu Val Thr Val Ser Ser Gly Gly
                405                 410                 415
Gly Gly Ser Gly Gly Gly Ser Gly Gly Gly Ser Gly Gly
            420                 425                 430
Gly Ser Gly Gly Gly Ser Gly Gly Gly Ser Glu Val Gln Leu
        435                 440                 445
Val Glu Ser Gly Gly Gly Leu Val Gln Pro Gly Gly Ser Leu Arg Leu
    450                 455                 460
Ser Cys Ala Ala Ser Gly Phe Thr Phe Ser Ser Tyr Thr Leu Ala Trp
465                 470                 475                 480
Val Arg Gln Ala Pro Gly Lys Gly Leu Glu Trp Val Ala Ala Ile Asp
                485                 490                 495
Ser Ser Ser Tyr Thr Tyr Ser Pro Asp Thr Val Arg Gly Arg Phe Thr
            500                 505                 510
Ile Ser Arg Asp Asn Ala Lys Asn Ser Leu Tyr Leu Gln Met Asn Ser
        515                 520                 525
```

```
Leu Arg Ala Glu Asp Thr Ala Val Tyr Tyr Cys Ala Arg Asp Ser Asn
        530                 535                 540

Trp Asp Ala Leu Asp Tyr Trp Gly Gln Gly Thr Thr Val Thr Val Ser
545                 550                 555                 560

Ser Gly Gly Gly Ser Gly Gly Gly Ser Gly Gly Gly Ser
                565                 570                 575

Asp Ile Gln Met Thr Gln Ser Pro Ser Ser Leu Ser Ala Ser Val Gly
                580                 585                 590

Asp Arg Val Thr Ile Thr Cys Lys Ala Ser Gln Asn Val Gly Thr Asn
                595                 600                 605

Val Gly Trp Tyr Gln Gln Lys Pro Gly Lys Ala Pro Lys Ala Leu Ile
        610                 615                 620

Tyr Ser Ala Ser Phe Arg Tyr Ser Gly Val Pro Ser Arg Phe Ser Gly
625                 630                 635                 640

Ser Gly Ser Gly Thr Asp Phe Thr Leu Thr Ile Ser Ser Leu Gln Pro
                645                 650                 655

Glu Asp Phe Ala Thr Tyr Tyr Cys Gln Gln Tyr Tyr Thr Tyr Pro Tyr
                660                 665                 670

Thr Phe Gly Gly Gly Thr Lys Val Glu Ile Lys His His His His His
        675                 680                 685

His

<210> SEQ ID NO 89
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Gly Gly Gly Ser Gly Gly
                165                 170                 175

Gly Gly Gly Ser Gly Gly Gly Ser Gly Gly Gly Ser Gly Gly
            180                 185                 190
```

-continued

```
Gly Gly Ser Gly Gly Gly Ser Glu Val Gln Leu Val Glu Ser Gly
            195                 200                 205
Gly Gly Leu Val Gln Pro Gly Gly Ser Leu Arg Leu Ser Cys Ala Ala
210                 215                 220
Ser Gly Phe Thr Phe Ser Ser Tyr Thr Leu Ala Trp Val Arg Gln Ala
225                 230                 235                 240
Pro Gly Lys Gly Leu Glu Trp Val Ala Ala Ile Asp Ser Ser Ser Tyr
                245                 250                 255
Thr Tyr Ser Pro Asp Thr Val Arg Gly Arg Phe Thr Ile Ser Arg Asp
            260                 265                 270
Asn Ala Lys Asn Ser Leu Tyr Leu Gln Met Asn Ser Leu Arg Ala Glu
        275                 280                 285
Asp Thr Ala Val Tyr Tyr Cys Ala Arg Asp Ser Asn Trp Asp Ala Leu
290                 295                 300
Asp Tyr Trp Gly Gln Gly Thr Thr Val Thr Val Ser Ser Gly Gly Gly
305                 310                 315                 320
Gly Ser Gly Gly Gly Gly Ser Gly Gly Gly Gly Ser Asp Ile Gln Met
                325                 330                 335
Thr Gln Ser Pro Ser Ser Leu Ser Ala Ser Val Gly Asp Arg Val Thr
            340                 345                 350
Ile Thr Cys Lys Ala Ser Gln Asn Val Gly Thr Asn Val Gly Trp Tyr
        355                 360                 365
Gln Gln Lys Pro Gly Lys Ala Pro Lys Ala Leu Ile Tyr Ser Ala Ser
370                 375                 380
Phe Arg Tyr Ser Gly Val Pro Ser Arg Phe Ser Gly Ser Gly Ser Gly
385                 390                 395                 400
Thr Asp Phe Thr Leu Thr Ile Ser Ser Leu Gln Pro Glu Asp Phe Ala
                405                 410                 415
Thr Tyr Tyr Cys Gln Gln Tyr Tyr Thr Tyr Pro Tyr Thr Phe Gly Gly
            420                 425                 430
Gly Thr Lys Val Glu Ile Lys Gly Gly Gly Gly Ser Gly Gly Gly Gly
        435                 440                 445
Ser Gly Gly Gly Gly Ser Glu Val Gln Leu Val Glu Ser Gly Gly Gly
450                 455                 460
Leu Val Gln Pro Gly Asn Ser Leu Arg Leu Ser Cys Ala Ala Ser Gly
465                 470                 475                 480
Phe Thr Phe Ser Lys Phe Gly Met Ser Trp Val Arg Gln Ala Pro Gly
                485                 490                 495
Lys Gly Leu Glu Trp Val Ser Ser Ile Ser Gly Ser Gly Arg Asp Thr
            500                 505                 510
Leu Tyr Ala Glu Ser Val Lys Gly Arg Phe Thr Ile Ser Arg Asp Asn
        515                 520                 525
Ala Lys Thr Thr Leu Tyr Leu Gln Met Asn Ser Leu Arg Pro Glu Asp
530                 535                 540
Thr Ala Val Tyr Tyr Cys Thr Ile Gly Gly Ser Leu Ser Val Ser Ser
545                 550                 555                 560
Gln Gly Thr Leu Val Thr Val Ser Ser Gly Gly Gly Ser Gly Gly
                565                 570                 575
Gly Gly Ser Gly Gly Gly Gly Ser Gln Val Gln Leu Gln Glu Ser Gly
            580                 585                 590
Gly Gly Leu Ala Gln Ala Gly Gly Ser Leu Ser Leu Ser Cys Ala Ala
        595                 600                 605
Ser Gly Phe Thr Val Ser Asn Ser Val Met Ala Trp Tyr Arg Gln Thr
```

-continued

```
                610                615                620
Pro Gly Lys Gln Arg Glu Phe Val Ala Ile Ile Asn Ser Val Gly Ser
625                630                635                640

Thr Asn Tyr Ala Asp Ser Val Lys Gly Arg Phe Thr Ile Ser Arg Asp
                645                650                655

Asn Ala Lys Asn Thr Val Tyr Leu Gln Met Asn Asn Leu Lys Pro Glu
                660                665                670

Asp Thr Ala Val Tyr Val Cys Asn Arg Asn Phe Asp Arg Ile Tyr Trp
            675                680                685

Gly Gln Gly Thr Gln Val Thr Val Ser Ser His His His His His His
        690                695                700

<210> SEQ ID NO 90
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Ala Gln Ala Gly Gly Ser Leu Ser Leu Ser Cys Ala Ala Ser Gly
        35                  40                  45

Phe Thr Val Ser Asn Ser Val Met Ala Trp Tyr Arg Gln Thr Pro Gly
    50                  55                  60

Lys Gln Arg Glu Phe Val Ala Ile Ile Asn Ser Val Gly Ser Thr Asn
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Asn Leu Lys Pro Glu Asp Thr
            100                 105                 110

Ala Val Tyr Val Cys Asn Arg Asn Phe Asp Arg Ile Tyr Trp Gly Gln
        115                 120                 125

Gly Thr Gln Val Thr Val Ser Ser Ala Pro Thr Ser Ser Ser Thr Lys
    130                 135                 140

Lys Thr Gln Leu Gln Leu Glu His Leu Leu Leu Asp Leu Gln Met Ile
145                 150                 155                 160

Leu Asn Gly Ile Asn Asn Tyr Lys Asn Pro Lys Leu Thr Arg Met Leu
                165                 170                 175

Thr Phe Lys Phe Tyr Met Pro Lys Lys Ala Thr Glu Leu Lys His Leu
            180                 185                 190

Gln Cys Leu Glu Glu Glu Leu Lys Pro Leu Glu Glu Val Leu Asn Leu
        195                 200                 205

Ala Gln Ser Lys Asn Phe His Leu Arg Pro Arg Asp Leu Ile Ser Asn
    210                 215                 220

Ile Asn Val Ile Val Leu Glu Leu Lys Gly Ser Glu Thr Thr Phe Met
225                 230                 235                 240

Cys Glu Tyr Ala Asp Glu Thr Ala Thr Ile Val Glu Phe Leu Asn Arg
                245                 250                 255

Trp Ile Thr Phe Cys Gln Ser Ile Ile Ser Thr Leu Thr Ser Gly Gly
            260                 265                 270
```

```
Pro Gly Pro Ala Gly Met Lys Gly Leu Pro Gly Ser Glu Val Gln Leu
            275                 280                 285
Val Glu Ser Gly Gly Gly Leu Val Gln Pro Gly Asn Ser Leu Arg Leu
            290                 295                 300
Ser Cys Ala Ala Ser Gly Phe Thr Phe Ser Lys Phe Gly Met Ser Trp
305                 310                 315                 320
Val Arg Gln Ala Pro Gly Lys Gly Leu Glu Trp Val Ser Ser Ile Ser
                325                 330                 335
Gly Ser Gly Arg Asp Thr Leu Tyr Ala Glu Ser Val Lys Gly Arg Phe
            340                 345                 350
Thr Ile Ser Arg Asp Asn Ala Lys Thr Thr Leu Tyr Leu Gln Met Asn
            355                 360                 365
Ser Leu Arg Pro Glu Asp Thr Ala Val Tyr Tyr Cys Thr Ile Gly Gly
            370                 375                 380
Ser Leu Ser Val Ser Ser Gln Gly Thr Leu Val Thr Val Ser Ser Gly
385                 390                 395                 400
Gly Gly Gly Ser Gly Gly Gly Ser Gly Gly Gly Ser Gly
            405                 410                 415
Gly Gly Ser Gly Gly Gly Ser Gly Gly Gly Ser Glu Val Gln
            420                 425                 430
Leu Val Glu Ser Gly Gly Gly Leu Val Gln Pro Gly Gly Ser Leu Arg
            435                 440                 445
Leu Ser Cys Ala Ala Ser Gly Phe Thr Phe Ser Ser Tyr Thr Leu Ala
            450                 455                 460
Trp Val Arg Gln Ala Pro Gly Lys Gly Leu Glu Trp Val Ala Ala Ile
465                 470                 475                 480
Asp Ser Ser Ser Tyr Thr Tyr Ser Pro Asp Thr Val Arg Gly Arg Phe
                485                 490                 495
Thr Ile Ser Arg Asp Asn Ala Lys Asn Ser Leu Tyr Leu Gln Met Asn
            500                 505                 510
Ser Leu Arg Ala Glu Asp Thr Ala Val Tyr Tyr Cys Ala Arg Asp Ser
            515                 520                 525
Asn Trp Asp Ala Leu Asp Tyr Trp Gly Gln Gly Thr Thr Val Thr Val
            530                 535                 540
Ser Ser Gly Gly Gly Gly Ser Gly Gly Gly Gly Ser Gly Gly Gly Gly
545                 550                 555                 560
Ser Asp Ile Gln Met Thr Gln Ser Pro Ser Ser Leu Ser Ala Ser Val
                565                 570                 575
Gly Asp Arg Val Thr Ile Thr Cys Lys Ala Ser Gln Asn Val Gly Thr
            580                 585                 590
Asn Val Gly Trp Tyr Gln Gln Lys Pro Gly Lys Ala Pro Lys Ala Leu
            595                 600                 605
Ile Tyr Ser Ala Ser Phe Arg Tyr Ser Gly Val Pro Ser Arg Phe Ser
            610                 615                 620
Gly Ser Gly Ser Gly Thr Asp Phe Thr Leu Thr Ile Ser Ser Leu Gln
625                 630                 635                 640
Pro Glu Asp Phe Ala Thr Tyr Tyr Cys Gln Gln Tyr Tyr Thr Tyr Pro
                645                 650                 655
Tyr Thr Phe Gly Gly Gly Thr Lys Val Glu Ile Lys His His His
            660                 665                 670
His His
```

<210> SEQ ID NO 91

```
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Thr Leu Ala Trp Val Arg Gln Ala Pro Gly
    50                  55                  60

Lys Gly Leu Glu Trp Val Ala Ala Ile Asp Ser Ser Tyr Thr Tyr
65                  70                  75                  80

Ser Pro Asp Thr Val Arg Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Asp Ser Asn Trp Asp Ala Leu Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Lys Ala Ser Gln Asn Val Gly Thr Asn Val Gly Trp Tyr Gln Gln
            180                 185                 190

Lys Pro Gly Lys Ala Pro Lys Ala Leu Ile Tyr Ser Ala Ser Phe Arg
        195                 200                 205

Tyr Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Tyr Tyr Thr Tyr Pro Tyr Thr Phe Gly Gly Gly Thr
                245                 250                 255

Lys Val Glu Ile Lys Gly Gly Gly Ser Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Ser Gly Gly Pro Gly Pro Ala Gly Met Lys Gly Leu Pro
    290                 295                 300

Gly Ser Ala Pro Thr Ser Ser Thr Lys Thr Gln Leu Gln Leu
305                 310                 315                 320

Glu His Leu Leu Leu Asp Leu Gln Met Ile Leu Asn Gly Ile Asn Asn
                325                 330                 335

Tyr Lys Asn Pro Lys Leu Thr Arg Met Leu Thr Phe Lys Phe Tyr Met
            340                 345                 350

Pro Lys Lys Ala Thr Glu Leu Lys His Leu Gln Cys Leu Glu Glu Glu
        355                 360                 365

Leu Lys Pro Leu Glu Glu Val Leu Asn Leu Ala Gln Ser Lys Asn Phe
```

```
                370                 375                 380
His Leu Arg Pro Arg Asp Leu Ile Ser Asn Ile Asn Val Ile Val Leu
385                 390                 395                 400

Glu Leu Lys Gly Ser Glu Thr Thr Phe Met Cys Glu Tyr Ala Asp Glu
                405                 410                 415

Thr Ala Thr Ile Val Glu Phe Leu Asn Arg Trp Ile Thr Phe Cys Gln
                420                 425                 430

Ser Ile Ile Ser Thr Leu Thr Ser Gly Gly Pro Gly Pro Ala Gly Met
                435                 440                 445

Lys Gly Leu Pro Gly Ser Glu Val Gln Leu Val Glu Ser Gly Gly Gly
                450                 455                 460

Leu Val Gln Pro Gly Asn Ser Leu Arg Leu Ser Cys Ala Ala Ser Gly
465                 470                 475                 480

Phe Thr Phe Ser Lys Phe Gly Met Ser Trp Val Arg Gln Ala Pro Gly
                485                 490                 495

Lys Gly Leu Glu Trp Val Ser Ser Ile Ser Gly Ser Gly Arg Asp Thr
                500                 505                 510

Leu Tyr Ala Glu Ser Val Lys Gly Arg Phe Thr Ile Ser Arg Asp Asn
                515                 520                 525

Ala Lys Thr Thr Leu Tyr Leu Gln Met Asn Ser Leu Arg Pro Glu Asp
                530                 535                 540

Thr Ala Val Tyr Tyr Cys Thr Ile Gly Gly Ser Leu Ser Val Ser Ser
545                 550                 555                 560

Gln Gly Thr Leu Val Thr Val Ser Ser Gly Gly Gly Gly Ser Gly Gly
                565                 570                 575

Gly Gly Ser Gly Gly Gly Gly Ser Gln Val Gln Leu Gln Glu Ser Gly
                580                 585                 590

Gly Gly Leu Ala Gln Ala Gly Gly Ser Leu Ser Leu Ser Cys Ala Ala
                595                 600                 605

Ser Gly Phe Thr Val Ser Asn Ser Val Met Ala Trp Tyr Arg Gln Thr
                610                 615                 620

Pro Gly Lys Gln Arg Glu Phe Val Ala Ile Ile Asn Ser Val Gly Ser
625                 630                 635                 640

Thr Asn Tyr Ala Asp Ser Val Lys Gly Arg Phe Thr Ile Ser Arg Asp
                645                 650                 655

Asn Ala Lys Asn Thr Val Tyr Leu Gln Met Asn Asn Leu Lys Pro Glu
                660                 665                 670

Asp Thr Ala Val Tyr Val Cys Asn Arg Asn Phe Asp Arg Ile Tyr Trp
                675                 680                 685

Gly Gln Gly Thr Gln Val Thr Val Ser Ser His His His His His His
                690                 695                 700

<210> SEQ ID NO 92
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
                20                  25                  30
```

Leu Ala Gln Ala Gly Gly Ser Leu Ser Leu Ser Cys Ala Ala Ser Gly
            35                  40                  45

Phe Thr Val Ser Asn Ser Val Met Ala Trp Tyr Arg Gln Thr Pro Gly
 50                  55                  60

Lys Gln Arg Glu Phe Val Ala Ile Ile Asn Ser Val Gly Ser Thr Asn
 65                  70                  75                  80

Tyr Ala Asp Ser Val Lys Gly Arg Phe Thr Ile Ser Arg Asp Asn Ala
                 85                  90                  95

Lys Asn Thr Val Tyr Leu Gln Met Asn Asn Leu Lys Pro Glu Asp Thr
                100                 105                 110

Ala Val Tyr Val Cys Asn Arg Asn Phe Asp Arg Ile Tyr Trp Gly Gln
            115                 120                 125

Gly Thr Gln Val Thr Val Ser Ser Gly Gly Gly Ser Gly Gly Gly
    130                 135                 140

Gly Ser Gly Gly Gly Ser Glu Val Gln Leu Val Glu Ser Gly Gly
145                 150                 155                 160

Gly Leu Val Gln Pro Gly Asn Ser Leu Arg Leu Ser Cys Ala Ala Ser
                165                 170                 175

Gly Phe Thr Phe Ser Lys Phe Gly Met Ser Trp Val Arg Gln Ala Pro
            180                 185                 190

Gly Lys Gly Leu Glu Trp Val Ser Ser Ile Ser Gly Ser Gly Arg Asp
        195                 200                 205

Thr Leu Tyr Ala Glu Ser Val Lys Gly Arg Phe Thr Ile Ser Arg Asp
    210                 215                 220

Asn Ala Lys Thr Thr Leu Tyr Leu Gln Met Asn Ser Leu Arg Pro Glu
225                 230                 235                 240

Asp Thr Ala Val Tyr Tyr Cys Thr Ile Gly Gly Ser Leu Ser Val Ser
                245                 250                 255

Ser Gln Gly Thr Leu Val Thr Val Ser Ser Gly Gly Pro Gly Pro
            260                 265                 270

Ala Gly Met Lys Gly Leu Pro Gly Ser Glu Val Gln Leu Val Glu Ser
            275                 280                 285

Gly Gly Gly Leu Val Gln Pro Gly Gly Ser Leu Arg Leu Ser Cys Ala
    290                 295                 300

Ala Ser Gly Phe Thr Phe Ser Ser Tyr Thr Leu Ala Trp Val Arg Gln
305                 310                 315                 320

Ala Pro Gly Lys Gly Leu Glu Trp Val Ala Ala Ile Asp Ser Ser Ser
                325                 330                 335

Tyr Thr Tyr Ser Pro Asp Thr Val Arg Gly Arg Phe Thr Ile Ser Arg
            340                 345                 350

Asp Asn Ala Lys Asn Ser Leu Tyr Leu Gln Met Asn Ser Leu Arg Ala
            355                 360                 365

Glu Asp Thr Ala Val Tyr Tyr Cys Ala Arg Asp Ser Asn Trp Asp Ala
    370                 375                 380

Leu Asp Tyr Trp Gly Gln Gly Thr Thr Val Thr Val Ser Ser Gly Gly
385                 390                 395                 400

Gly Gly Ser Gly Gly Gly Gly Ser Gly Gly Gly Gly Ser Asp Ile Gln
                405                 410                 415

Met Thr Gln Ser Pro Ser Ser Leu Ser Ala Ser Val Gly Asp Arg Val
            420                 425                 430

Thr Ile Thr Cys Lys Ala Ser Gln Asn Val Gly Thr Asn Val Gly Trp
            435                 440                 445

Tyr Gln Gln Lys Pro Gly Lys Ala Pro Lys Ala Leu Ile Tyr Ser Ala

```
            450                 455                 460
Ser Phe Arg Tyr Ser Gly Val Pro Ser Arg Phe Ser Gly Ser Gly Ser
465                 470                 475                 480

Gly Thr Asp Phe Thr Leu Thr Ile Ser Ser Leu Gln Pro Glu Asp Phe
                485                 490                 495

Ala Thr Tyr Tyr Cys Gln Gln Tyr Tyr Thr Tyr Pro Tyr Thr Phe Gly
                500                 505                 510

Gly Gly Thr Lys Val Glu Ile Lys Gly Gly Gly Ser Gly Gly Gly
            515                 520                 525

Gly Ser Gly Gly Gly Ser Gly Gly Gly Ser Gly Gly Gly
        530                 535                 540

Ser Gly Gly Gly Ser Ser Gly Gly Pro Gly Pro Ala Gly Met Lys
545                 550                 555                 560

Gly Leu Pro Gly Ser Ala Pro Thr Ser Ser Thr Lys Lys Thr Gln
                565                 570                 575

Leu Gln Leu Glu His Leu Leu Leu Asp Leu Gln Met Ile Leu Asn Gly
            580                 585                 590

Ile Asn Asn Tyr Lys Asn Pro Lys Leu Thr Arg Met Leu Thr Phe Lys
            595                 600                 605

Phe Tyr Met Pro Lys Lys Ala Thr Glu Leu Lys His Leu Gln Cys Leu
610                 615                 620

Glu Glu Glu Leu Lys Pro Leu Glu Glu Val Leu Asn Leu Ala Gln Ser
625                 630                 635                 640

Lys Asn Phe His Leu Arg Pro Arg Asp Leu Ile Ser Asn Ile Asn Val
                645                 650                 655

Ile Val Leu Glu Leu Lys Gly Ser Glu Thr Thr Phe Met Cys Glu Tyr
            660                 665                 670

Ala Asp Glu Thr Ala Thr Ile Val Glu Phe Leu Asn Arg Trp Ile Thr
            675                 680                 685

Phe Cys Gln Ser Ile Ile Ser Thr Leu Thr His His His His His
            690                 695                 700

<210> SEQ ID NO 93
<211> LENGTH: 689
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Thr Leu Ala Trp Val Arg Gln Ala Pro Gly
    50                  55                  60

Lys Gly Leu Glu Trp Val Ala Ala Ile Asp Ser Ser Ser Tyr Thr Tyr
65                  70                  75                  80

Ser Pro Asp Thr Val Arg Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110
```

-continued

Ala Val Tyr Tyr Cys Ala Arg Asp Ser Asn Trp Asp Ala Leu Asp Tyr
115                 120                 125

Trp Gly Gln Gly Thr Thr Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Lys Ala Ser Gln Asn Val Gly Thr Asn Val Gly Trp Tyr Gln Gln
            180                 185                 190

Lys Pro Gly Lys Ala Pro Lys Ala Leu Ile Tyr Ser Ala Ser Phe Arg
        195                 200                 205

Tyr Ser Gly Val Pro Ser Arg Phe Ser Gly Ser Gly Ser Gly Thr Asp
210                 215                 220

Phe Thr Leu Thr Ile Ser Ser Leu Gln Pro Glu Asp Phe Ala Thr Tyr
225                 230                 235                 240

Tyr Cys Gln Gln Tyr Tyr Thr Tyr Pro Tyr Thr Phe Gly Gly Gly Thr
                245                 250                 255

Lys Val Glu Ile Lys Gly Gly Gly Ser Gly Gly Gly Gly Ser Gly
            260                 265                 270

Gly Gly Ser Gly Gly Gly Ser Gly Gly Gly Ser Gly Gly
        275                 280                 285

Gly Gly Ser Glu Val Gln Leu Val Glu Ser Gly Gly Leu Val Gln
        290                 295                 300

Pro Gly Asn Ser Leu Arg Leu Ser Cys Ala Ala Ser Gly Phe Thr Phe
305                 310                 315                 320

Ser Lys Phe Gly Met Ser Trp Val Arg Gln Ala Pro Gly Lys Gly Leu
                325                 330                 335

Glu Trp Val Ser Ser Ile Ser Gly Ser Gly Arg Asp Thr Leu Tyr Ala
                340                 345                 350

Glu Ser Val Lys Gly Arg Phe Thr Ile Ser Arg Asp Asn Ala Lys Thr
            355                 360                 365

Thr Leu Tyr Leu Gln Met Asn Ser Leu Arg Pro Glu Asp Thr Ala Val
        370                 375                 380

Tyr Tyr Cys Thr Ile Gly Gly Ser Leu Ser Val Ser Ser Gln Gly Thr
385                 390                 395                 400

Leu Val Thr Val Ser Ser Ser Gly Gly Pro Gly Ala Gly Met Lys
                405                 410                 415

Gly Leu Pro Gly Ser Ala Pro Thr Ser Ser Ser Thr Lys Lys Thr Gln
                420                 425                 430

Leu Gln Leu Glu His Leu Leu Leu Asp Leu Gln Met Ile Leu Asn Gly
        435                 440                 445

Ile Asn Asn Tyr Lys Asn Pro Lys Leu Thr Arg Met Leu Thr Phe Lys
450                 455                 460

Phe Tyr Met Pro Lys Lys Ala Thr Glu Leu Lys His Leu Gln Cys Leu
465                 470                 475                 480

Glu Glu Glu Leu Lys Pro Leu Glu Glu Val Leu Asn Leu Ala Gln Ser
                485                 490                 495

Lys Asn Phe His Leu Arg Pro Arg Asp Leu Ile Ser Asn Ile Asn Val
            500                 505                 510

Ile Val Leu Glu Leu Lys Gly Ser Glu Thr Thr Phe Met Cys Glu Tyr
        515                 520                 525

Ala Asp Glu Thr Ala Thr Ile Val Glu Phe Leu Asn Arg Trp Ile Thr

Phe Cys Gln Ser Ile Ile Ser Thr Leu Thr Gly Gly Gly Ser Gly
545                 550                 555                 560

Gly Gly Gly Ser Gly Gly Gly Ser Gln Val Gln Leu Gln Glu Ser
                565                 570                 575

Gly Gly Gly Leu Ala Gln Ala Gly Gly Ser Leu Ser Leu Ser Cys Ala
                580                 585                 590

Ala Ser Gly Phe Thr Val Ser Asn Ser Val Met Ala Trp Tyr Arg Gln
            595                 600                 605

Thr Pro Gly Lys Gln Arg Glu Phe Val Ala Ile Ile Asn Ser Val Gly
            610                 615                 620

Ser Thr Asn Tyr Ala Asp Ser Val Lys Gly Arg Phe Thr Ile Ser Arg
625                 630                 635                 640

Asp Asn Ala Lys Asn Thr Val Tyr Leu Gln Met Asn Asn Leu Lys Pro
                645                 650                 655

Glu Asp Thr Ala Val Tyr Val Cys Asn Arg Asn Phe Asp Arg Ile Tyr
                660                 665                 670

Trp Gly Gln Gly Thr Gln Val Thr Val Ser Ser His His His His His
        675                 680                 685

His

<210> SEQ ID NO 94
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
                20                  25                  30

Leu Val Gln Ala Gly Gly Ser Leu Arg Leu Ser Cys Ala Ala Ser Gly
            35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Gly Ser Gly Gly Gly
    130                 135                 140

Gly Ser Gly Gly Gly Ser Ala Pro Thr Ser Ser Ser Thr Lys Lys
145                 150                 155                 160

Thr Gln Leu Gln Leu Glu His Leu Leu Leu Asp Leu Gln Met Ile Leu
                165                 170                 175

Asn Gly Ile Asn Asn Tyr Lys Asn Pro Lys Leu Thr Arg Met Leu Thr
            180                 185                 190

Phe Lys Phe Tyr Met Pro Lys Lys Ala Thr Glu Leu Lys His Leu Gln

```
                195                 200                 205
Cys Leu Glu Glu Glu Leu Lys Pro Leu Glu Val Leu Asn Leu Ala
        210                 215                 220

Gln Ser Lys Asn Phe His Leu Arg Pro Arg Asp Leu Ile Ser Asn Ile
225                 230                 235                 240

Asn Val Ile Val Leu Glu Leu Lys Gly Ser Glu Thr Thr Phe Met Cys
                245                 250                 255

Glu Tyr Ala Asp Glu Thr Ala Thr Ile Val Glu Phe Leu Asn Arg Trp
                260                 265                 270

Ile Thr Phe Cys Gln Ser Ile Ile Ser Thr Leu Thr Ser Gly Gly Pro
                275                 280                 285

Gly Pro Ala Gly Met Lys Gly Leu Pro Gly Ser Arg Gly Glu Thr Gly
        290                 295                 300

Pro Ala Ala Pro Gly Ser Glu Val Gln Leu Val Glu Ser Gly Gly Gly
305                 310                 315                 320

Leu Val Gln Pro Gly Asn Ser Leu Arg Leu Ser Cys Ala Ala Ser Gly
                325                 330                 335

Phe Thr Phe Ser Lys Phe Gly Met Ser Trp Val Arg Gln Ala Pro Gly
                340                 345                 350

Lys Gly Leu Glu Trp Val Ser Ser Ile Ser Gly Ser Gly Arg Asp Thr
        355                 360                 365

Leu Tyr Ala Glu Ser Val Lys Gly Arg Phe Thr Ile Ser Arg Asp Asn
        370                 375                 380

Ala Lys Thr Thr Leu Tyr Leu Gln Met Asn Ser Leu Arg Pro Glu Asp
385                 390                 395                 400

Thr Ala Val Tyr Tyr Cys Thr Ile Gly Gly Ser Leu Ser Val Ser Ser
                405                 410                 415

Gln Gly Thr Leu Val Thr Val Ser Ser Gly Gly Gly Ser Gly Gly
        420                 425                 430

Gly Gly Ser Gly Gly Gly Gly Ser Gly Gly Gly Gly Ser Gly Gly Gly
        435                 440                 445

Gly Ser Gly Gly Gly Gly Ser Glu Val Gln Leu Val Glu Ser Gly Gly
        450                 455                 460

Gly Leu Val Gln Pro Gly Gly Ser Leu Arg Leu Ser Cys Ala Ala Ser
465                 470                 475                 480

Gly Phe Thr Phe Ser Ser Tyr Thr Leu Ala Trp Val Arg Gln Ala Pro
                485                 490                 495

Gly Lys Gly Leu Glu Trp Val Ala Ala Ile Asp Ser Ser Ser Tyr Thr
        500                 505                 510

Tyr Ser Pro Asp Thr Val Arg Gly Arg Phe Thr Ile Ser Arg Asp Asn
        515                 520                 525

Ala Lys Asn Ser Leu Tyr Leu Gln Met Asn Ser Leu Arg Ala Glu Asp
        530                 535                 540

Thr Ala Val Tyr Tyr Cys Ala Arg Asp Ser Asn Trp Asp Ala Leu Asp
545                 550                 555                 560

Tyr Trp Gly Gln Gly Thr Thr Val Thr Val Ser Ser Gly Gly Gly Gly
                565                 570                 575

Ser Gly Gly Gly Gly Ser Gly Gly Gly Gly Ser Asp Ile Gln Met Thr
                580                 585                 590

Gln Ser Pro Ser Ser Leu Ser Ala Ser Val Gly Asp Arg Val Thr Ile
        595                 600                 605

Thr Cys Lys Ala Ser Gln Asn Val Gly Thr Asn Val Gly Trp Tyr Gln
        610                 615                 620
```

Gln Lys Pro Gly Lys Ala Pro Lys Ala Leu Ile Tyr Ser Ala Ser Phe
625                 630                 635                 640

Arg Tyr Ser Gly Val Pro Ser Arg Phe Ser Gly Ser Gly Ser Gly Thr
                645                 650                 655

Asp Phe Thr Leu Thr Ile Ser Ser Leu Gln Pro Glu Asp Phe Ala Thr
            660                 665                 670

Tyr Tyr Cys Gln Gln Tyr Tyr Thr Tyr Pro Tyr Thr Phe Gly Gly Gly
        675                 680                 685

Thr Lys Val Glu Ile Lys His His His His His His
690                 695                 700

<210> SEQ ID NO 95
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Gly Val Gly Ala Phe Arg Pro Tyr
        115                 120                 125

Arg Lys His Glu Trp Gly Gln Gly Thr Leu Val Thr Val Ser Arg Gly
130                 135                 140

Gly Gly Gly Ser Gly Gly Gly Ser Gly Gly Gly Gly Ser Ser Ser
145                 150                 155             160

Glu Leu Thr Gln Asp Pro Ala Val Ser Val Ala Leu Gly Gln Thr Val
                165                 170                 175

Arg Ile Thr Cys Gln Gly Asp Ser Leu Arg Ser Tyr Tyr Ala Ser Trp
            180                 185                 190

Tyr Gln Gln Lys Pro Gly Gln Ala Pro Val Leu Val Ile Tyr Gly Lys
        195                 200                 205

Asn Asn Arg Pro Ser Gly Ile Pro Asp Arg Phe Ser Gly Ser Ser Ser
210                 215                 220

Gly Asn Thr Ala Ser Leu Thr Thr Gly Ala Gln Ala Glu Asp Glu
225                 230                 235             240

Ala Asp Tyr Tyr Cys Asn Ser Ser Pro Phe Glu His Asn Leu Val Val
                245                 250                 255

Phe Gly Gly Gly Thr Lys Leu Thr Val Leu His His His His His His
            260                 265                 270

Glu Pro Glu Ala

<210> SEQ ID NO 96
<211> LENGTH: 279
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Gln Ser Gly Ala Glu
            20                  25                  30

Leu Val Arg Pro Gly Thr Ser Val Lys Val Ser Cys Lys Ala Ser Gly
        35                  40                  45

Tyr Ala Phe Thr Asn Tyr Leu Ile Glu Trp Val Lys Gln Arg Pro Gly
    50                  55                  60

Gln Gly Leu Glu Trp Ile Gly Val Ile Asn Pro Gly Ser Gly Gly Thr
65                  70                  75                  80

Asn Tyr Asn Glu Lys Phe Lys Gly Lys Ala Thr Leu Thr Ala Asp Lys
                85                  90                  95

Ser Ser Ser Thr Ala Tyr Met Gln Leu Ser Ser Leu Thr Ser Asp Asp
            100                 105                 110

Ser Ala Val Tyr Phe Cys Ala Arg Trp Arg Gly Asp Gly Tyr Tyr Ala
        115                 120                 125

Tyr Phe Asp Val Trp Gly Ala Gly Thr Thr Val Thr Val Ser Ser Gly
    130                 135                 140

Gly Gly Gly Ser Gly Gly Gly Ser Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Lys Ala Ser Gln Ser Val Asp Tyr Asp Gly Asp
            180                 185                 190

Ser Tyr Met Asn Trp Tyr Gln Gln Lys Pro Gly Gln Pro Pro Lys Leu
        195                 200                 205

Leu Ile Tyr Ala Ala Ser Asn Leu Glu Ser Gly Ile Pro Ala Arg Phe
    210                 215                 220

Ser Gly Ser Gly Ser Gly Thr Asp Phe Thr Leu Asn Ile His Pro Val
225                 230                 235                 240

Glu Glu Glu Asp Ala Ala Thr Tyr Tyr Cys Gln Gln Ser Asn Glu Asp
                245                 250                 255

Pro Tyr Thr Phe Gly Gly Gly Thr Lys Leu Glu Ile Lys His His His
            260                 265                 270

His His His Glu Pro Glu Ala
        275

<210> SEQ ID NO 97
<211> LENGTH: 279
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Met Asp Met Arg Val Pro Ala Gln Leu Leu Gly Leu Leu Leu Leu Trp

```
            1               5                  10                 15
        Leu Arg Gly Ala Arg Cys Gln Val Gln Leu Gln Gln Ser Gly Ala Glu
                        20                 25                 30

Leu Val Arg Pro Gly Thr Ser Val Lys Val Ser Cys Lys Ala Ser Gly
                        35                 40                 45

Tyr Ala Phe Thr Asn Tyr Leu Ile Glu Trp Val Lys Gln Arg Pro Gly
                        50                 55                 60

Gln Gly Leu Glu Trp Ile Gly Val Ile Asn Pro Gly Ser Gly Gly Thr
         65                 70                 75                 80

Asn Tyr Asn Glu Lys Phe Lys Gly Lys Ala Thr Leu Thr Ala Asp Lys
                        85                 90                 95

Ser Ser Ser Thr Ala Tyr Met Gln Leu Ser Ser Leu Thr Ser Asp Asp
                        100                105                110

Ser Ala Val Tyr Phe Cys Ala Arg Trp Arg Gly Asp Gly Tyr Tyr Ala
                        115                120                125

Tyr Phe Asp Val Trp Gly Ala Gly Thr Thr Val Thr Val Ser Ser Ser
                        130                135                140

Gly Gly Pro Gly Pro Ala Gly Met Lys Gly Leu Pro Gly Ser Asp Ile
        145                150                155                160

Val Leu Thr Gln Ser Pro Ala Ser Leu Ala Val Ser Leu Gly Gln Arg
                        165                170                175

Ala Thr Ile Ser Cys Lys Ala Ser Gln Ser Val Asp Tyr Asp Gly Asp
                        180                185                190

Ser Tyr Met Asn Trp Tyr Gln Gln Lys Pro Gly Gln Pro Pro Lys Leu
                        195                200                205

Leu Ile Tyr Ala Ala Ser Asn Leu Glu Ser Gly Ile Pro Ala Arg Phe
                        210                215                220

Ser Gly Ser Gly Ser Gly Thr Asp Phe Thr Leu Asn Ile His Pro Val
        225                230                235                240

Glu Glu Glu Asp Ala Ala Thr Tyr Tyr Cys Gln Gln Ser Asn Glu Asp
                        245                250                255

Pro Tyr Thr Phe Gly Gly Gly Thr Lys Leu Glu Ile Lys His His His
                        260                265                270

His His His Glu Pro Glu Ala
                        275

<210> SEQ ID NO 98
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Asp Met Arg Val Pro Ala Gln Leu Leu Gly Leu Leu Leu Leu Trp
        1               5                  10                 15

Leu Arg Gly Ala Arg Cys Asp Ile Val Leu Thr Gln Ser Pro Ala Ser
                        20                 25                 30

Leu Ala Val Ser Leu Gly Gln Arg Ala Thr Ile Ser Cys Lys Ala Ser
                        35                 40                 45

Gln Ser Val Asp Tyr Asp Gly Asp Ser Tyr Met Asn Trp Tyr Gln Gln
                        50                 55                 60

Lys Pro Gly Gln Pro Pro Lys Leu Leu Ile Tyr Ala Ala Ser Asn Leu
         65                 70                 75                 80
```

```
Glu Ser Gly Ile Pro Ala Arg Phe Ser Gly Ser Gly Ser Gly Thr Asp
                85                  90                  95

Phe Thr Leu Asn Ile His Pro Val Glu Glu Asp Ala Ala Thr Tyr
            100                 105                 110

Tyr Cys Gln Gln Ser Asn Glu Asp Pro Tyr Thr Phe Gly Gly Gly Thr
            115                 120                 125

Lys Leu Glu Ile Lys Gly Gly Gly Ser Gly Gly Gly Ser Gly
        130             135                 140

Gly Gly Gly Ser Gln Val Gln Leu Gln Gln Ser Gly Ala Glu Leu Val
145                 150                 155                 160

Arg Pro Gly Thr Ser Val Lys Val Ser Cys Lys Ala Ser Gly Tyr Ala
                165                 170                 175

Phe Thr Asn Tyr Leu Ile Glu Trp Val Lys Gln Arg Pro Gly Gln Gly
            180                 185                 190

Leu Glu Trp Ile Gly Val Ile Asn Pro Gly Ser Gly Gly Thr Asn Tyr
        195                 200                 205

Asn Glu Lys Phe Lys Gly Lys Ala Thr Leu Thr Ala Asp Lys Ser Ser
    210                 215                 220

Ser Thr Ala Tyr Met Gln Leu Ser Ser Leu Thr Ser Asp Asp Ser Ala
225                 230                 235                 240

Val Tyr Phe Cys Ala Arg Trp Arg Gly Asp Gly Tyr Tyr Ala Tyr Phe
                245                 250                 255

Asp Val Trp Gly Ala Gly Thr Thr Val Thr Val Ser Ser His His His
            260                 265                 270

His His His Glu Pro Glu Ala
        275

<210> SEQ ID NO 99
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Asp Met Arg Val Pro Ala Gln Leu Leu Gly Leu Leu Leu Leu Trp
1               5                   10                  15

Leu Arg Gly Ala Arg Cys Asp Ile Val Leu Thr Gln Ser Pro Ala Ser
            20                  25                  30

Leu Ala Val Ser Leu Gly Gln Arg Ala Thr Ile Ser Cys Lys Ala Ser
        35                  40                  45

Gln Ser Val Asp Tyr Asp Gly Asp Ser Tyr Met Asn Trp Tyr Gln Gln
    50                  55                  60

Lys Pro Gly Gln Pro Pro Lys Leu Leu Ile Tyr Ala Ala Ser Asn Leu
65                  70                  75                  80

Glu Ser Gly Ile Pro Ala Arg Phe Ser Gly Ser Gly Ser Gly Thr Asp
                85                  90                  95

Phe Thr Leu Asn Ile His Pro Val Glu Glu Asp Ala Ala Thr Tyr
            100                 105                 110

Tyr Cys Gln Gln Ser Asn Glu Asp Pro Tyr Thr Phe Gly Gly Gly Thr
            115                 120                 125

Lys Leu Glu Ile Lys Ser Gly Gly Pro Gly Pro Ala Gly Met Lys Gly
        130             135                 140

Leu Pro Gly Ser Gln Val Gln Leu Gln Gln Ser Gly Ala Glu Leu Val
145                 150                 155                 160
```

Arg Pro Gly Thr Ser Val Lys Val Ser Cys Lys Ala Ser Gly Tyr Ala
          165                 170                 175

Phe Thr Asn Tyr Leu Ile Glu Trp Val Lys Gln Arg Pro Gly Gln Gly
          180                 185                 190

Leu Glu Trp Ile Gly Val Ile Asn Pro Gly Ser Gly Thr Asn Tyr
          195                 200                 205

Asn Glu Lys Phe Lys Gly Lys Ala Thr Leu Thr Ala Asp Lys Ser Ser
          210                 215                 220

Ser Thr Ala Tyr Met Gln Leu Ser Ser Leu Thr Ser Asp Asp Ser Ala
225                 230                 235                 240

Val Tyr Phe Cys Ala Arg Trp Arg Gly Asp Gly Tyr Tyr Ala Tyr Phe
          245                 250                 255

Asp Val Trp Gly Ala Gly Thr Thr Val Thr Val Ser Ser His His His
          260                 265                 270

His His His Glu Pro Glu Ala
          275

<210> SEQ ID NO 100
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
            85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Gly Gly Gly Gly Ser
145                 150                 155                 160

Gly Gly Gly Gly Ser Gly Gly Gly Ser Glu Val Gln Leu Val Glu
            165                 170                 175

Ser Gly Gly Gly Leu Val Gln Pro Gly Asn Ser Leu Arg Leu Ser Cys
            180                 185                 190

Ala Ala Ser Gly Phe Thr Phe Ser Lys Phe Gly Met Ser Trp Val Arg
            195                 200                 205

Gln Ala Pro Gly Lys Gly Leu Glu Trp Val Ser Ser Ile Ser Gly Ser
        210                 215                 220

Gly Arg Asp Thr Leu Tyr Ala Glu Ser Val Lys Gly Arg Phe Thr Ile

```
              225                 230                 235                 240
Ser Arg Asp Asn Ala Lys Thr Thr Leu Tyr Leu Gln Met Asn Ser Leu
                245                 250                 255

Arg Pro Glu Asp Thr Ala Val Tyr Tyr Cys Thr Ile Gly Gly Ser Leu
                260                 265                 270

Ser Val Ser Ser Gln Gly Thr Leu Val Thr Val Ser Ser His His His
                275                 280                 285

His His His Glu Pro Glu Ala
                290                 295

<210> SEQ ID NO 101
<211> LENGTH: 765
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
                20                  25                  30

Gln Leu Gln Leu Glu His Leu Leu Leu Asp Leu Gln Met Ile Leu Asn
            35                  40                  45

Gly Ile Asn Asn Tyr Lys Asn Pro Lys Leu Thr Arg Met Leu Thr Phe
        50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Gly Gly Gly Gly Ser
145                 150                 155                 160

Gly Gly Gly Gly Ser Gly Gly Gly Ser Asp Ala His Lys Ser Glu
                165                 170                 175

Val Ala His Arg Phe Lys Asp Leu Gly Glu Glu Asn Phe Lys Ala Leu
            180                 185                 190

Val Leu Ile Ala Phe Ala Gln Tyr Leu Gln Gln Cys Pro Phe Glu Asp
        195                 200                 205

His Val Lys Leu Val Asn Glu Val Thr Glu Phe Ala Lys Thr Cys Val
    210                 215                 220

Ala Asp Glu Ser Ala Glu Asn Cys Asp Lys Ser Leu His Thr Leu Phe
225                 230                 235                 240

Gly Asp Lys Leu Cys Thr Val Ala Thr Leu Arg Glu Thr Tyr Gly Glu
                245                 250                 255

Met Ala Asp Cys Cys Ala Lys Gln Glu Pro Glu Arg Asn Glu Cys Phe
            260                 265                 270

Leu Gln His Lys Asp Asp Asn Pro Asn Leu Pro Arg Leu Val Arg Pro
        275                 280                 285
```

Glu Val Asp Val Met Cys Thr Ala Phe His Asp Asn Glu Glu Thr Phe
290                 295                 300

Leu Lys Lys Tyr Leu Tyr Glu Ile Ala Arg Arg His Pro Tyr Phe Tyr
305                 310                 315                 320

Ala Pro Glu Leu Leu Phe Phe Ala Lys Arg Tyr Lys Ala Ala Phe Thr
            325                 330                 335

Glu Cys Cys Gln Ala Ala Asp Lys Ala Ala Cys Leu Leu Pro Lys Leu
            340                 345                 350

Asp Glu Leu Arg Asp Glu Gly Lys Ala Ser Ser Ala Lys Gln Arg Leu
            355                 360                 365

Lys Cys Ala Ser Leu Gln Lys Phe Gly Glu Arg Ala Phe Lys Ala Trp
370                 375                 380

Ala Val Ala Arg Leu Ser Gln Arg Phe Pro Lys Ala Glu Phe Ala Glu
385                 390                 395                 400

Val Ser Lys Leu Val Thr Asp Leu Thr Lys Val His Thr Glu Cys Cys
            405                 410                 415

His Gly Asp Leu Leu Glu Cys Ala Asp Asp Arg Ala Asp Leu Ala Lys
            420                 425                 430

Tyr Ile Cys Glu Asn Gln Asp Ser Ile Ser Ser Lys Leu Lys Glu Cys
            435                 440                 445

Cys Glu Lys Pro Leu Leu Glu Lys Ser His Cys Ile Ala Glu Val Glu
450                 455                 460

Asn Asp Glu Met Pro Ala Asp Leu Pro Ser Leu Ala Ala Asp Phe Val
465                 470                 475                 480

Glu Ser Lys Asp Val Cys Lys Asn Tyr Ala Glu Ala Lys Asp Val Phe
            485                 490                 495

Leu Gly Met Phe Leu Tyr Glu Tyr Ala Arg Arg His Pro Asp Tyr Ser
            500                 505                 510

Val Val Leu Leu Leu Arg Leu Ala Lys Thr Tyr Glu Thr Thr Leu Glu
            515                 520                 525

Lys Cys Cys Ala Ala Ala Asp Pro His Glu Cys Tyr Ala Lys Val Phe
530                 535                 540

Asp Glu Phe Lys Pro Leu Val Glu Glu Pro Gln Asn Leu Ile Lys Gln
545                 550                 555                 560

Asn Cys Glu Leu Phe Glu Gln Leu Gly Glu Tyr Lys Phe Gln Asn Ala
            565                 570                 575

Leu Leu Val Arg Tyr Thr Lys Lys Val Pro Gln Val Ser Thr Pro Thr
            580                 585                 590

Leu Val Glu Val Ser Arg Asn Leu Gly Lys Val Gly Ser Lys Cys Cys
            595                 600                 605

Lys His Pro Glu Ala Lys Arg Met Pro Cys Ala Glu Asp Tyr Leu Ser
610                 615                 620

Val Val Leu Asn Gln Leu Cys Val Leu His Glu Lys Thr Pro Val Ser
625                 630                 635                 640

Asp Arg Val Thr Lys Cys Cys Thr Glu Ser Leu Val Asn Arg Arg Pro
            645                 650                 655

Cys Phe Ser Ala Leu Glu Val Asp Glu Thr Tyr Val Pro Lys Glu Phe
            660                 665                 670

Asn Ala Glu Thr Phe Thr Phe His Ala Asp Ile Cys Thr Leu Ser Glu
            675                 680                 685

Lys Glu Arg Gln Ile Lys Lys Gln Thr Ala Leu Val Glu Leu Val Lys
690                 695                 700

His Lys Pro Lys Ala Thr Lys Glu Gln Leu Lys Ala Val Met Asp Asp

```
                705                 710                 715                 720

Phe Ala Ala Phe Val Glu Lys Cys Cys Lys Ala Asp Asp Lys Glu Thr
                725                 730                 735

Cys Phe Ala Glu Glu Gly Lys Lys Leu Val Ala Ala Ser Gln Ala Ala
                740                 745                 750

Leu Gly Leu His His His His His His Glu Pro Glu Ala
                755                 760                 765

<210> SEQ ID NO 102
<211> LENGTH: 765
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
                20                  25                  30

Gln Leu Gln Leu Glu His Leu Leu Leu Asp Leu Gln Met Ile Leu Asn
            35                  40                  45

Gly Ile Asn Asn Tyr Lys Asn Pro Lys Leu Thr Arg Met Leu Thr Phe
        50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
                100                 105                 110

Val Ile Val Leu Glu Leu Lys Gly Ser Glu Thr Thr Phe Met Cys Glu
            115                 120                 125

Tyr Ala Asp Glu Thr Ala Thr Ile Val Glu Phe Leu Asn Arg Trp Ile
        130                 135                 140

Thr Phe Cys Gln Ser Ile Ile Ser Thr Leu Thr Gly Gly Gly Gly Ser
145                 150                 155                 160

Gly Gly Gly Gly Ser Gly Gly Gly Ser Asp Ala His Lys Ser Glu
                165                 170                 175

Val Ala His Arg Phe Lys Asp Leu Gly Glu Glu Asn Phe Lys Ala Leu
                180                 185                 190

Val Leu Ile Ala Phe Ala Gln Tyr Leu Gln Gln Cys Pro Phe Glu Asp
            195                 200                 205

His Val Lys Leu Val Asn Glu Val Thr Glu Phe Ala Lys Thr Cys Val
        210                 215                 220

Ala Asp Glu Ser Ala Glu Asn Cys Asp Lys Ser Leu His Thr Leu Phe
225                 230                 235                 240

Gly Asp Lys Leu Cys Thr Val Ala Thr Leu Arg Glu Thr Tyr Gly Glu
                245                 250                 255

Met Ala Asp Cys Cys Ala Lys Gln Glu Pro Glu Arg Asn Glu Cys Phe
                260                 265                 270

Leu Gln His Lys Asp Asp Asn Pro Asn Leu Pro Arg Leu Val Arg Pro
            275                 280                 285

Glu Val Asp Val Met Cys Thr Ala Phe His Asp Asn Glu Glu Thr Phe
        290                 295                 300
```

```
Leu Lys Lys Tyr Leu Tyr Glu Ile Ala Arg Arg His Pro Tyr Phe Tyr
305                 310                 315                 320

Ala Pro Glu Leu Leu Phe Phe Ala Lys Arg Tyr Lys Ala Ala Phe Thr
                325                 330                 335

Glu Cys Cys Gln Ala Ala Asp Lys Ala Ala Cys Leu Leu Pro Lys Leu
            340                 345                 350

Asp Glu Leu Arg Asp Glu Gly Lys Ala Ser Ser Ala Lys Gln Arg Leu
        355                 360                 365

Lys Cys Ala Ser Leu Gln Lys Phe Gly Glu Arg Ala Phe Lys Ala Trp
    370                 375                 380

Ala Val Ala Arg Leu Ser Gln Arg Phe Pro Lys Ala Glu Phe Ala Glu
385                 390                 395                 400

Val Ser Lys Leu Val Thr Asp Leu Thr Lys Val His Thr Glu Cys Cys
                405                 410                 415

His Gly Asp Leu Leu Glu Cys Ala Asp Asp Arg Ala Asp Leu Ala Lys
            420                 425                 430

Tyr Ile Cys Glu Asn Gln Asp Ser Ile Ser Ser Lys Leu Lys Glu Cys
        435                 440                 445

Cys Glu Lys Pro Leu Leu Glu Lys Ser His Cys Ile Ala Glu Val Glu
    450                 455                 460

Asn Asp Glu Met Pro Ala Asp Leu Pro Ser Leu Ala Ala Asp Phe Val
465                 470                 475                 480

Glu Ser Lys Asp Val Cys Lys Asn Tyr Ala Glu Ala Lys Asp Val Phe
                485                 490                 495

Leu Gly Met Phe Leu Tyr Glu Tyr Ala Arg Arg His Pro Asp Tyr Ser
            500                 505                 510

Val Val Leu Leu Leu Arg Leu Ala Lys Thr Tyr Glu Thr Thr Leu Glu
        515                 520                 525

Lys Cys Cys Ala Ala Ala Asp Pro His Glu Cys Tyr Ala Lys Val Phe
    530                 535                 540

Asp Glu Phe Lys Pro Leu Val Glu Glu Pro Gln Asn Leu Ile Lys Gln
545                 550                 555                 560

Asn Cys Glu Leu Phe Glu Gln Leu Gly Glu Tyr Lys Phe Gln Asn Ala
                565                 570                 575

Leu Leu Val Arg Tyr Thr Lys Lys Val Pro Gln Val Ser Thr Pro Thr
            580                 585                 590

Leu Val Glu Val Ser Arg Asn Leu Gly Lys Val Gly Ser Lys Cys Cys
        595                 600                 605

Lys His Pro Glu Ala Lys Arg Met Pro Cys Ala Glu Asp Tyr Leu Ser
    610                 615                 620

Val Val Leu Asn Gln Leu Cys Val Leu His Glu Lys Thr Pro Val Ser
625                 630                 635                 640

Asp Arg Val Thr Lys Cys Cys Thr Glu Ser Leu Val Asn Arg Arg Pro
                645                 650                 655

Cys Phe Ser Ala Leu Glu Val Asp Glu Thr Tyr Val Pro Lys Glu Phe
            660                 665                 670

Asn Ala Glu Thr Phe Thr Phe His Ala Asp Ile Cys Thr Leu Ser Glu
        675                 680                 685

Lys Glu Arg Gln Ile Lys Lys Gln Thr Ala Leu Val Glu Leu Val Lys
    690                 695                 700

His Lys Pro Lys Ala Thr Lys Glu Gln Leu Lys Ala Val Met Asp Asp
705                 710                 715                 720

Phe Ala Ala Phe Val Glu Lys Cys Cys Lys Ala Asp Asp Lys Glu Thr
```

```
                     725                 730                 735

Cys Phe Ala Glu Glu Gly Lys Lys Leu Val Ala Ala Ser Gln Ala Ala
            740                 745                 750

Leu Gly Leu His His His His His His Glu Pro Glu Ala
            755                 760                 765

<210> SEQ ID NO 103
<211> LENGTH: 765
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Asp Ala His Lys Ser Glu
                165                 170                 175

Val Ala His Arg Phe Lys Asp Leu Gly Glu Glu Asn Phe Lys Ala Leu
            180                 185                 190

Val Leu Ile Ala Phe Ala Gln Tyr Leu Gln Gln Cys Pro Phe Glu Asp
        195                 200                 205

His Val Lys Leu Val Asn Glu Val Thr Glu Phe Ala Lys Thr Cys Val
    210                 215                 220

Ala Asp Glu Ser Ala Glu Asn Cys Asp Lys Ser Leu His Thr Leu Phe
225                 230                 235                 240

Gly Asp Lys Leu Cys Thr Val Ala Thr Leu Arg Glu Thr Tyr Gly Glu
                245                 250                 255

Met Ala Asp Cys Cys Ala Lys Gln Glu Pro Glu Arg Asn Glu Cys Phe
            260                 265                 270

Leu Gln His Lys Asp Asp Asn Pro Asn Leu Pro Arg Leu Val Arg Pro
        275                 280                 285

Glu Val Asp Val Met Cys Thr Ala Phe His Asp Asn Glu Glu Thr Phe
    290                 295                 300

Leu Lys Lys Tyr Leu Tyr Glu Ile Ala Arg Arg His Pro Tyr Phe Tyr
305                 310                 315                 320
```

-continued

Ala Pro Glu Leu Leu Phe Phe Ala Lys Arg Tyr Lys Ala Ala Phe Thr
            325                 330                 335

Glu Cys Cys Gln Ala Ala Asp Lys Ala Ala Cys Leu Leu Pro Lys Leu
            340                 345                 350

Asp Glu Leu Arg Asp Glu Gly Lys Ala Ser Ser Ala Lys Gln Arg Leu
            355                 360                 365

Lys Cys Ala Ser Leu Gln Lys Phe Gly Glu Arg Ala Phe Lys Ala Trp
            370                 375                 380

Ala Val Ala Arg Leu Ser Gln Arg Phe Pro Lys Ala Glu Phe Ala Glu
385                 390                 395                 400

Val Ser Lys Leu Val Thr Asp Leu Thr Lys Val His Thr Glu Cys Cys
            405                 410                 415

His Gly Asp Leu Leu Glu Cys Ala Asp Asp Arg Ala Asp Leu Ala Lys
            420                 425                 430

Tyr Ile Cys Glu Asn Gln Asp Ser Ile Ser Ser Lys Leu Lys Glu Cys
            435                 440                 445

Cys Glu Lys Pro Leu Leu Glu Lys Ser His Cys Ile Ala Glu Val Glu
            450                 455                 460

Asn Asp Glu Met Pro Ala Asp Leu Pro Ser Leu Ala Ala Asp Phe Val
465                 470                 475                 480

Glu Ser Lys Asp Val Cys Lys Asn Tyr Ala Glu Ala Lys Asp Val Phe
            485                 490                 495

Leu Gly Met Phe Leu Tyr Glu Tyr Ala Arg Arg His Pro Asp Tyr Ser
            500                 505                 510

Val Val Leu Leu Leu Arg Leu Ala Lys Thr Tyr Glu Thr Thr Leu Glu
            515                 520                 525

Lys Cys Cys Ala Ala Ala Asp Pro His Glu Cys Tyr Ala Lys Val Phe
            530                 535                 540

Asp Glu Phe Lys Pro Leu Val Glu Glu Pro Gln Asn Leu Ile Lys Gln
545                 550                 555                 560

Asn Cys Glu Leu Phe Glu Gln Leu Gly Glu Tyr Lys Phe Gln Asn Ala
            565                 570                 575

Leu Leu Val Arg Tyr Thr Lys Lys Val Pro Gln Val Ser Thr Pro Thr
            580                 585                 590

Leu Val Glu Val Ser Arg Asn Leu Gly Lys Val Gly Ser Lys Cys Cys
            595                 600                 605

Lys His Pro Glu Ala Lys Arg Met Pro Cys Ala Glu Asp Tyr Leu Ser
            610                 615                 620

Val Val Leu Asn Gln Leu Cys Val Leu His Glu Lys Thr Pro Val Ser
625                 630                 635                 640

Asp Arg Val Thr Lys Cys Cys Thr Glu Ser Leu Val Asn Arg Arg Pro
            645                 650                 655

Cys Phe Ser Ala Leu Glu Val Asp Glu Thr Tyr Val Pro Lys Glu Phe
            660                 665                 670

Asn Ala Glu Thr Phe Thr Phe His Ala Asp Ile Cys Thr Leu Ser Glu
            675                 680                 685

Lys Glu Arg Gln Ile Lys Lys Gln Thr Ala Leu Val Glu Leu Val Lys
            690                 695                 700

His Lys Pro Lys Ala Thr Lys Glu Gln Leu Lys Ala Val Met Asp Asp
705                 710                 715                 720

Phe Ala Ala Phe Val Glu Lys Cys Cys Lys Ala Asp Asp Lys Glu Thr
            725                 730                 735

Cys Phe Ala Glu Glu Gly Lys Lys Leu Val Ala Ala Ser Gln Ala Ala

```
                    740                 745                 750
Leu Gly Leu His His His His His Glu Pro Glu Ala
        755                 760                 765

<210> SEQ ID NO 104
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Glu Val Gln Leu Val Glu
                165                 170                 175

Ser Gly Gly Gly Leu Val Gln Pro Gly Asn Ser Leu Arg Leu Ser Cys
            180                 185                 190

Ala Ala Ser Gly Phe Thr Phe Ser Lys Phe Gly Met Ser Trp Val Arg
        195                 200                 205

Gln Ala Pro Gly Lys Gly Leu Glu Trp Val Ser Ser Ile Ser Gly Ser
    210                 215                 220

Gly Arg Asp Thr Leu Tyr Ala Glu Ser Val Lys Gly Arg Phe Thr Ile
225                 230                 235                 240

Ser Arg Asp Asn Ala Lys Thr Thr Leu Tyr Leu Gln Met Asn Ser Leu
                245                 250                 255

Arg Pro Glu Asp Thr Ala Val Tyr Tyr Cys Thr Ile Gly Gly Ser Leu
            260                 265                 270

Ser Val Ser Ser Gln Gly Thr Leu Val Thr Val Ser Ser Gly Gly Gly
        275                 280                 285

Gly Ser Gly Gly Gly Gly Ser Gly Gly Gly Gly Ser Gly Gly Gly Gly
    290                 295                 300

Ser Gly Gly Gly Gly Ser Gly Gly Gly Gly Ser Ser Gly Gly Pro Gly
305                 310                 315                 320

Pro Ala Gly Met Lys Gly Leu Pro Gly Ser Glu Val Gln Leu Val Glu
                325                 330                 335
```

```
Ser Gly Gly Gly Leu Val Gln Pro Gly Ser Leu Arg Leu Ser Cys
            340                 345                 350

Ala Ala Ser Gly Phe Thr Phe Ser Ser Tyr Thr Leu Ala Trp Val Arg
        355                 360                 365

Gln Ala Pro Gly Lys Gly Leu Glu Trp Val Ala Ile Asp Ser Ser
370                 375                 380

Ser Tyr Thr Tyr Ser Pro Asp Thr Val Arg Gly Arg Phe Thr Ile Ser
385                 390                 395                 400

Arg Asp Asn Ala Lys Asn Ser Leu Tyr Leu Gln Met Asn Ser Leu Arg
                405                 410                 415

Ala Glu Asp Thr Ala Val Tyr Tyr Cys Ala Arg Asp Ser Asn Trp Asp
            420                 425                 430

Ala Leu Asp Tyr Trp Gly Gln Gly Thr Thr Val Thr Val Ser Ser Gly
        435                 440                 445

Gly Gly Gly Ser Gly Gly Gly Gly Ser Gly Gly Gly Gly Ser Asp Ile
    450                 455                 460

Gln Met Thr Gln Ser Pro Ser Ser Leu Ser Ala Ser Val Gly Asp Arg
465                 470                 475                 480

Val Thr Ile Thr Cys Lys Ala Ser Gln Asn Val Gly Thr Asn Val Gly
                485                 490                 495

Trp Tyr Gln Gln Lys Pro Gly Lys Ala Pro Lys Ala Leu Ile Tyr Ser
            500                 505                 510

Ala Ser Phe Arg Tyr Ser Gly Val Pro Ser Arg Phe Ser Gly Ser Gly
        515                 520                 525

Ser Gly Thr Asp Phe Thr Leu Thr Ile Ser Ser Leu Gln Pro Glu Asp
530                 535                 540

Phe Ala Thr Tyr Tyr Cys Gln Gln Tyr Tyr Thr Tyr Pro Tyr Thr Phe
545                 550                 555                 560

Gly Gly Gly Thr Lys Val Glu Ile Lys Gly Gly Gly Ser Gly Gly
                565                 570                 575

Gly Gly Ser Gly Gly Gly Gly Ser Gln Val Gln Leu Gln Glu Ser Gly
        580                 585                 590

Gly Gly Leu Ala Gln Ala Gly Gly Ser Leu Ser Leu Ser Cys Ala Ala
        595                 600                 605

Ser Gly Phe Thr Val Ser Asn Ser Val Met Ala Trp Tyr Arg Gln Thr
    610                 615                 620

Pro Gly Lys Gln Arg Glu Phe Val Ala Ile Ile Asn Ser Val Gly Ser
625                 630                 635                 640

Thr Asn Tyr Ala Asp Ser Val Lys Gly Arg Phe Thr Ile Ser Arg Asp
                645                 650                 655

Asn Ala Lys Asn Thr Val Tyr Leu Gln Met Asn Asn Leu Lys Pro Glu
            660                 665                 670

Asp Thr Ala Val Tyr Val Cys Asn Arg Asn Phe Asp Arg Ile Tyr Trp
        675                 680                 685

Gly Gln Gly Thr Gln Val Thr Val Ser Ser His His His His His
    690                 695                 700

Glu Pro Glu Ala
705

<210> SEQ ID NO 105
<211> LENGTH: 708
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 105

```
Met Asp Met Arg Val Pro Ala Gln Leu Leu Gly Leu Leu Leu Leu Trp
 1               5                  10                  15

Leu Arg Gly Ala Arg Cys Gln Val Gln Leu Gln Glu Ser Gly Gly Gly
             20                  25                  30

Leu Ala Gln Ala Gly Gly Ser Leu Ser Leu Ser Cys Ala Ala Ser Gly
         35                  40                  45

Phe Thr Val Ser Asn Ser Val Met Ala Trp Tyr Arg Gln Thr Pro Gly
     50                  55                  60

Lys Gln Arg Glu Phe Val Ala Ile Ile Asn Ser Val Gly Ser Thr Asn
 65                  70                  75                  80

Tyr Ala Asp Ser Val Lys Gly Arg Phe Thr Ile Ser Arg Asp Asn Ala
                 85                  90                  95

Lys Asn Thr Val Tyr Leu Gln Met Asn Asn Leu Lys Pro Glu Asp Thr
            100                 105                 110

Ala Val Tyr Val Cys Asn Arg Asn Phe Asp Arg Ile Tyr Trp Gly Gln
        115                 120                 125

Gly Thr Gln Val Thr Val Ser Ser Gly Gly Gly Ser Gly Gly Gly
    130                 135                 140

Gly Ser Gly Gly Gly Ser Ala Pro Thr Ser Ser Thr Lys Lys
145                 150                 155                 160

Thr Gln Leu Gln Leu Glu His Leu Leu Leu Asp Leu Gln Met Ile Leu
                165                 170                 175

Asn Gly Ile Asn Asn Tyr Lys Asn Pro Lys Leu Thr Arg Met Leu Thr
            180                 185                 190

Phe Lys Phe Tyr Met Pro Lys Lys Ala Thr Glu Leu Lys His Leu Gln
        195                 200                 205

Cys Leu Glu Glu Glu Leu Lys Pro Leu Glu Glu Val Leu Asn Leu Ala
    210                 215                 220

Gln Ser Lys Asn Phe His Leu Arg Pro Arg Asp Leu Ile Ser Asn Ile
225                 230                 235                 240

Asn Val Ile Val Leu Glu Leu Lys Gly Ser Glu Thr Thr Phe Met Cys
                245                 250                 255

Glu Tyr Ala Asp Glu Thr Ala Thr Ile Val Glu Phe Leu Asn Arg Trp
            260                 265                 270

Ile Thr Phe Cys Gln Ser Ile Ile Ser Thr Leu Thr Ser Gly Gly Pro
        275                 280                 285

Gly Pro Ala Gly Met Lys Gly Leu Pro Gly Ser Glu Val Gln Leu Val
    290                 295                 300

Glu Ser Gly Gly Gly Leu Val Gln Pro Gly Asn Ser Leu Arg Leu Ser
305                 310                 315                 320

Cys Ala Ala Ser Gly Phe Thr Phe Ser Lys Phe Gly Met Ser Trp Val
                325                 330                 335

Arg Gln Ala Pro Gly Lys Gly Leu Glu Trp Val Ser Ser Ile Ser Gly
            340                 345                 350

Ser Gly Arg Asp Thr Leu Tyr Ala Glu Ser Val Lys Gly Arg Phe Thr
        355                 360                 365

Ile Ser Arg Asp Asn Ala Lys Thr Thr Leu Tyr Leu Gln Met Asn Ser
    370                 375                 380

Leu Arg Pro Glu Asp Thr Ala Val Tyr Tyr Cys Thr Ile Gly Gly Ser
385                 390                 395                 400
```

Leu Ser Val Ser Ser Gln Gly Thr Leu Val Thr Val Ser Ser Gly Gly
                405                 410                 415

Gly Gly Ser Gly Gly Gly Gly Ser Gly Gly Gly Ser Gly Gly Gly
            420                 425                 430

Gly Ser Gly Gly Gly Ser Gly Gly Gly Ser Ser Gly Gly Pro
            435                 440                 445

Gly Pro Ala Gly Met Lys Gly Leu Pro Gly Ser Glu Val Gln Leu Val
450                 455                 460

Glu Ser Gly Gly Gly Leu Val Gln Pro Gly Ser Leu Arg Leu Ser
465                 470                 475                 480

Cys Ala Ala Ser Gly Phe Thr Phe Ser Ser Tyr Thr Leu Ala Trp Val
                485                 490                 495

Arg Gln Ala Pro Gly Lys Gly Leu Glu Trp Val Ala Ala Ile Asp Ser
            500                 505                 510

Ser Ser Tyr Thr Tyr Ser Pro Asp Thr Val Arg Gly Arg Phe Thr Ile
            515                 520                 525

Ser Arg Asp Asn Ala Lys Asn Ser Leu Tyr Leu Gln Met Asn Ser Leu
            530                 535                 540

Arg Ala Glu Asp Thr Ala Val Tyr Tyr Cys Ala Arg Asp Ser Asn Trp
545                 550                 555                 560

Asp Ala Leu Asp Tyr Trp Gly Gln Gly Thr Thr Val Thr Val Ser Ser
                565                 570                 575

Gly Gly Gly Gly Ser Gly Gly Gly Ser Gly Gly Gly Ser Asp
            580                 585                 590

Ile Gln Met Thr Gln Ser Pro Ser Ser Leu Ser Ala Ser Val Gly Asp
            595                 600                 605

Arg Val Thr Ile Thr Cys Lys Ala Ser Gln Asn Val Gly Thr Asn Val
610                 615                 620

Gly Trp Tyr Gln Gln Lys Pro Gly Lys Ala Pro Lys Ala Leu Ile Tyr
625                 630                 635                 640

Ser Ala Ser Phe Arg Tyr Ser Gly Val Pro Ser Arg Phe Ser Gly Ser
                645                 650                 655

Gly Ser Gly Thr Asp Phe Thr Leu Thr Ile Ser Ser Leu Gln Pro Glu
            660                 665                 670

Asp Phe Ala Thr Tyr Tyr Cys Gln Gln Tyr Tyr Thr Tyr Pro Tyr Thr
            675                 680                 685

Phe Gly Gly Gly Thr Lys Val Glu Ile Lys His His His His His
            690                 695                 700

Glu Pro Glu Ala
705

<210> SEQ ID NO 106
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Ala Gln Ala Gly Gly Ser Leu Ser Leu Ser Cys Ala Ala Ser Gly
        35                  40                  45

```
Phe Thr Val Ser Asn Ser Val Met Ala Trp Tyr Arg Gln Thr Pro Gly
    50                  55                  60

Lys Gln Arg Glu Phe Val Ala Ile Ile Asn Ser Val Gly Ser Thr Asn
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Asn Leu Lys Pro Glu Asp Thr
                100                 105                 110

Ala Val Tyr Val Cys Asn Arg Asn Phe Asp Arg Ile Tyr Trp Gly Gln
            115                 120                 125

Gly Thr Gln Val Thr Val Ser Ser Gly Gly Pro Gly Pro Ala Gly
    130                 135                 140

Met Lys Gly Leu Pro Gly Ser Ala Pro Thr Ser Ser Thr Lys Lys
145                 150                 155                 160

Thr Gln Leu Gln Leu Glu His Leu Leu Leu Asp Leu Gln Met Ile Leu
                165                 170                 175

Asn Gly Ile Asn Asn Tyr Lys Asn Pro Lys Leu Thr Arg Met Leu Thr
                180                 185                 190

Phe Lys Phe Tyr Met Pro Lys Lys Ala Thr Glu Leu Lys His Leu Gln
        195                 200                 205

Cys Leu Glu Glu Glu Leu Lys Pro Leu Glu Glu Val Leu Asn Leu Ala
    210                 215                 220

Gln Ser Lys Asn Phe His Leu Arg Pro Arg Asp Leu Ile Ser Asn Ile
225                 230                 235                 240

Asn Val Ile Val Leu Glu Leu Lys Gly Ser Glu Thr Thr Phe Met Cys
                245                 250                 255

Glu Tyr Ala Asp Glu Thr Ala Thr Ile Val Glu Phe Leu Asn Arg Trp
                260                 265                 270

Ile Thr Phe Cys Gln Ser Ile Ile Ser Thr Leu Thr Ser Gly Gly Pro
            275                 280                 285

Gly Pro Ala Gly Met Lys Gly Leu Pro Gly Ser Glu Val Gln Leu Val
    290                 295                 300

Glu Ser Gly Gly Gly Leu Val Gln Pro Gly Asn Ser Leu Arg Leu Ser
305                 310                 315                 320

Cys Ala Ala Ser Gly Phe Thr Phe Ser Lys Phe Gly Met Ser Trp Val
                325                 330                 335

Arg Gln Ala Pro Gly Lys Gly Leu Glu Trp Val Ser Ser Ile Ser Gly
                340                 345                 350

Ser Gly Arg Asp Thr Leu Tyr Ala Glu Ser Val Lys Gly Arg Phe Thr
        355                 360                 365

Ile Ser Arg Asp Asn Ala Lys Thr Thr Leu Tyr Leu Gln Met Asn Ser
    370                 375                 380

Leu Arg Pro Glu Asp Thr Ala Val Tyr Tyr Cys Thr Ile Gly Gly Ser
385                 390                 395                 400

Leu Ser Val Ser Ser Gln Gly Thr Leu Val Thr Val Ser Ser Gly Gly
                405                 410                 415

Gly Gly Ser Gly Gly Gly Gly Ser Gly Gly Gly Gly Ser Gly Gly Gly
            420                 425                 430

Gly Ser Gly Gly Gly Gly Ser Gly Gly Gly Gly Ser Ser Gly Gly Pro
        435                 440                 445

Gly Pro Ala Gly Met Lys Gly Leu Pro Gly Ser Glu Val Gln Leu Val
    450                 455                 460
```

-continued

Glu Ser Gly Gly Gly Leu Val Gln Pro Gly Ser Leu Arg Leu Ser
465                 470                 475                 480

Cys Ala Ala Ser Gly Phe Thr Phe Ser Ser Tyr Thr Leu Ala Trp Val
                485                 490                 495

Arg Gln Ala Pro Gly Lys Gly Leu Glu Trp Val Ala Ala Ile Asp Ser
            500                 505                 510

Ser Ser Tyr Thr Tyr Ser Pro Asp Thr Val Arg Gly Arg Phe Thr Ile
        515                 520                 525

Ser Arg Asp Asn Ala Lys Asn Ser Leu Tyr Leu Gln Met Asn Ser Leu
    530                 535                 540

Arg Ala Glu Asp Thr Ala Val Tyr Tyr Cys Ala Arg Asp Ser Asn Trp
545                 550                 555                 560

Asp Ala Leu Asp Tyr Trp Gly Gln Gly Thr Thr Val Thr Val Ser Ser
                565                 570                 575

Gly Gly Gly Gly Ser Gly Gly Gly Ser Gly Gly Gly Gly Ser Asp
            580                 585                 590

Ile Gln Met Thr Gln Ser Pro Ser Ser Leu Ser Ala Ser Val Gly Asp
        595                 600                 605

Arg Val Thr Ile Thr Cys Lys Ala Ser Gln Asn Val Gly Thr Asn Val
    610                 615                 620

Gly Trp Tyr Gln Gln Lys Pro Gly Lys Ala Pro Lys Ala Leu Ile Tyr
625                 630                 635                 640

Ser Ala Ser Phe Arg Tyr Ser Gly Val Pro Ser Arg Phe Ser Gly Ser
                645                 650                 655

Gly Ser Gly Thr Asp Phe Thr Leu Thr Ile Ser Ser Leu Gln Pro Glu
            660                 665                 670

Asp Phe Ala Thr Tyr Tyr Cys Gln Gln Tyr Tyr Thr Tyr Pro Tyr Thr
        675                 680                 685

Phe Gly Gly Gly Thr Lys Val Glu Ile Lys His His His His His His
    690                 695                 700

Glu Pro Glu Ala
705

<210> SEQ ID NO 107
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

```
Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
        130                 135                 140

Thr Phe Cys Gln Ser Ile Ile Ser Thr Leu Thr His His His His
145                 150                 155                 160

His

<210> SEQ ID NO 108
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Asp Leu Gln Met Ile Leu Asn
        35                  40                  45

Gly Ile Asn Asn Tyr Lys Asn Pro Lys Leu Thr Arg Met Leu Thr Phe
50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
        130                 135                 140

Thr Phe Cys Gln Ser Ile Ile Ser Thr Leu Thr Ser Gly Gly Pro Gly
145                 150                 155                 160

Pro Ala Gly Met Lys Gly Leu Pro Gly Ser Glu Val Gln Leu Val Glu
                165                 170                 175

Ser Gly Gly Gly Leu Val Gln Pro Gly Asn Ser Leu Arg Leu Ser Cys
            180                 185                 190

Ala Ala Ser Gly Phe Thr Phe Ser Lys Phe Gly Met Ser Trp Val Arg
        195                 200                 205

Gln Ala Pro Gly Lys Gly Leu Glu Trp Val Ser Ser Ile Ser Gly Ser
        210                 215                 220

Gly Arg Asp Thr Leu Tyr Ala Glu Ser Val Lys Gly Arg Phe Thr Ile
225                 230                 235                 240

Ser Arg Asp Asn Ala Lys Thr Thr Leu Tyr Leu Gln Met Asn Ser Leu
                245                 250                 255

Arg Pro Glu Asp Thr Ala Val Tyr Tyr Cys Thr Ile Gly Gly Ser Leu
            260                 265                 270

Ser Val Ser Ser Gln Gly Thr Leu Val Thr Val Ser Ser Gly Gly Gly
        275                 280                 285

Gly Ser Gly Gly Gly Gly Ser Gly Gly Gly Ser Gly Gly Gly Gly
        290                 295                 300
```

Ser Gly Gly Gly Gly Ser Gly Gly Gly Ser Ser Gly Gly Pro Gly
305                 310                 315                 320

Pro Ala Gly Met Lys Gly Leu Pro Gly Ser Glu Val Gln Leu Val Glu
            325                 330                 335

Ser Gly Gly Gly Leu Val Gln Pro Gly Gly Ser Leu Arg Leu Ser Cys
            340                 345                 350

Ala Ala Ser Gly Phe Thr Phe Ser Ser Tyr Thr Leu Ala Trp Val Arg
            355                 360                 365

Gln Ala Pro Gly Lys Gly Leu Glu Trp Val Ala Ala Ile Asp Ser Ser
370                 375                 380

Ser Tyr Thr Tyr Ser Pro Asp Thr Val Arg Gly Arg Phe Thr Ile Ser
385                 390                 395                 400

Arg Asp Asn Ala Lys Asn Ser Leu Tyr Leu Gln Met Asn Ser Leu Arg
            405                 410                 415

Ala Glu Asp Thr Ala Val Tyr Tyr Cys Ala Arg Asp Ser Asn Trp Asp
            420                 425                 430

Ala Leu Asp Tyr Trp Gly Gln Gly Thr Thr Val Thr Val Ser Ser Gly
            435                 440                 445

Gly Gly Gly Ser Gly Gly Gly Ser Gly Gly Gly Gly Ser Asp Ile
450                 455                 460

Gln Met Thr Gln Ser Pro Ser Ser Leu Ser Ala Ser Val Gly Asp Arg
465                 470                 475                 480

Val Thr Ile Thr Cys Lys Ala Ser Gln Asn Val Gly Thr Asn Val Gly
            485                 490                 495

Trp Tyr Gln Gln Lys Pro Gly Lys Ala Pro Lys Ala Leu Ile Tyr Ser
            500                 505                 510

Ala Ser Phe Arg Tyr Ser Gly Val Pro Ser Arg Phe Ser Gly Ser Gly
            515                 520                 525

Ser Gly Thr Asp Phe Thr Leu Thr Ile Ser Ser Leu Gln Pro Glu Asp
            530                 535                 540

Phe Ala Thr Tyr Tyr Cys Gln Gln Tyr Tyr Thr Tyr Pro Tyr Thr Phe
545                 550                 555                 560

Gly Gly Gly Thr Lys Val Glu Ile Lys Gly Gly Gly Ser Gly Gly
            565                 570                 575

Gly Gly Ser Gly Gly Gly Gly Ser Gln Val Gln Leu Gln Glu Ser Gly
            580                 585                 590

Gly Gly Leu Val Gln Ala Gly Gly Ser Leu Arg Leu Ser Cys Ala Ala
            595                 600                 605

Ser Gly Arg Ile Phe Ser Ile Asp Ile Met Ser Trp Tyr Arg Gln Ala
            610                 615                 620

Pro Gly Lys Gln Arg Glu Leu Val Ala Arg Ile Thr Arg Gly Gly Thr
625                 630                 635                 640

Ile Ser Tyr Asp Asp Ser Val Lys Gly Arg Phe Thr Ile Ser Arg Asp
            645                 650                 655

Asn Ala Lys Asn Thr Val Tyr Leu Gln Met Asn Ser Leu Lys Pro Glu
            660                 665                 670

Asp Thr Gly Val Tyr Tyr Cys Asn Ala Leu Tyr Gly Thr Asp Tyr Trp
            675                 680                 685

Gly Lys Gly Thr Gln Val Thr Val Ser Ser His His His His His
            690                 695                 700

Glu Pro Glu Ala
705

<210> SEQ ID NO 109
<211> LENGTH: 708
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Met Asp Met Arg Val Pro Ala Gln Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Gly Gly Ser Gly Gly Gly
    130                 135                 140

Gly Ser Gly Gly Gly Gly Ser Ala Pro Thr Ser Ser Ser Thr Lys Lys
145                 150                 155                 160

Thr Gln Leu Gln Leu Glu His Leu Leu Leu Asp Leu Gln Met Ile Leu
                165                 170                 175

Asn Gly Ile Asn Asn Tyr Lys Asn Pro Lys Leu Thr Arg Met Leu Thr
            180                 185                 190

Phe Lys Phe Tyr Met Pro Lys Lys Ala Thr Glu Leu Lys His Leu Gln
        195                 200                 205

Cys Leu Glu Glu Glu Leu Lys Pro Leu Glu Glu Val Leu Asn Leu Ala
    210                 215                 220

Gln Ser Lys Asn Phe His Leu Arg Pro Arg Asp Leu Ile Ser Asn Ile
225                 230                 235                 240

Asn Val Ile Val Leu Glu Leu Lys Gly Ser Glu Thr Thr Phe Met Cys
                245                 250                 255

Glu Tyr Ala Asp Glu Thr Ala Thr Ile Val Glu Phe Leu Asn Arg Trp
            260                 265                 270

Ile Thr Phe Cys Gln Ser Ile Ile Ser Thr Leu Thr Ser Gly Gly Pro
        275                 280                 285

Gly Pro Ala Gly Met Lys Gly Leu Pro Gly Ser Glu Val Gln Leu Val
    290                 295                 300

Glu Ser Gly Gly Gly Leu Val Gln Pro Gly Asn Ser Leu Arg Leu Ser
305                 310                 315                 320

Cys Ala Ala Ser Gly Phe Thr Phe Ser Lys Phe Gly Met Ser Trp Val
                325                 330                 335

Arg Gln Ala Pro Gly Lys Gly Leu Glu Trp Val Ser Ser Ile Ser Gly
            340                 345                 350

Ser Gly Arg Asp Thr Leu Tyr Ala Glu Ser Val Lys Gly Arg Phe Thr
        355                 360                 365

```
Ile Ser Arg Asp Asn Ala Lys Thr Thr Leu Tyr Leu Gln Met Asn Ser
        370                 375                 380

Leu Arg Pro Glu Asp Thr Ala Val Tyr Tyr Cys Thr Ile Gly Gly Ser
385                 390                 395                 400

Leu Ser Val Ser Ser Gln Gly Thr Leu Val Thr Val Ser Ser Gly Gly
                405                 410                 415

Gly Gly Ser Gly Gly Gly Gly Ser Gly Gly Gly Ser Gly Gly Gly
                420                 425                 430

Gly Ser Gly Gly Gly Ser Gly Gly Gly Ser Ser Gly Gly Pro
        435                 440                 445

Gly Pro Ala Gly Met Lys Gly Leu Pro Gly Ser Glu Val Gln Leu Val
        450                 455                 460

Glu Ser Gly Gly Gly Leu Val Gln Pro Gly Gly Ser Leu Arg Leu Ser
465                 470                 475                 480

Cys Ala Ala Ser Gly Phe Thr Phe Ser Ser Tyr Thr Leu Ala Trp Val
                485                 490                 495

Arg Gln Ala Pro Gly Lys Gly Leu Glu Trp Val Ala Ala Ile Asp Ser
                500                 505                 510

Ser Ser Tyr Thr Tyr Ser Pro Asp Thr Val Arg Gly Arg Phe Thr Ile
        515                 520                 525

Ser Arg Asp Asn Ala Lys Asn Ser Leu Tyr Leu Gln Met Asn Ser Leu
        530                 535                 540

Arg Ala Glu Asp Thr Ala Val Tyr Tyr Cys Ala Arg Asp Ser Asn Trp
545                 550                 555                 560

Asp Ala Leu Asp Tyr Trp Gly Gln Gly Thr Thr Val Thr Val Ser Ser
                565                 570                 575

Gly Gly Gly Gly Ser Gly Gly Gly Ser Gly Gly Gly Gly Ser Asp
        580                 585                 590

Ile Gln Met Thr Gln Ser Pro Ser Ser Leu Ser Ala Ser Val Gly Asp
        595                 600                 605

Arg Val Thr Ile Thr Cys Lys Ala Ser Gln Asn Val Gly Thr Asn Val
        610                 615                 620

Gly Trp Tyr Gln Gln Lys Pro Gly Lys Ala Pro Lys Ala Leu Ile Tyr
625                 630                 635                 640

Ser Ala Ser Phe Arg Tyr Ser Gly Val Pro Ser Arg Phe Ser Gly Ser
                645                 650                 655

Gly Ser Gly Thr Asp Phe Thr Leu Thr Ile Ser Ser Leu Gln Pro Glu
                660                 665                 670

Asp Phe Ala Thr Tyr Tyr Cys Gln Gln Tyr Tyr Thr Tyr Pro Tyr Thr
        675                 680                 685

Phe Gly Gly Gly Thr Lys Val Glu Ile Lys His His His His His His
        690                 695                 700

Glu Pro Glu Ala
705

<210> SEQ ID NO 110
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Asp Met Arg Val Pro Ala Gln Leu Leu Gly Leu Leu Leu Leu Trp
```

-continued

```
1               5                    10                   15
Leu Arg Gly Ala Arg Cys Gln Val Gln Leu Gln Glu Ser Gly Gly Gly
                20                  25                  30
Leu Val Gln Ala Gly Gly Ser Leu Arg Leu Ser Cys Ala Ala Ser Gly
                35                  40                  45
Arg Ile Phe Ser Ile Asp Ile Met Ser Trp Tyr Arg Gln Ala Pro Gly
                50                  55                  60
Lys Gln Arg Glu Leu Val Ala Arg Ile Thr Arg Gly Gly Thr Ile Ser
65                  70                  75                  80
Tyr Asp Asp Ser Val Lys Gly Arg Phe Thr Ile Ser Arg Asp Asn Ala
                85                  90                  95
Lys Asn Thr Val Tyr Leu Gln Met Asn Ser Leu Lys Pro Glu Asp Thr
                100                 105                 110
Gly Val Tyr Tyr Cys Asn Ala Leu Tyr Gly Thr Asp Tyr Trp Gly Lys
                115                 120                 125
Gly Thr Gln Val Thr Val Ser Ser Gly Gly Pro Gly Pro Ala Gly
                130                 135                 140
Met Lys Gly Leu Pro Gly Ser Ala Pro Thr Ser Ser Thr Lys Lys
145                 150                 155                 160
Thr Gln Leu Gln Leu Glu His Leu Leu Leu Asp Leu Gln Met Ile Leu
                165                 170                 175
Asn Gly Ile Asn Asn Tyr Lys Asn Pro Lys Leu Thr Arg Met Leu Thr
                180                 185                 190
Phe Lys Phe Tyr Met Pro Lys Lys Ala Thr Glu Leu Lys His Leu Gln
                195                 200                 205
Cys Leu Glu Glu Glu Leu Lys Pro Leu Glu Glu Val Leu Asn Leu Ala
                210                 215                 220
Gln Ser Lys Asn Phe His Leu Arg Pro Arg Asp Leu Ile Ser Asn Ile
225                 230                 235                 240
Asn Val Ile Val Leu Glu Leu Lys Gly Ser Glu Thr Thr Phe Met Cys
                245                 250                 255
Glu Tyr Ala Asp Glu Thr Ala Thr Ile Val Glu Phe Leu Asn Arg Trp
                260                 265                 270
Ile Thr Phe Cys Gln Ser Ile Ile Ser Thr Leu Thr Ser Gly Gly Pro
                275                 280                 285
Gly Pro Ala Gly Met Lys Gly Leu Pro Gly Ser Glu Val Gln Leu Val
                290                 295                 300
Glu Ser Gly Gly Leu Val Gln Pro Gly Asn Ser Leu Arg Leu Ser
305                 310                 315                 320
Cys Ala Ala Ser Gly Phe Thr Phe Ser Lys Phe Gly Met Ser Trp Val
                325                 330                 335
Arg Gln Ala Pro Gly Lys Gly Leu Glu Trp Val Ser Ser Ile Ser Gly
                340                 345                 350
Ser Gly Arg Asp Thr Leu Tyr Ala Glu Ser Val Lys Gly Arg Phe Thr
                355                 360                 365
Ile Ser Arg Asp Asn Ala Lys Thr Thr Leu Tyr Leu Gln Met Asn Ser
                370                 375                 380
Leu Arg Pro Glu Asp Thr Ala Val Tyr Tyr Cys Thr Ile Gly Gly Ser
385                 390                 395                 400
Leu Ser Val Ser Ser Gln Gly Thr Leu Val Thr Val Ser Ser Gly Gly
                405                 410                 415
Gly Gly Ser Gly Gly Gly Gly Ser Gly Gly Gly Gly Ser Gly Gly Gly
                420                 425                 430
```

```
Gly Ser Gly Gly Gly Ser Gly Gly Gly Ser Ser Gly Gly Pro
        435                 440                 445

Gly Pro Ala Gly Met Lys Gly Leu Pro Gly Ser Glu Val Gln Leu Val
    450                 455                 460

Glu Ser Gly Gly Gly Leu Val Gln Pro Gly Gly Ser Leu Arg Leu Ser
465                 470                 475                 480

Cys Ala Ala Ser Gly Phe Thr Phe Ser Ser Tyr Thr Leu Ala Trp Val
                485                 490                 495

Arg Gln Ala Pro Gly Lys Gly Leu Glu Trp Val Ala Ala Ile Asp Ser
            500                 505                 510

Ser Ser Tyr Thr Tyr Ser Pro Asp Thr Val Arg Gly Arg Phe Thr Ile
        515                 520                 525

Ser Arg Asp Asn Ala Lys Asn Ser Leu Tyr Leu Gln Met Asn Ser Leu
530                 535                 540

Arg Ala Glu Asp Thr Ala Val Tyr Tyr Cys Ala Arg Asp Ser Asn Trp
545                 550                 555                 560

Asp Ala Leu Asp Tyr Trp Gly Gln Gly Thr Thr Val Thr Val Ser Ser
                565                 570                 575

Gly Gly Gly Gly Ser Gly Gly Gly Ser Gly Gly Gly Gly Ser Asp
            580                 585                 590

Ile Gln Met Thr Gln Ser Pro Ser Ser Leu Ser Ala Ser Val Gly Asp
        595                 600                 605

Arg Val Thr Ile Thr Cys Lys Ala Ser Gln Asn Val Gly Thr Asn Val
    610                 615                 620

Gly Trp Tyr Gln Gln Lys Pro Gly Lys Ala Pro Lys Ala Leu Ile Tyr
625                 630                 635                 640

Ser Ala Ser Phe Arg Tyr Ser Gly Val Pro Ser Arg Phe Ser Gly Ser
                645                 650                 655

Gly Ser Gly Thr Asp Phe Thr Leu Thr Ile Ser Ser Leu Gln Pro Glu
            660                 665                 670

Asp Phe Ala Thr Tyr Tyr Cys Gln Gln Tyr Tyr Thr Tyr Pro Tyr Thr
        675                 680                 685

Phe Gly Gly Gly Thr Lys Val Glu Ile Lys His His His His His His
    690                 695                 700

Glu Pro Glu Ala
705

<210> SEQ ID NO 111
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
```

```
                65                  70                  75                  80
Leu Glu Glu Glu Leu Lys Pro Leu Glu Val Leu Asn Leu Ala Gln
                    85                  90                  95

Ser Lys Asn Phe His Leu Arg Pro Arg Asp Leu Ile Ser Asn Ile Asn
                100                 105                 110

Val Ile Val Leu Glu Leu Lys Gly Ser Glu Thr Thr Phe Met Cys Glu
            115                 120                 125

Tyr Ala Asp Glu Thr Ala Thr Ile Val Glu Phe Leu Asn Arg Trp Ile
130                 135                 140

Thr Phe Cys Gln Ser Ile Ile Ser Thr Leu Thr Ser Gly Gly Pro Gly
145                 150                 155                 160

Pro Ala Gly Leu Tyr Ala Gln Pro Gly Ser Glu Val Gln Leu Val Glu
                165                 170                 175

Ser Gly Gly Gly Leu Val Gln Pro Gly Asn Ser Leu Arg Leu Ser Cys
            180                 185                 190

Ala Ala Ser Gly Phe Thr Phe Ser Lys Phe Gly Met Ser Trp Val Arg
        195                 200                 205

Gln Ala Pro Gly Lys Gly Leu Glu Trp Val Ser Ser Ile Ser Gly Ser
210                 215                 220

Gly Arg Asp Thr Leu Tyr Ala Glu Ser Val Lys Gly Arg Phe Thr Ile
225                 230                 235                 240

Ser Arg Asp Asn Ala Lys Thr Thr Leu Tyr Leu Gln Met Asn Ser Leu
                245                 250                 255

Arg Pro Glu Asp Thr Ala Val Tyr Tyr Cys Thr Ile Gly Gly Ser Leu
            260                 265                 270

Ser Val Ser Ser Gln Gly Thr Leu Val Thr Val Ser Ser Gly Gly Gly
        275                 280                 285

Gly Ser Gly Gly Gly Gly Ser Gly Gly Gly Gly Ser Gly Gly Gly Gly
        290                 295                 300

Ser Gly Gly Gly Gly Ser Gly Gly Gly Ser Ser Gly Gly Pro Gly
305                 310                 315                 320

Pro Ala Gly Leu Tyr Ala Gln Pro Gly Ser Glu Val Gln Leu Val Glu
                325                 330                 335

Ser Gly Gly Gly Leu Val Gln Pro Gly Gly Ser Leu Arg Leu Ser Cys
            340                 345                 350

Ala Ala Ser Gly Phe Thr Phe Ser Ser Tyr Thr Leu Ala Trp Val Arg
        355                 360                 365

Gln Ala Pro Gly Lys Gly Leu Glu Trp Val Ala Ala Ile Asp Ser Ser
370                 375                 380

Ser Tyr Thr Tyr Ser Pro Asp Thr Val Arg Gly Arg Phe Thr Ile Ser
385                 390                 395                 400

Arg Asp Asn Ala Lys Asn Ser Leu Tyr Leu Gln Met Asn Ser Leu Arg
                405                 410                 415

Ala Glu Asp Thr Ala Val Tyr Tyr Cys Ala Arg Asp Ser Asn Trp Asp
            420                 425                 430

Ala Leu Asp Tyr Trp Gly Gln Gly Thr Thr Val Thr Val Ser Ser Gly
        435                 440                 445

Gly Gly Gly Ser Gly Gly Gly Gly Ser Gly Gly Gly Gly Ser Asp Ile
        450                 455                 460

Gln Met Thr Gln Ser Pro Ser Ser Leu Ser Ala Ser Val Gly Asp Arg
465                 470                 475                 480

Val Thr Ile Thr Cys Lys Ala Ser Gln Asn Val Gly Thr Asn Val Gly
                485                 490                 495
```

-continued

```
Trp Tyr Gln Gln Lys Pro Gly Lys Ala Pro Lys Ala Leu Ile Tyr Ser
                500                 505                 510

Ala Ser Phe Arg Tyr Ser Gly Val Pro Ser Arg Phe Ser Gly Ser Gly
            515                 520                 525

Ser Gly Thr Asp Phe Thr Leu Thr Ile Ser Ser Leu Gln Pro Glu Asp
        530                 535                 540

Phe Ala Thr Tyr Tyr Cys Gln Gln Tyr Thr Tyr Pro Tyr Thr Phe
545                 550                 555                 560

Gly Gly Gly Thr Lys Val Glu Ile Lys His His His His His His Glu
                565                 570                 575

Pro Glu Ala
```

<210> SEQ ID NO 112
<211> LENGTH: 579
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
                20                  25                  30

Gln Leu Gln Leu Glu His Leu Leu Leu Asp Leu Gln Met Ile Leu Asn
            35                  40                  45

Gly Ile Asn Asn Tyr Lys Asn Pro Lys Leu Thr Arg Met Leu Thr Phe
        50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
                100                 105                 110

Val Ile Val Leu Glu Leu Lys Gly Ser Glu Thr Thr Phe Met Cys Glu
            115                 120                 125

Tyr Ala Asp Glu Thr Ala Thr Ile Val Glu Phe Leu Asn Arg Trp Ile
        130                 135                 140

Thr Phe Cys Gln Ser Ile Ile Ser Thr Leu Thr Ser Gly Gly Pro Pro
145                 150                 155                 160

Gly Gly Pro Ala Gly Ile Gly Pro Gly Ser Glu Val Gln Leu Val Glu
                165                 170                 175

Ser Gly Gly Gly Leu Val Gln Pro Gly Asn Ser Leu Arg Leu Ser Cys
            180                 185                 190

Ala Ala Ser Gly Phe Thr Phe Ser Lys Phe Gly Met Ser Trp Val Arg
        195                 200                 205

Gln Ala Pro Gly Lys Gly Leu Glu Trp Val Ser Ser Ile Ser Gly Ser
    210                 215                 220

Gly Arg Asp Thr Leu Tyr Ala Glu Ser Val Lys Gly Arg Phe Thr Ile
225                 230                 235                 240

Ser Arg Asp Asn Ala Lys Thr Thr Leu Tyr Leu Gln Met Asn Ser Leu
                245                 250                 255

Arg Pro Glu Asp Thr Ala Val Tyr Tyr Cys Thr Ile Gly Gly Ser Leu
            260                 265                 270
```

Ser Val Ser Ser Gln Gly Thr Leu Val Thr Val Ser Ser Gly Gly
            275                 280                 285
Gly Ser Gly Gly Gly Ser Gly Gly Gly Ser Gly Gly Gly
        290                 295                 300
Ser Gly Gly Gly Ser Gly Gly Gly Ser Ser Gly Gly Pro Pro
305                 310                 315                 320
Gly Gly Pro Ala Gly Ile Gly Pro Gly Glu Val Gln Leu Val Glu
                325                 330                 335
Ser Gly Gly Gly Leu Val Gln Pro Gly Gly Ser Leu Arg Leu Ser Cys
                340                 345                 350
Ala Ala Ser Gly Phe Thr Phe Ser Ser Tyr Thr Leu Ala Trp Val Arg
            355                 360                 365
Gln Ala Pro Gly Lys Gly Leu Glu Trp Val Ala Ala Ile Asp Ser Ser
            370                 375                 380
Ser Tyr Thr Tyr Ser Pro Asp Thr Val Arg Gly Arg Phe Thr Ile Ser
385                 390                 395                 400
Arg Asp Asn Ala Lys Asn Ser Leu Tyr Leu Gln Met Asn Ser Leu Arg
                405                 410                 415
Ala Glu Asp Thr Ala Val Tyr Tyr Cys Ala Arg Asp Ser Asn Trp Asp
            420                 425                 430
Ala Leu Asp Tyr Trp Gly Gln Gly Thr Thr Val Thr Val Ser Ser Gly
            435                 440                 445
Gly Gly Gly Ser Gly Gly Gly Gly Ser Gly Gly Gly Gly Ser Asp Ile
        450                 455                 460
Gln Met Thr Gln Ser Pro Ser Ser Leu Ser Ala Ser Val Gly Asp Arg
465                 470                 475                 480
Val Thr Ile Thr Cys Lys Ala Ser Gln Asn Val Gly Thr Asn Val Gly
                485                 490                 495
Trp Tyr Gln Gln Lys Pro Gly Lys Ala Pro Lys Ala Leu Ile Tyr Ser
            500                 505                 510
Ala Ser Phe Arg Tyr Ser Gly Val Pro Ser Arg Phe Ser Gly Ser Gly
            515                 520                 525
Ser Gly Thr Asp Phe Thr Leu Thr Ile Ser Ser Leu Gln Pro Glu Asp
        530                 535                 540
Phe Ala Thr Tyr Tyr Cys Gln Gln Tyr Tyr Thr Tyr Pro Tyr Thr Phe
545                 550                 555                 560
Gly Gly Gly Thr Lys Val Glu Ile Lys His His His His His His Glu
                565                 570                 575

Pro Glu Ala

<210> SEQ ID NO 113
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Asp Met Arg Val Pro Ala Gln Leu Leu Gly Leu Leu Leu Leu Trp
1               5                   10                  15
Leu Arg Gly Ala Arg Cys Ala Pro Thr Ser Ser Ser Thr Lys Lys Thr
                20                  25                  30
Gln Leu Gln Leu Glu His Leu Leu Leu Asp Leu Gln Met Ile Leu Asn
            35                  40                  45

```
Gly Ile Asn Asn Tyr Lys Asn Pro Lys Leu Thr Arg Met Leu Thr Phe
        50                  55                  60

Lys Phe Tyr Met Pro Lys Ala Thr Glu Leu Lys His Leu Gln Cys
 65                  70                  75                  80

Leu Glu Glu Leu Lys Pro Leu Glu Val Leu Asn Leu Ala Gln
                    85                  90                  95

Ser Lys Asn Phe His Leu Arg Pro Arg Asp Leu Ile Ser Asn Ile Asn
                100                 105                 110

Val Ile Val Leu Glu Leu Lys Gly Ser Glu Thr Thr Phe Met Cys Glu
            115                 120                 125

Tyr Ala Asp Glu Thr Ala Thr Ile Val Glu Phe Leu Asn Arg Trp Ile
            130                 135                 140

Thr Phe Cys Gln Ser Ile Ile Ser Thr Leu Thr Ser Gly Gly Pro Ala
145                 150                 155                 160

Leu Phe Lys Ser Ser Phe Pro Pro Gly Ser Glu Val Gln Leu Val Glu
                165                 170                 175

Ser Gly Gly Gly Leu Val Gln Pro Gly Asn Ser Leu Arg Leu Ser Cys
                180                 185                 190

Ala Ala Ser Gly Phe Thr Phe Ser Lys Phe Gly Met Ser Trp Val Arg
            195                 200                 205

Gln Ala Pro Gly Lys Gly Leu Glu Trp Val Ser Ser Ile Ser Gly Ser
210                 215                 220

Gly Arg Asp Thr Leu Tyr Ala Glu Ser Val Lys Gly Arg Phe Thr Ile
225                 230                 235                 240

Ser Arg Asp Asn Ala Lys Thr Thr Leu Tyr Leu Gln Met Asn Ser Leu
                245                 250                 255

Arg Pro Glu Asp Thr Ala Val Tyr Tyr Cys Thr Ile Gly Gly Ser Leu
                260                 265                 270

Ser Val Ser Ser Gln Gly Thr Leu Val Thr Val Ser Ser Gly Gly Gly
            275                 280                 285

Gly Ser Gly Gly Gly Gly Ser Gly Gly Gly Ser Gly Gly Gly Gly
        290                 295                 300

Ser Gly Gly Gly Gly Ser Gly Gly Gly Ser Ser Gly Gly Pro Ala
305                 310                 315                 320

Leu Phe Lys Ser Ser Phe Pro Pro Gly Ser Glu Val Gln Leu Val Glu
                325                 330                 335

Ser Gly Gly Gly Leu Val Gln Pro Gly Gly Ser Leu Arg Leu Ser Cys
            340                 345                 350

Ala Ala Ser Gly Phe Thr Phe Ser Ser Tyr Thr Leu Ala Trp Val Arg
            355                 360                 365

Gln Ala Pro Gly Lys Gly Leu Glu Trp Val Ala Ala Ile Asp Ser Ser
370                 375                 380

Ser Tyr Thr Tyr Ser Pro Asp Thr Val Arg Gly Arg Phe Thr Ile Ser
385                 390                 395                 400

Arg Asp Asn Ala Lys Asn Ser Leu Tyr Leu Gln Met Asn Ser Leu Arg
                405                 410                 415

Ala Glu Asp Thr Ala Val Tyr Tyr Cys Ala Arg Asp Ser Asn Trp Asp
            420                 425                 430

Ala Leu Asp Tyr Trp Gly Gln Gly Thr Thr Val Thr Val Ser Ser Gly
            435                 440                 445

Gly Gly Gly Ser Gly Gly Gly Gly Ser Gly Gly Gly Ser Asp Ile
        450                 455                 460
```

```
Gln Met Thr Gln Ser Pro Ser Ser Leu Ser Ala Ser Val Gly Asp Arg
465                 470                 475                 480

Val Thr Ile Thr Cys Lys Ala Ser Gln Asn Val Gly Thr Asn Val Gly
                485                 490                 495

Trp Tyr Gln Gln Lys Pro Gly Lys Ala Pro Lys Ala Leu Ile Tyr Ser
            500                 505                 510

Ala Ser Phe Arg Tyr Ser Gly Val Pro Ser Arg Phe Ser Gly Ser Gly
        515                 520                 525

Ser Gly Thr Asp Phe Thr Leu Thr Ile Ser Ser Leu Gln Pro Glu Asp
    530                 535                 540

Phe Ala Thr Tyr Tyr Cys Gln Gln Tyr Tyr Thr Tyr Pro Tyr Thr Phe
545                 550                 555                 560

Gly Gly Gly Thr Lys Val Glu Ile Lys His His His His His His Glu
                565                 570                 575

Pro Glu Ala

<210> SEQ ID NO 114
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Asp Met Arg Val Pro Ala Gln Leu Leu Gly Leu Leu Leu Leu Trp
1               5                   10                  15

Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
    50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
    130                 135                 140

Thr Phe Cys Gln Ser Ile Ile Ser Thr Leu Thr Ser Gly Gly Pro Pro
145                 150                 155                 160

Leu Ala Gln Lys Leu Lys Ser Ser Pro Gly Ser Glu Val Gln Leu Val
                165                 170                 175

Glu Ser Gly Gly Gly Leu Val Gln Pro Gly Asn Ser Leu Arg Leu Ser
            180                 185                 190

Cys Ala Ala Ser Gly Phe Thr Phe Ser Lys Phe Gly Met Ser Trp Val
        195                 200                 205

Arg Gln Ala Pro Gly Lys Gly Leu Glu Trp Val Ser Ser Ile Ser Gly
    210                 215                 220

Ser Gly Arg Asp Thr Leu Tyr Ala Glu Ser Val Lys Gly Arg Phe Thr
225                 230                 235                 240
```

```
Ile Ser Arg Asp Asn Ala Lys Thr Thr Leu Tyr Leu Gln Met Asn Ser
            245                 250                 255

Leu Arg Pro Glu Asp Thr Ala Val Tyr Tyr Cys Thr Ile Gly Gly Ser
        260                 265                 270

Leu Ser Val Ser Ser Gln Gly Thr Leu Val Thr Val Ser Ser Gly Gly
        275                 280                 285

Gly Gly Ser Gly Gly Gly Ser Gly Gly Gly Ser Gly Gly Gly
    290                 295                 300

Gly Ser Gly Gly Gly Ser Gly Gly Gly Ser Ser Gly Gly Pro
305                 310                 315                 320

Pro Leu Ala Gln Lys Leu Lys Ser Ser Pro Gly Ser Glu Val Gln Leu
                325                 330                 335

Val Glu Ser Gly Gly Gly Leu Val Gln Pro Gly Gly Ser Leu Arg Leu
            340                 345                 350

Ser Cys Ala Ala Ser Gly Phe Thr Phe Ser Ser Tyr Thr Leu Ala Trp
            355                 360                 365

Val Arg Gln Ala Pro Gly Lys Gly Leu Glu Trp Val Ala Ala Ile Asp
        370                 375                 380

Ser Ser Ser Tyr Thr Tyr Ser Pro Asp Thr Val Arg Gly Arg Phe Thr
385                 390                 395                 400

Ile Ser Arg Asp Asn Ala Lys Asn Ser Leu Tyr Leu Gln Met Asn Ser
            405                 410                 415

Leu Arg Ala Glu Asp Thr Ala Val Tyr Tyr Cys Ala Arg Asp Ser Asn
        420                 425                 430

Trp Asp Ala Leu Asp Tyr Trp Gly Gln Gly Thr Thr Val Thr Val Ser
        435                 440                 445

Ser Gly Gly Gly Gly Ser Gly Gly Gly Gly Ser Gly Gly Gly Gly Ser
    450                 455                 460

Asp Ile Gln Met Thr Gln Ser Pro Ser Ser Leu Ser Ala Ser Val Gly
465                 470                 475                 480

Asp Arg Val Thr Ile Thr Cys Lys Ala Ser Gln Asn Val Gly Thr Asn
            485                 490                 495

Val Gly Trp Tyr Gln Gln Lys Pro Gly Lys Ala Pro Lys Ala Leu Ile
        500                 505                 510

Tyr Ser Ala Ser Phe Arg Tyr Ser Gly Val Pro Ser Arg Phe Ser Gly
        515                 520                 525

Ser Gly Ser Gly Thr Asp Phe Thr Leu Thr Ile Ser Ser Leu Gln Pro
        530                 535                 540

Glu Asp Phe Ala Thr Tyr Tyr Cys Gln Gln Tyr Tyr Thr Tyr Pro Tyr
545                 550                 555                 560

Thr Phe Gly Gly Gly Thr Lys Val Glu Ile Lys His His His His
                565                 570                 575

His Glu Pro Glu Ala
        580

<210> SEQ ID NO 115
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Asp Met Arg Val Pro Ala Gln Leu Leu Gly Leu Leu Leu Leu Trp
1               5                   10                  15
```

```
Leu Arg Gly Ala Arg Cys Ala Pro Thr Ser Ser Ser Thr Lys Lys Thr
            20                  25                  30

Gln Leu Gln Leu Glu His Leu Leu Leu Asp Leu Gln Met Ile Leu Asn
        35                  40                  45

Gly Ile Asn Asn Tyr Lys Asn Pro Lys Leu Thr Arg Met Leu Thr Phe
50                  55                  60

Lys Phe Tyr Met Pro Lys Lys Ala Thr Glu Leu Lys His Leu Gln Cys
65                  70                  75                  80

Leu Glu Glu Glu Leu Lys Pro Leu Glu Glu Val Leu Asn Leu Ala Gln
                85                  90                  95

Ser Lys Asn Phe His Leu Arg Pro Arg Asp Leu Ile Ser Asn Ile Asn
            100                 105                 110

Val Ile Val Leu Glu Leu Lys Gly Ser Glu Thr Thr Phe Met Cys Glu
        115                 120                 125

Tyr Ala Asp Glu Thr Ala Thr Ile Val Glu Phe Leu Asn Arg Trp Ile
130                 135                 140

Thr Phe Cys Gln Ser Ile Ile Ser Thr Leu Thr Ser Gly Gly Pro Pro
145                 150                 155                 160

Gly Gly Pro Ala Gly Ile Gly Ala Leu Phe Lys Ser Ser Phe Pro Pro
                165                 170                 175

Leu Ala Gln Lys Leu Lys Ser Ser Pro Gly Ser Glu Val Gln Leu Val
            180                 185                 190

Glu Ser Gly Gly Gly Leu Val Gln Pro Gly Asn Ser Leu Arg Leu Ser
        195                 200                 205

Cys Ala Ala Ser Gly Phe Thr Phe Ser Lys Phe Gly Met Ser Trp Val
210                 215                 220

Arg Gln Ala Pro Gly Lys Gly Leu Glu Trp Val Ser Ser Ile Ser Gly
225                 230                 235                 240

Ser Gly Arg Asp Thr Leu Tyr Ala Glu Ser Val Lys Gly Arg Phe Thr
                245                 250                 255

Ile Ser Arg Asp Asn Ala Lys Thr Thr Leu Tyr Leu Gln Met Asn Ser
            260                 265                 270

Leu Arg Pro Glu Asp Thr Ala Val Tyr Tyr Cys Thr Ile Gly Gly Ser
        275                 280                 285

Leu Ser Val Ser Ser Gln Gly Thr Leu Val Thr Val Ser Ser Gly Gly
290                 295                 300

Gly Gly Ser Gly Gly Gly Gly Ser Gly Gly Gly Gly Ser Gly Gly Gly
305                 310                 315                 320

Gly Ser Gly Gly Gly Gly Ser Gly Gly Gly Gly Ser Ser Gly Gly Pro
                325                 330                 335

Pro Gly Gly Pro Ala Gly Ile Gly Ala Leu Phe Lys Ser Ser Phe Pro
            340                 345                 350

Pro Leu Ala Gln Lys Leu Lys Ser Ser Pro Gly Ser Glu Val Gln Leu
        355                 360                 365

Val Glu Ser Gly Gly Gly Leu Val Gln Pro Gly Gly Ser Leu Arg Leu
370                 375                 380

Ser Cys Ala Ala Ser Gly Phe Thr Phe Ser Ser Tyr Thr Leu Ala Trp
385                 390                 395                 400

Val Arg Gln Ala Pro Gly Lys Gly Leu Glu Trp Val Ala Ala Ile Asp
                405                 410                 415

Ser Ser Ser Tyr Thr Tyr Ser Pro Asp Thr Val Arg Gly Arg Phe Thr
            420                 425                 430
```

```
Ile Ser Arg Asp Asn Ala Lys Asn Ser Leu Tyr Leu Gln Met Asn Ser
            435                 440                 445

Leu Arg Ala Glu Asp Thr Ala Val Tyr Tyr Cys Ala Arg Asp Ser Asn
450                 455                 460

Trp Asp Ala Leu Asp Tyr Trp Gly Gln Gly Thr Thr Val Thr Val Ser
465                 470                 475                 480

Ser Gly Gly Gly Gly Ser Gly Gly Gly Gly Ser Gly Gly Gly Gly Ser
                485                 490                 495

Asp Ile Gln Met Thr Gln Ser Pro Ser Ser Leu Ser Ala Ser Val Gly
            500                 505                 510

Asp Arg Val Thr Ile Thr Cys Lys Ala Ser Gln Asn Val Gly Thr Asn
        515                 520                 525

Val Gly Trp Tyr Gln Gln Lys Pro Gly Lys Ala Pro Lys Ala Leu Ile
530                 535                 540

Tyr Ser Ala Ser Phe Arg Tyr Ser Gly Val Pro Ser Arg Phe Ser Gly
545                 550                 555                 560

Ser Gly Ser Gly Thr Asp Phe Thr Leu Thr Ile Ser Ser Leu Gln Pro
                565                 570                 575

Glu Asp Phe Ala Thr Tyr Tyr Cys Gln Gln Tyr Tyr Thr Tyr Pro Tyr
            580                 585                 590

Thr Phe Gly Gly Gly Thr Lys Val Glu Ile Lys His His His His His
            595                 600                 605

His Glu Pro Glu Ala
    610

<210> SEQ ID NO 116
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
            35                  40                  45

Glu Glu Pro Gly Gly Leu Glu Trp Val Ser Ser Ile Ser Gly Ser Gly
50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Lys Pro Leu Gly Leu Gln Ala Arg Val Val Gly Gly Gly Thr Gln
130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
            165                 170                 175
```

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Ser Glu Val Gln Leu Val
                260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Gly Leu Val Gln Pro Gly
                405                 410                 415

Gly Ser Leu Thr Leu Ser Cys Ala Ala Ser Gly Arg Thr Phe Ser Ser
            420                 425                 430

Tyr Ala Met Gly Trp Phe Arg Gln Ala Pro Gly Lys Glu Arg Glu Phe
        435                 440                 445

Val Val Ala Ile Asn Trp Ala Ser Gly Ser Thr Tyr Tyr Ala Asp Ser
450                 455                 460

Val Lys Gly Arg Phe Thr Ile Ser Arg Asp Asn Ser Lys Asn Thr Leu
465                 470                 475                 480

Tyr Leu Gln Met Asn Ser Leu Arg Ala Glu Asp Thr Ala Val Tyr Tyr
                485                 490                 495

Cys Ala Ala Gly Tyr Gln Ile Asn Ser Gly Asn Tyr Asn Phe Lys Asp
            500                 505                 510

Tyr Glu Tyr Asp Tyr Trp Gly Gln Gly Thr Leu Val Thr Val Ser Ser
        515                 520                 525

His His His His His His
    530

<210> SEQ ID NO 117
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Ser Gly Gly Gly Gly Ser Gly Gly Val Val Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Gly Leu Val Gln Pro Gly
                405                 410                 415
```

```
Gly Ser Leu Thr Leu Ser Cys Ala Ala Ser Gly Arg Thr Phe Ser Ser
                420                 425                 430

Tyr Ala Met Gly Trp Phe Arg Gln Ala Pro Gly Lys Glu Arg Glu Phe
            435                 440                 445

Val Val Ala Ile Asn Trp Ala Ser Gly Ser Thr Tyr Tyr Ala Asp Ser
450                 455                 460

Val Lys Gly Arg Phe Thr Ile Ser Arg Asp Asn Ser Lys Asn Thr Leu
465                 470                 475                 480

Tyr Leu Gln Met Asn Ser Leu Arg Ala Glu Asp Thr Ala Val Tyr Tyr
                485                 490                 495

Cys Ala Ala Gly Tyr Gln Ile Asn Ser Gly Asn Tyr Asn Phe Lys Asp
                500                 505                 510

Tyr Glu Tyr Asp Tyr Trp Gly Gln Gly Thr Leu Val Thr Val Ser Ser
                515                 520                 525

His His His His His His
            530

<210> SEQ ID NO 118
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Val Val Gly Gly Gly Gly Thr Gln Thr Val Thr Gln Glu Pro Ser
1               5                   10                  15

Leu Thr Val Ser Pro Gly Gly Thr Val Thr Leu Thr Cys Ala Ser Ser
                20                  25                  30

Thr Gly Ala Val Thr Ser Gly Asn Tyr Pro Asn Trp Val Gln Gln Lys
            35                  40                  45

Pro Gly Gln Ala Pro Arg Gly Leu Ile Gly Gly Thr Lys Phe Leu Val
        50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Thr Lys
                100                 105                 110

Leu Thr Val Leu Gly Gly Gly Ser Gly Gly Gly Ser Gly Gly
            115                 120                 125

Gly Gly Ser Glu Val Gln Leu Val Glu Ser Gly Gly Gly Leu Val Gln
        130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
210                 215                 220

Ala Val Tyr Tyr Cys Val Arg His Ala Asn Phe Gly Asn Ser Tyr Ile
```

```
                225                 230                 235                 240
Ser Tyr Trp Ala Tyr Trp Gly Gln Gly Thr Leu Val Thr Val Ser Ser
                    245                 250                 255

Gly Gly Gly Gly Ser Gly Gly Ser Glu Val Gln Leu Val Glu Ser
                260                 265                 270

Gly Gly Gly Leu Val Gln Pro Gly Gly Ser Leu Thr Leu Ser Cys Ala
            275                 280                 285

Ala Ser Gly Arg Thr Phe Ser Ser Tyr Ala Met Gly Trp Phe Arg Gln
        290                 295                 300

Ala Pro Gly Lys Glu Arg Glu Phe Val Val Ala Ile Asn Trp Ala Ser
305                 310                 315                 320

Gly Ser Thr Tyr Tyr Ala Asp Ser Val Lys Gly Arg Phe Thr Ile Ser
                325                 330                 335

Arg Asp Asn Ser Lys Asn Thr Leu Tyr Leu Gln Met Asn Ser Leu Arg
            340                 345                 350

Ala Glu Asp Thr Ala Val Tyr Tyr Cys Ala Ala Gly Tyr Gln Ile Asn
        355                 360                 365

Ser Gly Asn Tyr Asn Phe Lys Asp Tyr Glu Tyr Asp Tyr Trp Gly Gln
    370                 375                 380

Gly Thr Leu Val Thr Val Ser Ser His His His His His His
385                 390                 395

<210> SEQ ID NO 119
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
            85                  90                  95

Pro Glu Asp Thr Ala Val Tyr Tyr Cys Thr Ile Gly Gly Ser Leu Ser
        100                 105                 110

Val Ser Ser Gln Gly Thr Leu Val Thr Val Ser Ser Gly Gly Gly Gly
    115                 120                 125

Lys Pro Leu Gly Leu Gln Ala Arg Val Val Gly Gly Gly Gly Thr Gln
        130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
            165                 170                 175

Tyr Pro Asn Trp Val Gln Gln Lys Pro Gly Gln Ala Pro Arg Gly Leu
        180                 185                 190
```

Ile Gly Gly Thr Lys Phe Leu Val Pro Gly Thr Pro Ala Arg Phe Ser
            195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Ser Glu Val Gln Leu Val
            260                 265                 270

Glu Ser Gly Gly Gly Leu Val Gln Pro Gly Gly Ser Leu Lys Leu Ser
    275                 280                 285

Cys Ala Ala Ser Gly Phe Thr Phe Asn Lys Tyr Ala Ile Asn Trp Val
290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
    355                 360                 365

Ala Asn Phe Gly Asn Ser Tyr Ile Ser Tyr Trp Ala Tyr Trp Gly Gln
370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Gly Leu Val Gln Pro Gly
                405                 410                 415

Gly Ser Leu Thr Leu Ser Cys Ala Ala Ser Arg Phe Met Ile Ser Glu
            420                 425                 430

Tyr His Met His Trp Val Arg Gln Ala Pro Gly Lys Gly Leu Glu Trp
    435                 440                 445

Val Ser Thr Ile Asn Pro Ala Gly Thr Thr Asp Tyr Ala Glu Ser Val
450                 455                 460

Lys Gly Arg Phe Thr Ile Ser Arg Asp Asn Ala Lys Asn Thr Leu Tyr
465                 470                 475                 480

Leu Gln Met Asn Ser Leu Lys Pro Glu Asp Thr Ala Val Tyr Tyr Cys
                485                 490                 495

Asp Ser Tyr Gly Tyr Arg Gly Gln Gly Thr Gln Val Thr Val Ser Ser
            500                 505                 510

His His His His His His
        515

<210> SEQ ID NO 120
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Leu Asp Gly Asn
    35                  40                  45

Glu Glu Pro Gly Gly Leu Glu Trp Val Ser Ser Ile Ser Gly Ser Gly
50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Ser Gly Gly Gly Gly Ser Gly Gly Val Val Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Gly Leu Val Gln Pro Gly
                405                 410                 415

Gly Ser Leu Thr Leu Ser Cys Ala Ala Ser Arg Phe Met Ile Ser Glu
            420                 425                 430

Tyr His Met His Trp Val Arg Gln Ala Pro Gly Lys Gly Leu Glu Trp
        435                 440                 445

```
Val Ser Thr Ile Asn Pro Ala Gly Thr Thr Asp Tyr Ala Glu Ser Val
    450                 455                 460

Lys Gly Arg Phe Thr Ile Ser Arg Asp Asn Ala Lys Asn Thr Leu Tyr
465                 470                 475                 480

Leu Gln Met Asn Ser Leu Lys Pro Glu Asp Thr Ala Val Tyr Tyr Cys
                485                 490                 495

Asp Ser Tyr Gly Tyr Arg Gly Gln Gly Thr Gln Val Thr Val Ser Ser
            500                 505                 510

His His His His His His
            515

<210> SEQ ID NO 121
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Val Val Gly Gly Gly Thr Gln Thr Val Thr Gln Glu Pro Ser
1               5                   10                  15

Leu Thr Val Ser Pro Gly Gly Thr Val Thr Leu Thr Cys Ala Ser Ser
                20                  25                  30

Thr Gly Ala Val Thr Ser Gly Asn Tyr Pro Asn Trp Val Gln Gln Lys
            35                  40                  45

Pro Gly Gln Ala Pro Arg Gly Leu Ile Gly Gly Thr Lys Phe Leu Val
50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
                100                 105                 110

Leu Thr Val Leu Gly Gly Gly Gly Ser Gly Gly Gly Ser Gly Gly
            115                 120                 125

Gly Gly Ser Glu Val Gln Leu Val Glu Ser Gly Gly Gly Leu Val Gln
            130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
            195                 200                 205

Lys Asn Thr Ala Tyr Leu Gln Met Asn Asn Leu Lys Thr Glu Asp Thr
            210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
                245                 250                 255

Gly Gly Gly Gly Ser Gly Gly Gly Ser Glu Val Gln Leu Val Glu Ser
            260                 265                 270

Gly Gly Gly Leu Val Gln Pro Gly Gly Ser Leu Thr Leu Ser Cys Ala
            275                 280                 285
```

```
Ala Ser Arg Phe Met Ile Ser Glu Tyr His Met His Trp Val Arg Gln
    290                 295                 300

Ala Pro Gly Lys Gly Leu Glu Trp Val Ser Thr Ile Asn Pro Ala Gly
305                 310                 315                 320

Thr Thr Asp Tyr Ala Glu Ser Val Lys Gly Arg Phe Thr Ile Ser Arg
                325                 330                 335

Asp Asn Ala Lys Asn Thr Leu Tyr Leu Gln Met Asn Ser Leu Lys Pro
                340                 345                 350

Glu Asp Thr Ala Val Tyr Tyr Cys Asp Ser Tyr Gly Tyr Arg Gly Gln
            355                 360                 365

Gly Thr Gln Val Thr Val Ser Ser His His His His His His
        370                 375                 380
```

<210> SEQ ID NO 122
<211> LENGTH: 503
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
                100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Asn Ser Leu Arg Leu
    130                 135                 140

Ser Cys Ala Ala Ser Gly Phe Thr Phe Ser Lys Phe Gly Met Ser Trp
145                 150                 155                 160

Val Arg Gln Ala Pro Gly Lys Gly Leu Glu Trp Val Ser Ser Ile Ser
                165                 170                 175

Gly Ser Gly Arg Asp Thr Leu Tyr Ala Asp Ser Val Lys Gly Arg Phe
                180                 185                 190

Thr Ile Ser Arg Asp Asn Ala Lys Thr Thr Leu Tyr Leu Gln Met Asn
        195                 200                 205

Ser Leu Arg Pro Glu Asp Thr Ala Val Tyr Tyr Cys Thr Ile Gly Gly
    210                 215                 220

Ser Leu Ser Val Ser Ser Gln Gly Thr Leu Val Thr Val Ser Ser Gly
225                 230                 235                 240

Gly Gly Gly Ser Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
```

```
            260                 265                 270
Ser Gly Phe Thr Phe Asn Lys Tyr Ala Ile Asn Trp Val Arg Gln Ala
        275                 280                 285
Pro Gly Lys Gly Leu Glu Trp Val Ala Arg Ile Arg Ser Lys Tyr Asn
    290                 295                 300
Asn Tyr Ala Thr Tyr Tyr Ala Asp Gln Val Lys Asp Arg Phe Thr Ile
305                 310                 315                 320
Ser Arg Asp Asp Ser Lys Asn Thr Ala Tyr Leu Gln Met Asn Asn Leu
                325                 330                 335
Lys Thr Glu Asp Thr Ala Val Tyr Tyr Cys Val Arg His Ala Asn Phe
            340                 345                 350
Gly Asn Ser Tyr Ile Ser Tyr Trp Ala Tyr Trp Gln Gly Thr Leu
        355                 360                 365
Val Thr Val Ser Ser Gly Gly Gly Ser Gly Gly Gly Ser Gly
    370                 375                 380
Gly Gly Ser Gln Thr Val Val Thr Gln Glu Pro Ser Leu Thr Val
385                 390                 395                 400
Ser Pro Gly Gly Thr Val Thr Leu Thr Cys Ala Ser Ser Thr Gly Ala
                405                 410                 415
Val Thr Ser Gly Asn Tyr Pro Asn Trp Val Gln Gln Lys Pro Gly Gln
            420                 425                 430
Ala Pro Arg Gly Leu Ile Gly Gly Thr Lys Phe Leu Val Pro Gly Thr
        435                 440                 445
Pro Ala Arg Phe Ser Gly Ser Leu Leu Gly Gly Lys Ala Ala Leu Thr
    450                 455                 460
Leu Ser Gly Val Gln Pro Glu Asp Glu Ala Glu Tyr Tyr Cys Thr Leu
465                 470                 475                 480
Trp Tyr Ser Asn Arg Trp Val Phe Gly Gly Gly Thr Lys Leu Thr Val
                485                 490                 495
Leu His His His His His His
            500

<210> SEQ ID NO 123
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Ser Lys Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Arg Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Val Ser Ser Gln Gly Thr Leu Val Thr
            100                 105                 110
```

Val Ser Ser Gly Gly Gly Ser Gly Gly Gly Ser Gly Gly Val
        115                 120                 125

Val Gly Gly Gly Thr Gln Thr Val Val Thr Gln Glu Pro Ser Leu
130                 135                 140

Thr Val Ser Pro Gly Gly Thr Val Thr Leu Thr Cys Ala Ser Ser Thr
145                 150                 155                 160

Gly Ala Val Thr Ser Gly Asn Tyr Pro Asn Trp Val Gln Gln Lys Pro
                165                 170                 175

Gly Gln Ala Pro Arg Gly Leu Ile Gly Thr Lys Phe Leu Val Pro
        180                 185                 190

Gly Thr Pro Ala Arg Phe Ser Gly Ser Leu Leu Gly Lys Ala Ala
        195                 200                 205

Leu Thr Leu Ser Gly Val Gln Pro Glu Asp Glu Ala Glu Tyr Tyr Cys
210                 215                 220

Thr Leu Trp Tyr Ser Asn Arg Trp Val Phe Gly Gly Gly Thr Lys Leu
225                 230                 235                 240

Thr Val Leu Gly Gly Gly Gly Ser Gly Gly Gly Ser Gly Gly Gly
                245                 250                 255

Gly Ser Glu Val Gln Leu Val Glu Ser Gly Gly Leu Val Gln Pro
        260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
        290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
                340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
370                 375                 380

Gly Gly Gly Ser Gly Gly Gly Ser Glu Val Gln Leu Val Glu Ser Gly
385                 390                 395                 400

Gly Gly Leu Val Gln Pro Gly Gly Ser Leu Thr Leu Ser Cys Ala Ala
                405                 410                 415

Ser Arg Phe Met Ile Ser Glu Tyr His Met His Trp Val Arg Gln Ala
        420                 425                 430

Pro Gly Lys Gly Leu Glu Trp Val Ser Thr Ile Asn Pro Ala Gly Thr
        435                 440                 445

Thr Asp Tyr Ala Glu Ser Val Lys Gly Arg Phe Thr Ile Ser Arg Asp
450                 455                 460

Asn Ala Lys Asn Thr Leu Tyr Leu Gln Met Asn Ser Leu Lys Pro Glu
465                 470                 475                 480

Asp Thr Ala Val Tyr Tyr Cys Asp Ser Tyr Gly Tyr Arg Gly Gln Gly
                485                 490                 495

Thr Gln Val Thr Val Ser Ser His His His His His
                500                 505

<210> SEQ ID NO 124
<211> LENGTH: 267
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 124

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Thr Leu Ala Trp Val Arg Gln Ala Pro Gly
    50                  55                  60

Lys Gly Leu Glu Trp Val Ala Ala Ile Asp Ser Ser Ser Tyr Thr Tyr
65                  70                  75                  80

Ser Pro Asp Thr Val Arg Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Asp Ser Asn Trp Asp Ala Leu Asp Tyr
        115                 120                 125

Trp Gly Gln Gly Thr Thr Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Lys Ala Ser Gln Asn Val Gly Thr Asn Val Gly Trp Tyr Gln Gln
            180                 185                 190

Lys Pro Gly Lys Ala Pro Lys Ala Leu Ile Tyr Ser Ala Ser Phe Arg
        195                 200                 205

Tyr Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Tyr Tyr Thr Tyr Pro Tyr Thr Phe Gly Gly Gly Thr
                245                 250                 255

Lys Val Glu Ile Lys His His His His His His
            260                 265
```

<210> SEQ ID NO 125
<211> LENGTH: 5
<212> TYPE: PRT
<213> ORGANISM: Unknown
<220> FEATURE:
<223> OTHER INFORMATION: Description of Unknown: Sortase A cleavage site
<220> FEATURE:
<221> NAME/KEY: MOD_RES
<222> LOCATION: (3)..(3)
<223> OTHER INFORMATION: Any amino acid

<400> SEQUENCE: 125

```
Leu Pro Xaa Thr Gly
1               5
```

<210> SEQ ID NO 126
<211> LENGTH: 25

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 'Gly Gly Gly
      Gly Ser' repeating units

<400> SEQUENCE: 126

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 127
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-5 'Gly Gly Gly
      Ser' repeating units

<400> SEQUENCE: 127

Gly Gly Gly Ser Gly Gly Gly Ser Gly Gly Gly Ser Gly Gly Gly Ser
1               5                   10                  15

Gly Gly Gly Ser
            20

<210> SEQ ID NO 128
<211> LENGTH: 7
<212> TYPE: PRT
<213> ORGANISM: Unknown
<220> FEATURE:
<223> OTHER INFORMATION: Description of Unknown:
      Protease-cleavable sequence

<400> SEQUENCE: 128

Gly Pro Leu Gly Val Arg Gly
1               5

<210> SEQ ID NO 129
<211> LENGTH: 8
<212> TYPE: PRT
<213> ORGANISM: Unknown
<220> FEATURE:
<223> OTHER INFORMATION: Description of Unknown:
      Protease-cleavable sequence

<400> SEQUENCE: 129

Ile Pro Val Ser Leu Arg Ser Gly
1               5

<210> SEQ ID NO 130
<211> LENGTH: 8
<212> TYPE: PRT
<213> ORGANISM: Unknown
<220> FEATURE:
<223> OTHER INFORMATION: Description of Unknown:
      Protease-cleavable sequence

<400> SEQUENCE: 130
```

Val Pro Leu Ser Leu Tyr Ser Gly
1               5

<210> SEQ ID NO 131
<211> LENGTH: 10
<212> TYPE: PRT
<213> ORGANISM: Unknown
<220> FEATURE:
<223> OTHER INFORMATION: Description of Unknown:
      Protease-cleavable sequence

<400> SEQUENCE: 131

Ser Gly Glu Ser Pro Ala Tyr Tyr Thr Ala
1               5                   10

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Gly Gly Gly Ser
1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Ser Gly Ser Gly Ser
1               5

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Ser Gly Gly Gly Ser Gly Gly Gly Ser Gly Gly Thr
1               5                   10

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Gly Gly Gly Ser Gly Gly Gly Ser Gly Gly Gly Gly Ser
1               5                   10                  15

<210> SEQ ID NO 136
<211> LENGTH: 6
<212> TYPE: PRT
<213> ORGANISM: Artificial Sequence

```
<220> FEATURE:
<223> OTHER INFORMATION: Description of Artificial Sequence: Synthetic
      6xHis tag

<400> SEQUENCE: 136

His His His His His His
1               5

<210> SEQ ID NO 137
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser
            115                 120
```